United States Patent
Yamashita et al.

(12) 
(10) Patent No.: US 6,699,881 B2
(45) Date of Patent: Mar. 2, 2004

(54) THIOL COMPOUNDS, THEIR PRODUCTION AND USE

(75) Inventors: Toshiro Yamashita, Tsukuba (JP); Hiroshi Nara, Suita (JP); Masayuki Takizawa, Tsukuba (JP); Koji Yoshimura, Tsukuba (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/161,289

(22) Filed: Jun. 3, 2002

(65) Prior Publication Data

US 2003/0078253 A1 Apr. 24, 2003

Related U.S. Application Data

(62) Division of application No. 09/787,623, filed as application No. PCT/JP99/05103 on Sep. 20, 1999, now Pat. No. 6,420,415.

(30) Foreign Application Priority Data

Sep. 21, 1998 (JP) ............................. 10-266037

(51) Int. Cl.[7] .................... C07D 211/98; C07D 207/50; A61K 31/4523; A61K 31/4025; A61P 19/02
(52) U.S. Cl. ...................... 514/318; 546/221; 546/216; 546/194; 514/327; 514/328
(58) Field of Search ................. 546/221, 216, 546/194; 514/318, 327, 328

(56) References Cited

U.S. PATENT DOCUMENTS

| | | | |
|---|---|---|---|
| 3,766,138 A | 10/1973 | Crivello | 528/170 |
| 3,855,239 A | 12/1974 | Crivello | 260/326.26 |
| 4,364,958 A | 12/1982 | Seres et al. | 424/276 |
| 4,874,874 A | 10/1989 | Kule et al. | 548/544 |
| 5,318,964 A | 6/1994 | Broadhurst et al. | 514/228.2 |
| 5,447,929 A | 9/1995 | Broadhurst et al. | 514/228.2 |

FOREIGN PATENT DOCUMENTS

| | | |
|---|---|---|
| EP | 0574758 | 12/1993 |
| WO | WO 96/20246 | 7/1996 |
| WO | WO 97/48685 | 12/1997 |
| WO | WO 98/03164 | 1/1998 |
| WO | WO 98/03166 | 1/1998 |
| WO | WO 98/08814 | 3/1998 |

OTHER PUBLICATIONS

T. J. Lobl et al. "SV40 Large T–Antigen Nuclear Signal Analogues: Successful Nuclear Targeting with Bovine Serum Albumin but Not Low Molecular Weight Fluorescent Conjugates", Biopolymers vol. 29, No. 1, pp. 197–203 (1990).

*Primary Examiner*—Mark L. Berch
*Assistant Examiner*—Kahsay Habte
(74) *Attorney, Agent, or Firm*—Elaine M. Ramesh; Mark Chao

(57) ABSTRACT

The present invention provides a compound represented by Formula:

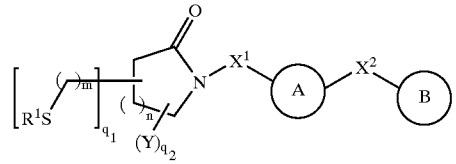

[1]

wherein ring A and ring B may be same or different and each is an optionally substituted homocyclic or heterocyclic ring and the like, each $R^1$ may be same or different and is a hydrogen atom, an optionally substituted hydrocarbon group, an acyl group, an optionally substituted heterocyclic group or $SR^2$, etc., $X^1$ is a bond, an optionally substituted divalent $C_{1-3}$ aliphatic hydrocarbon group or —$NR^3$—, etc, $X^2$ is a bond, an optionally substituted divalent $C_{1-3}$ aliphatic hydrocarbon group, —$NR^4$—, —O— or —$S(O)_p$— (wherein p is 0, 1 or 2), each Y may be same or different and is a hydrogen atom, an optionally substituted hydrocarbon group, a halogen atom, a carboxyl group, an acyl group, an optionally substituted hydroxy group, an optionally substituted amino group, $SR^5$, an oxo group, a thioxo group, an optionally substituted imino group, a nitro group, a cyano group, etc., each m may be same or different and is 0 or 1, n is an integer of 1 to 3, $q_1$ is an integer of 1 to 2n+4, $q_2$ is an integer of 0 to 2n+3, and the sum of $q_1$ and $q_2$ is 2n+4 or a salt thereof.

14 Claims, No Drawings

THIOL COMPOUNDS, THEIR PRODUCTION AND USE

This application is a divisional of U.S. patent application Ser. No. 09/787,623, now U.S. Pat. No. 6,420,415, issued Jul. 16, 2002 was the National Phase filing of International Patent Application No. PCT/JP99/05103, filed Sep. 20, 1999.

TECHNICAL FIELD

The present invention relates to a novel thiol derivative which has an excellent matrix metalloprotease inhibiting activity, and is useful as a therapeutic agent or a prophylactic agent against osteoarthritis and rheumatoid arthritis, and also as an agent for inhibiting the metastasis, the infiltration and the proliferation of various cancers.

BACKGROUND ART

A matrix metalloprotease (MMP) is an endopeptidase playing a physiologically important role in tissue reconstruction, and its protease activity is under strict control. However, such control is disturbed in pathological conditions to induce an excessive degradation of the extracellular matrix, thus being involved pathogenically in articular diseases such as osteoarthritis and rheumatoid arthritis, bone diseases such as osteoporosis, periodontosis, tumor infiltration or metastasis, corneal ulceration and the like.

At least 15 types of MMPs are now known, and are classified based on their primary structure and substrate specificity into 5 groups consisting of the collagenase group (MMP-1, 8, 13), the gelatinase group (MMP-2, 9), the stromelysin group (MMP-3, 10), the membrane-type MMP group (MT1, 2, 3, 4-MMP) and the miscellaneous group (MMP-7, 11, 12, 18). Among these groups, MMP-13 in the collagenase group is reported to be expressed exclusively in cartilage and bone tissues and produced at a higher level in articular diseases.

In addition, MMP-13 is assumed to be deeply involved in bone or articular diseases due to its higher collagen degrading activity when compared with other collagenases.

A large number of MMP inhibitors have been reported (Current Pharmaceutical Design, 2, 624–661 (1996)), Expert Opinion on Therapeutic Patents, 6, 1305–1315 (1996), and a large number of thiol derivatives were also reported recently (WO97-3783, WO97-38007, WO97-48685, EP818443, WO98-3164, WO98-3166, WO98-6696, WO98-8814, WO98-12211, WO98-23588, Bioorganic & Medicinal Chemistry Letters, 8, 1157–1162 (1998), Bioorganic & Medicinal Chemistry Letters, 8, 1163–1168 (1998)).

Those also reported in a large number are the compounds exhibiting inhibitory effects on MMP-13, which are classified broadly into hydroxamic acid derivatives (British Journal of Pharmacology, 121, 540–546 (1997), WO97-31892, WO98-15525, WO98-16506, WO98-16520), carboxylic acid derivatives (Journal of Clinical Investigation, 99, 1534–1545 (1997), WO98-6711, WO98-9934, WO98-17643) and thiol derivatives (WO98-3164, WO98-3166).

A novel compound which is more satisfactory when compared with conventional MMP inhibitors in terms of efficacy, duration and safety is desired.

DISCLOSURE OF INVENTION

In the course of research under the circumstances described above, we finally discovered that, due to the chemical structure characterized substantially by the substitution of the nitrogen atom on a ring represented by Formula:

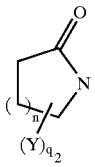

wherein each Y may be same or different and is a hydrogen atom, an optionally substituted hydrocarbon group, a halogen atom, a carboxyl group, an acyl group, an optionally substituted hydroxy group, an optionally substituted amino group, $SR^5$ (wherein $R^5$ is a hydrogen atom, an optionally substituted hydrocarbon group, an acyl group or an optionally substituted heterocyclic group), an oxo group, a thioxo group, an optionally substituted imino group, a nitro group or a cyano group, n is an integer of 1 to 3 and $q_2$ is an integer of 0 to 2n+3 with a group represented by Formula:

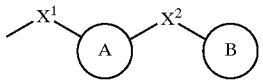

wherein ring A and ring B may be same or different and each is an optionally substituted homocyclic or heterocyclic ring, wherein the substituents on ring A (or ring B) are bound to the position capable of being substituted on ring B (or ring A) and taken together with ring A, ring B and $X^2$ to form a condensed ring, $X^1$ is a bond, an optionally substituted divalent $C_{1-3}$ aliphatic hydrocarbon group or —$NR^3$— (wherein $R^3$ is a hydrogen atom, an optionally substituted hydrocarbon group or an acyl group), $X^2$ is a bond, an optionally substituted divalent $C_{1-3}$ aliphatic hydrocarbon group, —$NR^4$— (wherein $R^4$ is a hydrogen atom, an optionally substituted hydrocarbon group or an acyl group), —O— or —$S(O)_p$— (wherein p is 0, 1 or 2); and also by the substitution on the carbon atom capable of being substituted on a ring represented by Formula:

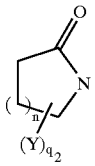

wherein each symbol has a meaning described above with a group represented by Formula:

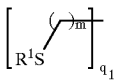

wherein each $R^1$ may be same or different and is a hydrogen atom, an optionally substituted hydrocarbon group, an acyl group, an optionally substituted heterocyclic group or $SR^2$ (wherein $R^2$ is a hydrogen atom, an optionally substituted hydrocarbon group, an acyl group or an optionally substituted heterocyclic group), each m may be same or different and is 0 or 1, $q_1$ is an integer of 1 to 2n+4, a compound represented by Formula:

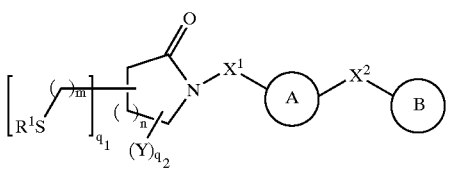

[1]

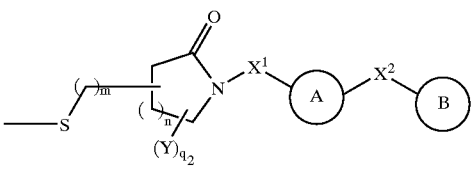

wherein ring A and ring B may be same or different and each is an optionally substituted homocyclic or heterocyclic ring, wherein the substituents on ring A (or ring B) is bound to the position capable of being substituted on ring B (or ring A) and taken together with ring A, ring B and $X^2$ to form a condensed ring, each $R^1$ may be same or different and is a hydrogen atom, an optionally substituted hydrocarbon group, an acyl group, an optionally substituted heterocyclic group or $SR^2$ (wherein $R^2$ is a hydrogen atom, an optionally substituted hydrocarbon group, an acyl group or an optionally substituted heterocyclic group), $X^1$ is a bond, an optionally substituted divalent $C_{1-3}$ aliphatic hydrocarbon group or $-NR^3-$ (wherein $R^3$ is a hydrogen atom, an optionally substituted hydrocarbon group or an acyl group), $X^2$ is a bond, an optionally substituted divalent $C_{1-3}$ aliphatic hydrocarbon group, $-NR^4-$ (wherein $R^4$ is a hydrogen atom, an optionally substituted hydrocarbon group or an acyl group), $-O-$ or $-S(O)_p-$ (wherein p is 0, 1 or 2), each Y may be same or different and is a hydrogen atom, an optionally substituted hydrocarbon group, a halogen atom, a carboxyl group, an acyl group, an optionally substituted hydroxy group, an optionally substituted amino group, $SR^5$ (wherein $R^5$ is a hydrogen atom, an optionally substituted hydrocarbon group, an acyl group or an optionally substituted heterocyclic group), an oxo group, a thioxo group, an optionally substituted imino group, a nitro group or a cyano group, each m may be same or different and is 0 or 1, n is an integer of 1 to 3, $q_1$ is an integer of 1 to 2n+4, $q_2$ is an integer of 0 to 2n+3, and the sum of $q_1$ and $q_2$ is 2n+4 or a salt thereof unexpectedly exhibits an excellent MMP inhibiting effect (especially an MMP13 inhibiting effect) resulting from its specific chemical structure in combination with excellent duration and safety, and such pharmacological effect is useful in a prophylactic and therapeutic agent against osteoarthritis, rheumatoidarthritis, osteoporosis, cancer, periodontosis or corneal ulcer, whereby establishing the invention.

Thus, the present invention is:

(1) a compound represented by Formula (I) shown above or a salt thereof (provided that when ring B is a nitrogen-containing heterocyclic ring then $X^2$ binds to a position capable of being substituted except for a nitrogen atom on ring B);

(2) a compound of the above (1) wherein each of ring A and ring B is an optionally substituted benzene ring;

(3) a compound of the above (1) wherein each $R^1$ may be same or different and is a hydrogen atom, an optionally substituted lower alkyl group, $-(C=O)-R^6$ (wherein $R^6$ is a hydrogen atom, an optionally substituted hydrocarbon group, an optionally substituted amino group or an optionally substituted hydroxy group) or $SR^2$ (wherein $R^2$ has a meaning defined in claim 1);

(4) a compound of the above (1) wherein each $R^1$ may be same or different and is represented by Formula:

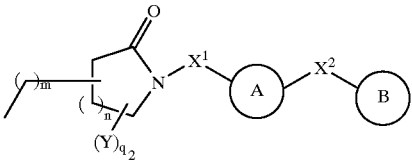

wherein each symbol has a meaning defined in the above (1), or by formula:

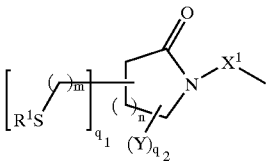

wherein each symbol has a meaning defined in the above (1);

(5) a compound of the above (1) wherein $X^1$ is an optionally substituted methylene group;

(6) a compound of the above (1) wherein $X^2$ is $-O-$;

(7) a compound of the above (1) wherein the group represented by Formula:

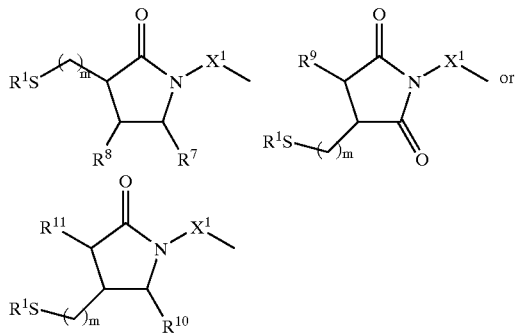

in Formula I is a group represented by Formula:

wherein each of $R^7$ to $R^{11}$ may be same or different and each is a hydrogen atom, an optionally substituted lower alkyl group, an optionally substituted hydroxy group, an optionally substituted amino group or $SR^{12}$ (wherein $R^{12}$ is a hydrogen atom, an optionally substituted hydrocarbon group, an acyl group or an optionally substituted heterocyclic group) and each of the other symbols has a meaning defined in the above (1);

(8) a compound of the above (1) wherein the group represented by Formula:

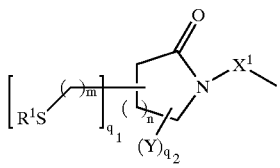

in Formula I is a group represented by Formula:

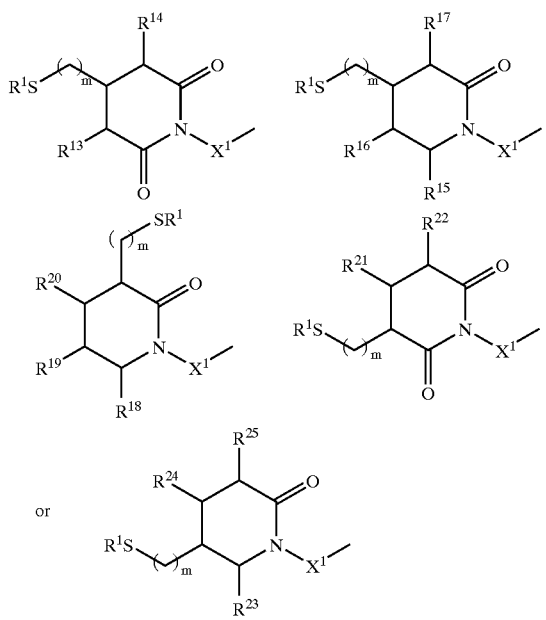

wherein each of $R^{13}$ to $R^{25}$ may be same or different and each is a hydrogen atom, an optionally substituted lower alkyl group, an optionally substituted hydroxy group, an optionally substituted amino group or $SR^{12}$ (wherein $R^{12}$ is a hydrogen atom, an optionally substituted hydrocarbon group, an acyl group or an optionally substituted heterocyclic group) and each of the other symbols has a meaning defined in the above (1);

(9) a compound of the above (1) wherein m is 0;

(10) a compound of the above (1) which is represented by Formula:

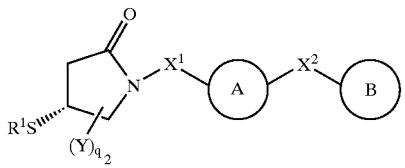

wherein each symbol has a meaning defined in the above (1);

(11) a method for producing a compound represented by Formula:

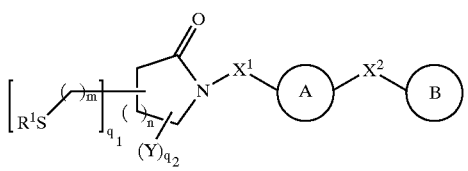

[1]

wherein each symbol has a meaning defined in the above (1) or a salt thereof, comprising reacting a compound represented by Formula:

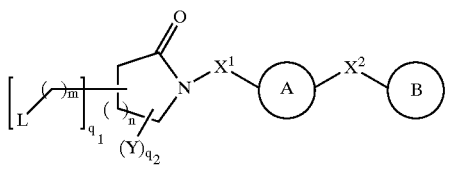

wherein L is a leaving group and each of the other symbols has a meaning defined in the above (1) or a salt thereof with a compound represented by Formula:

$R^1SH$ wherein $R^1$ has a meaning defined in the above (1) or a salt thereof;

(12) a method for producing a compound represented by Formula:

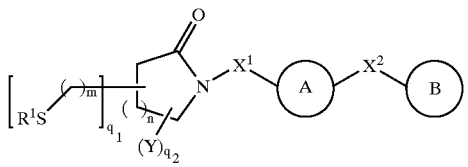

[1]

wherein each symbol has a meaning defined in the above (1) or a salt thereof, comprising reacting a compound represented by Formula:

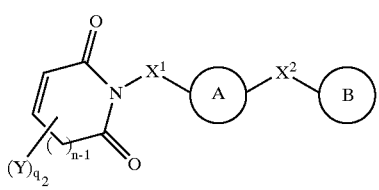

wherein each symbol has a meaning defined in the above (1) or a salt thereof, or a compound represented by Formula:

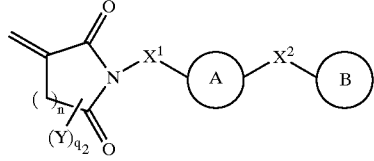

wherein each symbol has a meaning defined in the above (1) or a salt thereof, with a compound represented by Formula:

$R^1SH$ wherein R¹ has a meaning defined in the above (1) or a salt thereof;

(13) a pharmaceutical composition comprising a compound represented by Formula (I) or a salt thereof;

(14) a matrix metalloprotease inhibitor comprising a compound of the above (13) or a salt thereof; and,

(15) a prophylactic and therapeutic agent against osteoarthritis, rheumatoid arthritis, osteoporosis, cancer, periodontosis or corneal ulcer comprising a compound of the above (13) or a salt thereof.

When Compound (I) or a salt thereof contains an asymmetric carbon in its structure, its optically active forms and racemates are also encompassed in the invention, and Compound (I) or a salt thereof may be a hydrate or an anhydride.

The present invention is further detailed below.

Ring A and Ring B

Ring A and ring B may be same or different, and each is a homocyclic or heterocyclic ring having a same or different substituent. Furthermore, the substituents on ring A (or ring B) may be bound to the position capable of being substituted on ring B (or ring A) and taken together with ring A, ring B and X² to form a condensed ring.

A "homocyclic or heterocyclic ring" includes, for example, (i) an aromatic heterocyclic ring or a non-aromatic heterocyclic ring containing, in addition to carbon atoms, 1 or 2 kinds of heteroatoms selected from nitrogen, sulfur and oxygen atoms, preferably the number of heteroatoms is 1 to 3 and (ii) a cyclic hydrocarbon consisting of carbon atoms (homocyclic ring).

An "aromatic heterocyclic ring" may for example be a 5- or 6-membered aromatic heterocylic ring containing, in addition to carbon atoms, 1 to 3 heteroatoms selected from nitrogen, oxygen and sulfur atoms (for example, pyridine, pyrazine, pyrimidine, pyridazine, pyrrole, imidazole, pyrazole, triazole, thiophene, furan, thiazole, isothiazole, oxazole, isoxazole, etc.).

A preferred aromatic heterocyclic ring may for example be pyridine, pyrazine and thiophene rings as well as pyrrole and thiazole rings, etc.

Those preferred especially are (i) a nitrogen-containing heterocyclic ring containing, in addition to carbon atoms, 1 to 2 nitrogen atoms (for example, pyridine and pyrazine rings), or (ii) a 5-membered aromatic heterocyclic ring containing, in addition to carbon atoms, 1 sulfur atom (for example, thiophene ring).

A "non-aromatic heterocyclic ring" described above includes a 5- to 9-membered non-aromatic heterocylic ring, preferably a 5- to 6-membered non-aromatic heterocylic ring, containing, in addition to carbon atoms, 1 to 3 heteroatoms selected from nitrogen, oxygen and sulfur atoms.

Those "non-aromatic heterocyclic ring" may typically be tetrahydropyridine, dihydropyridine, tetrahydropyrazine, tetrahydropyrimidine, tetrahydropyridazine, dihydropyrane, dihydropyrrole, dihydroimidazole, dihydropyrazol, dihydrothiophene, dihydrofuran, dihydrothiazole, dihydroisothiazole, dihydrooxazole, dihydroisoxazole, piperidine, piperazine, hexahydropyrimidine, hexahydropyridazine, tetrahydropyrane, morpholine, pyrrolidine, imidazolidine, pyrazolidine, tetrahydrothiophene, tetrahydrofuran, tetrahydrothiazole, tetrahydroisothiazole, tetrahydrooxazole, tetrahydroisoxazole rings, etc.

A "cyclic hydrocarbon (homocyclic ring)" described above includes a 3- to 10-membered (preferably 5- to 9-membered) cyclic hydrocarbon, more preferably 5- to 6-membered cyclic hydrocarbon. Those which may be exemplified are benzene, a $C_{3-10}$ cycloalkene (for example, cyclobutene, cyclopentene, cyclohexene, cycloheptene, cyclooctene, etc.), a $C_{3-10}$ cycloalkane (for example cyclobutane, cyclopentane, cyclohexane, cycloheptane, cyclooctane, etc.), etc. A cycloalkene is preferably a $C_{5-6}$ cycloalkene (for example, cyclopentene, cyclohexene, etc.), while a cycloalkane is preferably a $C_{5-6}$ cycloalkane (for example, cyclohexane, cyclopentane, etc.), etc. Each of ring A and ring B is preferably a 6-membered homocyclic ring such as benzene and cyclohexene rings, etc., particularly a benzene ring.

A substituent which may be possessed by a "homocyclic or heterocyclic ring" represented by ring A and ring B may for example be:

(i) a halogen atom (for example, fluorine, chlorine, bromine, iodine atoms, etc.);

(ii) an optionally substituted alkyl group;

(iii) an optionally halogenated alkoxy group (for example, a $C_{1-6}$ alkoxy group which is substituted optionally with a halogen atom such as fluorine and chlorine atoms, such as methoxy, difluoromethoxy, trichloromethoxy, trifluoromethoxy, ethoxy, 2,2,2-trifluoroethoxy, perfluoroethoxy, propoxy, isopropoxy, butoxy, isobutoxy, t-butoxy, perfluorobutoxy, pentyloxy, hexyloxy groups);

(iv) an optionally halogenated alkylthio group (for example, a $C_{1-6}$ alkylthio group (especially a $C_{1-4}$ alkylthio group) which is substituted optionally with a halogen atom such as fluorine and chlorine atoms, etc., such as methylthio, difluoromethylthio, trifluoromethylthio, ethylthio, propylthio, isopropylthio, butylthio groups, etc.);

(v) an aryl group (for example, a $C_{6-14}$ aryl group such as phenyl, naphthyl, anthryl, phenanthryl groups, etc.);

(vi) an acyloxy group (for example a $C_{1-3}$ acyloxy group, etc. such as formyloxy, acetoxy, propionyloxy groups, etc.);

(vii) a hydroxy group;

(viii) a nitro group;

(ix) a cyano group;

(x) an amino group;

(xi) a mono- or dialkylamino group (for example, a mono- or di-$C_{1-6}$ alkylamino group (especially, mono- or di-$C_{1-4}$ alkylamino group) such as methylamino, ethylamino, propylamino, dimethylamino, diethylamino groups, etc.);

(xii) a cyclic amino group (for example, a 5- to 9-membered cyclic amino group optionally containing, in addition to carbon atoms, 1 to 3 heteroatoms such as nitrogen, sulfur and oxygen atoms (for example, pyrrolidino, piperidino, morpholino groups, etc.), etc.;

(xiii) an acylamino group (for example, a $C_{1-6}$ alkyl-carbonylamino group such as formylamino group, or acetylamino, propionylamino, butyrylamino groups, etc.);

(xiv) a lower alkyl-substituted carbamoylamino group (such as ethylcarbamoylamino group, etc.);

(xv) an alkylsulfonylamino group (for example, a $C_{1-6}$ alkylsulfonylamino group, etc. such as methylsulfonylamino, ethylsulfonylamino, propylsulfonylamino groups, etc.);

(xvi) an alkoxycarbonyl group (for example, a $C_{1-6}$ alkoxycarbonyl group, etc. such as methoxycarbonyl, ethoxycarbonyl, propoxycarbonyl, butoxycarbonyl, isobutoxycarbonyl groups, etc.);

(xvii) a carboxyl group;

(xviii) an alkylcarbonyl group (for example a $C_{1-6}$ alkylcarbonylgroup, etc. such as methylcarbonyl; ethylcarbonyl, butylcarbonyl groups, etc.);

(xix) a carbamoyl group;

(xx) amono- or dialkylcarbamoyl group (for example, a mono- or di-$C_{1-6}$ alkylcarbamoyl group, etc. such as methylcarbamoyl, ethylcarbamoyl, propylcarbamoyl, butylcarbamoyl, diethylcarbamoyl, dibutylcarbamoyl groups, etc.);

(xxi) an alkylsulfonyl group (for example, a $C_{1-6}$ alkylsulfonyl group, etc. such as methylsulfonyl, ethylsulfonyl, propylsulfonyl groups, etc.);

(xxii) an oxo group;

(xxiii) a thioxo group, etc.

An "optionally substituted alkyl group" means, for example:

(a) a straight or branched alkyl group having 1 to 6 carbon atoms such as methyl, ethyl, propyl, isopropyl, butyl, isobutyl, sec-butyl and tert-butyl, etc.;

(b) a halogenated $C_{1-6}$ alkyl group (forexample, chloromethyl, difluoromethyl, trichloromethyl, trifluoromethyl, 2-bromoethyl, 2,2,2-trifluoroethyl, perfluoroethyl, 3,3,3-trifluoropropyl and perfluorobutyl groups, etc.);

(c) an amino group-substituted $C_{1-6}$ alkyl group (for example, aminomethyl and 2-aminoethyl groups, etc.);

(d) amono- or di-$C_{1-6}$ alkylamino-substituted $C_{1-6}$ alkyl group (for example, methylaminomethyl, dimethylaminomethyl, 2-methylaminoethyl and 2-dimethylaminoethyl groups, etc.);

(e) a carboxyl group-substituted $C_{1-6}$ alkyl group (for example, carboxymethyl and carboxyethyl groups, etc.);

(f) a $C_{1-6}$ alkoxycarbonyl-substituted $C_{1-6}$ alkyl group (for example, methoxycarbonylethyl and ethoxycarbonylethyl groups, etc.);

(g) a hydroxy group-substituted $C_{1-6}$ alkyl group (for example, hydroxymethyl and hydroxyethyl groups, etc.);

(h) a $C_{6-14}$ aryl group-substituted $C_{1-6}$ alkyl group (for example, benzyl, etc.);

(i) a $C_{1-6}$ alkoxy group-substituted $C_{1-6}$ alkyl group (for example, methoxymethyl, methoxyethyl, etc.); or, (j) a $C_{7-15}$ aralkyloxy group-substituted $C_{1-6}$ alkyl group (for example, benzyloxymethyl, etc.), etc.

A substituent which may be possessed by ring A and ring B may for example be a halogen atom, an optionally substituted alkyl group, an optionally halogenated alkoxy group, a mono- or dialkylamino group, an optionally halogenated alkylthio group, etc.

A substituent which may be possessed favorably by ring A and ring B includes a halogen atom, an optionally substituted $C_{1-4}$ alkyl group, an optionally halogenated $C_{1-4}$ alkoxy group, a mono- or di-$C_{1-4}$ alkylamino group, an optionally halogenated $C_{1-4}$ alkylthio group, etc.

Among those listed above, a halogen atom, an optionally substituted $C_{1-4}$ alkyl group and an optionally halogenated $C_{1-4}$ alkoxy group are employed preferably.

A substituent on ring A and ring B may be on any position capable of being substituted on the ring, and when two or more substituents are present, they may be same or different and the number of such substituents may be 1 to about 4. The number of the substituents is preferably 1 to about 3.

When each of ring A and ring B has a nitrogen atom, a quaternary ammonium salt may be formed together with an anion such as, for example, a halogen ion (such as Cl$^-$, Br$^-$, I$^-$), sulfate ion, hydroxy ion, etc.

Each of ring A and ring B is preferably an optionally substituted benzene ring.

A substituent on an "optionally substituted benzene" means, for example, one exemplified above as a substituent on ring A and ring B.

A condensed ring formed whena substituent on ring A (or ring B) is bound to a position capable of being substituted on ring B (or ring A) and taken together with ring A, ring B and $X^2$ described later may for example be fluorene, anthracene, dibenzofuran, dibenzopyrane, dibenzodioxane, carbazol, acridine, phenothiazine, etc., in detail a tricyclic condensed ring represented by Formula:

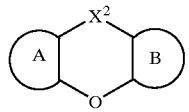

wherein each of ring A and ring B has a meaning defined above, and $x^2$ has a meaning defined later being preferred.

One exemplified more preferably is a tricyclic condensed ring represented by Formula:

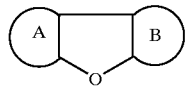

wherein each of ring A and ring B has a meaning defined above.

Group "$R^1$"

Each $R^1$ may be same or different and is a hydrogen atom, an optionally substituted hydrocarbon group, an acyl group, an optionally substituted heterocyclic group or $SR^2$ (wherein $R^2$ is a hydrogen atom, an optionally substituted hydrocarbon group, an acyl group or an optionally substituted heterocyclic group).

A "hydrocarbon group" in an "optionally substituted hydrocarbon group" represented by $R^1$ may for example be an alkyl group, an alkenyl group, an alkynyl group, a cycloalkyl group and an aryl group, with an alkyl group, a cycloalkyl group and an aryl group, especially an alkyl group, being preferred.

An "alkyl group" is a straight or branched chain of 1 to 6 carbon atoms, preferably, a straight or branched alkyl group having 1 to 4 carbon atoms such as methyl, ethyl, propyl, isopropyl, butyl, isobutyl, sec-butyl, tert-butyl, etc.

An "alkenyl group" may for example be an alkenyl group having 2 to 6 carbon atoms such as ethenyl, propenyl, isopropenyl, butenyl, isobutenyl, sec-butenyl and the like, with an alkenyl group having 2 to 4 carbon atoms such as ethenyl, propenyl and isopropenyl being employed preferably.

An "alkynyl group" may for example be an alkynyl group having 2 to 6 carbon atoms such as ethynyl, propynyl, isopropynyl, butynyl, isobutynyl, sec-butynyl and the like, with an alkynyl group having 2 to 4 carbon atoms such as ethynyl, propynyl and isopropynyl being employed preferably.

A "cycloalkyl group" may for example be a $C_{3-8}$ cycloalkyl group such as cyclopropyl, cyclobutyl, cyclopentyl, cyclohexyl, etc., with a $C_{3-6}$ cycloalkyl group such as cyclopropyl and cyclobutyl being employed preferably.

An "aryl group" may for example be an aryl group having 6 to 14 carbon atoms such as phenyl, naphthyl, anthryl, phenanthryl, etc., with an aryl group having 6 to 10 carbon atoms such as phenyl and naphthyl being employed preferably.

A "substituent" on an "optionally substituted hydrocarbon group" may for example be:

(i) a halogen atom (for example, fluorine, chlorine, bromine, iodine atoms, etc.);

(ii) an optionally substituted alkyl group;

(iii) a cycloalkyl group (for example, a $C_{3-8}$ cycloalkyl group, etc. such as cyclopopyl, cyclobutyl, cyclopentyl, cyclohexyl, etc.);

(iv) an optionally substituted aryl group;

(v) an optionally halogenated alkoxy group (for example, a $C_{1-6}$ alkoxy group, etc. which is substituted optionally with a halogen atom such as fluorine and chlorine atoms, etc., such as methoxy, difluoromethoxy, trichloromethoxy, trifluoromethoxy, ethoxy, 2,2,2-trifluoroethoxy, perfluoroethoxy, propoxy, isopropoxy, butoxy, isobutoxy, t-butoxy, perfluorobutoxy, pentyloxy, hexyloxy groups, $C_{3-8}$ cycloalkyloxy and heterocyclyloxy groups, etc.);

(vi) a nitro group;

(vii) a cyano group;

(viii) a hydroxy group;

(ix) an aryloxy group (for example, a $C_{6-14}$ aryloxy group, etc. such as phenoxy and naphthyloxy groups, etc.);

(x) an aralkyloxy group (for example, a $C_{6-14}$ aryl group-$C_{1-4}$ alkyloxy group, etc. such as benzyloxy and phenethyloxy groups, etc.);

(xi) an optionally halogenated alkylthio group (for example, a $C_{1-6}$ alkylthio group (especially $C_{1-4}$ alkylthio group, etc.) which is substituted optionally with a halogen atom such as fluorine and chlorine, such as methylthio, difluoromethylthio, trifluoromethylthio, ethylthio, propylthio, isopropylthio, butylthio groups);

(xii) an amino group;

(xiii) an amino group which is mono- or disubstituted by a formyl group or an optionally substituted alkyl group (for example, a mono- or di-$C_{1-6}$ alkylamino group (especially mono- or di-$C_{1-4}$ alkylamino group) such as methylamino, ethylamino, propylamino, dimethylamino, diethylamino groups, etc., formylamino group, pyrimidinylmethylamino group, etc.);

(xiv) a cyclic amino group (for example, a 5- to 9-membered cyclic amino group optionally containing 1 to 3 heteroatoms such as oxygen and sulfur atoms in addition to nitrogen atoms (for example, pyrrolidino, piperidino and morpholino groups, etc.);

(xv) an alkylcarbonylamino group (for example, a $C_{1-6}$ alkylcarbonylamino group, etc. such as acetylamino, propionylamino and butyrylamino groups, etc.);

(xvi) an alkoxycarbonylamino group (for example, a $C_{1-6}$ alkoxycarbonylamino group, etc. such as ethoxycarbonylamino group, etc.);

(xvii) an arylcarbonylamino group (for example, a $C_{6-14}$ arylcarbonylamino group, etc. such as benzoylamino group, etc.);

(xviii) an acyloxy group (for example, a $C_{1-3}$ acyloxy group, etc. such as formyloxy, acetoxy and propionyloxy groups, etc.);

(xvix) an aminocarbonyloxy group;

(xx) a mono- or dialkylaminocarbonyloxy group (for example, a mono- or di-$C_{1-6}$ alkylaminocarbonyloxy group, etc. such as methylaminocarbonyloxy, ethylaminocarbonyloxy, dimethylaminocarbonyloxy and diethylaminocarbonyloxy groups, etc.);

(xxi) an alkylsulfonylamino group (for example, a $C_{1-6}$ alkylsulfonylamino group, etc. such as methylsulfonylamino, ethylsulfonylamino and propylsulfonylamino groups, etc.);

(xxii) an alkoxycarbonyl group (for example, a $C_{1-6}$ alkoxycarbonyl group, etc. such as methoxycarbonyl, ethoxycarbonyl, propoxycarbonyl, butoxycarbonyl and isobutoxycarbonyl groups, etc.);

(xxiii) an aralkyloxycarbonyl group (for example, a $C_{7-15}$ aralkyloxycarbonyl group, etc. such as benzyloxycarbonyl group, etc.);

(xxiv) an aryloxycarbonyl group (for example a $C_{6-14}$ aryloxycarbonyl group, etc. such as phenoxycarbonyl group, etc.);

(xxv) a carboxyl group;

(xxvi) an alkylcarbonyl group (for example, a $C_{1-6}$ alkylcarbonyl group, etc. such as methylcarbonyl, ethylcarbonyl and butylcarbonyl groups, etc.);

(xxvii) a cycloalkylcarbonyl group (for example, a $C_{3-8}$ cycloalkylcarbonyl group, etc. such as cyclopentylcarbonyl and cyclohexylcarbonyl groups, etc.);

(xxviii) an arylcarbonyl group (for example, a $C_{6-14}$ arylcarbonyl group, etc. such as benzoyl group, etc.);

(xxix) a carbamoyl group;

(xxx) a thiocarbamoyl group;

(xxxi) a mono- or dialkylcarbamoyl group (for example, a mono- or di-$C_{1-6}$ alkylcarbamoyl group, etc. such as methylcarbamoyl, ethylcarbamoyl, propylcarbamoyl, butylcarbamoyl, diethylcarbamoyl and dibutylcarbamoyl groups, etc.);

(xxxii) an alkylsulfonyl group (for example, a $C_{1-6}$ alkylsulfonyl group, etc. such as methylsulfonyl, ethylsulfonyl and propylsulfonyl groups, etc.);

(xxxiii) a cycloalkylsulfonyl group (for example, a $C_{3-8}$ cycloalkylsulfonyl group, etc. such as cyclopentylsulfonyl and cyclohexylsulfonyl groups, etc.);

(xxxiv) an arylsulfonyl group (for example, a $C_{6-14}$ arylsulfonyl group, etc. such as phenylsulfonyl and naphthylsulfonyl groups, etc.);

(xxxv) an aralkylsulfonyl group (for example a $C_{7-15}$ aralkylsulfonyl group, etc. such as benzylsulfonyl group, etc.); and, (xxxvi) an optionally substituted 5- or 6-membered heterocyclic group, etc.

An "optionally substituted 5- or 6-membered heterocyclic group" as a "substituent" on an "optionally substituted hydrocarbon" represented by $R^1$ may for example be a 5- or 6-membered aromatic heterocyclic group, a saturated or unsaturated 5- or 6-membered non-aromatic heterocyclic group, etc.

Such "5- or 6-membered aromatic heterocyclic group" may for example be furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc.

A "5- or 6-membered non-aromatic heterocyclic group" described above may for example be pyrrolidinyl, tetrahydrofuryl, tetrahydrothienyl, piperidyl, tetrahydropyranyl, morpholinyl, thiomorpholinyl and piperazinyl, etc.

Such non-aromatic heterocyclic group may further be condensed with other aromatic or non-aromatic homocyclic or heterocyclic rings.

A "substituent" on an "optionally substituted 5- or 6-membered heterocyclic group" represented as a "substituent" on an "optionally substituted hydrocarbon" may for example be one exemplified as a "substituent" on an "optionally substituted homocyclic or heterocyclic ring" represented by ring A and ring B described above.

In addition, a group represented by formula:

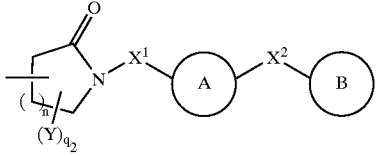

wherein each symbol has a meaning defined above may also be exemplified as an "optionally substituted hydrocarbon group" represented by $R^1$.

The number of the substituents on an "optionally substituted hydrocarbon group" represented by $R^1$ is 1 to about 5 (preferably 1 to 2), and when two or more substituents are present they may be same or different.

An "optionally substituted alkyl group" described as a "substituent" on an "optionally substituted hydrocarbon group" represented by $R^1$ may for example be an "optionally substituted alkyl group" exemplified as a substituent possessed optionally by a "homocyclic or heterocyclic ring" represented by ring A and ring B described above.

An "aryl group" in an "optionally substituted aryl group" described as a "substituent" on an "optionally substituted hydrocarbon group" represented by $R^1$ may for example be an aryl group having 6 to 14 carbon atoms such as phenyl, naphthyl, anthryl and phenanthryl, etc., which an aryl having 6 to 10 carbon atoms such as phenyl and naphthyl being employed preferably.

A "substituent" on an "optionally substituted aryl group" described as a "substituent" on an "optionally substituted hydrocarbon group" represented by $R^1$ may for example be (i) a halogen atom such as fluorine and chlorine, etc., (ii) an optionally halogenated $C_{1-4}$ alkyl group such as methyl, ethyl and trifluoromethyl group, etc., or (iii) a $C_{1-4}$ alkoxy group, etc. such as methoxy and ethoxy groups, etc.

An "acyl group" represented by $R^1$ may for example be —(C=O)—$R^6$, —$SO_2$—$R^6$, —SO—$R^6$, —(C=O)$NR^6R^{27}$, —(C=O)O—$R^6$, —(c=S)O—$R^6$, —(C=S)$NR^6R^{27}$, —(P=O)(O$R^6$)$_2$, —(P=O)(O$R^6$)(O $^{27}$) (wherein $R^6$ is a hydrogen atom or an optionally substituted hydrocarbon group, an optionally substituted amino group or an optionally substituted hydroxy group, and $R^{27}$ is a hydrogen atom or a lower alkyl group (for example, a $C_{1-6}$ alkyl group such as methyl, ethyl, propyl, isopropyl, butyl, isobutyl, sec-butyl, tert-butyl, pentyl and hexyl, etc., with a $C_{1-3}$ alkyl group such as methyl, ethyl, propyl and isopropyl, etc. being preferred)), etc.

An "optionally substituted hydrocarbon group" represented by $R^6$ may for example be one exemplified as an "optionally substituted hydrocarbon group" represented by $R^1$ described above.

A "substituent" on an "optionally substituted amino group" represented by $R^6$ may for example be an optionally substituted hydrocarbon group, an optionally substituted hydroxy group and an acyl group, etc.

An "optionally substituted hydrocarbon group" as a "tubstituent" on an "optionally substituted amino group represented by $R^6$ may for example be one exemplified as an "optionally substituted hydrocarbon group" represented by $R^1$ described above.

An "optionally substituted hydroxy group" as a "substituent" on an "optionally substituted amino group" represented by $R^6$ may for example be (i) a hydroxy group, (ii) a $C_{1-6}$ alkoxy group (for example, methoxy, ethoxy, propoxy, isopropoxy, butoxy and t-butoxy groups, etc.), (iii) a $C_{6-14}$ aryloxy group (for example, phenyloxy and naphthyloxy groups, etc.), (iv) a $C_{1-6}$ alkylcarbonyloxy group (for example, formyloxy, acetoxy and propionyloxy groups, etc.), and (v) a $C_{6-14}$ arylcarbonyloxy group (for example, benzyloxy and naphthylcarbonyloxy groups, etc.), etc., with a hydroxy group and a $C_{1-6}$ alkoxy group (for example, methoxy, ethoxy, propoxy and isopropoxy groups, etc.) being preferred.

An "acyl group" as a "substituent" on an "optionally substituted amino group" represented by $R^6$ may for example be —(C=O)—$R^{28}$, —$SO_2$—$R^{28}$, —SO—$R^{28}$, —(C=O)$NR^{28}R^{29}$, —(C=O)O—$R^{28}$, —(C=S)O—$R^{28}$, —(C=S)$NR^{28}R^{29}$ (wherein $R^{28}$ is a hydrogen atom or an optionally substituted hydrocarbon group, and $R^{29}$ is a hydrogen atom or a lower alkyl group (for example, a $C_{1-6}$ alkyl group, etc. such as methyl, ethyl, propyl, isopropyl, butyl, isobutyl, sec-butyl, tert-butyl, pentyl and hexyl, etc., with a $C_{1-3}$ alkyl group such as methyl, ethyl, propyl and isopropyl, etc. being preferred)), etc.

An "optionally substituted hydrocarbon group" represented by $R^{28}$ may for example be one exemplified as an "optionally substituted hydrocarbon group" represented by $R^1$ described above.

Each of "$C_{1-6}$ alkoxy group", "$C_{6-14}$ aryloxy group", "$C_{1-6}$ alkylcarbonyloxy group" and "$C_{6-14}$ arylcarbonyloxy group" exemplified as an "optionally substituted hydroxy group" as a "substituent" on an "optionally substituted amino group" represented by $R^6$ may further be substituted by one similar to a "substituent" on an "optionally substituted hydrocarbon group" represented by $R^1$ described above, and such substituent is preferably a halogen atom (for example, fluorine, chlorine and bromine, etc.).

An "optionally substituted hydroxy group" represented by $R^6$ described above may for example be one exemplified as an "optionally substituted hydroxy group" as a "substituent" on an "optionally substituted amino group" represented by $R^6$ described above.

Otherwise, $R^6$ and $R^{27}$ may be taken together to form a cyclic amino group (for example, a 5- to 9-membered cyclic amino group which may contain 1 to 3 heteroatoms such as oxygen and sulfur atoms in addition to nitrogen atoms (for example, pyrrolidino, piperidino and morpholino groups, etc.), etc.).

A "heterocyclic group" in an "optionally substituted heterocyclic group" represented by $R^1$ may for example be an aromatic heterocyclic group, a saturated or unsaturated non-aromatic heterocyclic group containing as an ring member atom (ring atom), in addition to carbon atoms, at least one (preferably 1 to 4, more preferably 1 to 2) atom of 1 to 3 heteroatoms selected from oxygen, sulfur and nitrogen atoms.

Such "aromatic heterocyclic group" may for example be 5- or 6-membered aromatic monocyclic heterocyclic group (for example furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl, etc.), etc. and an 8- to 12-membered aromatic condensed heterocyclic group such as an aromatic condensed heterocyclic group (for example, benzofuranyl, isobenzofuranyl, benzothienyl, indolyl, isoindolyl, 1H-indazolyl, benzindazolyl, benzoxazolyl, 1,2-benzoisoxazolyl, benzothiazolyl, benzopyranyl, 1,2-benzoisothiazolyl, 1H-benzotriazolyl, quinolyl, isoquinolyl, cinnolinyl, quinazolyl, quinoxanyl, phthalazinyl, naphthylidinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrenyl, indolydinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl, etc.) (preferably, a heterocyclic ring formed by condensing a 5- or 6-membered aromatic monocyclic heterocyclic group described above with a benzene ring, or a heterocyclic ring formed by condensing the same or different 2 heterocyclic rings of 5- or 6-membered aromatic monocyclic heterocyclic groups described above).

A "non-aromatic heterocyclic group" described above may for example be a 3- to 8-membered (preferably 5- to 6-membered) saturated or unsaturated (preferably saturated) non-aromatic heterocyclic group, etc. such as oxylanyl, azetidinyl, oxetanyl, thietanyl, pyrrolidinyl, tetrahydrofuryl, tetrahydrothienyl, piperidyl, tetrahydropyranyl, morpholinyl, thiomorpholinyl and piperazinyl.

A "substituent" on are "optionally substituted heterocyclic group" represented by $R^1$ may for example be one exemplified as a substituent which may be possessed by a "homocyclic or heterocyclic ring" represented by ring A and ring B, as well as a group represented by Y (Y has a meaning defined above) in Formula (I) shown above and a group represented by Formula:

wherein each symbol has a meaning defined above.

A "substituent" on an "optionally substituted heterocyclic group" represented by $R^1$ may be on any position capable of being substituted on a ring, and when two or more substituents are present then they may be same or different and the number of them may be 1 to about 3. The number of the substituents is preferably 1 to about 2.

An "optionally substituted hydrocarbon group" represented by $R^2$ in "$SR^2$ (wherein R is a hydrogen atom, an optionally substituted hydrocarbon group, an acyl group or an optionally substituted heterocyclic group)" represented by $R^1$ may for example be one exemplified as an "optionally substituted hydrocarbon group" represented by $R^1$ described above.

An "acyl group" represented by $R^2$ in "$SR^2$ (wherein $R^2$ is a hydrogen atom, an optionally substituted hydrocarbon group, an acyl group or an optionally substituted heterocyclic group)" represented by $R^1$ may for example be one exemplified as an "acyl group" represented by RX described above.

An "optionally substituted heterocyclic group" represented by $R^2$ in "$SR^2$ (wherein $R^2$ is a hydrogen atom, an optionally substituted hydrocarbon group, an acyl group or an optionally substituted heterocyclic group)" represented by Rlmayfor example be one exemplified as an "optionally substituted heterocyclic group" represented by $R^1$ described above.

Those employed preferably as $R^1$ may for example be a hydrogen atom, an optionally substituted lower alkyl group, —(C=O)—$R^6$ (wherein $R^6$ has a meaning defined above) or $SR^2$ (wherein $R^2$ has a meaning defined above).

An "optionally substituted lower alkyl group" as a preferred example of $R^1$ may for example be:

(a) a straight or branched alkyl group having 1 to 6 carbon atoms such as methyl, ethyl, propyl, isopropyl, butyl, isobutyl, sec-butyl and tert-butyl;

(b) a halogenated $C_{1-6}$ alkyl group (for example, chloromethyl, difluoromethyl, trichloromethyl, trifluoromethyl, 2-bromoethyl, 2,2,2-trifluoroethyl, perfluoroethyl, 3,3,3-trifluoropropyl and perfluorobutyl groups, etc.);

(c) an amino group-substituted $C_{1-6}$ alkyl group (for example, aminomethyl and 2-aminoethyl groups, etc.);

(d) amono- or di-$C_{1-6}$ alkylamino group-substituted $C_{1-6}$ alkyl group (for example, methylaminomethyl, dimethylaminomethyl, 2-methylaminoethyl and 2-dimethylaminoethyl groups, etc.);

(e) a carboxyl group-substituted $C_{1-6}$ alkyl group (for example, carboxymethyl and carboxyethyl groups, etc.);

(f) a $C_{1-6}$ alkoxycarbonyl group-substituted $C_{1-6}$ alkyl group (for example, methoxycarbonylethyl, ethoxycarbonylethyl and t-butoxycarbonylmethyl groups, etc.);

(g) a hydroxy group-substituted $C_{1-6}$ alkyl group (for example, hydroxymethyl and hydroxyethyl groups, etc.);

(h) a $C_{6-14}$ aryl group-substituted $C_{1-6}$ alkyl group (for example, benzyl, etc.);

(i) a $C_{1-6}$ alkoxy group-substituted $C_{1-6}$ alkyl group (for example, methoxymethyl, methoxyethyl, etc.); or, (j) a $C_{7-15}$ aralkyloxy group-substituted $C_{1-6}$ alkyl group (for example, benzyloxymethyl, etc.), etc. More preferably, $R^1$ is (1) a hydrogen atom, (2) a $C_{1-6}$ alkyl group substituted optionally with [1] a $C_{1-6}$ alkoxycarbonyl group (especially, ethoxycarbonyl, t-butoxycarbonyl, etc.), or with [2] a $C_{6-14}$ aryl group (especially phenyl, etc.), or, (3) —(C=O)—$R^{6a}$ (wherein $R^{6a}$ is a $C_{1-6}$ alkyl group (especially methyl, etc.) or a $C_{6-14}$ aryl group (especially phenyl, etc.), etc.), etc.

Furthermore, a group represented by Formula:

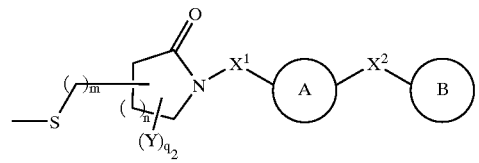

wherein each symbol has a meaning defined above, or by Formula:

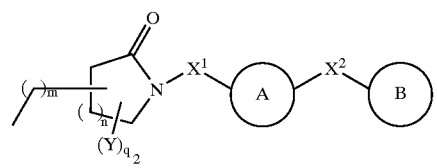

wherein each symbol has a meaning defined above may also be mentioned to be preferable as $R^1$.

Group "X¹"

X¹ is a bond, an optionally substituted divalent $C_{1-3}$ aliphatic hydrocarbon group or —NR³— (wherein R³ is a hydrogen atom, an optionally substituted hydrocarbon group or an acyl group).

A "divalent $C_{1-3}$ aliphatic hydrocarbon group" in an "optionally substituted divalent $C_{1-3}$ aliphatic hydrocarbon group" is a group obtained by removing (2 in total of) hydrogen atoms each one of which is binding to a same or different carbon atoms in a saturated or unsaturated $C_{1-3}$ aliphatic hydrocarbon. Those exemplified typically are:

(i) a $C_{1-3}$ alkylene group (for example, —CH₂—, —CH₂CH₂—, —CH₂CH₂CH₂—, —CH(CH₃)—CH₂—, etc.);

(ii) a $C_{2-3}$ alkenylene group (for example —CH=CH—, —CH=CH—CH₂—, etc.);

(iii) a $C_{2-3}$ alkynylene group (for example,

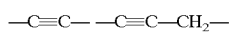

etc.).

Among those listed above, a $C_{1-3}$ alkylene group (for example, —CH₂—, —CH₂CH₂—, —CH₂CH₂CH₂— or —CH(CH₃)—CH₂—, etc.) are employed frequently. Preferably, —CH₂— is employed.

A "substituent" on an "optionally substituted divalent $C_{1-3}$ aliphatic hydrocarbon group" represented by X¹ may for example be one exemplified as a "substituent " on an "optionally substituted hydrocarbon group" represented by R¹ described above (provided that a group represented by Formula:

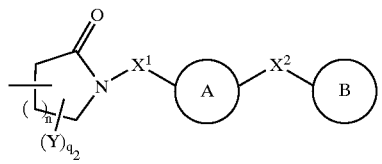

wherein each symbol has a meaning defined above as a substituent on an optionally substituted hydrocarbon group represented by R¹ is excluded from the substituents on an "optionally substituted divalent $C_{1-3}$ aliphatic hydrocarbon group"), as well as an oxo group and a thioxo group, etc.

An "optionally substituted hydrocarbon group" represented by "R³" in "—NR³—" represented by X¹ may for example be one exemplified as an "optionally substituted hydrocarbon group" represented by R¹ described above (provided that a group represented by Formula:

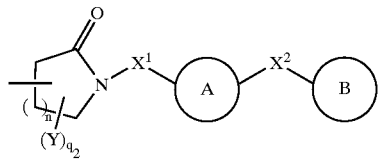

wherein each symbol has a meaning defined above as a substituent a hydrocarbon group represented by R¹ is excluded from the substituents on a hydrocarbon group represented by R¹).

An "acyl group" represented by "R³" in "—NR³—" represented by X¹ may for example be one exemplified as an "acyl group" represented by R¹ described above.

X¹ is preferably an optionally substituted methylene group. A "substituent" on such "optionally substituted methylene group" may for example be one exemplified as a "substituent" on an "optionally substituted divalent $C_{1-3}$ aliphatic hydrocarbon group" represented by X¹.

A particularly preferred X¹ is an unsubstituted methylene group.

Group "X²"

X² is a bond, an optionally substituted divalent $C_{1-3}$ aliphatic hydrocarbon group, —NR⁴ — (wherein R⁴ is a hydrogen atom, an optionally substituted hydrocarbon group or an acyl group), —O— or —S(O)$_p$— (wherein p is 0, 1 or 2).

An "optionally substituted divalent $C_{1-3}$ aliphatic hydrocarbon group" represented by X² may for example be one exemplified as an "optionally substituted divalent $C_{1-3}$ aliphatic hydrocarbon group" represented by X¹ described above.

An "acyl group" represented by "R⁴" in "—NR⁴— represented by X² may for example be one exemplified as an "acyl group" represented by R¹ described above.

X² is preferably —O—.

Group "Y"

Each Y may be same or different and is a hydrogen atom, an optionally substituted hydrocarbon group, a halogen atom, a carboxyl group, an acyl group, an optionally substituted hydroxy group, an optionally substituted amino group, SR⁵ (wherein R⁵ is a hydrogen atom, an optionally substituted hydrocarbon group, an acyl group or an optionally substituted heterocyclic group), an oxo group, a thioxo group, an optionally substituted imino group, a nitro group or a cyano group.

An "optionally substituted hydrocarbon group" represented by Y may for example be one exemplified as an "optionally substituted hydrocarbon group" represented by R³ described above.

A "halogen atom" represented by Y may for example be fluorine, chlorine, bromine, iodine, etc.

An "acyl group" represented by Y may for example be one exemplified as an "acyl group" represented by R¹ described above.

An "optionally substituted hydroxy group" represented by Y may for example be one exemplified as an "optionally substituted hydroxy group" as a "substituent" on an "optionally substituted amino group" represented by R⁶ described above.

An "optionally substituted amino group" represented by Y may for example be one exemplified as an "optionally substituted amino group" represented by R⁶ described above.

An "optionally substituted hydrocarbon group" as "R⁵" in "SR⁵" represented by Y may for example be one exemplified as an "optionally substituted hydrocarbon group" represented by R³ described above.

An "acyl group" as "R⁵" in "SR⁵" represented by Y may for example be one exemplified as an "acyl group" represented by R¹ described above.

An "optionally substituted heterocyclic group" as "R⁵" in "SR⁵" represented by Y may for example be one exemplified as an "optionally substituted heterocyclic group" represented by R¹ described above (provided that, among the examples of a "substituent" in an "optionally substituted heterocyclic group" represented by R¹ described above, a group represented by Y (wherein Y has a meaning defined above)and a group represented by Formula:

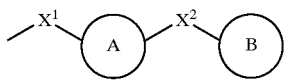

wherein each symbol has a meaning defined above are excluded from the substituents on an "optionally substituted heterocyclic group" represented by $R^5$).

A substituent on an "optionally substituted imino group" represented by Y may for example be one exemplified as an "optionally substituted hydrocarbon group" or an "acyl group" represented by $R^4$.

Those employed preferably as Y may for example be a hydrogen atom, an optionally substituted lower alkyl group, an optionally substituted hydroxy group, an optionally substituted amino group, $SR^{12}$ (wherein $R^{12}$ is a hydrogen atom, an optionally substituted hydrocarbon group, an acyl group or an optionally substituted heterocyclic group) or an oxo group, etc.

An "optionally substituted lower alkyl group" described above as a preferred example of Y may for example be:

(a) a straight or branched alkyl group having 1 to 6 carbon atoms such as methyl, ethyl, propyl, isopropyl, butyl, isobutyl, sec-butyl and tert-butyl, etc.;

(b) a halogenated $C_{1-6}$ alkyl group (for example, chloromethyl, difluoromethyl, trichloromethyl, trifluoromethyl, 2-bromoethyl, 2,2,2-trifluoroethyl, perfluoroethyl, 3,3,3-trifluoropropyl and perfluorobutyl groups, etc.);

(c) an amino group-substituted $C_{1-6}$ alkyl group (for example, aminomethyl and 2-aminoethyl groups, etc.);

(d) a mono- or di-$C_{1-6}$ alkylamino group-substituted $C_{1-6}$ alkyl group (for example, methylaminomethyl, dimethylaminomethyl, 2-methylaminoethyl and 2-dimethylaminoethyl groups, etc.);

(e) a carboxyl group-substituted $C_{1-6}$ alkyl group (for example, carboxymethyl and carboxyethyl groups, etc.);

(f) a $C_{1-6}$ alkoxycarbonyl group-substituted $C_{1-6}$ alkyl group (for example, methoxycarbonylethyl, ethoxycarbonylethyl and t-butoxycarbonylmethyl groups);

(g) a hydroxy group-substituted $C_{1-6}$ alkyl group (for example, hydroxymethyl and hydroxyethyl groups, etc.);

(h) a $C_{6-14}$ aryl group-substituted $C_{1-6}$ alkyl group (for example, benzyl, etc.);

(i) a $C_{1-6}$ alkoxy group-substituted $C_{1-6}$ alkyl group (for example, methoxymethyl, methoxyethyl, etc.); or, (j) a $C_{7-15}$ aralkyloxy group-substituted $C_{1-6}$ alkyl group (for example, benzyloxymethyl, etc.), etc.

An "optionally substituted hydroxy group" described above as a preferred example of Y may for example be one exemplified as an "optionally substituted hydroxy group" as a "substituent" on an "optionally substituted amino group" represented by $R^6$ described above.

An "optional substituted amino group" described above as a preferred example of Y may for example be one exemplified as an "optionally substituted amino group" represented by $R^6$ described above.

An "optionally substituted hydrocarbon group" as "$R^{12}$" in "$SR^{12}$" described above as a preferred example of Y may for example be one exemplified as an "optionally substituted hydrocarbon group" represented by $R^3$ described above.

An "acyl group" as "$R^{12}$" in "$SR^{12}$" represented as Y may for example be one exemplified as an "acyl group" represented by $R^1$ described above.

An "optionally substituted heterocyclic group" as "$R^{12}$" in "$SR^{12}$" represented by Y may for example be one exemplified as an "optionally substituted heterocyclic group" represented by $R^1$ described above (provided that among the examples of a "substituent" in an "optionally substituted heterocyclic group" represented by $R^1$ described above, a group represented by Y (wherein Y has a meaning defined above) and a group represented by Formula:

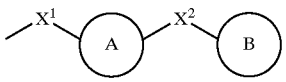

wherein each symbol has a meaning defined above are excluded from the substituents on an "optionally substituted heterocyclic group" represented by $R^{12}$).

More preferably, Y may for example be an unsubstituted $C_{1-6}$ alkyl group (for example, methyl, ethyl, propyl, isopropyl, butyl, isobutyl, sec-butyl, tert-butyl, etc.), a hydroxy group-substituted $C_{1-6}$ alkyl group (for example, hydroxymethyl and hydroxyethyl groups, etc.), an alkoxy group-substituted $C_{1-6}$ alkyl group (for example, benzyloxymethyl and methoxymethyl groups, etc.) as well as an oxo group.

Number "m"

Each m may be same or different and is 0 or 1. m is preferably 0.

Number "n"

Each n is an integer of 1 to 3. n is preferably 1 to 2, especially 1.

Numbers "$q_1$ and $q_2$"

$q_1$ is an integer of 1 to 2n+4, $q_2$ is an integer of 0 to 2n+3, and the sum of $q_1$ and $q_2$ is 2n+4.

Preferably $q_1$ is 1.

Partial structure of compound represented by Formula [I]

A preferred group represented by Formula

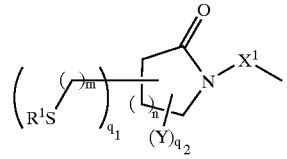

which is a partial structure of Formula [I] shown above may for example be a group represented by Formula:

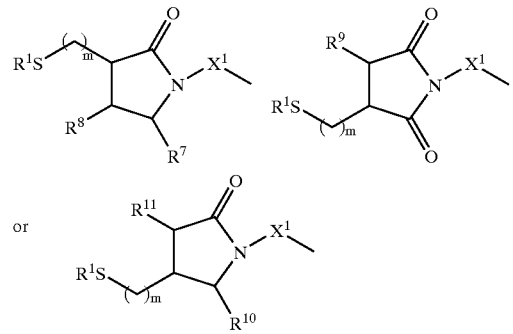

wherein each of $R^7$ to $R^{11}$ may be same or different and each is a hydrogen atom, an optionally substituted lower alkyl group, an optionally substituted hydroxy group, an optionally substituted amino group or $SR^{12}$ (wherein $R^{12}$ has a meaning defined above) and each of other symbols has a meaning defined above.

An "optionally substituted lower alkyl group" represented by each of $R^7$ to $R^{11}$" may for example be:

(a) a straight or branched alkyl group having 1 to 6 carbon atoms such as methyl, ethyl, propyl, isopropyl, butyl, isobutyl, sec-butyl and tert-butyl, etc.;

(b) a halogenated $C_{1-6}$ alkyl group (for example, chloromethyl, difluoromethyl, trichloromethyl, trifluoromethyl, 2-bromoethyl, 2,2,2-trifluoroethyl, perfluoroethyl, 3,3,3-trifluoropropyl and perfluorobutyl groups, etc.);

(c) an amino group-substituted $C_{1-6}$ alkyl group (for example, aminomethyl and 2-aminoethyl groups, etc.);

(d) a mono- or di-$C_{1-6}$ alkylamino group-substituted $C_{1-6}$ alkyl group (for example, methylaminomethyl, dimethylaminomethyl, 2-methylaminoethyl and 2-dimethylaminoethyl groups, etc.);

(e) a carboxyl group-substituted $C_{1-6}$ alkyl group (for example, carboxymethyl and carboxyethyl groups, etc.);

(f) a $C_{1-6}$ alkoxycarbonyl group-substituted $C_{1-6}$ alkyl group (for example, methoxycarbonylethyl, ethoxycarbonylethyl and t-butoxycarbonylmethyl groups, etc.);

(g) a hydroxy group-substituted $C_{1-6}$ alkyl group (for example, hydroxymethyl and hydroxyethyl groups, etc.);

(h) a $C_{6-14}$ aryl group-substituted $C_{1-6}$ alkyl group (for example, benzyl, etc.);

(i) a $C_{1-6}$ alkoxy group-substituted $C_{1-6}$ alkyl group (for example, methoxymethyl, methoxyethyl, etc.); or, (j) a C7–15 aralkyloxy group-substituted $C_{1-6}$ alkyl group (for example, benzyloxymethyl, etc.), etc.

An "optionally substituted hydroxy group" represented by each of $R^7$ to $R^{11}$ may for example be one exemplified as an "optionally substituted hydroxy group" as a "substituent" on an "optionally substituted amino group" represented by $R^6$ described above.

An "optionally substituted amino group" represented by each of $R^7$ to $R^{11}$ may for example be one exemplified as an "optionally substituted amino group" represented by $R^6$ described above.

More preferably, each of $R^7$ to $R^{11}$ may for example be an unsubstituted $C_{1-6}$ alkyl group (for example, methyl, ethyl, propyl, isopropyl, butyl, isobutyl, sec-butyl, tert-butyl), a hydroxy group-substituted $C_{1-6}$ alkyl group (for example, hydroxymethyl and hydroxyethyl groups, etc.), an alkoxy group-substituted $C_{1-6}$ alkyl group (for example, benzyloxymethyl and methoxymethyl groups, etc.) as well as an oxo group.

A most preferred group represented by Formula:

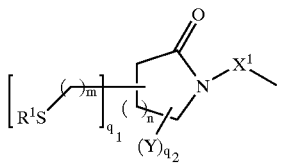

which is a partial structure of Formula [I] shown above may for example be a group represented by Formula:

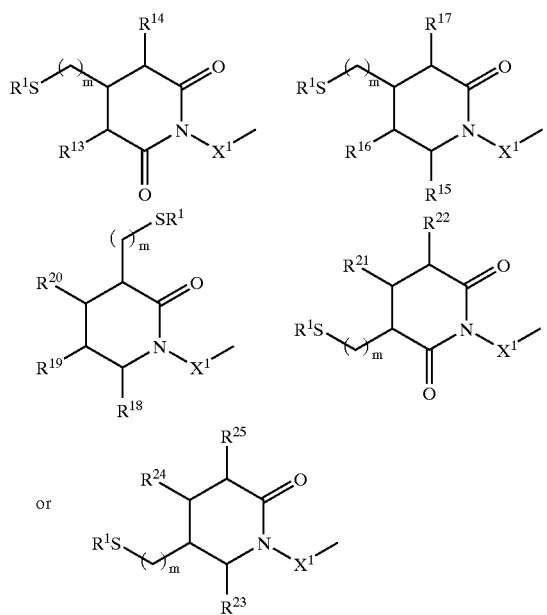

or wherein each of $R^{13}$ to $R^{25}$ may be same or different and each is a hydrogen atom, an optionally substituted lower alkyl group, an optionally substituted hydroxy group, an optionally substituted amino group or $SR^{12}$ (wherein $R^{12}$ has a meaning defined above).

An "optionally substituted lower alkyl group" represented by each of $R^{13}$ to $R^{25}$ may for example be:

(a) a straight or branched alkyl group having 1 to 6 carbon atoms such as methyl, ethyl, propyl, isopropyl, butyl, isobutyl, sec-butyl and tert-butyl, etc.;

(b) a halogenated $C_{1-6}$ alkyl group (for example, chloromethyl, difluoromethyl, trichloromethyl, trifluoromethyl, 2-bromoethyl, 2,2,2-trifluoroethyl, perfluoroethyl, 3,3,3-trifluoropropyl and perfluorobutyl groups, etc.);

(c) an amino group-substituted $C_{1-6}$ alkyl group (for example, aminomethyl and 2-aminoethyl groups, etc.);

(d) a mono- or di-$C_{1-6}$ alkylamino group-substituted $C_{1-6}$ alkyl group (for example, methylaminomethyl, dimethylaminomethyl, 2-methylaminoethyl and 2-dimethylaminoethyl groups, etc.);

(e) a carboxyl group-substituted $C_{1-6}$ alkyl group (for example, carboxymethyl and carboxyethyl groups, etc.);

(f) a $C_{1-6}$ alkoxycarbonyl group-substituted $C_{1-6}$ alkyl group (for example, methoxycarbonylethyl, ethoxycarbonylethyl and t-butoxycarbonylmethyl groups, etc.);

(g) a hydroxy group-substituted $C_{1-6}$ alkyl group (for example, hydroxymethyl and hydroxyethyl groups, etc.);

(h) a $C_{6-14}$ aryl group-substituted $C_{1-6}$ alkyl group (for example, benzyl, etc.);

(i) a $C_{1-6}$ alkoxy group-substituted $C_{1-6}$ alkyl group (for example, methoxymethyl, methoxyethyl, etc.); or, (j) a $C_{7-15}$ aralkyloxy group-substituted $C_{1-6}$ alkyl group (for example, benzyloxymethyl, etc.), etc.

An "optionally substituted hydroxy group" represented by each of $R^{13}$ to $R^{25}$ may for example be one exemplified as an "optionally substituted hydroxy group" as a "substituent" on an "optionally substituted amino group" represented by $R^6$ described above.

An "optionally substituted amino group" represented by each of $R^{13}$ to $R^{25}$ may for example be one exemplified as an "optionally substituted amino group" represented by $R^6$ described above.

More preferably, each of $R^{13}$ to $R^{25}$ may for example be an unsubstituted $C_{1-6}$ alkyl group (for example, methyl, ethyl, propyl, isopropyl, butyl, isobutyl, sec-butyl, tert-butyl, etc.), a hydroxy group-substituted $C_{1-6}$ alkyl group (for example, hydroxymethyl and hydroxyethyl groups, etc.), an alkoxy group-substituted $C_{1-6}$ alkyl group (for example, benzyloxymethyl and methoxymethyl groups, etc.) as well as an oxo group.

Among the groups represented by Formula:

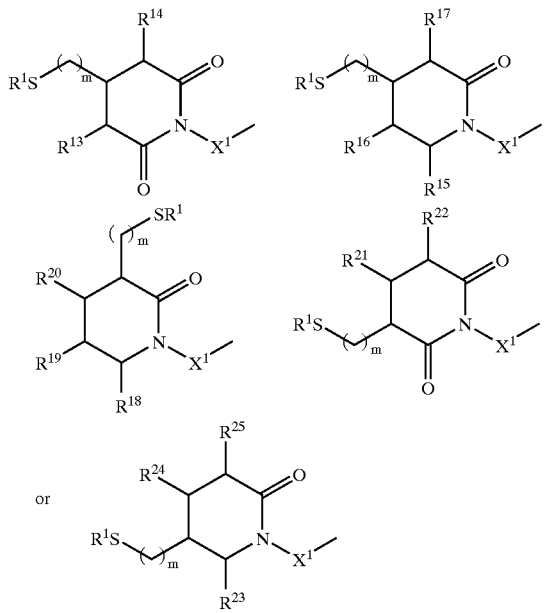

or wherein each symbol has a meaning defined above, each of which is exemplified as a preferred group represented by Formula:

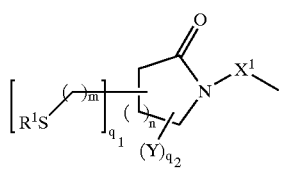

which is a partial structure of Formula [I] shown above, one preferred particularly may for example be a group represented by Formula:

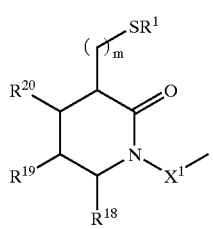

wherein each symbol has a meaning defined above.

Preferred examples of a compound represented by Formula [I] may for example be the compounds represented later by Formula [Ia], [Ib], [Ic], [Id], [Ie], [If], [Ig], [Ih], [Ii], [XXXIV] and [XXXVII].

One preferred particularly is a compound represented by Formula [I] wherein both of ring A and ring B are benzene rings, $R^1$ is an acyl group, $X^1$ is methylene, $X^2$ is an oxygen atom and n is 1.

Optical isomers of compound represented by Formula [I]

While a compound represented by Formula [I] or a salt thereof can exist as an optical isomer when it contains an asymmetric carbon in its structure, a preferable optical isomer may for example be a compound represented by Formula:

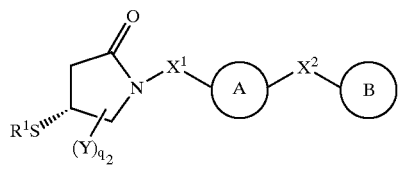

wherein each symbol has a meaning defined above or a salt thereof.

A method for producing compound (I) according to the invention or a salt thereof is discussed below.

Compound (I) according to the invention or a salt thereof can be produced by methods (A) to (N) described below.

(Method A) A compound represented by Formula:

[Ia]

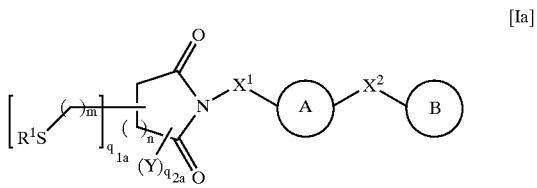

wherein $q_{1a}$ is an integer of 1 to 2n+2, $q_{2a}$ is an integer of 0 to 2n+1, and the sum of $q_{1a}$ and $q_{2a}$ is 2n+2 and each of other symbols has a meaning defined above which is encompassed within compound (I) of the invention or a salt thereof can be produced for example by reacting a compound represented by Formula:

(II)

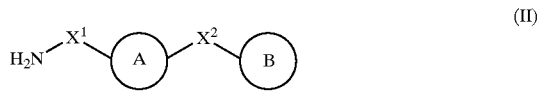

wherein each symbol has a meaning defined above or a salt thereof with a compound represented by Formula:

(III)

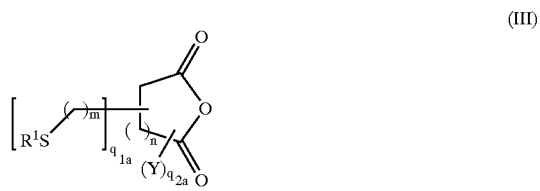

wherein $q_{1a}$ is an integer of 1 to 2n+2, $q_{2a}$ is an integer of 0 to 2n+1, and the sum of $q_{1a}$ and $q_{2a}$ is 2n+2 or a salt thereof or with a compound represented by Formula:

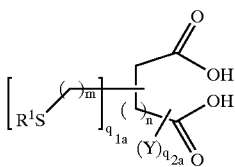

(IV)

wherein each symbol has a meaning defined above or a salt thereof.

In this reaction, one mole of compound [II] or a salt thereof is reacted usually with 1 to 5 moles, preferably 1 to 3 moles of compound [III] or a salt thereof or compound [IV] or a salt thereof.

A reaction solvent is an aromatic hydrocarbon such as benzene, toluene and xylene, etc., an organic acid such as acetic acid, etc., an organic acid anhydride such as acetic anhydride, etc. and an amide such as N,N-dimethylformamide and N,N-dimethylacetamide, etc.

This reaction is conducted usually under a dehydrating condition. The addition of an acid in this reaction allows the reaction to proceed advantageously. Such acid is preferably an inorganic acid such as hydrochloric acid and sulfuric acid, etc. and an organic acid such as methanesulfonic acid, benzenesulfonic acid, toluenesulfonic acid, oxalic acid, fumaric acid and maleic acid, etc. While the amount of an acid employed may vary depending on the types of the compound and the solvent employed as well as other reaction conditions, it is usually 0.01 to 1 mole, preferably 0.05 to 0.1 mole per 1 mole of the compound.

The reaction temperature is usually 0 to 200° C., preferably 50 to 150° C.

The reaction time is usually 30 minutes to 48 hours, preferably 1 to 24 hours.

Compound [II] is produced for example by method N described below, and compound [III] or [IV] is commercially available or may be a sulfur-substituted acid anhydride and a dicarboxylic acid produced for example in method D described below.

(Method B) Compound (I) or a salt thereof according to the invention can be produced for example by reacting a compound represented by Formula:

(II)

wherein each symbol has a meaning defined above or a salt thereof with a compound represented by Formula:

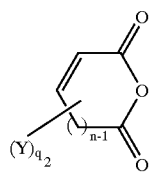

(V)

wherein each symbol has a meaning defined above or a salt thereof or with a compound represented by Formula:

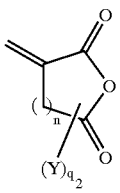

(VI)

wherein each symbol has a meaning defined above or a salt thereof to produce a compound represented by Formula:

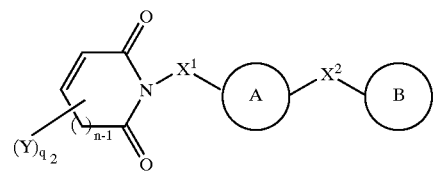

(VII)

wherein each symbol has a meaning defined above or a salt thereof or a compound represented by Formula:

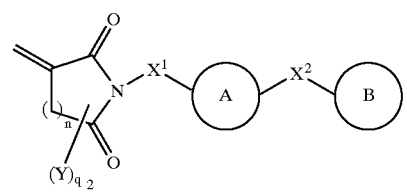

(VIII)

wherein each symbol has a meaning defined above or a salt thereof, followed by reacting a compound represented by Formula [VII] or [VIII] shown above or a salt thereof with a compound represented by $R^1SH$ (wherein $R^1$ has a meaning defined above) or a salt thereof.

In order to react a compound represented by Formula [II] or a salt thereof with a compound represented by Formula [V] or [VI] or a salt thereof to form a compound represented by Formula [VII] or [VIII] or a salt thereof, a method similar to (method A) described above may be employed.

In a reaction to produce a compound represented by Formula [I] or a salt thereof from a compound represented by Formula [VII] or [VIII] or a salt thereof, 1 to 5 moles, preferably 1 to 3 moles of a compound represented by $R^1SH$ (wherein $R^1$ has a meaning defined above) is used per 1 mole of a compound represented by Formula [VII] or [VIII] or a salt thereof.

$R^1SH$ may for example be an inorganic sulfide such as hydrogen sulfide, sodium hydrogen sulfide and sodium sulfide, etc. and their salts, an organic sulfur-containing acid such as thioacetic acid and thiobenzoic acid, etc. and their salts, an aliphatic mercaptan such as methylmercaptan, benzylmercaptan, triphenylmethylmercaptan and 3-mercaptopropionic acid derivatives, etc., an aromatic mercaptan such as thiophenol and a thiourea.

A reaction solvent is an alcohol such as methanol and ethanol, etc., an ether such as dioxane and tetrahydrofuran, etc., an aromatic hydrocarbon such as benzene, toluene and xylene, etc., an ester such as ethyl acetate, etc., a halogenated hydrocarbon such as chloroform and dichloromethane, etc., a nitrile such as acetonitrile, etc., an amide such as N,N-dimethylformamide and N,N-dimethylacetamide, etc. and a sulfoxide such as dimethylsulfoxide, etc.

The addition of a base in this reaction allows the reaction to proceed advantageously. Such base is an inorganic base (alkaline metal hydroxide such as sodium hydroxide and potassium hydroxide, etc., alkaline metal hydrogen carbonate such as sodium hydrogen carbonate and potassium hydrogen carbonate, etc., alkaline metal carbonate such as sodium carbonate and potassium carbonate, etc., alkaline metal hydride such as sodium hydride and potassium hydride, etc., sodium amide, alkoxide such as sodium methoxide and sodium ethoxide, etc.) and an organic base (amine such as trimethylamine, triethylamine and diisopropylethylamine, cyclic amine such as pyridine, etc.), etc.

Instead of using a base in this reaction, a compound represented by $R^1SH$ (wherein $R^1$ has a meaning defined above) or a salt thereof may be converted for example into an alkaline metal salt or an alkaline earth metal salt, which may then be reacted with a compound represented by Formula [VII] or [VIII] or a salt thereof.

While the amount of a base employed may vary depending on the types of the compound and the solvent employed as well as other reaction conditions, it is usually 1 to 10 moles, preferably 1 to 5 moles per 1 mole of a compound represented by $R^1SH$ (wherein $R^1$ has a meaning defined above) or a salt thereof. The reaction temperature is usually −50 to 200° C., preferably −20 to 100° C. The reaction time may vary depending on the type of the compound and the reaction temperature, and is usually 1 to 72 hours, preferably 1 to 24 hours.

(Method C) A compound represented by Formula:

peroxide such as m-chloroperbenzoic acid and peracetic acid, etc. or hydrogen peroxide or an air oxidation, etc.

In this reaction, usually 1 to 5 moles, preferably 1 to 2 moles of an oxidizing agent is employed per 1 mole of compound [IX] or a salt thereof.

A reaction solvent is an ether such as dioxane and tetrahydrofuran, etc., an aromatic hydrocarbon such as benzene, toluene and xylene, etc., an ester such as ethyl acetate, etc., a halogenated hydrocarbon such as chloroform and dichloromethane, etc., a nitrile such as acetonitrile, etc., an amide such as N,N-dimethylformamide and N,N-dimethylacetamide, etc. and a sulfoxide such as dimethylsulfoxide, etc.

The addition of a base in this reaction allows the reaction to proceed advantageously. Such base is an inorganic base (alkaline metal hydroxide such as sodium hydroxide and potassium hydroxide, etc., alkaline metal hydrogen carbonate such as sodium hydrogen carbonate and potassium hydrogen carbonate, etc., alkaline metal carbonate such as sodium carbonate and potassium carbonate, etc., halide such as sodium iodide and potassium iodide, etc., alkaline metal hydride such as sodium hydride and potassium hydride, etc., sodium amide, alkoxide such as sodium methoxide and sodium ethoxide, etc.) and an organic base (amine such as trimethylamine, triethylamine and diisopropylethylamine, etc., cyclic amine such as pyridine, etc.). While the amount of a base employed may vary depending on the types of the compound and the solvent employed as well as other reaction conditions, it is usually 0.1 to 20 moles, preferably 1 to 2 moles per 1 mole of compound [IX] or a salt thereof.

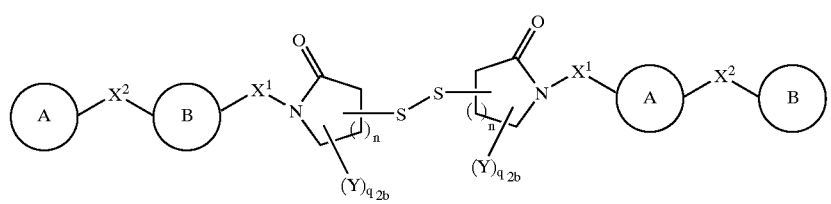

[Ib]

wherein $q_{2b}$ is 2n+3 and each of other symbols has a meaning defined above which is encompassed within compound (I) of the invention or a salt thereof can be produced for example by reacting a compound represented by Formula:

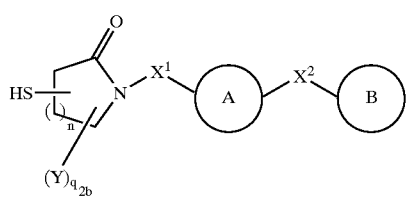

[IX]

wherein each symbol has a meaning defined above or a salt thereof with an oxidizing agent.

An oxidizing agent employed in this reaction may be an ordinary disulfide bond-forming reagent found in "SHINJIKKENKAGAKUKOZA", Vol. 15, Oxidation and Reduction (MARUZEN), for example, a halogen such as chlorine, bromine and iodine, etc., an N-halogen carboxylimide such as N-chlorosuccinimide, etc. or a sulfonamide, a metallic oxidizer such as a chromic acid, lead tetraacetate, potassium permanganate and iron chloride, etc., an organic The reaction temperature is usually −20 to 200° C., preferably 0 to 100° C. The reaction time is usually 1 minute to 24 hours, preferably 1 minute to 5 hours.

(Method D) A compound represented by Formula:

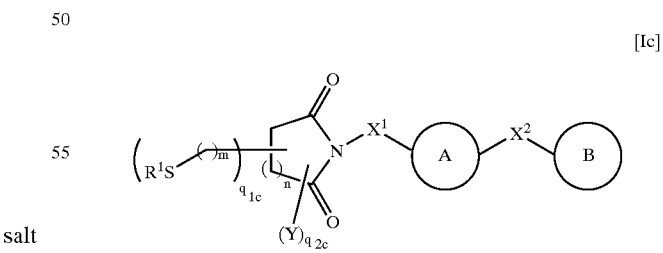

[Ic]

wherein $q_{1c}$ is an integer of 1 to 2n+2, $q_{2c}$ is an integer of 0 to 2n+1, and the sum of $q_{1c}$ and $q_{2c}$ is 2n+2 which is encompassed within compound (I) of the invention or a salt thereof can be produced for example by reacting a compound represented by Formula:

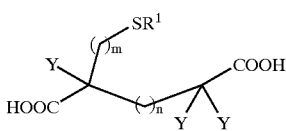

wherein each symbol has a meaning defined above or a salt thereof with a compound represented by Formula:

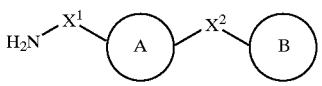

wherein each symbol has a meaning defined above or a salt thereof.

In this reaction, compound [X] or a salt thereof is first reacted with various acid anhydrides or acid halides to form a corresponding acid anhydride. A reagent employed is an acid anhydride or an acid halide of an ordinary organic acid such as acetic acid and benzoic acid, etc.

This reaction employs 1 to 50 moles of a reagent per 1 mole of compound [X] or a salt thereof. While the reaction solvent is an aromatic hydrocarbon such as benzene, toluene and xylene, etc., an organic acid such as acetic acid, etc., a nitrile such as acetonitrile, etc. and an amide such as N,N-dimethylformamide and N,N-dimethylacetamide, etc., it May be an acid anhydride itself employed as a reagent. While the reaction temperature may vary depending on compound [X] or a salt thereof employed as well as other reaction conditions, it is 0 to 200° C., preferably 20 to 150° C. The reaction time is 30 minutes to 24 hours, preferably 1 to 10 hours. An acid anhydride thus obtained and compound [II] or a salt thereof are subjected to a method similar to that in (Method A) described above to produce compound [Ic] or a salt thereof.

Among compounds represented as compounds [Ic], one wherein $R^1$ is other than an acyl group can be hydrolyzed with an acid or a base to produce a compound wherein $R^1$ is H.

An acid which may be employed may for example be an inorganic acid such as hydrochloric acid, sulfuric acid and nitric acid, etc., and a base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., sodium amide, an alkoxide such as sodium methoxide and sodium ethoxide, etc., ammonia, an organic amine such as methylamine and ethylamine, etc.

This reaction is conducted in a 20 to 50 volumes of an aqueous solution of an inorganic acid described above (usually at 10 to 30%) per 1 g of a compound among compounds [Ic] wherein $R^1$ is an acyl group, or in an aqueous solution containing 3 to 10 moles of a base described above per 1 mole of a compound among compounds [Ic] wherein $R^1$ is an acyl group. In view of the solubility of a compound, the reaction may be performed in an aqueous solution described above which is supplemented with an organic solvent, or the reaction may be performed in an organic solvent. An organic solvent which may be employed is an alcohol such as methanol clnd ethanol, etc., an organic acid such as acetic acid, etc., an ether such as dioxane and tetrahydrofuran, etc., a nitrile such as acetonitrile, etc., an amide such as N,N-dimethylformamide and N,N-dimethylacetamide, etc. and a sulfoxide such as dimethylsulfoxide, etc.

While the reaction temperature may vary depending on the compound among compounds [Ic] wherein $R^1$ is an acyl group as well as other conditions, it is usually 0 to 200° C., preferably 20 to 150° C. The reaction time is 30 minutes to 48 hours, preferably 1 to 24 hours.

Alternatively, a compound represented by Formula (X) shown above or a salt thereof can be produced also by reacting a compound represented by Formula:

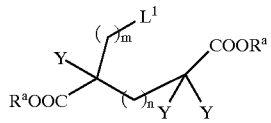

wherein $L^1$ is a leaving group, each $R^a$ may be same or different and is an optionally substituted hydrocarbon group, and Y has a meaning defined above or a salt thereof with a sulfur-containing nucleophilic agent followed by a hydrolysis.

A leaving group represented by $L^1$ in compound [XI] may for example be hydroxy, a halogen atom (for example, chlorine, bromine and iodine, etc.), a substituted sulfonyloxy (for example, methanesulfonyloxy and p-toluenesulfonyloxy, etc.), an acyloxy (such as acetoxy and benzoyloxy, etc.), and an oxy group substituted by a heterocyclic ring or an aryl group (such as succinimide, benzotriazole, quinoline and 4-nitrophenyl, etc.).

An optionally substituted hydrocarbon group represented by $R^6$ may for example be one exemplified as an "optionally substituted hydrocarbon group" represented by $R^1$ described above, with a $C_{1-4}$ alkyl group such as methyl, ethyl and propyl, etc. being employed preferably.

A sulfur-containing nucleophilic agent is an inorganic sulfide such as hydrogen sulfide, sodium hydrogen sulfide and sodium sulfide, etc., an organic sulfur-containing acid such as thioacetic acid and thiobenzoic acid, etc. as well as their salts, a mercaptan such as benzylmercaptan, triphenylmethylmercaptan and 3-mercaptopropionic acid derivatives, etc. and a thiourea. A base may for example be an inorganic base (alkaline metal hydroxide such as sodium hydroxide and potassium hydroxide, etc., alkaline metal hydrogen carbonate such as sodium hydrogen carbonate and potassium hydrogen carbonate, etc., alkaline metal carbonate such as sodium carbonate and potassium carbonate, etc., a cesium salt such as cesium carbonate, etc., alkaline metal hydride such as sodium hydride and potassium hydride, etc., sodium amide, alkoxide such as sodium methoxide and sodium ethoxide, etc.) and an organic base (amine such as trimethylamine, triethylamine and diisopropylethylamine, cyclic amine such as pyridine, etc.).

In this reaction, 1 to 5 moles, preferably 1 to 3 moles of an sulfur-containing nucleophilic agent is employed per 1 mole of compound [XI] or a salt thereof. A base is employed also in an amount of 1 to 5 moles, preferably 1 to 3 moles.

A reaction solvent is an alcohol such as methanol and ethanol, etc., an ether such as dioxane and tetrahydrofuran, etc., an aromatic hydrocarbon such as benzene, toluene and xylene, etc., an ester such as ethyl acetate, etc., a halogenated hydrocarbon such as chloroform and dichloromethane, etc., a nitrile such as acetonitrile, etc., an amide such as N,N-dimethylformamide and N,N-dimethylacetamide, etc. and a sulfoxide such as dimethylsulfoxide, etc.

While the reaction temperature may vary depending on the compound employed as well as other conditions, it is −20 to 200° C., preferably 0 to 150° C. The reaction time is usually 5 minutes to 24 hours, preferably 5 minutes to 6 hours.

A sulfur-substituted product thus obtained is hydrolyzed with an acid or a base to yield compound [X] or a salt thereof.

An acid which may be employed is an inorganic acid such as hydrochloric acid, sulfuric acid and nitric acid, etc., and a base is an inorganic base (alkaline metal hydroxide such as sodium hydroxide and potassium hydroxide, etc., alkaline metal hydrogen carbonate such as sodium hydrogen carbonate and potassium hydrogen carbonate, etc., alkaline metal carbonate such as sodium carbonate and potassium carbonate, etc.).

This reaction is conducted in a 20 to 50 volumes of an aqueous solution of an inorganic acid described above (usually at 10 to 30%) per 1 g of a sulfur-substituted product, or in an aqueous solution containing 3 to 10 moles of a base described above per 1 mole of a sulfur-substituted product. In view of the solubility of a compound, the reaction may be performed in an aqueous solution described above which is supplemented with an organic solvent. An organic solvent which may be employed is an alcohol such as methanol and ethanol, etc., an organic acid such as acetic acid, etc., an ether such as dioxane and tetrahydrofuran, etc., a nitrile such as acetonitrile, etc., an amide such as N,N-dimethylformamide and N,N-dimethylacetamide, etc. and a sulfoxide such as dimethylsulfoxide, etc.

While the reaction temperature may vary depending on the sulfur-substituted product employed as well as other conditions, it is 0 to 200° C., preferably 20 to 150° C. The reaction time is 30 minutes to 48 hours, preferably 1 to 24 hours.

Compound [XI] may be a commercially available halogenated dicarboxylic acid derivative, a product obtained from a corresponding aminodicarboxylic acid derivative by substituting an amino group with a halogen according to a method known in a literature such as Heterocycles, 24(5), 1331 (1986) or Journal of Organic Chemistry, 58(5), 1159 (1993), etc., or a product obtained from a corresponding hydroxy form by converting into an appropriate leaving group according to a method known in a literature such as an acylation or alkylation described for example in Organic Functional Group Preparations (Academic Press).

(Method E) A compound represented by Formula:

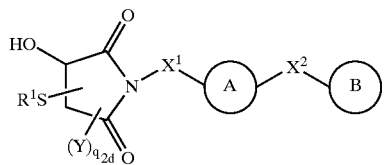

[Id]

wherein $q_{2d}$ is 0 to 2 and each of other symbols has a meaning defined above which is encompassed within compound (I) of the invention or a salt thereof can be produced for example by reacting a compound represented by Formula:

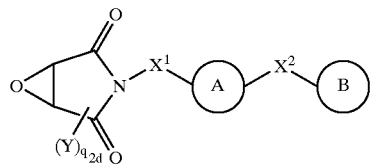

[XII]

wherein each symbol has a meaning defined above or a salt thereof with a compound represented by $R^1SH$ wherein $R^1$ has a meaning defined above or a salt thereof in the presence of a base.

In this reaction, 1 to 5 moles, preferably 1 to 3 moles of a compound represented by $R^1SH$ wherein $R^1$ has a meaning defined above or a salt thereof and 1 to 5 moles, preferably 1 to 3 moles of a base are employed per 1 mole of Compound [XII] or a salt thereof. A compound represented by $R^1SH$ wherein $R^1$ has a meaning defined above which is employed may for example be an inorganic sulfide such as hydrogen sulfide, sodium hydrogen sulfide and sodium sulfide, etc., an aliphatic mercaptan such as methylmercaptan, a ethylmercaptan and mercaptopropionic acid derivatives, etc., an organic sulfur-containing acid such as thioacetic acid and thiobenzoic acid, etc., an aromatic mercaptan such as thiophenol, etc. and a thiourea, etc.

A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkoxide such as sodium methoxide and sodium ethoxide, etc., an amine such as trimethylamine, triethylamine and diisopropylethylamine, etc., a cyclic amine such as pyridine, etc.

A reaction solvent which may be employed is an alcohol such as methanol and ethanol, etc., an ether such as dioxane and tetrahydrofuran, etc., an aromatic hydrocarbon such as benzene, toluene and xylene, etc., an ester such as ethyl acetate, etc., a halogenated hydrocarbon such as chloroform and dichloromethane, etc., a nitrile such as acetonitrile, etc., an amide such as N,N-dimethylformamide and N,N-dimethylacetamide, etc. and a sulfoxide such as dimethylsulfoxide, etc. Instead of using a base in this reaction, a compound represented by $R^1SH$ may be converted for example into an alkaline metal salt or an alkaline earth metal salt, which may then be reacted with compound [XII] or a salt thereof.

While the reaction temperature may vary depending on compound [XII] or a salt thereof employed as well as other reaction conditions, it is −20 to 200° C., preferably 0 to 150° C. The reaction time is 5 minutes to 24 hours, preferably 5 minutes to 6 hours.

A compound represented by Formula [XII] or a salt thereof may be produced also for example by reacting a compound represented by Formula:

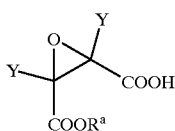

wherein each symbol has a meaning defined above or a salt thereof with a compound represented by Formula:

wherein each symbol has a meaning defined above or a salt thereof to form an amide followed by a hydrolysis and an imidation.

In this reaction, compound [XIII] or a salt thereof is first condensed with compound [II] or a salt thereof to form an amide.

This process may be in accordance with a known amidation such as a method described in "JIKKENKAGAKUKOZA", Vol.22, Organic Synthesis IV (MARUZEN). A condensing agent may for example be dicyclohexylcarbodiimide (DCC), diethyl cyanophosphate (DEPC) and diphenylphosphorylazide (DPPA), etc.

When using such a condensing agent, an ordinary solvent (for example, ethers, esters, hydrocarbons, amides and sulfoxides, etc. including tetrahydrofuran, dioxane, dimethoxyethane, ethyl acetate, benzene, toluene, N,N-dimethylformamide, dimethylsulfoxide, etc.) is employed.

This reaction may be promoted in the presence of a base at a temperature of −10 to 100° C., preferably 0 to 60° C.

The reaction time is usually 30 minutes to 96 hours, preferably 1 to 72 hours. The amount of compound [II] or a salt thereof and a condensing agent employed is 1 to 5 moles, preferably 1 to 3 moles per 1 mole of compound [XIII] or a salt thereof.

A base may for example be an alkylamine such as triethylamine, etc. and a cyclic amine such as N-methylmorpholine and pyridine, etc., and is used in an amount of 1 to 5 moles, preferably 1 to 3 moles per 1 mole of compound [XIII] or a salt thereof.

An ester thus obtained can be hydrolyzed to obtain a carboxylic acid. A hydrolysis may be effected using an acid or a base.

An acid which may be employed may for example be an inorganic acid such as hydrochloric acid, sulfuric acid and nitric acid, and a base may for example be an inorganic base (alkaline metal hydroxide such as sodium hydroxide and potassium hydroxide, etc., alkaline metal hydrogen carbonate such as sodium hydrogen carbonate and potassium hydrogen carbonate, etc., alkaline metal carbonate such as sodium carbonate and potassium carbonate, etc.).

This reaction is conducted in a 20 to 50 volumes of an aqueous solution of an inorganic acid described above (usually at 10 to 30%) per 1 g of an ester, or in an aqueous solution containing 3 to 10 moles of a base described above per 1 mole of an ester. In view of the solubility of a compound, the reaction may be performed in an aqueous solution described above which is supplemented with an organic solvent. An organic solvent which may be employed is an alcohol such as methanol and ethanol, etc., an organic acid such as acetic acid, etc., an ether such as dioxane and tetrahydrofuran, etc., a nitrile such as acetonitrile, etc., an amide such as N,N-dimethylformamide, etc. and N,N-dimethylacetamide and a sulfoxide such as dimethylsulfoxide, etc.

While the reaction temperature may vary depending on the ester employed as well as other conditions, it is 0 to 200° C., preferably 20 to 150° C. The reaction time is 30 minutes to 48 hours, preferably 1 to 24 hours.

A carboxylic acid thus obtained can be condensed to yield compound [XII] or a salt thereof.

This reaction employs 10 to 50 volumes of a condensing agent as a reaction solvent per 1 g of a carboxylic acid. A condensing agent is an anhydride of an ordinary organic acid such as acetic anhydride and benzoic anhydride, etc. The addition of a base in this reaction allows the reaction to proceed advantageously.

A base which may be employed is preferably an alkaline metal salt of an organic acid corresponding to a condensing agent employed such as sodium acetate and potassium acetate. The amount is 0.1 to 1 mole based on a carboxylic acid.

While the reaction temperature may vary depending on the carboxylic acid employed as well as other conditions, it is 20 to 200° C., preferably 50 to 150° C. The reaction time is 5 minutes to 24 hours, preferably 5 minutes to 5 hours.

As compound [VIII], a commercially available epoxysuccinic acid derivative is mainly employed.

(Method F) A compound represented by Formula:

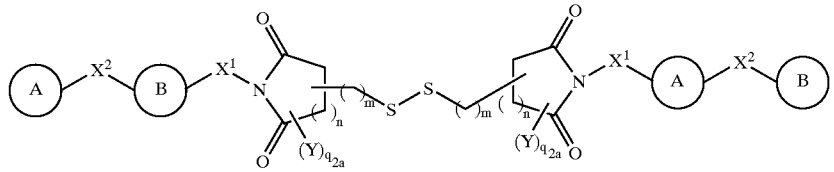

wherein $q_{2e}$ is 2n+1 and each of other symbols has a meaning defined above which is encompassed within compound (I) of the invention or a salt thereof can be produced for example by subjecting a compound represented by Formula:

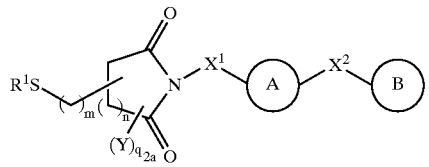

wherein each symbol has a meaning defined above or a salt thereof to a method similar to that in method C described above in the presence of a base.

A compound represented by Formula (XIV) or a salt thereof can be produced also by reacting a compound represented by Formula:

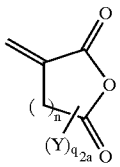

[XV]

wherein each symbol has a meaning defined above or a salt thereof with a compound represented by Formula:

[II]

wherein each symbol has a meaning defined above or a salt thereof to form an amide followed by reacting with a compound represented by R¹SH wherein R¹ has a meaning defined above or a salt thereof followed by an amidation.

In this amidation, 1 mole of compound [XV] or a salt thereof is reacted with 1 to 5 moles, preferably 1 to 2 moles of compound [II] or a salt thereof.

A reaction solvent may for example be an alcohol such as methanol and ethanol, etc., an ether such as dioxane and tetrahydrofuran, etc., an aromatic hydrocarbon such as benzene, toluene and xylene, etc., an ester such as ethyl acetate, etc., a halogenated hydrocarbon such as chloroform and dichloromethane, etc., a nitrile such as acetonitrile, etc., an amide such as N,N-dimethylformamide and N,N-dimethylacetamide, etc. and a sulfoxide such as dimethylsulfoxide, etc.

While the reaction temperature may vary depending on compound [XV] or a salt thereof as well as other conditions, it is −20 to 100° C., preferably 0 to 100° C. The reaction time is 5 minutes to 5 hours, preferably 5 minutes to 1 hour.

An amide thus obtained can be converted into an adduct by a method similar to that in (Method B) described above, and then condensed by a method similar to that in (Method E), whereby producing compound [XIV] or a salt thereof.

As compound [XV], a commercially available itaconic anhydride derivative is mainly employed.

(Method G) Compound (I) according to the invention or a salt thereof can be produced for example by reacting a compound represented by Formula:

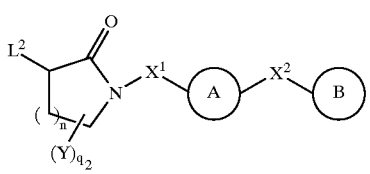

[XVI]

wherein L² is a leaving group and each of other symbols has a meaning defined above or a salt thereof with a compound represented by R¹SH wherein R¹ has a meaning defined above or a salt thereof in the presence of a base.

A leaving group represented by L² described above may for example be one exemplified as a leaving group as represented by L¹ described above.

A compound represented by Formula (XVI) or a salt thereof can be produced for example from a compound represented by Formula:

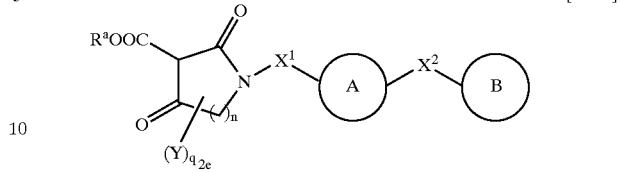

[XVII]

wherein each symbol has a meaning defined above or a salt thereof.

Thus, compound [XVI] or a salt thereof can be produced by decarboxylating compound [XVII] or a salt thereof and then reacting a dicarbonyl compound thus formed in situ with a nucleophilic agent or a reducing agent to form a hydroxy product which is then converted into a leaving group.

A decarboxylation is performed in 1 to 100 volumes, preferably 20 to 50 volumes of a solvent per 1 g of compound [XVII]. While a solvent which may preferably be employed is a nitrile such as acetonitrile, etc., those also employed are an ether such as dioxane and tetrahydrofuran, etc., an aromatic hydrocarbon such as benzene, toluene and xylene, etc., an ester such as ethyl acetate, etc., a halogenated hydrocarbon such as chloroform and dichloromethane, etc., an amide such as N,N-dimethylformamide and N,N-dimethylacetamide, etc., a sulfoxide such as dimethylsulfoxide, etc. as well as water.

While the reaction temperature may vary depending on compound [XVII] or a salt thereof employed as well as other conditions, it is 0 to 200° C., preferably 20 to 150° C. The reaction time is 5 minutes to 24 hours, preferably 5 minutes to 1 hour.

In a nucleophilic reaction and a reducing reaction, a nucleophilic agent or a reducing agent is employed in an amount of 1 to 5 moles, preferably 1 to 3 moles per 1 mole of compound [XVII] or a salt thereof. A nucleophilic agent may be an organic metal reagent such as organic lithium, organic zinc, organic aluminum, Grignard reagent, etc. While a reducing agent may preferably be a metal hydride such as sodium borohydride as lithium aluminum hydride, etc., it may be a reagent capable of reducing a ketone compound to an alcohol, such as one described in "SHINJIKKENKAGAKUKOZA", Vol.15, Oxidation and Reduction (MARUZEN).

A solvent which may be employed may for example be an alcohol such as methanol and ethanol, etc., an ether such as dioxane and tetrahydrofuran, etc., an aromatic hydrocarbon such as benzene, toluene and xylene, etc., an ester such as ethyl acetate, etc., a halogenated hydrocarbon such as chloroform and dichloromethane, etc., a nitrile such as acetonitrile, etc., an amide such as N,N-dimethylformamide and N,N-dimethylacetamide, etc. and a sulfoxide such as dimethylsulfoxide, etc.

While the reaction temperature may vary depending on the reagent employed as well as other conditions, it is −100 to 200° C., preferably −78 to 100° C. The reaction time is 5 minutes to 24 hours, preferably 5 minutes to 10 hours.

A resultant hydroxy product can be converted into any of various leaving groups to produce compound [XVI]. Such leaving group may for example be a halogen atom (for example, chlorine, bromine and iodine, etc.), a substituted sulfonyloxy (for example, methanesulfonyloxy and p-toluenesulfonyloxy, etc.), an acyloxy (for example, acetoxy and benzoyloxy, etc.) and an oxy group which is substituted with a heterocyclic or aryl group (such as succinimide, benzotriazole, quinoline and 4-nitrophenyl, etc.), etc.

A halogen atom may for example be a halide of an inorganic acid, such as thionyl chloride, thionyl bromide, phosphorus trichloride, phosphorus pentachloride and phosphorus oxychloride, etc. and a halogenated hydrogen acid such as hydrochloric acid and hydrobromic acid, etc. Other leaving groups can be produced by known methods such as those described in method D for producing compound [XI].

For example, a latter reaction employing an acylation employs 1 to 5 moles, preferably 1 to 2 moles of a corresponding halide and 1 to 5 moles, preferably 1 to 3 moles of a base per 1 mole of a hydroxy product or a salt thereof. Some base, such as pyridine, can serve also as a solvent.

A solvent may for example be an ether such as dioxane and tetrahydrofuran, etc., an aromatic hydrocarbon such as benzene, toluene and xylene, etc., an ester such as ethyl acetate, etc., a halogenated hydrocarbon such as chloroform and dichloromethane, etc., a nitrile such as acetonitrile, etc., an amide such as N,N-dimethylformamide and N,N-dimethylacetamide, etc. and a sulfoxide such as dimethylsulfoxide, etc.

A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkoxide such as sodium methoxide and sodium ethoxide, etc., an amine such as trimethylamine, triethylamine and diisopropylethylamine, etc., a cyclic amine such as pyridine, etc.

While the reaction temperature may vary depending on the substrate employed as well as other conditions, it is −20 to 200° C., preferably 0 to 100° C. The reaction time is 30 minutes to 48 hours, preferably 1 to 24 hours.

A resultant compound can be subjected to a method similar to that in (Method D) described above to react with any of various sulfur-containing nucleophilic agents to produce compound [I] wherein $R^1$ is not H or a salt thereof and also to be deprotected to produce compound [I] wherein $R^1$ is H or a salt thereof.

Alternatively, a compound represented by Formula (XVII) or a salt thereof can be produced for example by reacting a compound represented by Formula:

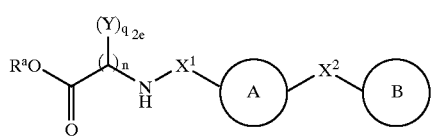

[XVIII]

wherein each symbol has a meaning defined above or a salt thereof with a compound represented by Formula:

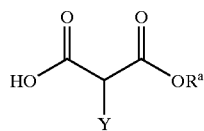

[XIX]

wherein each symbol has a meaning defined above or a salt thereof, or with a compound represented by Formula:

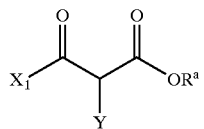

[XX]

wherein $X_1$ is a halogen atom and each of other symbols has a meaning defined above or a salt thereof to form an amide, which is then subjected to a treatment with a base.

A halogen atom represented by $X^1$ may for example be fluorine, chlorine, bromine and iodine, etc.

In this reaction, compound [XVIII] or a salt thereof can be condensed with compound [XIX] or a salt thereof using a condensing agent or its halide [XX] or a salt thereof can be reacted in the presence of a base to form an amide. The former reaction can be performed similarly to (Method E) described above.

The latter reaction employs 1 to 5 moles, preferably 1 to 2 moles of compound [XX] or a salt thereof per 1 mole of compound [XVIII] or a salt thereof. A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkoxide such as sodium methoxide and sodium ethoxide, etc., an amine such as trimethylamine, triethylamine and diisopropylethylamine, etc., a cyclic amine such as pyridine, etc. The amount of a base employed is I to 10 moles, preferably 1 to 5 moles per 1 moles of compound [XVIII] or a salt thereof. Some base, such as pyridine, can serve also as a solvent.

A solvent may for example be an ether such as dioxane and tetrahydrofuran, etc., an aromatic hydrocarbon such as benzene, toluene and xylene, etc., an ester such as ethyl acetate, etc., a halogenated hydrocarbon such as chloroform and dichloromethane, etc., a nitrile such as acetonitrile, etc., an amide such as N,N-dimethylformamide and N,N-dimethylacetamide, etc. and a sulfoxide such as dimethylsulfoxide, etc. While the reaction temperature may vary depending on compound [XVIII] or a salt thereof employed as well as other conditions, it is −20 to 200° C., preferably 0 to 100° C. The reaction time is 5 minutes to 48 hours, preferably 5 minutes to 24 hours.

A resultant amide can be subjected to a treatment with a base to produce compound [XVII] or a salt thereof.

This reaction employs 1 to 3 moles, preferably 1 to 2 moles of a base per 1 mole of an amide. A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkoxide such as sodium methoxide and sodium ethoxide, etc. A solvent which may be employed may for example be an alcohol such as methanol and ethanol, etc., an ether such as dioxane and tetrahydrofuran, etc., an aromatic hydrocarbon such as benzene, toluene and xylene, etc., an ester such as ethyl acetate, etc., a halogenated hydrocarbon such as chloroform and dichloromethane, etc., a nitrile such as acetonitrile, etc., an amide such as N,N-dimethylformamide and N,N-dimethylacetamide, etc. and a sulfoxide such as dimethylsulfoxide, etc. While the reaction temperature may vary depending on the amide employed as well as other conditions, it is −20 to 200° C., preferably 0 to 100° C. The reaction time is 5 minutes to 48 hours, preferably 10 minutes to 5 hours.

Alternatively, a compound represented by Formula (XVIII) or a salt thereof can be produced for example by reacting a compound represented by Formula:

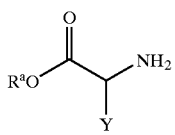

[XXI]

wherein each symbol has a meaning defined above or a salt thereof with a compound represented by Formula:

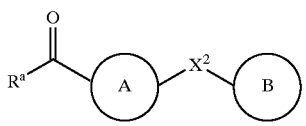

[XXII]

wherein each symbol has a meaning defined above or a salt thereof.

Compound [XVIII] or a salt thereof can be produced from compound [XXI] or a salt thereof and a carbonyl compound [XXII] by an in situ production of an imine which is then reduced by an appropriate reducing agent.

A reducing agent is preferably sodium borohydride, lithium borohydride, sodium cyanoborohydride and sodium triacetoxyborohydride.

In this reaction, 1 to 5 moles, preferably 1 to 2 moles of carbonyl compound [XXII] and 0.5 to 10 moles, preferably 0.5 to 3 moles of a reducing agent per 1 mole of compound [XXI] or a salt thereof. A reaction solvent may for example be an alcohol such as methanol and ethanol, etc., an ether such as dioxane and tetrahydrofuran, etc., an aromatic hydrocarbon such as benzene, toluene and xylene, etc., an ester such as ethyl acetate, etc., a halogenated hydrocarbon such as chloroform and dichloromethane, etc., a nitrile such as acetonitrile, etc., an amide such as N,N-dimethylformamide and N,N-dimethylacetamide, etc. and a sulfoxide such as dimethylsulfoxide, etc.

When producing an imine, a dehydrating condition using a molecular sieve or an addition of an acid serves to promote the reaction. An acid employed here is preferably acetic acid and trifluoroacetic acid, etc. While the reaction temperature in this imine production may vary depending on compound [XXI] or a salt thereof as well as other conditions, it is 0 to 200° C., preferably 0 to 150° C. The reaction time is 30 minutes to 48 hours, preferably 1 hour to 24 hours.

The reaction temperature in the reducing reaction is −20 to 150° C., preferably 0 to 100° C. The reaction time is 30 minutes to 24 hours, preferably 30 minutes to 12 hours.

Compound [XXI] is mainly a commercially available amino acid derivative, while compound [XXII] is produced by method N or a commercially available product. (Method H) A compound represented by Formula:

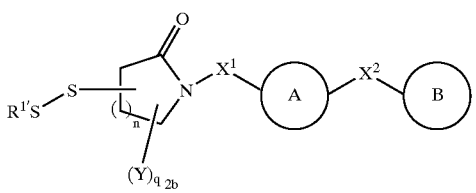

[If]

wherein $R^1$ is an optionally substituted hydrocarbon group, an acyl group or an optionally substituted heterocyclic group, and each of other symbols has a meaning defined above which is encompassed within compound (I) of the invention or a salt thereof can be produced for example by reacting a compound represented by Formula:

$R^{1'}SH$ [XXIII]

wherein $R^1$ has a meaning defined above or a salt thereof with a compound represented by Formula (IX) described above or a salt thereof by a method similar to (Method C) described above or by a method known per se.

Alternatively, a compound represented by Formula (XXIII) or a salt thereof is commercially available or can be produced from a compound represented by Formula:

$R^{1'}X_1$ [XXIV]

wherein each symbol has a meaning defined above or a salt thereof in accordance with a method known in a literature (for example, methods exemplified in Organic Chemistry of Bivalent Sulfur, Vol.1, p32 (Chem. Publ. Co., New York), Organic Functional Group Preparations, 1 (Academic), etc.).

An "optionally substituted hydrocarbongroup" represented by Formula $R^1$ may for example be one exemplified as an "optionally substituted hydrocarbon group" represented by $R^1$ described above. An "acyl group" represented by Formula $R^1$ may for example be one exemplified as an "acyl group" represented by $R^1$ described above.

An "optionally substituted heterocyclic group" represented by Formula $R^1$ may for example be one exemplified as an "optionally substituted heterocyclic group" represented by $R^1$ described above.

(Method I) A compound represented by Formula:

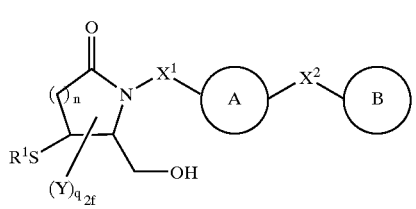

[Ig]

wherein $q_{2f}$ is 0 to 2n+2 and each of other symbols has a meaning defined above which is encompassed within compound (I) of the invention or a salt thereof can be produced for example by subjecting a compound represented by Formula:

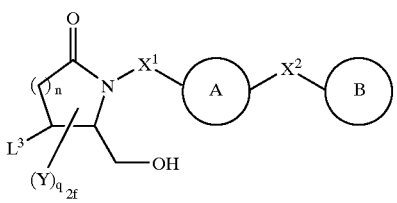

[XXV]

wherein L³ is a leaving group and each of other symbols has a meaning defined above or a salt thereof and a compound represented by R¹SH wherein R¹ has a meaning defined above or a salt thereof to a nucleophilic reaction.

A leaving group represented by L³ may for example be one exemplified as a leaving group represented by L¹ described above.

This reaction can be performed in accordance with a method similar to (Method G) described above.

Alternatively, a compound represented by Formula (XXV) or a salt thereof can be produced for example by converting a secondary hydroxy group of a compound represented by Formula:

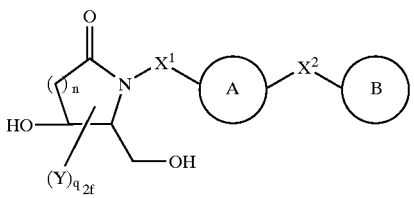

[XXVI]

wherein each symbol has a meaning defined above or a salt thereof to a leaving group.

In this reaction, a primary hydroxy group of compound [XXVI] or a salt thereof is first protected to form a protected intermediate.

While a protective group employed in this reaction may be any of the protective groups for a hydroxy group employed generally, it is preferably a triphenylmethyl group, a diphenylmethyl group, a t-butyldimethylsilyl group or a t-butyldiphenylsilyl group, etc. having a large steric hindrance, since a secondary hydroxy group exists simultaneously. In the reaction, a halide having a substituent listed above, such as a triphenylmethyl chloride, etc., is condensed with compound [XXVI] or a salt thereof in the presence of a base to form a protected intermediate.

In this reaction, 1 to 5 moles, preferable 1 to 3 moles of a halide and 1 to 10 moles, preferably 1 to 5 moles of a base are employed per 1 mole of compound [XXVI] or a salt thereof.

A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkoxide such as sodium methoxide and sodium ethoxide, etc., an amine such as trimethylamine, triethylamine and diisopropylethylamine, etc., a cyclic amine such as pyridine, etc.

A solvent may for example be an ether such as dioxane and tetrahydrofuran, etc., an aromatic hydrocarbon such as benzene, toluene and xylene, etc., an ester such as ethyl acetate, etc., a halogenated hydrocarbon such as chloroform Ho and dichloromethane, etc., a nitrile such as acetonitrile, etc., an amide such as N,N-dimethylformamide and N,N-dimethylacetamide, etc. and a sulfoxide such as dimethylsulfoxide, etc.

While the reaction temperature may vary depending on the substrate employed as well as other conditions, it is −20 to 200° C., preferably 0 to 100° C. The reaction time is 1 to 48 hours, preferably 1 to 24 hours.

An intermediate thus obtained can be subjected to a method similar to that in (Method G) described above to convert a secondary hydroxy group into a leaving group.

An active intermediate thus obtained is deprotected to yield compound [XXV] or a salt thereof.

In this reaction, a deprotection is effected under an acidic condition or as a catalytic hydrogenation. A catalyst employed in a catalytic hydrogenation may for example be a platinum catalyst such as platinum black, platinum oxide and Pt/C, etc., a palladium catalyst such as palladium black, palladium oxide, palladium barium sulfate, Pd/C, etc. and nickel catalyst such as reduced nickel, oxidized nickel, Raney nickel, Urushibara nickel catalyst, etc.

A solvent is preferably an alcohol such as methanol, ethanol, propanol and isopropanol, etc., an ether such as tetrahydrofuran and dioxane, etc. and an ester such as ethyl acetate, etc.

The reaction temperature is 0° C. to 200° C., preferably 20° C. to 110° C. The reaction time is usually 0.5 to 48 hours, preferably 1 to 16 hours. While a reaction is performed usually in an atmospheric pressure, it can be performed under pressure (3 to 10 atm) if necessary.

While the amount of a catalyst employed may vary depending on the type of the catalyst employed, it is usually 0.1 to 20% by weight based on an active intermediate or a salt thereof.

An acid employed in a deprotection under an acidic condition may for example be an inorganic acid such as hydrochloric acid, sulfuric acid and nitric acid, etc., and an ordinary organic acid such as formic acid, acetic acid, trifluoroacetic acid and methanesulfonic acid, etc. as well as a Lewis acid.

A reaction solvent may for example be an alcohol such as methanol and ethanol, etc., an ether such as dioxane and tetrahydrofuran, etc., an aromatic hydrocarbon such as benzene, toluene and xylene, etc., an ester such as ethyl acetate, etc., a halogenated hydrocarbon such as chloroform and dichloromethane, etc., a nitrile such as acetonitrile, etc., an amide such as N,N-dimethylformamide and N,N-dimethylacetamide, etc. and a sulfoxide such as dimethylsulfoxide, etc.

This reaction employs 1 to 100 moles, preferably 1 to 10 moles of an acid described above per 1 mole of an active intermediate. Some acid can serve also as a solvent.

While the reaction temperature may vary depending on the substrate employed as well as other conditions, it is −20 to 200° C., preferably 0 to 100° C. The reaction time is usually 5 minutes to 24 hours, preferably 5 minutes to 10 hours.

A compound represented by Formula (XXVI) or a salt thereof can be produced for example by subjecting a compound represented by Formula:

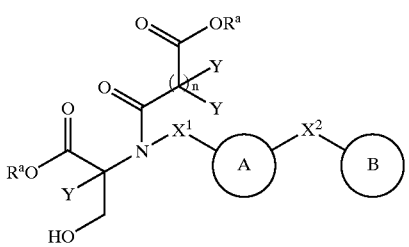

[XXVII]

wherein each symbol has a meaning defined above or a salt god thereof to a reaction similar to that in Method G or to a method known per se.

A compound represented by Formula (XXVII) or a salt thereof can be produced for example by subjecting a compound represented by Formula:

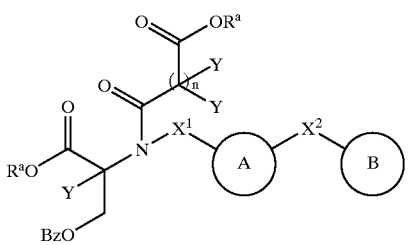

[XXVIII]

wherein each symbol has a meaning defined above or a salt thereof to a deprotection.

While this reaction can be performed various methods, for example, the reductive method similar to catalytic hydrogenation is preferably employed.

A compound represented by Formula (XXVIII) or a salt thereof can be produced for example by subjecting a compound represented by Formula:

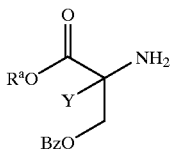

[XXIX]

wherein each symbol has a meaning defined above or a salt thereof to a reaction similar to that in Method G or to a method known per se.

As Compound [XXIX], a commercially available amino acid derivative such as serine, etc. is employed mainly.

(Method J) A compound represented by Formula:

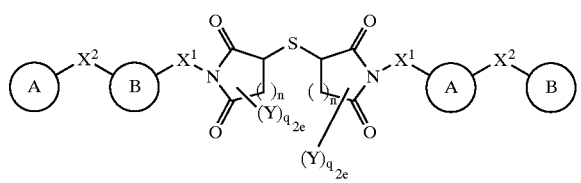

[Ih]

wherein each symbol has a meaning defined above which is encompassed within compound (I) of the invention or a salt thereof can be produced for example by reacting a compound represented by Formula:

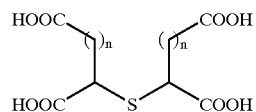

[XXX]

wherein each symbol has a meaning defined above or a salt thereof with a compound represented by Formula:

[II]

wherein each symbol has a meaning defined above or a salt thereof.

This reaction can be performed by a method in (Method A) described above or an analogous method.

As compound [XXX], a commercially available thiodisuccinic acid may for example be employed.

(Method K) A compound represented by Formula:

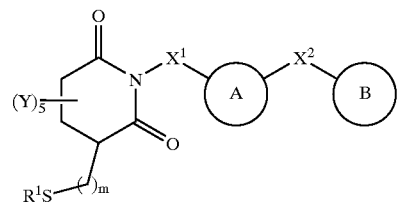

[Ii]

wherein each symbol has a meaning defined above which is encompassed within compound (I) of the invention or a salt thereof can be produced for example by reacting a compound represented by Formula:

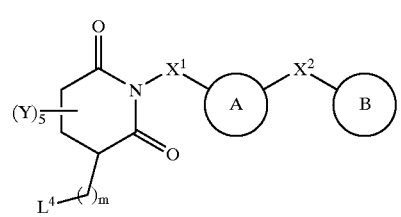

[XXXI]

wherein $L^4$ is a leaving group and each of other symbols has a meaning defined above or a salt thereof with a compound represented by $R^1SH$ wherein $R^1$ has a meaning defined above or a salt thereof.

A leaving group represented by $L^4$ may for example be one exemplified as a leaving group represented by $L^1$ described above.

This reaction can be performed by a method similar to that in (Method G) described above.

Alternatively, a compound represented by Formula (XXXI) or a salt thereof can also be produced for example by reacting a compound represented by Formula:

[XXXII]

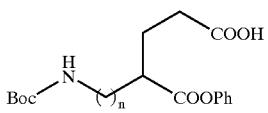

or a salt thereof with a compound represented by Formula:

[II]

wherein each symbol has a meaning defined above or a salt thereof to form an imide followed by a deprotection to form an amino product and a conversion of an amino group to a halogen.

In this reaction, compound [XXXII] or a salt thereof is first condensed with compound [II] or a salt thereof by a method similar to that in (Method E) described above to produce imide. In this process, a cyclization occurs simultaneously.

A deprotection of an imide thus obtained yields an amino product or a salt thereof. This reaction is performed using 1 g of an imide product in 10 volumes of an appropriate organic acid solvent or an inorganic aqueous solution or a mixture. An organic acid is preferably trifluoroacetic acid, etc. An inorganic acid is preferably hydrochloric acid, sulfuric acid, etc.

The reaction temperature is −20 to 100° C., preferably −20 to 50° C. The reaction time is usually 1 minute to 24 hours, preferably 1 minute to 12 hours.

A resultant amino product or a salt thereof can be substituted by a halogen by a method known in literature, such as methods described in Heterocycles, 24(5), 1331 (1986) and Journal of Organic Chemistry, 58(5), 1159 (1993) to produce compound [XXXI]

In this reaction, 1 to 10 moles, preferably 1 to 3 moles of a diazotizing agent such as sodium nitrite, etc. is reacted per 1 mole of an amino product or a salt thereof in the presence of 1 to 100 moles of a haloacid. A haloacid is preferably hydrochloric acid, hydrobromic acid and hydroiodic acid, etc.

As a reaction solvent, a nitrile such as acetonitrile, etc. and water are preferred.

The reaction temperature is −50 to 100° C., preferably −20 to 50° C. The reaction time is 30 minutes to 24 hours, preferably 30 minutes to 12 hours. Alternatively, a compound represented by Formula (XXXII) or a salt thereof can be produced for example by a compound represented by Formula:

[XXXIII]

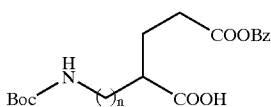

by a method known in a literature (Tetrahedron Asymmetry, 6(6), 1249 (1995)).

(Method L) A compound represented by Formula:

[XXXIV]

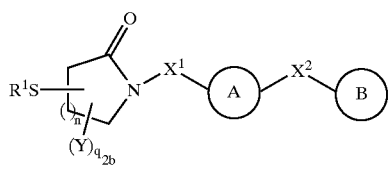

wherein each symbol has a meaning defined above which is encompassed within compound (I) of the invention or a salt thereof can be produced for example by reacting a compound represented by Formula:

[XXXV]

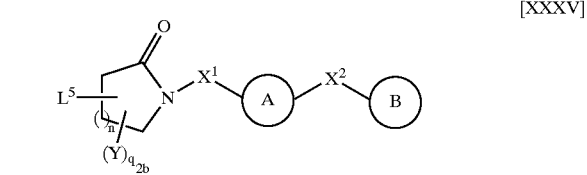

wherein $L^5$ is a leaving group and each of other symbols has a meaning defined above or a salt thereof with a compound represented by $R^1SH$ wherein $R^1$ has a meaning defined above or a salt thereof.

This reaction can be performed by a method described in (Method G) or an analogous method.

A leaving group represented by $L^5$ may for example be one exemplified as a leaving group represented by $L^1$ described above.

Alternatively, a compound represented by Formula (XXXV) or a salt can also be produced for example by reacting a compound represented by Formula:

[XXXVI]

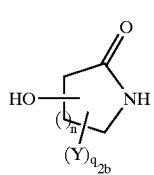

wherein each symbol has a meaning defined above or a salt thereof with a compound represented by Formula:

(IIa)

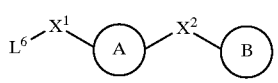

wherein $L^6$ is a leaving group and each of other symbols has a meaning defined above or a salt thereof to convert a hydroxy group into a leaving group.

A leaving group represented by $L^6$ may for example be a halogen atom (for example, chlorine, bromine and iodine, etc.), a substituted sulfonyloxy (for example, methanesulfonyloxy and p-toluenesulfonyloxy, etc.), an acyloxy (such as acetoxy and benzoyloxy, etc.), and an oxy group substituted by a heterocyclic ring or an aryl group (such as succinimide, benzotriazole, quinoline and 4-nitrophenyl, etc.).

Compound [XXXVI] or a salt thereof may be used as a free form, it may be subjected to a reaction as an alkaline metal salt such as lithium, sodium and potassium salts, etc.

In this reaction, 1 to 10 moles, preferably 1 to 5 moles of compound [IIa] or a salt thereof is reacted per 1 mole of compound [XXXVI] or a salt thereof.

Usually, the reaction is performed in a solvent. Such solvent may for example be a halogenated hydrocarbon such as dichloromethane and chloroform, etc., a nitrile such as acetonitrile, etc., an ether such as dimethoxyethane and tetrahydrofuran, etc. as well as dimethylformamide, dimethylsulfoxide and hexamethylphosphoramide, etc.

The addition of a base in this reaction allows the reaction to proceed advantageously. Such base may for example be sodium hydrogen carbonate, potassium hydrogen carbonate, sodium carbonate, potassium carbonate, sodium hydride, potassium hydride, sodium amide, sodium methoxide, triethylamine, diisopropylethylamine and pyridine, etc.

While the amount of a base may vary depending on the types of the compound and the solvent employed as well as other reaction conditions, it is usually 1 to 10 moles, preferably 1 to 5 moles per 1 mole of compound [XXXVI] or a salt thereof. The reaction temperature is about −50 to 200° C., preferably −20 to 150° C. While the reaction time varies depending on the type of the compound and the reaction temperature, it is 1 to 72 hours, preferably 1 to 24 hours.

Compound [XXXVI] may be any of commercially available hydroxy-substituted 5-membered and 6-membered amides such as (S)-4-hydroxypyrrolidin-2-one, (R)-4-hydroxypyrrolidin-2-one (DAISO), 3-hydroxypiperidin-2-one (Aldrich), etc., or may be produced by a method known in literatures such as Synthesis, 614 (1978), Tetrahedron Asymmetry, 3(11), 1431 (1992), etc.

Compound [IIa] may be a commercially available product or may be produced by Method N.

(Method M) A compound represented by Formula:

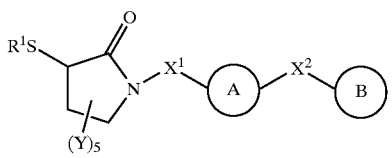

[XXXVII]

wherein each symbol has a meaning defined above which is encompassed within compound (I) of the invention or a salt thereof can be produced for example from a compound represented by Formula:

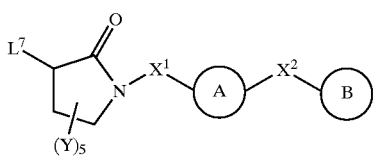

[XXXVIII]

wherein L is a leaving group and each of other symbols has a meaning defined above or a salt thereof by a method similar to Method G described above.

A leaving group represented by $L^7$ may for example be one exemplified as-a leaving-group represented by $L^1$ described above.

Alternatively, a compound represented by Formula [XXXVIII] or a salt thereof can also be produced for example by subjecting a compound represented by Formula:

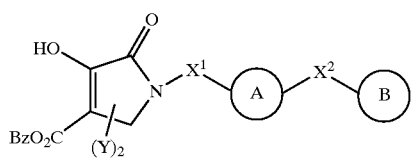

[XXXIX]

wherein Bz is a benzyl group and each of other symbols has a meaning defined above or a salt thereof to a catalytic hydrogenation by a method known per se (for example a method similar to Method I described above) to obtain a saturated hydroxy form which is then converted into a leaving group.

Compound [XXXIX] or a salt thereof can be produced also in accordance with a method known in a literature (Journal of American Chemical Society, 75, 3413 (1953)). For example, a compound represented by Formula:

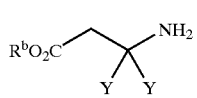

[XXXX]

wherein $R^b$ is an optionally substituted hydrocarbon group and Y has a meaning defined above or a salt thereof is subjected to a method similar to Method G described above to form a reduced amino product which is then reacted with a diester derivative of oxalic acid in the presence of a base.

An optionally substituted hydrocarbon group represented by $R^b$ may for example be one exemplified as an optionally substituted hydrocarbon group represented by $R^1$ described above, with a benzyl group being preferred.

In this reaction, a diester of oxalic acid and a base are employed in amounts of 1 to 3 moles, preferably 1 to 2 moles per 1 mole of a reduced amino product.

While various diester derivatives of oxalic acid may be employed, a benzyl derivative capable of being deprotected by a catalytic hydrogenation is preferred.

A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkoxide such as sodium methoxide and sodium ethoxide, etc., an amine such as trimethylamine, triethylamine and diisopropylethylamine, etc., a cyclic amine such as pyridine, etc.

A reaction solvent may for example be an alcohol such as methanol and ethanol, etc., an ether such as dioxane and tetrahydrofuran, etc., an aromatic hydrocarbon such as benzene, toluene and xylene, etc., an ester such as ethyl acetate, etc., a halogenated hydrocarbon such as chloroform ahd dichloromethane, etc., a nitrile such as acetonitrile, etc., an amide such as N,N-dimethylformamide and N,N-dimethylacetamide, etc. and a sulfoxide such as dimethylsulfoxide, etc. as well as water, etc.

While the reaction temperature may vary depending on the substrate employed as well as other conditions, it is 0 to 200° C., preferably 0 to 150° C. The reaction time is 1 to 24 hours, preferably 1 to 12 hours.

(Method N) A compound represented by Formula:

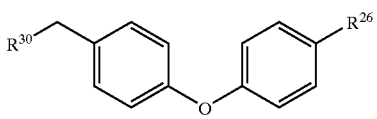

[XXXXI]

or a salt thereof, wherein R has a meaning similar to that of a substituent on ring B in Formula [I] shown above and $R^{30}$ is an amino group or a halogen which is encompassed within a compound [II] or [IIa] described above or a salt thereof can be produced for example by subjecting a compound represented by Formula:

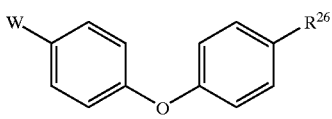

[XXXXII]

wherein $R^{26}$ has a meaning defined above and W is a cyano group or an aldehyde group or a salt thereof to a reduction or a halogenation which is known per se.

Compound [XXXXII] wherein W is a nitrile was reduced by a known method, such as one using an appropriate reducing agent described for example in "SHINJIKKENKAGAKUKOZA", Vol. 15, Oxidation and Reduction (MARUZEN) to form a benzylamine product [XXXXI]. As a reducing agent, an ordinary nitrile reducing reagent such as a metal hydride including lithium aluminum hydride, etc.

In this reaction 0.5 to 3 moles, preferably 0.5 to 1mole of a reducing agent is employed per 1 mole of Compound [XXXXII].

As a reaction solvent, an ether such as dioxane and tetrahydrofuran, etc. and an aromatic hydrocarbon such as benzene, toluene and xylene, etc. may be employed.

The reaction temperature is −50 to 100° C., preferably 0 to 80° C. The reaction time is 0.5 to 24 hours, preferably 0.5 to 12 hours. A compound [XXXXII] wherein W was an aldehyde was subjected to a known method such as those described in "JIKKENKAGAKUKOZA", Vol. 20, (MARUZEN) and Journal of American Chemical Society, 81, 475 (1959) by converting into an oxime using hydroxylamine followed by a reduction with an appropriate reducing agent to yield a benzylamine product [XXXXI].

An oxime production uses 1 to 3 moles, preferably 1 to 2 moles of hydroxylamine per 1 mole of an aldehyde. This reaction is promoted by an addition of a base. Such base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., sodium amide, an alkoxide such as sodium methoxide and sodium ethoxide, etc., an amine such as trimethylamine, triethylamine and diisopropylethylamine, etc., a cyclic amine such as pyridine, etc. The amount employed is 1 to 5 moles, preferably 1 to 3 moles per 1 mole of an aldehyde.

A reaction solvent may for example be an alcohol such as methanol and ethanol, etc., an ether such as dioxane and tetrahydrofuran, etc., a nitrile such as acetonitrile, etc., an amide such as N,N-dimethylformamide and N,N-dimethylacetamide, etc., a sulfoxide such as dimethylsulfoxide, etc. as well as water, etc. The reaction temperature is 0 to 200° C., preferably 0 to 150° C., and the reaction time is 1 to 48 hours, preferably 1 to 24 hours.

In addition to a catalytic hydrogenation, any ordinary oxime reducing agent such as a metal hydride including lithium aluminum hydride, etc. can be employed as a reducing agent as described in "SHINJIKKENKAGAKUKOZA", Vol.15, Oxidation and Reduction (MARUZEN). The reaction condition is similar to that for reducing a nitrile.

When W is an aldehyde, an appropriate reducing agent was used to form a hydroxy product and then the hydroxy group was halogenated using a halogenating agent to obtain a benzyl halide [XXXXI]. A reducing agent may be an ordinary aldehyde reducing agent described in "SHINJIKKENKAGAKUKOZA", Vol.15; Oxidation and Reduction, with sodium borohydride and lithium aluminum hydride, etc. being employed preferably. The reaction condition is similar to that for a nitrile described above.

A halogenating agent may for example be a halide of an inorganic acid, such as thionyl chloride, thionyl bromide, phosphorus trichloride, phosphorus pentachloride and phosphorus oxychloride, etc. and a halogenated hydrogen acid such as hydrochloric acid and hydrobromic acid, etc.

In this reaction, 1 to 3 moles, preferably 1 to 1.5 moles of a halogenating agent is employed per 1 mole of an alcohol.

This reaction is promoted by an addition of a base. Such base may for example be an amine such as trimethylamine, triethylamine and diisopropylethylamine, etc. and a cyclic amine such as pyridine, etc.

A reaction solvent may for example be an ether such as dioxane and tetrahydrofuran, etc., an aromatic hydrocarbon such as benzene, toluene and xylene, etc., an ester such as ethyl acetate, etc., and a halogenated hydrocarbon such as chloroform and dichloromethane, etc.

The reaction temperature is −50 to 100° C., preferably −20 to 50° C. The reaction time is 30 minutes to 24 hours, preferably 30 minutes to 10 hours.

Alternatively, compound [XXXXII] may be a commercially available product or may be produced from a compound represented by Formula:

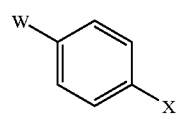

[XXXXIII]

wherein W has a meaning defined above and X is a halogen atom or a salt thereof and a compound represented by Formula:

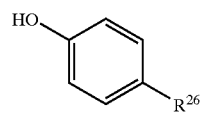

[XXXXIV]

wherein $R^{26}$ has a meaning defined above or a salt thereof by a method known per se ((Journal of Organic Chemistry, 59(18), 5414 (1994), Bioorganic and Medicinal Chemistry, 6, 15 (1998)) as well as an analogous method.

Compound (I) obtained by any method described above as a free form may be converted in accordance with a standard procedure for example into a salt with an inorganic acid (for example, hydrochloric acid, sulfuric acid and hydrobromic acid, etc.), an organic acid (for example, methanesulfonic acid, benzenesulfonic acid, toluenesulfonic acid, oxalic acid, fuumaric acid, maleic acid and tartaric acid, etc.), an inorganic base (for example, alkaline metal such as sodium and potassium, etc., alkaline earth metal such as calcium and magnesium, etc., aluminum and ammonium, etc.) or an organic base (for example, trimethylamine, triethylamine, pyridine, picoline, ethanolamine, diethanolamine, triethanolamine, dicyclohexylamine and N,N'-dibenzylethylenediamine, etc.), while compound (I) obtained as a salt may be converted into a free form or other salts according to a standard procedure.

Compound (I) or a salt thereof thus obtained can be purified and recovered using a separation/purification method known per se (for example, condensation, solvent extraction, column chromatography and recrystallization, etc.).

A starting compound for compound (I) according to the invention may be in a form of a salt, including a salt with an inorganic acid (for example, hydrochloric acid, phosphoric acid, hydrobromic acid and sulfuric acid, etc.) and a salt with an organic acid (for example, acetic acid, formic acid, propionic acid, fumaric acid, maleic acid, succinic acid, tartaric acid, citric acid, malic acid, oxalic acid, benzoic acid, methanesulfonic acid and benzenesulfonic acid, etc.). When any of these compound carries an acidic group such as —COOH, etc., a salt with an inorganic base (for example, an alkaline metal or an alkaline earth metal such as sodium, potassium, calcium and magnesium, ammonia, etc.) or with an organic base (for example, tri-$C_{1-3}$ alkylamine such as triethylamine, etc.) may be formed.

In each of the reactions described above, when a starting compound carries as a substituent an amino group, a carboxyl group or a hydroxyl group, then such group is derivatized with a protective group employed ordinarily in a peptide chemistry, which is cleaved after a reaction if desired to yield an intended compound.

A protective group for an amino group may for example be an optionally substituted $C_{1-6}$ alkylcarbonyl (for example, formyl, methylcarbonyl and ethylcarbonyl, etc.), phenylcarbonyl, a $C_{1-6}$ alkyloxycarbonyl (for example, methoxycarbonyl and ethoxycarbonyl, etc.), phenyloxycarbonyl (for example, benzoxycarbonyl), $C_{7-10}$ aralkylcarbonyl (for example, benzyloxycarbonyl), trityl, phthaloyl, etc. A substituent on each of the groups listed above may be a halogen atom (for example, fluorine, chlorine, bromine and iodine, etc.), a $C_{1-6}$ alkylcarbonyl (for example, methylcarbonyl, ethylcarbonyl and butylcarbonyl, etc.) and a nitro group, which may occur 1 to about 3 times.

A protective group for a carboxyl group may for example be an optionally substituted $C_{1-6}$ alkyl (for example, methyl, ethyl, n-propyl, i-propyl, n-butyl and t-butyl, etc.), phenyl, trityl and silyl, etc. A substituent on each of the groups listed above may be a halogen atom (for example, fluorine, chlorine, bromine and iodine, etc.), a $C_{16}$ alkylcarbonyl (for example, formyl, methylcarbonyl, ethylcarbonyl and butylcarbonyl, etc.) and a nitro group, which may occur 1 to about 3 times.

A protective group for a hydroxyl group may for example be an optionally substituted $C_{1-6}$ alkyl (for example, methyl, ethyl, n-propyl, i-propyl, n-butyl and tert-butyl, etc.), phenyl, a $C_{7-10}$ aralkyl (for example, benzyl, etc.), a $C_{16}$ alkylcarbonyl (for example, formyl, methylcarbonyl and ethylcarbonyl, etc.), phenyloxycarbonyl (for example, benzoxycarbonyl, etc.), $C_{7-10}$ aralkylcarbonyl (for example, benzyloxycarbonyl, etc.), pyranyl, furanyl, silyl, etc. A substituent on each of the groups listed above may be a halogen atom (for example, fluorine, chlorine, bromine and iodine, etc.), a $C_{1-6}$ alkyl, phenyl, a $C_{7-10}$ aralkyl, nitro, etc., which may occur 1 to about 4 times.

A method for cleaving a protective group is a method known per se or an analogous method, such as a treatment for example with an acid, a base, a reduction, UV light, hydrazine, phenylhydrazine, sodium N-methyldithiocarbamate, tetrabutylammonium fluoride, palladium acetate, etc.

Compound (I) or a salt thereof according to the invention has an excellent MMP inhibiting effect, especially an MMP-13 inhibiting effect.

In addition, compound (I) or a salt thereof according to the invention has low toxicity and is safe.

Accordingly, compound (I) or a salt thereof according to the invention having an excellent MMP inhibiting effect, especially an MMP-13 inhibiting effect, is useful as a safe prophylactic and therapeutic agent in a mammal (for example, mouse, rat, hamster, rabbit, cat, dog, cattle, sheep, monkey and human) against osteoarthritis, rheumatoid arthritis, osteoporosis, cancer, periodontosis, corneal ulcer, pathologic bone resorption (such as Behcet's disease), nephritis, arteriosclerosis, pulmonary emphysema, cirrhosis, autoimmune disease (Crohn's disease and Sjogren's disease), cancer metastasis, contraception, etc.

A formulation containing compound (I) or a salt thereof according to the invention may be in various dosage forms such as a solid form including powder, granule, tablet, capsule, etc., and a liquid form including syrup, emulsion or solution for injection, etc.

A prophylactic and therapeutic formulation according to the invention can be produced by a customary method such as mixing, kneading, granulation, compaction, coating, sterilization and emulsifying depending on the type of the formulation. The production of a formulation may be in accordance for example with each section in the General Rule of the Formulation under Japanese Pharmacopeia.

While the amount of compound (I) or a salt thereof in a formulation according to the invention may vary depending on the type of the formulation, it is usually 0.01 to 100% by weight, preferably 0.1 to 50% by weight, more preferably 0.5 to 20% by weight based on the total weight of the formulation.

When compound (I) or a salt thereof is used as a pharmaceutical described above, it may be used as it is or is treated by a standard method if necessary with a pharmaceutically acceptable carrier such as an excipient (for example, starch, lactose, sugar, calcium carbonate and calcium phosphate), a binder (for example, starch, gum arabic, carboxymethyl cellulose, hydroxypropyl cellulose, crystalline cellulose, alginic acid, gelatin and polyvinylpyrrolidone), a lubricant (for example, stearic acid, magnesium stearate, calcium stearate and talc), a disintegrant (for example, calcium carboxymethyl cellulose and talc), a diluent (for example, water for injection and physiological saline) together with appropriate additives (stabilizer, preservative, colorant, flavor, solubilizing agent, emulsifier, buffer, osmotic agent), and administered orally or parenterally in a solid dosage form such as powder, fine powder, granule, tablet, capsule and the like, as well as a liquid form such as an injection formulation. While the dose may vary depending on the types of compound (I) or a pharmaceutically acceptable salt thereof, the administration route, the condition and the age of a patient, a preferred daily dose per kg body weight as compound (I) or a salt thereof is about 0.005 to 50 mg, preferably about 0.05 to 10 mg, more preferably about 0.2 to 4 mg, which may be divided into 1 to 3 times a day.

BEST MODE FOR CARRYING OUT THE INVENTION

EXAMPLE

The present invention is further described in detail in the following Examples and Comparatives, which are not intended to restrict the invention and may be modified without departing from the scope of the invention.

An elution in column chromatography in each Example was performed under the observation by a TLC (thin layer chromatography) unless otherwise specified. In a TLC observation, a 60 $F_{254}$ from Merck was employed as a TLC plate. A detection was made by an Uw detector or by means of a color development with a phosphomolybdic acid. As silica gel for column chromatography, silica gel 60 (70 to 230 mesh size) from Merck was employed. As preparative TLC plate, a 60 $F_{254}$ from Merck was employed. As a column for high performance liquid chromatography, a YMC Pack ODS SH-343-5 or a YMC Pack ODS S-363 I-15 (YMC) was employed. A room temperature referred herein means a temperature from 10° C. to 35° C.

NMR (Nuclear Magnetic Resonance) spectra were measured using a *VARIAN* model Gemini-200 spectrometer ($^1$H-NMR:200 MHz) or a *BRUKER* model DPX-300 U.S. patent application Ser. No. 10/161,289 spectrometer ($^1$H-NMR:300 MHz). An internal standard was tetramethylsilane and all δ values are represented in ppm. Abbreviations employed here are described below. $CDCl_3$: deutero chloroform, $DMSO-d_6$: deutero dimethylsulfoxide, Hz: Hertz J: Coupling constant, m: Multiplet, q: Quartet, t: Triplet, d: Doublet, s: Singlet, br: Broad, dd: Double doublet, dq: Double quartet.

Example 1

3-Mercapto-1-(4-phenoxybenzylpyrrolidine-2,5-dione 0.50 g (2.1 mmol) of 4-phenoxybenzylamine hydrochloride was dissolved in 50 ml of chloroform, and washed with a saturated aqueous sodium hydrogen carbonate. After drying over anhydrous magnesium sulfate, chloroform was concentrated under reduced pressure to obtain a residue which was treated with 50 ml of toluene and 0.38 g (2.6 mmol) of thiomalic acid and then heated under reflux with dehydration for 5 hours. After concentrating toluene, the residue was treated with 50 ml of acetic acid and heated under reflux overnight, and then the reaction mixture was concentrated to obtain a residue which was subjected to column chromatography on silica gel using chloroform as an fluent, and the effluent was concentrated into dryness to obtain 0.21 g (yield: 32%) of 3-mercapto-1-(4-phenoxybenzyl)pyrrolidine-2,5-dione as a colorless oil.
$^1$H-NMR (200 MHz, $CDCl_3$)
δ: 7.40–6.90 (9H, m), 4.70 (1H, d, J=14.0 Hz), 4.58 (1H, d, J=14.0 Hz), 3.95–3.86 (1H, m), 3.17 (1H dd, J=18.6, 9.0 Hz), 2.57 (1H, dd, J=18.6, 4.2 Hz), 2.56 (1H, d, J=4.6 Hz)

Example 2

3-Ethylthio-1-(4-Phenoxybenzyl)Pyrrolidine-2,5-Dione (1) 5.90 g (29.6 mmol) of 4-phenoxybenzylamine and 2.94 g (30 mmol) of maleic anhydride were dissolved in 50 ml of acetic acid and stirred at 130° C. overnight. The reaction mixture was concentrated to obtain a residue which was subjected to column chromatography on silica gel using chloroform as an eluent, and the effluent was concentrated into dryness to obtain 2.60 g (yield: 32%) of 4-phenoxybenzylmaleimide as a white powder.
$^1$H-NMR (200 MHz, $CDCl_3$)
δ: 7.40–6.90 (9H, m), 6.71 (2H, s), 4.65 (2H, s)

(2) 0.10 g (0.36 mmol) of 4-phenoxybenzylmaleimide was dissolved in 10 ml of ethanol, treated with 0.040 g (0.43 mmol) of ethylmercaptan and stirred at room temperature for 4 hours. The reaction mixture was concentrated to obtain a residue which was subjected to column chromatography on silica gel using chloroform as an eluent, and the effluent was concentrated into dryness to obtain 0.10 g (yield: 82%) of 3-ethylthio-1-(4-phenoxybenzylpyrrolidine-2,5-dione as a colorless oil.
$^1$H-NMR (200 MHz, $CDCl_3$)
δ: 7.40–6.90 (9H, m), 4.68 (1H, d, J=14.0 Hz), 4.60 (1H, d, J=14.0 Hz), 3.75 (1H, dd, J=9.0, 3.7 Hz), 3.15 (1H, dd, J=18.0, 9.0 Hz), 2.95–2.65 (2H, m), 2.54 (1H, dd, J=18.0, 3.7 Hz), 1.29 (3H, t, J=7.4 Hz)

Example 3

3-[2-(Ethoxycarbonyl)Ethylthio]-1-(4-phenoxybenzyl)pyrrolidine-2,5-Dione

By a method similar to that in Example 2, starting from 0.10 g (0.36 mmol) of 4-phenoxybenzylmaleimide and 0.06 g (0.43 mmol) of ethyl 3-mercaptopropionate, 0.14 g (yield: 95%) of 3-[2-(ethoxycarbonyl)ethylthio]-1-(4-phenoxybenzyl)pyrrolidine-2,5-dione was obtained as a colorless oil.
$^1$H-NMR (200 MHz, $CDCl_3$)
δ: 7.40–6.90 (9H, m), 4.68 (1H, d, J=14.0 Hz), 4.60 (1H, d, J=14.0 Hz), 4.16 (2H, q, J=7.1 Hz), 3.80 (1H dd, J=10.0, 3.8Hz), 3.26–2.94 (3H, m), 2.68 (2H, t, J=6.0 Hz), 2.51 (1H, dd, J=18.0, 4.0Hz), 1.26 (3H, t, J=7.2 Hz)

Example 4

3-Benzylthio-1-(4-phenoxybenzyl)pyrrolidine-2, 5-dione

By a method similar to that in Example 2, starting from 0.28 g (1.0 mmol) of 4-phenoxybenzylmaleimide and 0.12 g (1.0 mmol) of benzylmercaptan, 0.42 g of 3-benzylthio-1-(4-phenoxybenzyl)pyrrolidine-2,5-dione was obtained almost quantitatively as a colorless oil.
$^1$H-NMR (300 MHz, $CDCl_3$)
δ: 7.39–7.25 (9H, m), 7.10 (1H, m), 7.02–6.91 (4H, M), 4.66 (1H, d, J=14.1 Hz), 4.60 (1H, d, J=14.1 Hz), 4.20 (1H, d, J=13.5 Hz), 3.84 (1H, d, J=13.5 Hz), 3.51 (1H, dd, J=9.2, 3.8 Hz), 2.97 (1H, dd, J=18.8, 9.2 Hz), 2.41 (1H, dd, J=18.8, 3.8 Hz)

Example 5

3-Acetylthio-1-(4-Phenoxybenzyl)Pyrrolidine-2,5-dione 1.00 g (5.70 mmol, Aldrich) of S-acetylmercaptosuccinic anhydride was dissolved in 30 ml of acetic acid, treated with 1.20 g (5.70 mmol) of 4-phenoxybenzylamine hydrochloride and 795 μl(5.70 mmol) of triethylamine, and then heated at 100° C. for 14 hours with stirring. The reaction mixture was concentrated under reduced pressure to obtain a residue which was purified three times by column chromatography on silica gel (eluent: ethyl acetate: hexane (20:80), chloroform and ethyl acetate: hexane (20:80)) to obtain an intended fraction which was then concentrated under reduced pressure to obtain 0.80 g (yield: 40%) of 3-acetylthio-1-(4-phenoxybenzyl)pyrrolidine-2,5-dione as a yellow oil.
$^1$H-NMR (300 MHz, $CDCl_3$)
δ: 7.37 (2H, d, J=8.5 Hz), 7.32 (2H, d, J=7.6Hz), 7.11 (1H, t, J=7.6Hz), 7.00 (2H, d, J=8.5 Hz), 6.94 (2H, d, J=8.5 Hz), 4.72 (1H, d, J=14.1Hz), 4.65 (1H, d, J=14.1 Hz), 4.23

(1H, dd, J=9.6, 5.6 Hz), 3.25 (1H, dd, J=18.5, 9.6 Hz), 2.72 (1H, dd, J=18.5, 5.6 Hz), 2.39 (3H, s)

Example 6

3-Benzoylthio-1-(4-phenoxybenzyl)pyrrolidine-2,5-dione

By a method similar to that in Example 2, starting from 1.00 g (3.60mmol) of 4-phenoxybenzylmaleimide and 0.50 g (3.60 mmol) of thiobenzoic acid, 0.87 g (yield: 58%) of 3-benzoylthio-1-(4-phenoxybenzyl)pyrrolidine-2,5-dione was obtained as a white powder.

$^1$H-NMR (300 MHz, CDCl$_3$)

δ: 7.91 (2H, d, J=7.4 Hz), 7.62 (1H dd, J=7.6, 7.6Hz), 7.47 (2H, dd, J=7.7, 7.6 Hz), 7.41 (2H, d, J=8.5 Hz), 7.33 (2H, dd, J=7.7, 7.6 Hz), 7.11 (1H dd, J=7.6, 7.4Hz) 7.01 (2H, d, J=8.5 Hz), 6.95 (2H, d, J=8.5 Hz), 4.78 (1H, d, J=14.1 Hz), 4.70 (1H, d, J=14.1 Hz), 4.41 (1H dd, J=9.5, 5.5 Hz), 3.34 (1H, dd, J=18.5, 9.5 Hz), 2.84 (1H, dd, J=18.5, 5.5 Hz)

Example 7

3-Acetylthio-4-methyl-1-(4-phenoxybenzyl) pyrrolidine-2,5-dione (1) 3.00 g of 2-amino-3-methylsuccinic acid (Sigma, 20.4 mmol) was dissolved in 163 ml of 2.5 N hydrobromic acid, cooled to −10° C., treated with 7.28 g (61.2 mmol) of potassium bromide, treated with 3.52 g (51.0 mmol) of sodium nitrite with stirring over a period of 1.5 hours, and then stirred at −5° C. for further 1.5hours. After adding sodium chloride, the mixture was extracted five times with ethyl acetate and dried over anhydrous sodium sulfate. After concentrating into dryness, the residue was dissolved in 100 ml of ethanol, treated with 1.00 ml of concentrated sulfuric acid, and heated under ref lux for 10 hours. After concentrating, the residue was dissolved in ethyl acetate and washed with saturated aqueous sodium hydrogen carbonate, water and saturated brine, and then dried over anhydrous sodium sulfate. After concentrating, the residue was subjected to column chromatography on silica gel using hexane: ethyl acetate (95:5) as an eluent and the effluent was concentrated to obtain 4.53 g (yield: 83%) diethyl 2-bromo-3-methylsuccinate as a colorless oil.

$^1$H-NMR (300 MHz, CDCl$_3$)

:4.44 (1H, d, J=9.4 Hz), 4.23 (2H, m), 4.16 (2H, q, J=7.2 Hz), 3.12 (1H, dq, J=9.4, 7.2 Hz), 1.40 (3H, d, J=7.2 Hz), 1.29 (3H, t, J=7.2 Hz), 1.25 (3H, t, J=7.2 Hz)

(2) 2.27 g (8.49 mmol) of diethyl 2-bromo-3-methylsuccinate was dissolved in 110 ml of ethanol, treated with 1.45 g (12.7 mmol) of potassium thioacetate, and stirred at 50° C. for 2 hours, and 0.49 g (4.25 mmol) of potassium thioacetate was further added and the mixture was stirred at 50° C. for 1 hour. The reaction mixture was concentrated, dissolved in ethyl acetate, washed with water and saturated brine and dried over anhydrous sodium sulfate. After concentrating, the residue was subjected to column chromatography on silica gel using hexane: ethyl acetate (90:10–80:20) as an eluent, and the effluent was concentrated into dryness to obtain 1.80 g (yield: 80%) of diethyl 2-acethylthio-3-methylsuccinate as a colorless oil.

$^1$H-NMR (300 MHz, CDCl$_3$)

δ: 4.56 (1H, d, J=5.7 Hz), 4.17 (4H, m), 3.24 (1H, dq, J=5.7, 7.2 Hz), 2.39 (3H, s), 1.26 (3H, t, J=7.2 Hz), 1.26 (3H, d, J=7.2 Hz), 1.26 (3H, t, J=7.2 Hz)

(3) 1.80 g (6.86 mmol) of diethyl 2-acethylthio-3-methylsuccinate was dissolved in 20.0 ml of acetic acid and 20.0 ml of conc. hydrochloric acid, and stirred at 100° C. for 1.5 hours. The reaction mixture was concentrated, treated with toluene, concentrated, precipitated from ether-hexane to obtain 1.00 g (yield: 89%) of 2-mercapto-3-methylsuccinic acid as a white powder.

$^1$H-NMR (300 MHz, DMSO-d$_6$)

δ: 3.42 (1H, m), 3.13 (1H, m), 2.71 (1H, m), 1.15 (3H, d, J=7.2 Hz)

(4) 0.950 g (5.79 mmol) of 2-mercapto-3-methylsuccinic acid was dissolved in 15.0 ml of acetic anhydride and stirred at 100° C. for 1 hour. The reaction mixture was concentrated, treated with toluene, concentrated into dryness to obtain 0.963 g (yield: 88%) of 3-acetylthio-4-methylsuccinic anhydride as a colorless oil.

$^1$H-NMR (300 MHz, CDCl$_3$)

δ: 3.93 (1H, d, J=8.3 Hz), 3.17 (1H, m), 2.44 (3H, s), 1.49 (3H, d, J=7.2 Hz)

(5) 0.930 g (4.90 mmol) of 3-acetylthio-4-methylsuccinic anhydride was dissolved in 25.0 ml of dichloromethane, and 1.16 g (4.94 mmol) of 4-phenoxybenzylamine hydrochloride and 1.03 ml (7.41 mmol) of triethylamine were added and the mixture was stirred at room temperature for 2 hours and then the reaction mixture was concentrated into dryness. The residue was dissolved in 15.0 ml of acetic anhydride, treated with 1.00 g of sodium acetate, and then stirred at 100° C. for 20 minutes. After concentrating the reaction mixture, the residue was dissolved in ethyl acetate, washed with water and saturated brine, and then dried over anhydrous sodium sulfate. After concentrating, the residue was subjected to column chromatography on silica gel using hexane: ethyl acetate (75:25) as an eluent, and the effluent was concentrated into dryness to obtain 0.491 g (yield: 27%) of 3-acethylthio-4-methyl-1-(4-phenoxybenzyl)pyrrolidine-2,5-dione as a colorless oil.

$^1$H-NMR (300 MHz, CDCl$_3$)

δ: 7.35 (4H, m), 7.11 (1H, m), 7.00 (2H, m), 6.94 (2H, d, J=8.7Hz), 4.72 (1H, d, J=14.1 Hz), 4.63 (1H, d, J=14.1 Hz), 3.85 (1H, d, J=6.4 Hz), 2.85 (1H, m), 2.40 (3H, s), 1.40 (3H, d, J=7.2 Hz)

Example 8

3-Mercapto-4-methyl-1-(4-phenoxybenzyl) pyrrolidine-2,5-dione 0.360 g (0.974 mmol) of 3-acethylthio-4-methyl-1-(4-phenoxybenzyl)pyrrolidine-2,5-dione obtained in Example 7 was dissolved in 20 ml of acetic acid and 10.0 ml of conc. hydrochloric acid, and stirred at 100° C. for 30 minutes. The reaction mixture was treated with toluene and concentrated into dryness to obtain a residue, which was then subjected to column chromatography on silica gel using hexane: ethyl acetate (80:20) as an eluent, and the effluent was concentrated into dryness to obtain 0.208 g (yield: 65%) of 3-mercapto-4-methyl-1-(4-phenoxybenzyl)pyrrolidine-2,5-dione as a colorless oil.

$^1$H-NMR (300 MHz, CDCl$_1$)

δ: 7.33 (4H, m), 7.11 (1H, m), 7.00 (2H, m), 6.93 (2H, d, J=8.3Hz), 4.67 (1H, d, J=13.9 Hz), 4.61 (1H, d, J=13.9 Hz), 3.48 (1H, dd, J=5.3, 5.3 Hz), 2.67 (1H, dq, J=5.3, 7.2 Hz), 2.44 (1H, d, J=5.3 Hz), 1.41 (3H, d, J=7.2 Hz)

Example 9

3-Hydroxy-4-[2-(methoxycarbonyl)ethylthio]-1-(4-phenoxybenzyl)pyrrolidine-2,5-dione (1) 10.0 g (75.7 mmol, TOKYO KASEI KOGYO) of cis-epoxysuccinic acid was dissolved in 200 ml of ethanol and treated with 2.00 ml of conc. sulfuric acid and heated under reflux for 4 hours. The reaction mixture was concentrated, dissolved in ethyl acetate, and washed with water and saturated brine. After drying over anhydrous sodium sulfate followed by concentrating into dryness, 13.5 g (yield: 95%) of a diethylester product was obtained as a colorless oil.

$^1$H-NMR (300 MHz, CDCl$_1$)

δ: 4.27 (4H, q, J=7.2 Hz), 3.70 (2H, s), 1.31 (6H, t, J=7.2 Hz)

(2) 4.00 g (21.30 mmol) of the diethylester product thus obtained was dissolved in 200 ml of ethanol, treated with 21.30 ml (21.30 mmol) of a 1N aqueous solution of sodium hydroxide and then stirred at room temperature for 2 hours. The reaction mixture was concentrated, treated with saturated brine, adjusted at pH 2.0 with 1N hydrochloric acid, and then extracted five times with ethyl acetate. The ethyl acetate layer was washed with saturated brine, dried over anhydrous sodium sulfate, and concentrated into dryness to obtain 1.92 g (yield: 56%) of ethylhydrogen-cis-epoxysuccinic acid as a colorless oil.

$^1$H-NMR (300 MHz, CDCl$_3$)

δ: 4.32 (2H, m), 3.80 (1H, d, J=4.5 Hz), 3.76 (1H, d, J=4.9 Hz), 1.33 (3H, t, J=7.2 Hz)

(3) 0.679 g (4.24 mmol) of ethylhydrogen-cis-epoxysuccinic acid was dissolved in 20.0 ml of N,N-dimethylformamide, and then 0.845 g (4.24 mmol) of 4-phenoxybenzylamine, 0.634 ml (4.24 mmol) of diethyl cyanomalate and 0.591 ml (4.24 mmol) of triethylamine were added and the mixture was stirred at room temperature for 2 hours. The reaction mixture was concentrated, dissolved in ethyl acetate, washed with 10% aqueous citric acid, saturated aqueous sodium hydrogen carbonate, water and saturated brine and then dried over anhydrous sodium sulfate. After concentrating, the residue was subjected to column chromatography on silica gel using hexane: ethyl acetate (70:30) as an eluent, and the effluent was concentrated into dryness to obtain 0.870 g (yield: 60%) of ethyl-cis-3-(4-phenoxybenzylcarbamoyl)-2-oxylane-carboxylate as a colorless oil.

$^1$H-NMR (300 MHz, CDCl$_3$)

δ: 7.34 (2H, m), 7.25 (2H, d, J=8.5Hz), 7.11 (1H, m), 6.98 (4H, m), 6.77 (1H, m) 4.45 (1H, dd, J=14.7, 6.4 Hz), 4.35 (1H, dd, J=14.7, 5.7 Hz), 4.16 (2H, q, J=7.2 Hz), 3.74 (1H, d, J=4.9 Hz), 3.72 (1H, d, J=4.9 Hz), 1.25 (3H, t, J=7.2 Hz)

(4) 0.770 g (2.26 mmol) of ethyl-cis-3-(4-phenoxybenzylcarbamoyl)-2-oxylane-carboxylate was dissolved in 30 ml of methanol, treated with 2.49 ml (2.49 mmol) of a 1N aqueous solution of sodium hydroxide and stirred at room temperature for 2 hours. The reaction mixture was adjusted at pH 2.0, concentrated, diluted with ethyl acetate, and washed with water and saturated brine. After drying over anhydrous sodium sulfate followed by concentrating into dryness, 0.650 g (yield: 92%) of cis-3-(4-phenoxybenzylcarbamoyl)-2-oxylanecarboxylic acid was obtained as a white powder.

$^1$H-NMR (300 MHz, DMSO-d$_6$)

δ: 8.54 (1H, m), 7.38 (2H, m), 7.27 (2H, d, J=8.3 Hz), 7.13 (1H m), 6.98 (2H, m), 6.94 (2H, d, J=8.3 Hz), 4.29 (1H, dd, J=15.1, 6.4 Hz), 4.23 (1H, dd, J=l5.1, 5.7Hz), 3.79 (1H, d, J=4.9 Hz), 3.76 (1H, d, J=4.9 Hz)

(5) 0.250 g (0.80 mmol) of cis-3-(4-phenoxybenzylcarbamoyl)-2-oxylanecarboxylic acid was dissolved in 5.00 ml of acetic anhydride, treated with 0.250 g of sodium acetate, and stirred at 120° C. for 5 minutes. The reaction mixture was concentrated, dissolved in ethyl acetate, washed with water and saturated brine, and then dried over anhydrous sodium sulfate. After concentrating, the residue was subjected to column chromatography on silica gel using hexane: ethyl acetate (70:30–60:40) as an eluent, and the effluent was concentrated and precipitated from hexane-ethyl acetate to obtain 0.129 g (yield: 55%) of 3,4-epoxy-1-(4-phenoxybenzyl)pyrrolidine-2,5-dione as a white powder.

$^1$H-NMR (300 MHz, CDCl$_1$)

δ: 7.33 (2H, m), 7.26 (2H, d, J=8.3Hz), 7.11 (1H, m), 6.99 (2H, m), 6.93 (2H, d, J=8.7 Hz), 4.54 (2H, s), 4.05 (2H s)

(6) 0.220 g (0.740 mmol) of 3,4-epoxy-1-(4-phenoxybenzyl)pyrrolidine-2,5-dione was dissolved in 10.0 ml of N,N-dimethylformamide, treated with 0.309 g (2.24 mmol) of potassium carbonate and 0.248 ml (2.24 mmol) of methyl 3-mercaptopropionate, and then stirred at room temperature for 10 minutes. After adding 3N hydrochloric acid, the mixture was extracted twice with ethyl acetate. The ethyl acetate layer was washed with water and saturated brine, and dried over anhydrous sodium sulfate. After concentrating, the residue was subjected to column chromatography on silica gel using hexane: ethyl acetate (50:50) as an eluent, and the effluent was concentrated into dryness to obtain 0.153 g (yield: 49%) of 3-hydroxy-4-[2-(methoxycarbonyl)ethylthio]-1-(4-phenoxybenzyl)pyrrolidine-2,5-dione as a colorless oil.

$^1$H-NMR (300 MHz, CDCl$_3$)

δ: 7.34 (4H, m), 7.12 (1H, m), 7.00 (2H, m), 6.93 (2H, d, J=8.3Hz), 4.67 (1H, d, J=14.1 Hz), 4.63 (1H, d, J=14.1 Hz), 4.46 (1H, n), 3.78 (1H, d, J=5.3 Hz), 3.71 (3H, s), 3.48 (1H, d, J=3.0 Hz), 3.09 (2H, m), 2.75 (2H, t, J=7.0 Hz)

Example 10

3-Acethylmethyl-1-(4-phenoxybenzyl)pyrrolidine-2,5-dione 1.90 g (8.90 mmol) of 4-phenoxybenzylamine hydrochloride was dissolved in ethyl acetate, and washed with saturated aqueous sodium carbonate. The organic layer was concentrated under reduced pressure, dissolved in 100 ml of toluene, treated with 1.00 g (8.90 mmol) of itaconic anhydride, and stirred at room temperature for 4 hours. 2.50 ml (19.8 mmol) of triethylamine and 1.30 ml (19.8 mmol) of thioacetic acid were added, and the mixture was stirred for further 16 hours at room temperature. The reaction mixture was concentrated under reduced pressure, dissolved in ethyl acetate, washed twice with water, dilute hydrochloric acid, water and then saturated brine, and the organic layer was dried over anhydrous sodium sulfate. After concentrating under reduced pressure, the residue was subjected to column chromatography on silica gel, and the fraction eluted with ethyl acetate: hexane (10:90–50:50) was concentrated, dissolved in 50 ml of toluene, treated with 10 ml of acetic anhydride, and then stirred with heating at 100° C. for 3 hours. The reaction mixture was concentrated under reduced pressure and the residue was subjected to column chromatography on silica gel, and the fraction eluted with ethyl acetate: hexane (20:80–30:70) was purified again by high pressure liquid chromatography (eluent: 60% acetonitrile/0.05% trifluoroacetic acid). Desired fractions were concentrated under reduced pressure, extracted twice with ethyl acetate, and the organic layer obtained was washed with saturated brine and dried over anhydrous sodium sulfate. This solution was concentrated under reduced pressure to obtain 0.536 g (yield: 16%) of 3-acethylmethyl-1-(4-phenoxybenzyl)pyrrolidine-2,5-dione as a tan oil.

¹H-NMR (300 MHz, CDCl₁)
δ: 7.33 (4H, m), 7.11 (1H, t, J=7.4 Hz), 6.99 (2H, d, J=7.7 Hz), 6.93 (2H, d, J=8.6 Hz), 4.65 (1H, d, J=14.1 Hz), 4.59 (1H, d, J=14.1 Hz), 3.42 (1H, dd, J=13.4, 4.1 Hz), 3.25–3.09 (2H, m), 2.83 (1H, dd, J=18.4, 8.8 Hz), 2.45 (1H, dd, J=18.4, 4.8Hz), 2.34 (3H, s)

Example 11

3-[(Tetrahydro-2-furanyl)methyldithio]-1-(4-phenoxybenzyl)pyrrolidine-2,5-dione 5.00 g (30.0 mmol) of tetrahydrofurfuryl bromide was dissolved in 30 ml of ethanol, and 2.30 g (30.0 mmol) of thiourea was added and the mixture was heated under ref lux for 16 hours. The reaction mixture was concentrated under reduced pressure, and then dissolved in 30 ml of a 1N aqueous solution of sodium hydroxide and heated at 100° C. for 1.5 hours. After cooling and extracting with ethyl acetate, the organic layer was washed with water and saturated brine, and then dried over anhydrous sodium sulfate. This solution was concentrated under reduced pressure to obtain 0.208 g of a tan oil. The oil thus obtained was dissolved in 20 ml of methanol, and treated with 0.552 g (1.80 mmol) of 3-mercapto-1-(4-phenoxybenzyl)pyrrolidine-2,5-dione obtained in Example 1, 0.178 g (1.80 mmol) of triethylamine and excessive iodine, and then stirred at room temperature for 1 hour. After concentrating under reduced pressure, the residue was dissolved in ethyl acetate, washed with water, an aqueous solution of sodium thiosulfate and saturated brine, and then dried over anhydrous sodium sulfate. After concentrating under reduced pressure, the residue was purified three times by column chromatography on silica gel (eluent: ethyl acetate: hexane (30:70–50:50), chloroform and ethyl acetate: hexane (20:80)) followed by high pressure liquid chromatography (eluent: 60% acetonitrile/0.05% trifluoroacetic acid) for a further purification. Desired fractions were concentrated under reduced pressure and extracted twice with ethyl acetate, and the organic layers obtained were combined and washed with saturated aqueous sodium hydrogen carbonate and saturated brine, and then dried over anhydrous sodium sulfate. This solution was 2 concentrated under reduced pressure to obtain 0.045 g (yield 6%) of 3-[(tetrahydro-2-furanyl)methyldithio]-1-(4-phenoxybenzyl)pyrrolidine-2,5-dione as a tan oil.

¹H-NMR (300 MHz, CDCl₃)
δ: 7.38 (2H, d, J=8.5 Hz), 7.31 (2H d, J=7.9Hz), 7.11 (1H, m), 6.99 (2H, d, J=7.9 Hz), 6.93 (2H, d, J=8.5 Hz), 4.70 (0.5H, d, J=14.0 Hz), 4.69(0.5H, d, J=14.0 Hz), 4.63 (0.5H, d, J=14.0 Hz), 4.62 (0.5H, d, J=14.0 Hz), 4.09–3.68 (4H, m), 3.17 (0.5H, dd, J=18.8, 2.6 Hz), 3.14 (0.5H, dd, J=18.8, 2.7 Hz), 2.95 (0.5H, dd, J=18.8, 4.2 Hz), 2.92 (0.5H, dd, J=18.8, 4.2 Hz), 2.81 (0.51H, dd, J=13.4, 6.7 Hz), 2.67 (1H, m), 2.52 (0.5H, dd, J=13.4, 7.4 Hz), 2.06–1.82 (3H, m), 1.61–1.43 (1H, m)

Example 12

3,3'-Dithiobis[1-(4-phenoxybenzyl)pyrrolidine-2,5-dione 0.100 g (0.35 mmol) of 3-mercapto-1-(4-phenoxybenzyl)pyrrolidine-2,5-dione obtained in Example 1 was dissolved in 100 ml of ethanol and treated with 0.15 g (0.60 mmol) of iodine and then allowed to stand at room temperature for 1 hour. The reaction mixture was concentrated under reduced pressure and purified by a high pressure liquid chromatography (eluent: 60% acetonitrile/0.01 M phosphate buffer (pH 6.3)). Desired fractions were concentrated under reduced pressure, extracted twice with ethyl acetate, and the organic phase obtained was washed with saturated brine, and dried over anhydrous sodium sulfate. This solution was concentrated under reduced pressure to obtain 0.062 g (yield: 31%) of 3,3'-dithiobis[1-(4-phenoxybenzyl)pyrrolidine-2,5-dione as a white powder.

¹H-NMR (300 MHz, CDCl₃)
δ: 7.33 (8H, m), 7.11 (2H, td, J=7.6, 2.6 Hz), 6.95 (8H, m), 4.63 (4H, brs.), 4.02 (1H, dd, J=9.2, 4.8 Hz), 3.82 (1H, dd, J=9.1, 4.6 Hz), 3.13 (1H, dd, J=18.9, 9.1 Hz), 3.03 (1H, dd, J=18.8, 9.2 Hz), 2.86 (1H, dd, J=18.9, 4.6 Hz), 2.74 (1H, dd, J=18.8, 4.8 Hz)

Example 13

3,3'-[Dithiobis(methylene)]bis[1-(4-phenoxybenzyl) pyrrolidine-2,5-dione]

0.300 g (0.80 mmol) of 3-acethylmethyl-1-(4-phenoxybenzyl)pyrrolidine-2, 5-dione obtained in Example 10 was dissolved in 3 ml of methanol, and 3 ml of a 28% solution of sodium methoxide in methanol was added and the mixture was stirred at room temperature for 20 minutes. The reaction mixture was made acidic with 1N hydrochloric acid, and then treated further with water. The mixture was extracted twice with ethyl acetate, and the organic phase obtained was washed with saturated aqueous sodium carbonate and saturated brine, and dried over anhydrous sodium sulfate. After concentrating under reduced pressure, the residue was subjected to column chromatography on silica gel, and the fraction eluted with ethyl acetate: hexane (50:50) was concentrated under reduced pressure to obtain 0.059 g (yield: 20%) of 3,3'-[dithiobis(methylene)]bis[1-(4-phenoxybenzyl)pyrrolidine-2,5-dione] as a colorless oil.

¹H-NMR (300 MHz, CDCl₃)
δ: 7.33 (8H, t, J=8.5 Hz), 7.10 (2H, t, J=7.5 Hz), 6.99 (4H, d, J=8.6 Hz), 6.92 (4H, d, J=8.6 Hz), 4.63 (2H, s), 4.62 (2H, s), 3.10–2.74 (8H, m), 2.59 (1H, dd, J=18.3, 5.0 Hz), 2.53 (1H, dd, J=18.3, 5.0 Hz)

Example 14

3,3'-[Thiobis[1-(4-phenoxybenzyl)pyrrolidine-2,5-dione]

1.00 g (4.20 mmol) of 4-phenoxybenzylamine hydrochloride was dissolved in ethyl acetate, and washed with saturated aqueous sodium hydrogen carbonate. The organic layer was concentrated under reduced pressure, dissolved in 50 ml of toluene, treated with 0.506 g (1.90 mmol, TOKYO KASEI) of thiodisuccinic acid, and heated under reflux for 4 hours with dehydrating. The reaction mixture was concentrated under reduced pressure, dissolved in ethyl acetate, washed with water and saturated brine, and dried over anhydrous sodium sulfate. After concentrating, the residue was subjected to column chromatography on silica gel, and the fraction eluted with ethyl acetate: hexane (20:80–30:70) was concentrated under reduced pressure to obtain 0.180 g (yield: 8%) of 3,3'-[thiobis[1-(4-phenoxybenzyl)pyrrolidine-2,5-dione] as a yellow oil.

¹H-NMR (300 MHz, CDCl₃) δ: 7.33 (8H, m), 7.11 (2H, m), 6.95 (8H, m), 4.64 (4H, brs), 4.61 (1H, dd, J=9.3 4.3 Hz), 4.08 (1H, dd, J=9.3, 4.3 Hz), 3.16 (2H, dd, J=18.8, 9.3 Hz), 2.71 (1H, dd, J=18.8, 4.3 Hz), 2.43 (1H, dd, J=18.8, 4.3 Hz)

Example 15

4-Acetylthio-1-(4-phenoxybenzyl)pyrrolidin-2-one (1) 2.79 g (20.0 mmol) of glycine ethyl ester hydrochloride was dissolved in 30 ml of methanol, 3.23 g (20.0 mmol) of triethylamine was added and the mixture was stirred at room temperature for 10 minutes, and then 3.96 g (20.0 mmol) of 4-phenoxybenzaldehyde was added and the mixture was stirred for 5 hours.0.378 g (10.0 mmol) of sodium borohydride was added in portions and the mixture was stirred at room temperature for 2 hours, and then the reaction mixture was concentrated, treated with saturated aqueous sodium hydrogen carbonate, and extracted with ethyl acetate. The ethyl acetate layer was washed with water, concentrated to obtain a residue which was then treated with 50 ml of ether and 10 ml of a 4N solution of hydrogen chloride in ethyl acetate and then stirred at room temperature for 30 minutes. The precipitate was collected by filtration, and washed with ether to obtain 5.49 g (yield: 85%) of a hydrochloride of a reduced amino product as a white powder.

$^1$H-NMR (200 MHz, DMSO-$d_6$)

δ: 10.2–9.6 (1H, m), 7.62–6.97 (9H, m), 4.30–4.10 (4H, m), 4.00–3.82 (2H, m), 1.23 (3H, t, J=7.1 Hz)

(2) 5.00 g (16.0 mmol) the amine product thus obtained was dissolved in 50 ml of chloroform, treated with 3.46 g (34.0 mmol) of triethylamine with cooling on ice, stirred for 10 minutes, treated dropwise with 2.57 g (17.0 mmol) of ethyl malonyl chloride and then stirred at room temperature overnight. The mixture was made acidic with 2N hydrochloric acid and then extracted, and the chloroform layer was washed with water, concentrated, subjected to column chromatography on silica gel eluting with hexane: ethyl acetate=70:30) to obtain 3.40 g (yield: 55%) of an amide product as a pale yellow oil.

$^1$H-NMR (200 MHz, CDCl$_3$)

δ: 7.40–6.90 (1H, m), 4.65 (1H, s), 4.61 (1H, s), 4.27–4.10 (4H, m), 4.06 (1H, s), 3.98 (1H, s), 3.58 (1H, s), 3.48 (1H, s), 1.35–1.20 (6H, m)

(3) 3.40 g (8.51 mmol) of the amide product thus obtained was dissolved in 30 ml of ethanol, treated with 2.90 ml (8.51 mmol) of a 20% solution of sodium ethoxide in ethanol, and stirred at room temperature for 1 hour. The reaction mixture was concentrated at low temperature and the residue was made acidic with 2N hydrochloric acid and then extracted with ethyl acetate. The ethyl acetate layer was washed with water and concentrated at low temperature, and the residue was treated with ethyl acetate: hexane (1:5) and stirred for 10 minutes, and then the precipitate was collected by filtration and washed with the same solution to obtain 2.34 g (78%) of a pyrrolidin-2-one product as a white powder.

$^1$H-NMR (200 MHz, CDCl$_3$)

δ: 7.40–6.90 (9H, m), 4.57 (2H, s), 4.41 (2H, q, J=7.1Hz), 3.88 (2H, s), 1.41 (3H, t, J=7.1 Hz)

(4) 0.350 g (1.00 mmol) of the pyrrolidin-2-one product thus obtained was dissolved in 10 ml of acetonitrile, treated with 0.5 ml of water and stirred at 90° C. for 30 minutes. The reaction mixture was concentrated, treated with 10 ml of methanol, treated with 0.038 g (1.00 ml) of sodium borohydride in portions at room temperature and stirred for 1 hour. The reaction mixture was concentrated, and the residue was treated with ethyl acetate and saturated aqueous sodium hydrogen carbonate and then extracted. The ethyl acetate layer was washed with water, concentrated, a subjected to column chromatography on silica gel eluting with methanol: chloroform (3:97) to obtain 0.280 g (yield: 99%) of an alcohol product as a colorless oil.

$^1$H-NMR (200 MHz, CDCl$_3$)

δ: 7.40–6.90 (9H, m), 4.57–4.45 (1H, m), 4.45 (2H, s), 3.53 (1H, dd, J=10.7, 5.7 Hz), 3.21 (1H, dd, J=10.7, 2.1 Hz), 2.75 (1H, dd, J=17.4, 6.5 Hz), 2.44 (1H, dd, J=17.4 2.5 Hz), 2.32–2.24 (1H, m)

(5) 0.120 g (0.42 mmol) of the alcohol product thus obtained was dissolved in 10 ml of pyridine, treated with 0.115 g (1.00 mmol) of methanesulfonyl chloride and stirred at 50° C. for 2 hours. The reaction mixture was concentrated, and the residue was made acidic with 2N hydrochloric acid and then extracted with ethyl acetate. The ethyl acetate layer was washed with water and concentrated, and the residue was combine with a mixture of hexane: ethyl acetate (5:1) and stirred for 30 minutes. The precipitate was collected by filtration and washed with the same solution to obtain 0.120 g (yield: 79%) of a mesylate product as a white powder.

$^1$H-NMR (200 MHz, CDCl$_3$)

δ: 7.40–6.95 (9H, m), 5.35–5.25 (1H, m), 4.47 (2H, brs), 3.67 (1H, dd, J=12.0, 5.6 Hz), 3.53 (1H, dd, J=12.0, 2.2 Hz), 3.02 (3H, s), 2.89 (1H, dd, J=17.9, 6.7 Hz) 2.71 (1H, dd, J=17.9, 2.7 Hz)

(6) 0.090 g (0.25 mmol) of themesylate product thus obtained was dissolved in 5 ml of N,N-dimethylf ormamide, treated with 0.085 g (0.75 mmol) of potassium thioacetate and stirred at 70° C. for 1 hour. The reaction mixture was poured into water and extracted with ethyl acetate, and the ethyl acetate layer was washed with water and concentrated to obtain a residue which was subjected to column chromatography on silica gel eluting with hexane: ethyl acetate (60:40) to obtain 0.055 g (yield: 64%) of 4-acethylthio-1-(4-phenoxybenzyl)pyrrolidin-2-one as a white powder.

$^1$H-NMR (200 MHz, CDCl$_3$)

δ: 7.40–6.95 (9H, m), 4.44 (2H, brs), 4.13–3.98 (1H, m), 3.76 (1H, dd, J=10.7, 7.5 Hz), 3.17 (1H, dd, J=10.7, 4.9 Hz), 2.92 (1H, dd, J=17.4, 8.9 Hz), 2.42 (1H, dd, J=17.4, 6.0 Hz), 2.32 (3H, s)

Example 16

4-Benzoylthio-l-(4-phenoxybenzyl)pyrrolidin-2-one 0.100 g (0.28 mmol) of the mesylate product obtained in Example 15, 0.046 g (0.66 mmol) of thiobenzoic acid and 0.092 g (0.66 mmol) of potassium carbonate were dissolved in 10 ml of N,N-dimethylformamide and stirred at 80° C. for 2 hours. The residue was poured into water and extracted with ethyl acetate. The ethyl acetate layer was washed with water and concentrated, and the residue was subjected to column chromatography on silica gel eluting with hexane-:ethyl acetate (70:30) to obtain 0.052 g (yield: 46%) of 4-benzoylthio-1-(4-phenoxybenzyl)pyrrolidin-2-one as a white powder.

$^1$H-NMR (200 MHz, CDCl$_3$)

δ: 7.92–6.90 (14H, m), 4.47 (2H, s), 4.33–4.20 (1H, mn), 3.88 (1H, dd, J=10.7, 7.5 Hz), 3.29 (1H, dd, J=10.7, 4.8 Hz), 3.03 (1H, dd, J=17.4, 9.0 Hz), 2.56 (1H, dd, J=17.4, 5.9 Hz)

Example 17

4-Mercapto-1-(4-phenoxybenzyl)pyrrolidin-2-one 25 mg (0.07 mmol) of 4-acetylthio-1-(4-phenoxybenzyl) pyrrolidin-2-one was dissolved in a mixture of 5 ml of acetic acid and 1 ml of conc. hydrochloric acid, and stirred at 100° C. for 2 hours. The reaction mixture was concentrated, and the residue was treated with ethyl acetate and saturated aqueous sodium hydrogen carbonate and extracted. The ethyl acetate layer was washed with water and concentrated, and the residue was subjected to column chromatography on silica gel eluting with chloroform to obtain 20 mg (yield: 95%) of 4-mercapto-1-(4-phenoxybenzyl)pyrrolidin-2-one as a colorless oil.

$^1$H-NMR (200 MHz, CDCl$_3$)

δ: 7.40–6.93 (9H, m), 4.48 (1H, d, J=14.7 Hz), 4.40 (1H, d, J=14.7 Hz), 3.66 (1H, dd, J=9.8, 7.1 Hz), 3.61–3.47 (1H, m), 3.17 (1H, dd, J=9.8, 4.8 Hz), 2.92 (1H, dd, J=17.1, 8.1 Hz), 2.42 (1H, dd, J=17.1, 6.1 Hz), 1.87 (1H, d, J=6.8 Hz)

Example 18

4-Pivaloyloxymethylthio-1-(4-phenoxybenzyl)pyrrolidin-2-one 80 mg (0.27 mmol) of 4-mercapto-1-(4-phenoxybenzyl)pyrrolidin-2-one obtained in Example 17 was dissolved in 15 ml of chloroform, treated with 11 mg (0.27 mmol) of sodium hydride (60% in oil) and 41 mg (0.27 mmol) of pivaloyloxymethyl chloride, and stirred at room temperature for 1 hour. Water was added slowly, followed by extraction, and the chloroform layer was washed and concentrated, and the residue was subjected to column chromatography on silica gel eluting with hexane: acetate (70:30) to obtain 63 mg (yield: 78%) of 4-pivaloyloxymethylthio-1-(4-phenoxybenzyl)pyrrolidin-2-one as a colorless oil.

$^1$H-NMR (200 MHz, CDCl$_3$)

δ: 7.40–6.93 (1H, m), 4.48 (1H, d, J=14.8 Hz), 4.39 (1H, d, J=14.8 Hz), 4.02–3.90 (1H, m), 3.77 (1H, m),3.77 (1H, dd, J=10.6, 7.4 Hz), 3.13 (1H, dd, J=10.6, 4.6 Hz), 2.93 (1H, dd, J=17.4, 8.9 Hz), 2.43 (1H, dd, J=17.4, 5.8 Hz), 1.20 (9H, s)

Example 19

4,4'-Dithiobis[1-(4-phenoxybenzyl)pyrrolidin-2-one]

30 ml of ethyl acetate and 30 ml of water were added to a separatory funnel, to which 80 mg (0.27 mmol) of 4-mercapto-2-(4-phenoxybenzyl)pyrrolidin-2-one, 68 mg (0.27 mmol) of iodine and 45 mg (0.27 mmol) of potassium iodide were added and shaken at room temperature for 5 minutes. After a partition, the ethyl acetate layer was washed with an aqueous solution of sodium hydrogen sulfite followed by water, and then concentrated into dryness. The residue was diluted with hexane and stirred, and the precipitate was collected by filtration t obtain 63 mg (yield: 78%) of 4,4'-dithiobis[1-(4-phenoxybenzyl)piperidin-2-one] as a white powder.

$^1$H-NMR (200 MHz, CDCl$_3$)

δ: 7.40–6.90 (18H, m), 4.50 (1H, d, J=14.7 Hz), 4.48 (1H, d, J=14.7 Hz), 4.38 (1H, d, J=14.7 Hz), 4.35 (1H d, J=14.7 Hz), 3.65–3.53 (2H, m), 3.53–3.37 (2H, m), 3.31–3.22 (2H, m), 2.85 (1H, dd, J=8.0, 2.9 Hz), 2.77 (1H, dd, J=7.8, 3.1 Hz), 2.49 (2H, dd, J=17.6, 4.4 Hz)

Example 20

Trans-4-acetylthio-5-hydroxymethyl-1-(4-phenoxybenzyl)pyrrolidin-2-one (1) 13.5 ml (185 mmol) of thionyl chloride was added dropwise to 52 ml of methanol with ice-cooling over 30 minutes, 10.0 g (51.2 mmol) of O-benzyl-D,L-serine was added and the mixture was stirred at room temperature for 15 hours. The reaction mixture was concentrated, treated with toluene, concentrated, treated with methanol, concentrated, treated with ether to precipitate, whereby obtaining 12.0 g (yield: 95%) of O-benzyl-D,L-serine methyl ester hydrochloride as a white powder.

$^1$H-NMR (300 MHz, DMSO-d$_6$)

δ: 8.71 (3H, s), 7.35 (5H, m), 4.58 (1H, d, J=12.1 Hz), 4.49 (1H, d, J=12.1 Hz), 4.35 (1H, t, J=3.4 Hz), 3.85 (2H, d, J=3.4 Hz), 3.74 (3H, s)

(2) 9.50 g (38.7 mmol) of O-benzyl-D,L-serine methyl ester hydrochloride was dissolved in 160 ml of methanol, treated with 8.09 ml (58.1 mmol) of triethylamine and 6.78 ml (38.7 mmol) of 4-phenoxybenzaldehyde, and then stirred at room temperature for 20 hours.1.46 g (38.7 mmol) of sodium borohydride was added and the mixture was stirred at room temperature for 2.5 hours. The reaction mixture was concentrated, treated with ethyl acetate, washed with water and saturated brine, and then dried over anhydrous sodium sulfate. After concentrating followed by column chromatography on silica gel eluting with hexane: ethyl acetate (80:20–60:40) followed by concentrating into dryness, 13.0 g (yield: 86%) of N—(4-phenoxybenzyl)—O-benzyl-D,L-serine methyl ester as a colorless oil.

$^1$H-NMR (300 MHz, CDCl$_3$)

δ: 7.30 (9H, m), 7.08 (1H, m), 6.98 (4H, m), 4.54 (1H, d, J=12.4 Hz), 4.50 (1H, d, J=12.4 Hz), 3.86 (1H, d, J=12.8 Hz), 3.73 (3H, s), 3.70 (3H, m), 3.51 (1H, t, J=4.9 Hz)

(3) 13.0 g (33.2 mmol) of N—(4-phenoxybenzyl)—O-benzyl-D,L-serine methyl ester was dissolved in 130 ml of chloroform, treated with 5.55 ml (39.8 mmol) of triethylamine and 5.10 ml (39.8 mmol) of ethyl malonyl chloride with cooling on ice, and stirred at room temperature for 1 hour. The reaction mixture was concentrated, treated with ethyl acetate, washed with water and saturated brine and then dried over anhydrous sodium sulfate. After concentrating followed by column chromatography on silica gel eluting with hexane: ethyl acetate (70:30–60:40) followed by concentrating into dryness, 14.3 g (yield: 85%) of N—(ethylmalonyl)—N—(4-phenoxybenzyl)—O-benzyl-D,L-serine methyl ester as a colorless oil.

$^1$H-NMR (300 MHz, CDCl$_3$)

δ: 7.28 (9H, m), 7.12 (1H, m), 6.98 (4H, m), 4.72 (3H, m), 4.41 (2H, s), 4.18 (2H, q, J=7.2 Hz), 3.97 (2H, m), 3.71 (3H, s), 3.47 (1H, d, J=15.3 Hz), 3.39 (1H, d, J=15.3 Hz), 1.25 (3H, t, J=7.2 Hz)

(4) 2.40 g (4.75 mmol) of N—(ethylmalonyl)—N—(4-phenoxybenzyl)—O—benzyl-D,L-serine methyl ester was dissolved in 30.0 ml of methanol, treated with 240 mg of 10% Palladium on activated charcoal and 30 ml of conc. hydrochloric acid, and stirred under hydrogen atmosphere at room temperature for 2 hours. After filtrating the catalyst off followed by concentrating into dryness, 1.90 g (yield: 96%) of N—(ethylmalonyl)—N—(4-phenoxybenzyl)-D,L-serine methyl ester as a colorless oil.

$^1$H-NMR (300 MHz, CDCl$_3$)

δ: 7.33 (4H, m), 7.13 (1H, m), 7.01 (4H, m), 4.64 (1H, d, J=16.8 Hz), 4.58 (1H, d, J=16.8 Hz), 4.21 (2H, q, J=7.2 Hz), 4.13 (2H, m), 3.93 (1H, m), 3.72 (3H, s), 3.56 (1H, d, J=15.8 Hz), 3.45 (1H, d, J=15.8 Hz), 1.29 (3H, t, J=7.2 Hz)

(5) 1.90 g (4.57 mmol) of N—(ethylmalonyl)—N—(4-phenoxybenzyl)-D,L-serine methyl ester was dissolved in 20.0 ml of ethanol, treated with 1.79 ml (4.57 mmol) of a 20% solution of sodium ethoxide in ethanol and stirred at room temperature for 1 hour. The reaction mixture was concentrated, treated with ethyl acetate, washed with 10% aqueous citric acid, water and then with saturated brine, and dried over anhydrous sodium sulfate. The reaction mixture was concentrated and dissolved in 30.0 ml of methanol, 159 mg (4.20 mmol) of sodium borohydride was added with stirring, and then the mixture was stirred further for 1 hour at room temperature. After adding 1N hydrochloric acid followed by extracting twice with ethyl acetate, the ethyl acetate layer was washed with water and saturated brine and dried over anhydrous sodium sulfate. After concentrating followed by column chromatography on silica gel eluting with chloroform: methanol (95:5) followed by concentrating into dryness, 520 mg (yield 36%) of cis-4-hydroxy-5-hydroxymethyl-1-(4-phenoxybenzyl)pyrrolidin-2-one as a white powder.

$^1$H-NMR (300 MHz, CDCl$_3$)

δ: 7.34 (2H, m), 7.19 (2H, d, J=8.3 Hz), 7.11 (1H, m), 6.97 (4H, m), 4.97 (1H, d, J=15.1 Hz), 4.61 (1H, m), 4.07 (1H, d, J=15.1 Hz), 3.92 (2H, m), 3.55 (1H, m), 3.49 (1H, m), 3.06 (1H, s), 2.76 (1H, dd, J=17.2, 7.5 Hz), 2.54 (1H, dd, J=17.2, 4.9 Hz)

(6) 500 mg (1.60 mmol) of cis-4-hydroxy-5-hydroxymethyl-1-(4-phenoxybenzyl)pyrrolidin-2-one was dissolved in 15.0 ml of chloroform, treated with 491 mg (1.76 mmol) of trityl chloride, 401 µl (2.88 mmol) of triethylamine and 7.82 mg (0.064 mmol) of 4-dimethylaminopyridine, and stirred at room temperature for 9 hours. The reaction mixture was concentrated, treated with ethyl acetate, washed with water and saturated brine, and dried over anhydrous sodium sulfate. After concentrating followed by column chromatography on silica gel eluting with hexane: ethyl acetate (70:30–60:40) followed by concentrating into dryness, 700 mg (yield: 79%) of cis-4-hydroxy-1-(4-phenoxybenzyl)-5-trityloxymethylpyrrolidin-2-one as a colorless oil.

$^1$H-NMR (300 MHz, CDCl$_3$)

δ: 7.33 (19H, m), 7.11 (1H, m), 6.98 (2H, m), 6.87 (2H, d, J=8.3 Hz), 4.94 (1H, d, J=14.7 Hz), 4.55 (1H, m), 3.58 (2H, m), 3.47 (1H, dd, J=10.0, 3.4 Hz), 3.40 (1H, dd, J=10.0, 5.7 Hz), 2.77 (1H, dd, J=17.3, 7.9 Hz), 2.63 (1H, dd, J=17.3, 5.7 Hz), 2.48 (1H, d, J=6.8 Hz)

(7) 350 mg (0.630 mmol) of cis-4-hydroxy-1-(4-phenoxybenzyl)-5-trityloxymethylpyrrolidin-2-one was dissolved in 14.0 ml of chloroform, treated with 439 µl (3.15 mmol) of triethylamine and 244 µl (3.15 mmol) of methanesulfonyl chloride and stirred at room temperature for 1 hour. The reaction mixture was concentrated, treated with ethyl acetate, washed with water and saturated brine, and then dried over anhydrous sodium sulfate. After concentrating followed by column chromatography on silica gel eluting with hexane: ethyl acetate (40:60–30:70) followed by concentrating into dryness, 400 mg (yield: 100%) of cis-4-methanesulfonyloxy-1-(4-phenoxybenzyl)-5-trityloxymethylpyrrolidin-2-one was obtained as a colorless oil.

$^1$H-NMR (300 MHz, CDCl$_3$)

δ: 7.41 (6H, m), 7.31 (11H, m), 7.12 (1H, m), 6.99 (2H, m), 6.88 (4H, m), 5.29 (1H, m), 4.95 (1H, d, J=15.1 Hz), 3.69 (1H, m), 3.52 (1H, dd, J=10.6, 2.6 Hz), 3.39 (1H, dd, J=10.6, 4.1 Hz), 3.31 (1H, d, J=15.1 Hz), 3.11 (1H, dd, J=16.6, 7.2 Hz), 2.92 (3H, s), 2.85 (1H, dd, J=16.6, 7.9 Hz)

(8) 400 mg (0.630 mmol) of cis-4-methanesulfonyloxy-1-(4-phenoxybenzyl)-5-trityloxymethylpyrrolidin-2-one was dissolved in 2.00 ml of ether, treated with 4.00 ml of formic acid, and stirred at room temperature for 1 hour. After concentrating the reaction mixture followed by column chromatography on silica gel eluting with hexane: ethyl acetate (10:90–0:100) followed by concentrating into dryness, 121 mg (yield: 49%) of cis-5-hydroxymethyl-4-methanesulfonyloxy-1-(4-phenoxybenzyl)pyrrolidin-2-one as a colorless oil.

$^1$H-NMR (300 MHz, CDCl$_3$)

δ: 7.35 (2H, m), 7.21 (2H, d, J=8.3 Hz), 7.12 (1H, m), 7.01 (2H, m), 6.96 (2H, d, J=8.7 Hz), 5.35 (1H, m), 4.90 (1H, d, J=15.1 Hz), 4.13 (1H, d, J=15.1 Hz), 3.89 (2H, m), 3.77 (1H, m), 3.10 (3H, s), 2.84 (2H, m), 2.04 (1H, s)

(9) 121 mg (0309 mmol) of cis-5-hydroxymethyl-4-methanesulfonyloxy-1-(4-phenoxybenzyl)pyrrolidin-2-one was dissolved in 5 ml of N,N-dimethylformamide, treated with 70.6 mg (0.618 mmol) of potassium thioacetate, stirred at 50° C. for 1.5 hours, treated further with 141 mg (1.24 mmol) of potassium thioacetate, and stirred at 70° C. for 3 hours. The reaction mixture was concentrated, treated with ethyl acetate, washed with water and saturated brine, and then dried over anhydrous sodium sulfate. After concentrating followed by column chromatography on silica gel eluting with hexane: ethyl acetate (10:90) followed by concentrating into dryness, 17.1 mg (yield: 15%) of trans-4-acetylthio-5-hydroxymethyl-1-(4-phenoxybenzyl)pyrrolidin-2-one as a colorless oil.

$^1$H-NMR (300 MHz, CDCl$_3$)

δ: 7.34 (2H, m), 7.21 (2H, d, J=8.3 Hz), 7.11 (1H, m), 6.98 (4H, m), 4.90 (1H, d, J=15.3 Hz), 4.11 (1H, d, J=15.3 Hz), 4.03 (1H, m), 3.80 (1H, dd, J=12.3, 3.2 Hz), 3.71 (1H, dd, J=12.3, 2.5 Hz), 3.38 (1H, m), 3.10 (1H, dd, J=17.3, 9.0 Hz), 2.37 (1H, dd, J=17.3, 4.1 Hz), 2.30 (3H, s)

Example 21

(S)-4-Acetylthio-1-(4-phenoxybenzyl)pyrrolidin-2-one (1) 700 mg (6.9 mmol, DAISO) of (R)-4-hydroxy-2-pyrrolidone and 4.50 g (20.8 mmol) of 4-phenoxybenzyl chloride were dissolved in 6.0 ml of dimethylsulfoxide, treated with 1.20 g of powdered potassium hydroxide with cooling on ice and then stirred at room temperature for 14 hours. After adding ethyl acetate followed by washing 6 times with water and then with saturated brine, the ethyl acetate layer was dried over anhydrous sodium sulfate and concentrated under reduced pressure, and the residue was subjected to column chromatography on silica gel eluting with ethyl acetate: methanol (100:0–99:1) to obtain 365 mg (yield: 19%) of (R)-4-hydroxy-1-(4-phenoxybenzyl)pyrrolidin-2-one as a light brown oil.

$^1$H-NMR (300 MHz, CDCl$_3$)

δ: 7.36–6.95 (9H, m), 4.51–4.48 (1H, m), 4.45 (2H, s), 3.53 (1H, dd, J=10.8, 5.6 Hz), 3.21 (1H, dd, J=10.8, 1.9 Hz), 2.75 (1H, dd, J=17.3, 6.5 Hz), 2.44 (1H, dd, J=17.3, 2.2 Hz), 2.07 (1H, brs).

(2) To a mixture of 300 mg (1.1 mmol) of (R)-4-hydroxy-1-(4-phenoxybenzyl)pyrrolidin-2-one, 207 µl (1.5 mmol) of triethylamine and 1.5 ml of chloroform, a mixture of 115 µl (1.5 mmol) of methanesulfonyl chloride and 1.5 ml of chloroform was added dropwise with cooling on ice, and the mixture was stirred for 30 minutes with cooling on ice. The reaction mixture was concentrated under reduced pressure and the residue obtained was treated with ethyl acetate and washed 6 times with water followed by saturated brine, and then the ethyl acetate layer was dried over anhydrous sodium sulfate and concentrated under reduced pressure to obtain 372 mg (yield: 97%) of (R)-4-methanesulfonyloxy-1-(4-phenoxybenzyl)pyrrolidin-2-one as a brown oil.

$^1$H-NMR (300 MHz, CDCl$_3$)

δ: 7.37–6.96 (9H, m), 5.32–5.27 (1H, m), 4.50 (1H, d, J=14.7 Hz), 4.44 (1H, d, J=14.7 Hz), 3.66 (1H, dd, J=11.9, 5.7 Hz), 3.52 (1H, dd, J=11.9, 2.0 Hz), 3.02 (3H, s), 2.87 (1H, dd, J=17.9, 6.8 Hz), 2.71 (1H, dd, J=17.9, 2.5 Hz).

(3) To a solution of 89 µl (1.2 mmol) of thioacetic acid in 1.0 ml of methanol, 369 mg (1.1 mmol) of cesium carbonate was added at room temperature, and the mixture was concentrated under reduced pressure, and the residue was treated with 2.0 ml of N,N-dimethylformamide to obtain a solution of cesium thioacetate. This solution was added to a mixture of 372 mg (1.0 mmol) of (R)-4-methanesulfonyloxy-1-(4-phenoxybenzyl)pyrrolidin-2-one obtained above and 3.0 ml of N,N-dimethylformamide, and the mixture was stirred at room temperature for 6 hours, and then treated with 15 μl (0.2 mmol) of thioacetic acid and 67 mg (0.2 mmol) of cesium carbonate. After stirring at room temperature for 15 hours followed by adding ethyl acetate followed by washing 6 times with water and then with saturated brine, the ethyl acetate layer was dried over anhydrous sodium sulfate, concentrated under reduced pressure to obtain a residue which is then subjected to column chromatography on silica gel eluding with ethyl acetate: hexane (18:82) to obtain a crude product which was then purified by preparative thin layer silica gel chromatography (eluent: ethyl acetate: hexane (1:1) solution) to obtain 80.3 mg (yield: 23%) of (S)-4-acethylthio-1-(4-phenoxybenzyl) pyrrolidin-2-one as a colorless oil.

$^1$H-NMR (300 MHz, CDCl$_3$)

δ: 7.36–6.94 (9H, m), 4.45 (1H, d, J=14.7 Hz), 4.39 (1H, d, J=14.7 Hz), 4.07–4.02 (1H, m), 3.74 (1H, dd, J=10.6, 7.5 Hz), 3.16 (1H, dd, J=10.6, 4.9 Hz), 2.90 (1H, dd, J=17.4, 8.9 Hz), 2.41 (1H, dd, J=17.4, 6.0 Hz), 2.31 (3H, s).

Example 22

(S)-4-Mercapto-1-(4-phenoxybenzyl)pyrrolidin-2-one

A mixture of 8 mg (0.02 mmol) of (S)-4-acethylthio-1-(4-phenoxybenzyl)pyrrolidin-2-one obtained in Example 21, 0.1 ml of conc. hydrochloric acid and 0.1 ml of acetic acid was stirred at 100° C. for 20 minutes. The reaction mixture was treated with ethyl acetate, washed 5 times with water and then with saturated brine, and the ethyl acetate layer was dried over anhydrous sodium sulfate and concentrated under reduced pressure to obtain 6.9 mg (yield: 99%) of (S)-4-mercapto-1-(4-phenoxybenzyl)pyrrolidin-2-one as a colorless oil.

$^1$H-NMR (300 MHz, CDCl$_3$)

δ: 7.37–6.95 (9H, m), 4.47 (1H, d, J=14.6 Hz), 4.40 (1H, d, J=14.7 Hz), 3.65 (1H, dd, J=10.0, 7.2 Hz), 3.60–3.48 (1H, m), 3.16 (1H, dd, J=10.0, 5.1 Hz), 2.91 (1H, dd, J=17.1, 8.1 Hz), 2.41 (1H, dd, J=17.1, 6.2 Hz), 1.87 (1H, d, J=6.7 Hz).

Example 23

(4S, 4'S)-4,4'-Dithiobis[1-(4-phenoxybenzyl)pyrrolidin-2-one]

A mixture of 4 mg (0.01 mmol) of (S)-4-acethylthio-1-(4-phenoxybenzyl)pyrrolidin-2-one obtained in Example 21, 2 drops of conc. hydrochloric acid and 2 drops of acetic acid was stirred at 100° C. for 5 minutes. The reaction mixture was treated with ethyl acetate, washed 2 times with water, 0.25 M potassium iodide-iodine solution, a 5% aqueous solution of sodium sulfite and then with saturated brine, and the ethyl acetate layer was dried over anhydrous sodium sulfate and concentrated under reduced pressure to obtain 2 mg (yield: 30%) of (4S, 4'S)-4,4'-dithiobis[1-(4-phenoxybenzyl)pyrrolidin-2-one] as a pale yellow powder.

$^1$H-NMR (300 MHz, CDCl$_3$)

δ: 7.36–6.94 (18H, m), 4.47 (2H, d, J=14.7 Hz), 4.38 (2H, d, J=14.7 Hz), 3.61 (2H, dd, J=10.7, 6.9 Hz), 3.53–3.47 (2H, m), 3.27 (2H, dd, J=10.7, 3.5 Hz), 2.82 (2H, dd, J=17.5, 8.2 Hz), 2.49 (2H, dd, J=17.5, 4.4 Hz).

Example 24

(R)-4-Acetylthio-1-(4-phenoxybenzyl)pyrrolidin-2-one

By a method similar to that in Example 21 and starting from (S)-4-hydroxy-2-pyrrolidone (DAISO), (R)-4-acetylthio-1-(4-phenoxybenzyl)pyrrolidin-2-one was obtained as a pale yellow oil.

(S)-4-Hydroxy-1-(4-phenoxybenzyl)pyrrolidin-2-one (yield:21%)

$^1$H-NMR (300 MHz, CDCl$_3$)

δ: 7.37–6.94 (9H, m), 4.54–4.48 (1H, m), 4.48 (1H, d, J=14.6 Hz), 4.42 (1H, d, J=14.6 Hz), 3.53 (1H, dd, J=10.8, 6.5 Hz), 3.21 (1H, dd, J=10.8, 2.1 Hz), 2.75 (1H, dd, J=17.3, 6.5 Hz), 2.44 (1H, d, J=17.3, 2.4 Hz), 2.05 (1H, brs).

(S)-4-Methanesulfonyloxy-1-(4-phenoxybenzyl)pyrrolidin-2-one (yield:98%)

$^1$H-NMR (300 MHz, CDCl$_3$)

δ: 7.37–6.96 (9H, m), 5.32–5.27 (1H, m), 4.49 (1H, d, J=14.7 Hz), 4.43 (1H, d, J=14.7 Hz), 3.66 (1H, dd, J=11.9, 5.7 Hz), 3.52 (1H, dd, J=11.9, 2.0 Hz), 3.02 (3H, s), 2.88 (1H, dd, J=17.9, 6.8 Hz), 2.71 (1H, dd, J=17.9, 2.5 Hz).

(R)-4-Acetylthio-1-(4-phenoxybenzyl)pyrrolidin-2-one (yield:44%)

$^1$H-NMR (300 MHz, CDCl$_3$)

δ: 7.37–6.95 (9H, m), 4.46 (1H, d, J=14.6 Hz), 4.40 (1H, d, J=14.6 Hz), 4.11–4.01 (1H, m), 3.75 (1H, dd, J=10.6, 7.5 Hz), 3.17 (1H, dd, J=10.6, 4.9 Hz), 2.91 (1H, dd, J=17.4, 9.0 Hz), 2.42 (1H, dd, J=17.4, 6.0 Hz), 2.32 (3H, s).

Example 25

(R)-4-Mercapto-1-(4-phenoxybenzyl)pyrrolidin-2-one

By a method similar to that in Example 22 and starting from 10 mg (0.03 mmol) of (R)-4-acetylthio-1-(4-phenoxybenzyl)pyrrolidin-2-one obtained in Example 24, 8.1 mg (yield: 92%) of (R)-4-mercapto-1-(4-phenoxybenzyl)pyrrolidin-2-one was obtained as a colorless oil.

$^1$H-NMR (300 MHz, CDCl$_3$)

δ: 7.37–6.95 (9H, m), 4.47 (1H, d, J=14.7 Hz), 4.40 (1H, d, J=14.7 Hz), 3.65 (1H, dd, J=10.0, 7.2 Hz), 3.60–3.48 (1H, m), 3.16 (1H, dd, J=10.0, 5.1 Hz), 2.91 (1H, dd, J=17.1, 8.1 Hz), 2.42 (1H, dd, J=17.0, 6.2 Hz), 1.87 (1H, d, J=6.7 Hz).

Example 26

(4H, 4'R)-4,4'-Dithiobis[1-(4-phenoxybenzyl)pyrrolidin-2–one]

By a method similar to that in Example 23 and starting from 10 mg (0.03 mmol) of (R)-4-acetylthio-1-(4-phenoxybenzyl)pyrrolidin-2-one obtained in Example 24, 6.9 mg (yield: 79%) of (4H, 4'R)-4,4'-dithiobis[1-(4-phenoxybenzyl)pyrrolidin-2–one] as a white powder.

$^1$H-NMR (300 MHz, CDCl$_3$)

δ: 7.36–6.94 (18H, m), 4.46 (2H, d, J=14.7 Hz), 4.42 (2H, d, J=14.7 Hz), 3.60 (2H, dd, J=10.7, 6.9 Hz), 3.52–3.45 (2H, m), 3.27 (2H, dd, J=10.7, 3.5 Hz), 2.81 (2H, dd, J=17.5, 8.2 Hz), 2.48 (2H, dd, J=17.5, 4.4 Hz).

Example 27

3-Acetylthio-1-(4-phenoxybenzyl)pyrrolidin-2-one (1) A mixture of 3.20 g (16.2 mmol) of 4-phenoxybenzaldehyde, 6.00 g (17.0 mmol) of β-alanine benzyl ester p-toluenesulfonate, 2.40 ml (17.1 mmol) of triethylamine and 150.0 ml of methanol was stirred at room temperature for 22 hours, and then treated with 0.517 g (13.7 mmol) of sodium borohydride in portions. After stirring at room temperature for 10 minutes and concentrating under reduced pressure, the residue obtained was treated with ethyl acetate, washed 3 times with saturated aqueous sodium hydrogen carbonate, once with water and then with saturated brine, and the ethyl acetate layer was dried over anhydrous sodium sulfate and concentrated under reduced pressure to obtain 5.70 g (yield: 98%) of an amine product as a colorless oil.

$^1$H-NMR (300 MHz, CDCl$_3$)

δ: 7.35–6.93 (14H, m), 5.13 (2H, s), 3.76 (2H, s), 2.92 (2H, t, J=6.3 Hz), 2.59 (2H, t, J=6.4 Hz)

(2) To a mixture of 5.70 g (15.9 mmol) of the amine product thus obtained, 4.50 g (16.7 mmol) of benzyl oxalate and 150 ml of tetrahydrofuran, 667 mg (16.7 mmol) of sodium hydride (60% in oil) which had previously been washed three times with hexane was added, and the mixture was heated at 95° C. for 2 hours with stirring, cooled and concentrated under reduced pressure to obtain a residue which was then treated with ethyl acetate and washed three times with 6N hydrochloric acid and 6N hydrochloric acid-saturated brine, and the ethyl acetate layer was dried over anhydrous sodium sulfate and concentrated under reduced pressure to obtain a residue which was then treated with ethyl acetate, and the precipitate formed was collected by filtration to obtain 3.10 g (yield: 47%) of a benzyl ester product as a white powder.

$^1$H-NMR (300 MHz, CDCl$_3$)

δ: 8.80 (1H, brs), 7.38–6.94 (14H, m), 5.26 (2H, s), 4.63 (2H, s), 3.89 (2H, s).

(3) A mixture of 3.50 g (8.40 mmol) of the benzyl ester product thus-obtained, 1.80 g of 10% palladium on activated charcoal, 100 ml of ethyl acetate and 100 ml of ethanol was stirred under hydrogen atmosphere at room temperature for 3 hours. After filtering insolubles off and concentrating under reduced pressure, the residue obtained was treated with ethyl acetate, washed twice with saturated aqueous sodium hydrogen carbonate and saturated brine, and the ethyl acetate layer was dried over anhydrous sodium sulfate and concentrate under reduced pressure to obtain a residue which was then treated with ethyl acetate, and then the precipitate formed was collected by filtration to obtain 1.70 g (yield: 72%) of 3-hydroxy-1-(4-phenoxybenzyl)pyrrolidin-2-one as a white powder.

$^1$H-NMR (300 MHz, DMSO-d$_6$)

δ: 7.41–6.96 (9H, m), 5.56 (1H, d, J=5.6 Hz), 4.37 (1H, d, J=15.2 Hz), 4.31 (1H, d, J=5.2 Hz), 4.19–4.12 (1H, m), 3.22–3.06 (2H, m), 2.31–2.21 (1H, m), 1.76–1.63 (1H, m).

(4) To a mixture of 50 mg of 3-hydroxy-1-(4-phenoxybenzyl)pyrrolidin-2-one, 15 μl (0.2 mmol) of methanesulfonyl chloride and 1.0 ml of chloroform, 54 μl (0.2 mmol) of triethylamine was added and the mixture was stirred at room temperature for 5 minutes and concentrated under reduced pressure, and the residue obtained was treated with ethyl acetate and washed three times with water and then with saturated brine, and the ethyl acetate layer was dried over anhydrous sodium sulfate and concentrated under reduced pressure, and the residue obtained was purified by preparative thin layer silica gel chromatography (eluent: ethyl acetate: hexane (33:67)) to obtain 52 mg (yield: 81%) of 3-methanesulfonyl-1-(4-phenoxybenzyl)pyrrolidin-2-one as a colorless oil.

$^1$H-NMR (300 MHz, CDCl$_3$)

δ: 7.38–6.96 (9H, m), 5.23 (1H, t, J=7.8 Hz), 4.47 (1H, d, J=14.6 Hz), 4.41 (1H, d, J=14.5 Hz), 3.41–3.21 (2H, m), 3.31 (3H, s), 2.61–2.50 (1H, m), 2.30–2.17 (1H, m).

(5) A mixture of 52 mg (0.1 mmol) of 3-methanesulfonyl-1-(4-phenoxybenzyl)pyrrolidin-2-one, 20 mg (0.2 mmol) of potassium thioacetate and 1.0 ml of N,N-dimethylformamide was stirred at room temperature for 12 hours and concentrated under reduced pressure, and the residue obtained was treated with ethyl acetate, and washed three times with water and then with saturated brine, and the ethyl acetate layer was dried over anhydrous sodium sulfate and concentrated under reduced pressure to obtain 41 mg (yield: 84%) of 3-acetylthio-1-(4-phenoxybenzyl)pyrrolidin-2-one as a colorless oil.

$^1$H-NMR (300 MHz, CDCl$_3$)

δ: 7.37–6.95 (9H, m), 4.50 (1H, d, J=14.6 Hz), 4.41 (1H, d, J=14.6 Hz), 4.25 (1H, t, J=8.6 Hz), 3.35–3.23 (2H, m), 2.65–2.54 (1H, m), 2.39 (3H, s), 2.07–1.94 (1H, m).

Example 28

3-Benzoylthio-1-(4-phenoxybenzyl)pyrrolidin-2-one

To a solution of 64 μl (0.5 mmol) of thiobenzoic acid in 1.0 ml of methanol, 24 mg (0.2 mmol) of cesium carbonate was added and the solvent was distilled off under reduced pressure to obtain cesium thiobenzoate. This salt was added to a mixture of 163 mg (0.452 mmol) of 3-methanesulfonyloxy-1-(4-phenoxybenzyl)pyrrolidin-2-one obtained in Example 27 and 2.0 ml of N,N-dimethylformamide, and the mixture was stirred at room temperature for 3 days, and then 64 μl (0.5 mmol) of thiobenzoic acid and 24 mg (0.2 mmol) of cesium carbonate were added. After stirring at room temperature further for 3 hours, 64 μl (0.5 mmol) of thiobenzoic acid and 24 mg (0.2 mmol) of cesium carbonate were added, and then ethyl acetate was added, and the mixture was washed twice with saturated aqueous sodium hydrogen carbonate, water and then saturated brine, and the ethyl acetate layer was dried over anhydrous sodium sulfate and concentrated under reduced pressure to obtain a residue which was then purified by preparative thin layer silica gel chromatography (eluent: ethyl acetate: hexane (1:1)) to obtain 133 mg (yield: 73%) of 3-benzoylthio-1-(4-phenoxybenzyl)pyrrolidin-2-one as a colorless oil.

$^1$H-NMR (300 MHz, CDCl$_3$)

δ: 7.98–7.95 (2H, m), 7.59–6.97 (12H, m), 4.54 (1H, d, J=14.8 Hz), 4.47 (1H, t, J=8.3 Hz), 4.46 (1H, d, J=14.8 Hz), 3.42–3.30 (2H, m), 2.78–2.65 (1H, m), 2.17–2.05 (1H, m)

Example 29

3-Mercapto-1-(4-phenoxybenzyl)pyrrolidin-2-one

A mixture of 41.2 mg (0.1 mmol) of 3-acethylthio-1-(4-phenoxybenzyl)pyrrolidin-2-one obtained in Example 27, 0.5 ml of conc. hydrochloric acid and 0.5 ml of acetic acid was stirred at 100° C. for 8 minutes, and cooled and concentrated under reduced pressure, and the residue obtained was treated with ethyl acetate, washed 3 times with water and then with saturated brine, and the ethyl acetate layer was dried over anhydrous sodium sulfate and concentrated under reduced pressure to obtain 35.6 mg (yield: 98%) of 3-mercapto-1-(4-phenoxybenzyl)pyrrolidin-2-one as a colorless oil.

¹H-NMR (300 MHz, CDCl$_3$)

δ: 7.37–6.95 (9H, m), 4.48 (1H, d, J=14.6 Hz), 4.40 (1H, d, J=14.6 Hz), 3.72–3.66 (1H, m), 3.40–3.19 (2H, m), 2.52–2.39 (1H, m), 2.32 (1H, d, J=4.3 Hz), 1.96–1.85 (1H, m).

Example 30

4-Acetylthio-1-(4-(4'-fluorophenoxy)benzyl)pyrrolidin-2-one (1) 10.0 g (83.9 mmol) of 4-amino-3-hydroxybutyric acid was dissolved in 400 ml of xylene, and treated with 124 ml (587 mmol) of hexamethyldisilazane and 1 drop of trimethylsilyl chloride and then heated under reflux for 16.5 hours. The reaction mixture was concentrated, and the residue was washed with diisopropyl ether to obtain 12.6 g (yield: 87%) of 4-trimethylsilyloxypyrrolidin-2-one as a tan powder.

¹H-NMR (300 MHz, CDCl$_3$)

δ: 6.62 (1H, brs), 4.52 (1H, brs), 3.57 (1H, brd), 3.23 (1H, brd), 2.52 (1H, m), 2.25 (1H, m), 0.11 (94 brs)

(2) 5.0 g (40.3 mmol) of 4-fluorobenzaldehyde, 4.5 g (40.3 mmol) of 4-fluorophenol and 5.6 g (40.3 mmol) of potassium carbonate were dissolved in 100 ml of N,N-dimethylformamide, and stirred at 120" C. for 14.5 hours. A cold water was added to the reaction mixture, which was then extracted twice with ethyl acetate, and the organic layer obtained was washed with water and saturated brine, and then dried over anhydrous sodium sulfate. After concentrating under reduced pressure followed by column chromatography on silica gel, the fraction eluted with hexane: ethyl acetate (97:3) was concentrated under reduced pressure and the residue was washed with hexane to obtain 7.7 g (yield: 88%) of 4-(4'-fluorophenoxy)benzaldehyde as a white powder.

¹H-NMR (300 MHz, CDCl$_3$)

δ: 9.93 (1H, s), 7.85 (2H, d, J=8.8 Hz), 7.09 (2H, d, J=7.9 Hz), 7.05 (2H, d, J=7.9 Hz), 7.03 (2H, d, J=8.8 Hz)

(3) 2.0 g (9.3 mmol) of 4-(4'-fluorophenoxy)benzaldehyde was dissolved in 40 ml of methanol, treated slowly with 422 mg (11.2 mmol) of sodium borohydride and then stirred at room temperature for 2 hours. The reaction mixture was made acidic with a dilute hydrochloric acid, concentrated under reduced pressure and extracted twice with ethyl acetate, and the organic layer obtained was washed with water and saturated brine, and then dried over anhydrous sodium sulfate. After concentrating under reduced pressure, the residue was washed with hexane to obtain 1.7 g (yield: 85%) of 4-(41-fluorophenoxy)benzylalcohol as a white powder.

¹H-NMR (300 MHz, CDCl$_3$)

δ: 7.33 (2H, d, J=8.7 Hz), 7.01 (2H, d, J=10.3 Hz), 6.99 (2H, d, J=8.7 Hz), 6.96 (2H, d, J=10.3 Hz), 4.67 (2H, d, J=5.6 Hz), 1.64 (1H, t, J=5.6 Hz)

(4) 1.7 g (7.9 mmol) of 4-(4'-fluorophenoxy)benzylalcohol was dissolved in chloroform and stirred on an ice bath. 639 μl (7.9 mmol) of pyridine and 632 μl (8.7 mmol) of thionyl chloride were added slowly, and the mixture was stirred on an ice bath for 0.5 hours and then at room temperature for 2 hours. The reaction mixture was concentrated under reduced pressure, treated with water and extracted twice with ethyl acetate, and then the organic layer obtained was washed with water and saturated brine, and dried over anhydrous sodium sulfate. After concentrating under reducer pressure, 1.7 g (yield: 91%) of 4-(4'-fluorophenoxy)benzyl chloride was obtained as a colorless oil.

¹H-NMR (300 MHz, CDCl$_3$)

δ: 7.33 (21H, d, J=8.6 Hz), 7.01 (2H, d, J=7.6 Hz), 6.99 (2H d, J=7.6 Hz), 6.93 (2H, d, J=8.6 Hz), 4.56 (2H, s)

(5) 1.25 g (7.2 mmol) of 4-trimethylsilyloxypyrrolidin-2-one and 1.70 g (7.2 mmol) of 4-(4'-fluorophenoxy)benzyl chloride were dissolved in 20.0 ml of dimethyl sulfoxide, and 475 mg (7.2 mmol) of pulverized potassium hydroxide and a catalytic amount of potassium iodide were added, and the mixture was stirred at room temperature for 5.5 hours. The reaction mixture was treated with water and extracted twice with ethyl acetate, and the organic layer obtained was washed 4 times with water and then with saturated brine, and dried over anhydrous sodium sulfate. After concentrating under reduced pressure followed by column chromatography on silica gel eluting with chloroform: methanol (92:8), 914 mg (yield: 42%) of 4-hydroxy-1-(4-(4-fluorophenoxy)benzyl)pyrrolidin-2-one was obtained as a tan powder.

¹H-NMR (300 MHz, CDCl$_3$)

δ:7.20 (2H, d, J=8.6 Hz), 7.01 (2H, d, J=10.6 Hz), 6.99 (2H, d, J=10.6 Hz), 6.92 (2H, d, J=8.6 Hz), 4.91 (141 m), 4.49 (1H, d, J=14.9 Hz), 4.41 (1H, d, J=14.8 Hz) 3.53 (1H, dd, J=10.8, 5.6 Hz), 3.21 (1H, dd, J=10.8, 2.0 Hz), 2.75 (1H, dd, J=17.4, 6.6 Hz), 2.44 (1H, dd, J=17.4, 2.4 Hz), 2.10 (1H, d, J=4.3 Hz)

(6) 914 mg (3.0 mmol) of 4-hydroxy-1-(4-(4'-fluorophenoxy)benzyl)pyrrolidin-2-one was dissolved in 20 ml of pyridine, treated with 464 μl (6.0 mmol) of methanesulfonyl chloride and stirred at 50° C. for 1 hour. The reaction mixture was treated with water and extracted twice with ethyl acetate, and the organic layer obtained was washed twice with water and then with saturated brine, and then the ethyl acetate layer was dried over anhydrous sodium sulfate. After concentrating under reduced pressure, the residue was precipitated from hexane-ethyl acetate to obtain 926 mg (yield: 81%) of 4-methanesulfonyloxy-1-(4-'4'-fluorophenoxy)benzyl)pyrrolidin-2-one as a grayish tan powder.

¹H-NMR (300 MHz, CDCl$_3$)

δ: 7.19 (2H, d, J=8.5 Hz), 7.02 (2H, d, J=10.7 Hz), 7.00 (2H, d, J=10.7 Hz), 6.93 (2H, d, J=8.5 Hz), 5.29 (1H, m), 4.49 (1H, d, J=14.9 Hz), 4.43 (1H, d, J=14.8 Hz), 3.66 (1H, dd, J=1.9, 5.7 Hz), 3.52 (1H, dd, J=1.9, 2.0 Hz), 3.03 (3H, s), 2.75 (1H, dd, J=17.9, 6.8 Hz), 2.71 (1H, dd, J=17.9, 2.6 Hz)

(7) 925 mg (2.4 mmol) of 4-methanesulfonyloxy-1-(4-'4'-fluorophenoxy)benzyl)pyrrolidin-2-one was dissolved in 30 ml of ethanol, treated with 822 mg (7.2 mmol) of potassium thioacetate and heated under reflux for 1 hour. The reaction mixture was concentrated under reduced pressure, treated with water and extracted twice with ethyl acetate, and the organic layer obtained was washed with water and saturated brine, and then dried over anhydrous sodium sulfate. After concentrating under reduced pressure, the residue was subjected to column chromatography on silica gel eluting with hexane: ethyl acetate (70:30) to obtain 834 mg (yield: 97%) of 4-acetylthio-1-(4-(4'-fluorophenoxy)benzyl)pyrrolidin-2-one as a pale yellow oil.

¹H-NMR (300 MHz, CDCl$_3$)

δ: 7.18 (2H, d, J=8.6 Hz), 7.02 (2H, d, J=9.7 Hz), 7.00 (2H, d, J=9.7 Hz), 6.92 (2H d, J=8.6 Hz), 4.45 (1H, d, J=15.1 Hz), 4.40 (1H, d, J=15.1Hz), 4.05 (1H, m), 3.75 (1H, dd, J=10.6, 7.6 Hz), 3.17 (1H, dd, J=10.6, 5.0 Hz), 2.91 (1H, dd, J=17.4, 9.0 Hz), 2.42 (1H, dd, J=17.4, 6.1 Hz), 2.32 (3H, s)

Example 31

4-Mercapto-1-(4-(4'-fluorophenoxy)benzyl)pyrrolidin-2-one 250 mg (0.7 mmol) of 4-acetylthio-1-(4-(4'-fluorophenoxy)benzyl)pyrrolidin-2-one obtained in Example 30 was dissolved in a mixture of 4 m of acetic acid and 1 ml of conc. hydrochloric acid, and stirred at 100° C. for 3 hours. The reaction mixture was concentrated under reduced pressure, treated with ethyl acetate and washed twice with water and then with saturated brine, and the organic layer was dried over anhydrous sodium sulfate. After concentrating under reduced pressure, the residue was subjected to column chromatography on silica gel eluting with hexane: ethyl acetate (70:30–50:50) to obtain 163 mg (yield: 73%) of 4-mercapto-1-(4-(4'-fluorophenoxy)benzyl)pyrrolidin-2-one as a colorless oil.
$^1$H-NMR (300 MHz, CDCl$_3$)
δ: 7.21 (2H, d, J=8.6 Hz), 7.02 (2H, d, J=10.2 Hz), 7.00 (2H, d, J=10.2 Hz), 6.93 (2H, d, J=8.6 Hz), 4.47 (1H, d, J=14.7 Hz), 4.39 (1H, d, J=14.7 Hz), 3.65 (1H, dd, J=10.0, 7.2 Hz), 3.54 (1H, m), 3.16 (1H, dd, J=10.0, 5.0 Hz), 2.92 (1H, dd, J=17.1, 8.1 Hz), 2.42 (1H, dd, J=17.1, 6.1 Hz), 1.86 (1H, d, J=6.7 Hz)

Example 32

4-Acetylthio-1-(4-(4'-chlorophenoxy)benzyl)pyrrolidin-2-one

By a method similar to that in Example 30 and starting from 1.72 g (6.8 mmol) of 4-(4'-chlorophenoxy)benzyl chloride prepared from 4-fluorobenzaldehyde and 4-chlorophenol and 1.20 g (6.8 mmol) of 4-trimethylsilyloxypyrrolidin-2-one, 702 mg (yield: 27%) of 4-acetylthio-1-(4-(4'-chlorophenoxy)benzyl)pyrrolidin-2-one was obtained as a pale tan powder.
$^1$H-NMR (300 MHz, CDCl$_3$)
δ: 7.30 (2H, d, J=8.9 Hz), 7.20 (2H, d, J=8.5 Hz), 6.96 (2H, d, J=8.5 Hz), 6.94 (2H, d, J=8.9 Hz), 4.46 (1H, d, J=15.2 Hz), 4.41 (1H, d, J=15.2 Hz), 4.06 (1H, m), 3.76 (1H, dd, J=10.6, 7.5 Hz), 3.18 (1H, dd, J=10.6, 5.0 Hz), 2.92 (1H, dd, J=17.4, 9.0 Hz) 2.43 (1H, dd, J=17.4, 6.1 Hz), 2.32 (3H, s)

Example 33

4-Mercaoto-1-(4-(4'-chlorophenoxy)benzyl)pyrrolidin-2-one

By a method similar to that in Example 31 and starting from 253 mg (0.7 mmol) of 4-acetylthio-1-(4-(4'-chlorophenoxy)benzyl)pyrrolidin-2-one obtained in Example 32, 209 mg (yield: 93%) of 4-mercaoto-1-(4-(4'-chlorophenoxy)benzyl)pyrrolidin-2-one was obtained as a colorless oil.
$^1$H-NMR (300 MHz, CDCl$_3$)
δ: 7.29 (2H, d, J=8.8 Hz), 7.22 (2H, d, J=8.5 Hz), 6.96 (2H, d, J=8.5 Hz), 6.94 (2H, d, J=8.8 Hz), 4.48 (1H, d, J=14.7 Hz), 4.40 (1H, d, J=14.7 Hz), 3.66 (1H, dd, J=10.0, 7.2 Hz), 3.55 (14 m), 3.17 (1H, dd, J=10.0, 5.0 Hz), 2.92 (1H, dd, J=17.1, 8.1 Hz), 2.42 (1H, dd, J=17.1, 6.1 Hz), 1.87 (1H, J=6.7 Hz)

Example 34

4-Acetylthio-1-(4-(4'-bromophenoxy)benzyl)pyrrolidin-2-one

By a method similar to that in Example 30 and starting from 1.92 g (6.5 mmol) of 4-(4'-bromophenoxy)benzyl chloride prepared from 4-fluorobenzaldehyde and 4-bromophenol and 1.10 g (6.5 mmol) of 4-trimethylsilyloxypyrrolidin-2-one, 955 mg (yield: 35%) of 4-acetylthio-1-(4-(4'-bromophenoxy)benzyl)pyrrolidin-2-one was obtained as a pale tan powder. $^1$H-NMR (300 MHz, CDCl$_3$)
δ: 7.44 (2H, d, J=8.9 Hz), 7.20 (2H, d, J=8.5 Hz), 6.96 (2H, d, J=8.5 Hz), 6.89 (2H, d, J=8.9 Hz), 4.46 (1H, d, J=14.9 Hz), 4.41 (1H d, J=14.9 Hz), 4.06 (1H, m), 3.76 (1H, dd, J=10.6, 7.5 Hz), 3.18 (1H, dd, J=10.6, 5.0 Hz), 2.92 (1H, dd, J=17.4, 9.0 Hz), 2.43 (1H, dd, J=17.4, 6.1 Hz), 2.32 (3H, s)

Example 35

4-Mercapto-1-(4-(4'-bromophenoxy)benzyl)pyrrolidin-2-one

By a method similar to that in Example 31 and starting from 330 mg (0.8 mmol) of 4-acetylthio-1-(4-(4'-bromophenoxy)benzyl)pyrrolidin-2-one obtained in Example 34, 240 mg (yield: 79%) of 4-mercaoto-1-(4-(4'-bromophenoxy)benzyl)pyrrolidin-2-one was obtained as a colorless oil. $^1$H-NMR (300 MHz, CDCl$_3$)
δ: 7.44 (2H, d, J=8.9 Hz), 7.23 (2H, d, J=8.6 Hz), 6.96 (2H, d, J=8.6 Hz), 6.88 (2H, d, J=8.9 Hz), 4.48 (1H, d, J=14.8 Hz), 4.40 (1H, d, J=14.8 Hz), 3.66 (1H, dd, J=10.0, 7.2 Hz), 3.55 (1H, m), 3.17 (1H, dd, J=10.0, 5.0 Hz), 2.92 (1H, dd, J=17.1, 8.1 Hz), 2.43 (1H, dd, J=17.1, 6.1 Hz), 1.87 (1H, d, J=6.7 Hz)

Example 36

4-Acetylthio-1-(4-(4'-methoxyphenoxy)benzyl)pyrrolidin-2-one

By a method similar to that in Example 30 and starting from 1.75 g (7.0 mmol) of 4-(4'-methoxyphenoxy)benzyl chloride prepared from 4-fluorobenzaldehyde and 4-methoxyphenol and 1.21 g (7.0 mmol) of 4-trimethylsilyloxypyrrolidin-2-one, 866 mg (yield: 33%) of 4-acetylthio-1-(4-(4'-methoxyphenoxy)benzyl)pyrrolidin-2-one was obtained as a pale tan powder. $^1$H-NMR (300 MHz, CDCl3)
δ: 7.15 (2H, d, J=8.4 Hz), 6.98 (2H d, J=9.0 Hz), 6.89 (2H, d, J=8.4 Hz), 6.89 (2H, d, J=9.0 Hz), 4.45 (1H, d, J=15.1 Hz), 4.38 (1H, d, J=15.1 Hz), 4.05 (1H, m), 3.81 (3H, s), 3.74 (1H, dd, J=10.6, 7.6 Hz), 3.16 (1H, dd, J=10.6, 5.0 Hz), 2.91 (1H, dd, J=17.4, 9.0 Hz), 2.41 (1H, dd, J=17.4, 6.0 Hz), 2.31 (3H, s)

Example 37

4-Mercapto-1-(4-(4'-methoxyphenoxy)benzyl)pyrrolidin-2-one

By a method similar to that in Example 31 and starting from 291 mg (0.9 mmol) of 4-acetylthio-1-(4-(4'-methoxyphenoxy)benzyl)pyrrolidin-2-one obtained in Example 36, 291 mg (yield: 98%) of 4-mercaoto-1-(4-(4'-methoxyphenoxy)benzyl)pyrrolidin-2-one was obtained as a colorless oil.
$^1$H-NMR (300 MHz, CDCl1)
δ: 7.17 (2H, d, J=8.4 Hz), 6.98 (2H, d, J=9.0 Hz), 6.90 (2H, d, J=8.4 Hz), 6.89 (2H, d, J=9.0 Hz), 4.45 (1H, d, J=14.7 Hz), 4.39 (1H, d, J=14.7 Hz), 3.81 (3H, s) 3.64 (1H, dd, J=10.0, 7.3 Hz), 3.53 (1H, m), 3.15 (1H, dd, J=10.0, 5.1 Hz), 2.91 (1H, dd, J=17.1, 8.1 Hz), 2.42 (1H, dd, J=17.1, 6.2 Hz), 1.86 (1H, d, J=6.8 Hz)

Example 38

Trans-4-acetylthio-5-benzyloxymethyl-1-(4-phenoxybenzyl)pyrrolidin-2-one (1) 14.3 g (28.3 mmol) of N-(ethylmalonyl)-N-(4-phenoxybenzyl)—O—benzyl-D,L-serine methyl ester synthesized in Example 20 was dissolved in 140 ml of ethanol, treated with 11.1 ml (28.3 mmol) of a 20% solution of sodium ethoxide in ethanol and stirred at room temperature for 1 hour. The reaction mixture was concentrated under reduced pressure, treated with 10% aqueous citric acid and extracted twice with ethyl acetate and the organic layer was washed twice with water and then with saturated brine, and dried over anhydrous sodium sulfate. After concentrating under reducer pressure into dryness, the residue was dissolved in 220 ml of acetonitrile, treated with 700 ml of water and heated under reflux for 1 hour. The reaction mixture was concentrated under reduced pressure, dissolved in 165 ml of methanol, treated with 987 mg (26.1 mmol) of sodium borohydride in portions with stirring, and then stirred at room temperature further for 1 hour. The reaction mixture was concentrated under reduced pressure, treated with water and then extracted three times with ethyl acetate. The organic layer was washed twice with water and then with saturated brine, and dried over anhydrous sodium sulfate. After concentrating under reduced pressure, the residue was subjected to column chromatography on silica gel eluting with hexane: ethyl acetate (20:80–0:100) to obtain 8.32 g (yield: 73%) of cis-5-benzyloxymethyl-4-hydroxy-1-(4-phenoxybenzyl)pyrrolidin-2-one as a colorless oil.

$^1$H-NMR (300 MHz, CDCl$_3$)

δ: 7.34 (7H, m), 7.12 (3H, m), 6.98 (2H, m), 6.92 (2H, d, J=8.3 Hz), 4.80 (1H, d, J=15.3 Hz), 4.53 (1H, m), 4.48 (1H, d, J=11.9 Hz), 4.40 (1H, d, J=11.9 Hz), 4.00 (1H, d, J=15.3 Hz), 3.71 (1H, m), 3.65 (2H, m), 2.74 (1H, dd, J=17.0, 7.9 Hz), 2.53 (1H, dd, J=17.0, 6.0 Hz)

(2) 500 mg (1.24 mmol) of cis-5-benzyloxymethyl-4-hydroxy-1-(4-phenoxybenzyl)pyrrolidin-2-one was dissolved in 20 ml of chloroform, treated with 864 µl (6.20 mmol) of triethylamine and 480 µl (6.20 mmol) of methanesulfonyl chloride with cooling on ice and then stirred at room temperature for 1 hour. The reaction mixture was concentrated under reduced pressure, treated with ethyl acetate, washed with water and saturated brine, and then dried over anhydrous sodium sulfate. After concentrating under reduced pressure followed by column chromatography on silica gel eluting with hexane: ethyl acetate (30:70–20:80), 560 mg (yield: 94%) of cis-5-benzyloxymethyl-4-methanesulfonyloxy-1-(4-phenoxybenzyl)pyrrolidin-2-one as a colorless oil.

$^1$H-NMR (300 MHz, CDCl$_3$)

δ: 7.34 (7H, m), 7.13 (3H m), 7.00 (2H, m), 6.92 (2H, d, J=8.7 Hz), 5.27 (1H, m) 4.85 (1H, d, J=15.1 Hz), 4.47 (1H, d, J=11.9 Hz), 4.42 (1H, d, J=11.9 Hz), 4.06 (1H, d, J=15.1 Hz), 3.82 (1H, m), 3.66 (2H, m), 2.98 (3H, s), 2.91 (1H, dd, J=17.0, 6.6 Hz), 2.76 (1H, dd, J=17.0, 7.9 Hz)

(5) 560 mg (1.16 mmol) of 5-benzyloxymethyl-4-methanesulfonyloxy-1-(4-phenoxybenzyl)pyrrolidin-2-one was dissolved in 20 ml of ethanol, treated with 265 mg (2.32 mmol) of potassium thioacetate, heated under ref lux for 4 hours, treated further with 265 mg (2.32 mmol) of potassium thioacetate, and then heated under ref lux for 2 hours. The reaction mixture was concentrated under reduced pressure, treated with ethyl acetate, washed with water and saturated brine, and then dried over anhydrous sodium sulfate. After concentrating under reduced pressure followed by column chromatography on silica gel eluting with hexaneg: ethyl acetate (60:40–50:50), 245 mg (yield: 46%) of trans-4-acetylthio-5-benzyloxymehyl-1-(4-phenoxybenzyl)pyrrolidin-2-one as a colorless oil. $^1$H-NMR (300 MHz, CDC$_{13}$)

δ: 7.32 (7H, m), 7.14 (2H, d, J=8.7 Hz), 7.10 (1H, m), 6.98 (2H, m), 6.92 (2H, d. J=8.7 Hz), 4.88 (1H, d, J=15.3 Hz), 4.49 (1H, d, J=12.1 Hz), 4.39 (1H, d, J=12.1 Hz), 3.99 (1H, d, J=15.3 Hz), 3.99 (1H, m), 3.57 (2H, m), 3.45 (1H, m), 3.13 (1H, dd, J=17.8, 9.1 Hz), 2.33 (1H, m), 2.29 (3H, s)

Example 39

Trans-5-benzyloxymethyl-4-mercapto-1-(4-phenoxybenzyl)pyrrolidin-2-one 145 mg (0.314 mmol) of trans-4-acetylthio-5-benzyloxymehyl-1-(4-phenoxybenzyl)pyrrolidin-2-one obtained in Example 38 was dissolved in a mixture of 1 ml of acetic acid and 1 ml of conc. hydrochloric acid, and stirred at 100° C. for 20 minutes. The reaction mixture was poured into an iced water and extracted twice with ethyl acetate, and the organic layer obtained was washed twice with water and then with saturated brine, and dried over anhydrous sodium sulfate. After concentrating under reduced pressure followed by column chromatography on silica gel eluting with hexane: ethyl acetate (50:50), 34.2 mg (yield: 26%) of trans-5-benzyloxymethyl-4-mercapto-1-(4-phenoxybenzyl)pyrrolidin-2-one was obtained as a colorless oil.

$^1$H-NMR (300 MHz, CDCl$_3$)

δ: 7.33 (7H, m), 7.15 (2H, d, J=8.7 Hz), 7.10 (1H, m), 6.98 (2H, m), 6.92 (2H, d, J=8.7 Hz), 4.91 (1H, d, J=15.1 Hz), 4.46 (1H, d, J=11.9 Hz), 4.42 (1H, d, J=11.9 Hz), 3.97 (1H, d, J=15.1 Hz), 3.50 (2H, m), 3.42 (2H, m), 3.05 (1H, dd, J=17.3, 7.9 Hz), 2.36 (1H, dd, J=17.3, 4.9 Hz), 1.79 (1H, d, J=6.8 Hz).

Example 40

4-Acetylthio-1-(3-phenoxybenzyl)pyrrolidin-2-one

By a method similar to that in Example 30 and starting from 1.23 g (5.6 mmol) of 3-phenoxybenzyl chloride prepared from 3-phenoxybenzaldehydr (TOKYO KASEI) and 0.97 g (5.6 mmol) of 4-trimethylsilyloxypyrrolidin-2-one, 704 mg (yield: 37%) of 4-acetylthio-1-(3-phenoxybenzyl)pyrrolidin-2-one was obtained as a colorless oil.

$^1$H-NMR (300 MHz, CDCl$_3$)

δ: 7.38–7.28 (3H, m), 7.12 (1H, t, J=7.4 Hz), 7.02–6.86 (5H, m), 4.48 (1H, d, J=14.9 Hz), 4.39 (1H, d, J=14.9 Hz), 4.05 (1H, m), 3.75 (1H, dd, J=10.6, 7.5 Hz), 3.17 (1H, dd, J=10.6, 4.9 Hz), 2.91 (1H, dd, J=17.4, 8.9 Hz), 2.41 (1H, dd, J=17.4, 5.9 Hz), 2.31 (3H, s)

Example 41

4-Mercapto-1-(3-phenoxybenzyl)pyrrolidin-2-one

By a method similar to that in Example 31 and starting from 200 mg (0.59 mmol) of 4-acetylthio-1-(3-phenoxybenzyl)pyrrolidin-2-one obtained in Example 40, 104 mg (yield 59%) of 4-mercapto-1-(3-phenoxybenzyl)pyrrolidin-2-one was obtained as a colorless oil.

$^1$H-NMR (300 MHz, CDCl$_3$)

δ: 7.38–7.26 (3H, m), 7.12 (1H, t, J=7.4 Hz), 7.03–6.87 (5H, m), 4.48 (1H, d, J=14.9 Hz), 4.40 (1H, d, J=14.9 Hz), 3.65 (1H, dd, J=10.1, 7.2 Hz), 3.53 (1H, m), 3.16 (1H, dd, J=10.1, 5.0 Hz), 2.91 (1H, dd, J=17.1, 8.1 Hz), 2.41 (1H, dd, J=17.1, 6.1 Hz), 1.84 (1H, d, J=6.8 Hz).

Example 42 and Example 43

3-Acetylthio-1-(4-phenoxybenzyl)piperidine-2,6-dione and 3-acetylthio-1-[4-(4-bromophenoxy)benzyl]piperidine-2,6-dione (1) A mixture of 4.91 g (14.9 mmol) of ethyl α-phenyl N-t-butyloxycarbonylglutamate prepared by the method known in literature (Tetrahedron Asymmetry, Vol.6, No.6, pp1249–1252, 1995), 4.28 g (22.3 mmol) of 1-ethyl-3-(3-dimethylaminopropyl)carbodiimide hydrochloride, 15.8 ml (113.1 mmol) of triethylamine, 3.56 (17.9 mmol) of 4-phenoxybenzylamine and 77 ml of chloroform was stirred at 55° C. for 30 minutes, treated with 2.41 g (17.9 mmol) of 1-hydroxybenzotriazole and stirred at 55° C. for two days. The reaction mixture was concentrated under reduced pressure, and the residue was treated with ethyl acetate, washed three times with saturated aqueous sodium hydrogen carbonate, once with saturated brine, three times with a 10% aqueous solution of citric acid and then once with saturated brine. The ethyl acetate layer was dried over anhydrous sodium sulfate and concentrated under reduced pressure, and the residue was subjected to column chromatography on silica gel eluting with hexane: ethyl acetate (25:75) to obtain 1.46 g (yield: 24%) of 3-(t-butyloxycarbonylamino)-1-(4-phenoxybenzyl)piperidine-2,6-dione as a brown oil.

$^1$H-NMR (300 MHz, CDCl$_3$)

δ: 7.35–6.89 (9H, m), 5.40 (1H, brs), 4.93 (1H, d, J=13.8 Hz), 4.88 (1H, d, J=13.8 Hz), 4.31–4.26 (1H, m), 2.93–2.85 (1H, m), 2.78–2.66 (1H, m), 2.51–2.47 (1H, m), 1.88–1.73 (1H, m), 1.46 (9H, s).

(2) Immediately after dissolving 1.21 g (3.0 mmol) of 3-(t-butyloxycarbonylamino)-1-(4-phenoxybenzyl)piperidine-2,6-dione in 15 ml of trifluoroacetic acid, the solution was concentrated under reduced pressure to obtain a residue which was then treated with ethyl acetate and washed successively with saturated aqueous sodium hydrogen carbonate, water and saturated brine, and the ethyl acetate layer was dried over anhydrous sodium sulfate and concentrated under reduced pressure to obtain a residue which was then treated with ethyl acetate, and the precipitate formed was collected by filtration, whereby obtaining 823 mg (yield: 90%) of 3-amino-1-(4-phenoxybenzyl)piperidine-2,6-dione as a pale blue powder.

$^1$H-NMR (300 MHz, CDCl$_3$)

δ: 7.36–6.89 (9H, m), 4.91 (2H, s), 3.53 (1H, dd, J=12.4, 5.1 Hz), 2.94–2.85 (1H, m), 2.74–2.61 (1H, m), 2.27–2.18 (1H, m), 1.87–1.72 (1H, m).

(3) 800 mg (2.6 mmol) of 3-amino-1-(4-phenoxybenzyl)piperidine-2,6-dione was suspended in 2 ml of ethyl acetate, and then immediately after adding 2 ml of a 25% solution of hydrogen bromide in acetic acid the mixture was concentrated under reduced pressure to obtain a residue to which then ethyl acetate was added, and the precipitate formed was collected by filtration to give 881 mg of 3-amino-i-(4-phenoxybenzyl)piperidine-2,6-dione hydrobromide. A mixture of 1.20 g (3.1 mmol) of 3-amino-i-(4-phenoxybenzyl)piperidine-2,6-dione hydrobromide thus obtained, 7 ml (61.4 mmol) of 8.84 N aqueous hydrogen bromide, 7 ml of acetonitrile and 7 ml of water was cooled to −5° C., and treated dropwise over 1 hour with an aqueous solution prepared by mixing 1.83 g (15.4 mmol) of potassium bromide and 530 mg (7.7 mmol) of sodium nitrite with 10 ml of water thereafter, 21 ml of acetonitrile and 14 ml of water were added, and the mixture was stirred at room temperature for 1 hour. The reaction mixture was concentrated under reduced pressure, and the residue was treated with ethyl acetate, washed twice with water and then with saturated brine. The ethyl acetate layer was dried over anhydrous sodium sulfate and concentrated under reduced pressure, and the residue was subjected to column chromatography on silica gel eluting with ethyl acetate: hexane (10:90) to obtain 424 mg of a mixture (of about 2:1) of 3-bromo-1-(4-phenoxybenzyl)piperidine-2,6-dione and 3-bromo-1-[4-(4-bromophenoxy)benzyl]piperidine-2,6-dione as a pale purple oil.

$^1$H-NMR (300 MHz, CDCl$_3$)

δ: 7.43–7.40 (0.7H, m), 7.12–7.07 (0.7H, m), 7.35–6.85 (7.3H, m), 4.97 (1H, d, J=13.8 Hz), 4.88 (1H, d, J=13.8 Hz), 4.72 (1H, t, J=3.1 Hz), 3.12–3.00 (1H, m), 2.81–2.73 (1H, m), 2.44–2.20 (2H, m).

(4) A mixture consisting of 200 mg of the mixture (of about 2:1) of 3-bromo-1-(4-phenoxybenzyl)piperidine-2,6-dione and 3-bromo-1-[4-(4-bromophenoxy)benzyl]piperidine-2,6-dione, 67 mg (0.6 mmol) of potassium thioacetate and 2 ml of N,N-dimethylformamide was stirred at room temperature for 30 minutes and concentrated under reduced pressure, and the residue obtained was treated with ethyl acetate and washed three times with water and then with saturated brine, and the ethyl acetate layer was dried over anhydrous sodium sulfate and concentrated under reduced pressure, and the residue obtained was subjected to high pressure liquid chromatography (eluent: 65% acetonitrile/0.01 N phosphate buffer (pH6.3)) to obtain 108 mg of 3-acetylthio-1-(4-phenoxybenzyl)piperidine-2,6-dione as a pale blue oil and 63 mg of 3-acetylthio-1-[4-(4-bromophenoxy)benzyl]piperidine-2,6-dione as a pale red oil.

3-Acetylthio-1-(4-phenoxybenzyl)piperidine-2,6-dione (Example 42)

$^1$H-NMR (300 MHz, CDCl$_3$)

δ: 7.35–6.90 (9H, m), 4.96 (1H, d, J=13.7 Hz), 4.88 (1H, d, J=13.8 Hz), 4.45 (1H, dd, J=9.7, 4.9 Hz), 2.91–2.70 (2H, m), 2.42 (3H, s), 2.32–2.26 (1H, m), 2.14–2.23 (1H, m), 2.14–2.01 (1H, m).

3-Acetylthio-1-[4-(4-bromophenoxy)benzyl]piperidine-2,6-dione (Example 43)

$^1$H-NMR (300 MHz, CDCl$_3$)

δ: 7.42–7.27 (4H, m), 6.91–6.85 (4H, m), 4.95 (1H, d, J=13.8 Hz), 4.88 (1H, d, J=13.8 Hz), 4.44 (1H, dd, J=9.8, 4.9 Hz), 2.90–2.70 (2H, m), 2.41 (3H, s), 2.34–2.23 (1H, m), 2.14–2.01 (1H, m).

Example 44

3-Benzoylthio-1-(4-phenoxybenzyl)piperidine-2,6-dione 100 mg of a mixture (of about 5:1) of 3-bromo-1-(4-phenoxybenzyl)piperidine-2,6-dione and 3-bromo-1-[4-(4-bromophenoxy)benzyl]piperidine-2,6-dione obtained similarly to Example 42 was processed similarly to 28 to obtain 86 mg of 3-benzoylthio-1-(4-phenoxybenzyl)piperidine-2,6-dione as a pale yellow oil.

$^1$H-NMR (300 MHz, CDCl$_3$)

δ: 8.00–7.95 (2H, m), 7.65–6.86 (12H, m), 5.00 (1H, d, J=13.7 Hz), 4.93 (1H, d, J=13.7 Hz), 4.67 (1H, dd, J=9.7, 4.9), 2.98–2.76 (2H, m), 2.44–2.13 (2H, m).

Example 45

Mixture of 3-mercapto-1-(4-phenoxybenzyl)piperidine-2,6-dione and 1-[4-(4-bromophenoxy)benzyl]-3-mercaptopiperidine-2,6-dione A mixture consisting of 150 mg of a mixture (of about 2:1) of 3-bromo-1-(4-phenoxybenzyl)piperidine-2,6-dione and 3-bromo-1-[4-(4-bromophenoxy)benzyl]piperidine-2,6-dione obtained similarly to Example 42, 50 mg (0.04 mmol) of potassium thioacetate and 2 ml of N,N-dimethylformamide was stirred at room temperature for 45 minutes and concentrated under reduced pressure, and the residue obtained was treated with ethyl acetate and washed twice with water and then with saturated brine. The ethyl acetate layer was dried over anhydrous sodium sulfate and concentrated under reduced pressure, and the residue obtained was dissolved in a mixture of 1 ml of acetic acid and 1 ml of conc. hydrochloric acid, and stirred at 100° C. for 25 minutes. After concentrating under reduced pressure, the residue obtained was treated with ethyl acetate, washed three times with water, saturated aqueous sodium hydrogen carbonate, phosphate buffer (pH6.8) and then saturated brine, and the ethyl acetate layer was dried over anhydrous sodium sulfate and concentrated under reduced pressure to obtain a residue, which was then purified by preparative thin layer silica gel chromatography (eluent: ethyl acetate: hexane (2:1)) to obtain a mixture (of about 2:1) of 3-mercapto-1-(4-phenoxybenzyl)piperidine-2,6-dione and 1-[4-(4-bromophenoxy)benzyl]-3-mercaptopiperidine-2,6-dione.

$^1$H-NMR (300 MHz, CDCl$_3$)

δ: 7.43–7.40(0.7H, m), 7.15–7.07 (0.7H, m), 7.35–6.85 (7.3H m), 4.96 (1H, d, J=13.8 Hz), 4.89 (1H, d, J=13.8 Hz), 3.97–3.93 (1H, m), 2.99–2.88 (1H, m), 2.75–2.65 (1H, m), 2.40 (1H, d, J=4.6 Hz), 2.39–2.27 (1H, m), 2.09–1.96 (1H, m).

Example 46

3-Acetylthio-1-(4-phenoxybenzyl)piperidin-2-one (1) To a mixture of 700 mg of 3-hydroxy-2-piperidone (6.1 ammol, Aldrich), 512 mg (9.1 mmol) of pulverized potassium hydroxide and 6 ml of dimethylsulfoxide, 1.33 g (6.1 mmol) of phenoxybenzyl chloride was added with cooling on ice, and the mixture was stirred at room temperature for 16 hours. After adding ethyl acetate, the mixture was washed with 1N hydrochloric acid, 6 times with water and then with saturated brine. The ethyl acetate layer was dried over anhydrous sodium sulfate and concentrated under reduced pressure, and the residue was subjected to column chromatography on silica gel eluting with ethyl acetate: n-hexane (20:80) to obtain 781 mg (yield: 43%) of 3-hydroxy-1-(4-phenoxybenzyl)piperidin-2-one as a pale yellow oil.

$^1$H-NMR (300 MHz, CDCl$_3$)

δ: 7.35–6.95 (9H, m), 4.60 (1H, d, J=14.5 Hz), 4.49 (1H, d, J=14.5 Hz), 4.13–4.06 (1H, m), 3.26–3.22 (2H, m), 2.30–2.26 (1H, m), 1.93–1.69 (4H, m).

(2) 909 mg (3.1 mmol) of 3-hydroxy-1-(4-phenoxybenzyl)piperidin-2-one was processed similarly to Example 21 to obtain 1.13 g (yield: 99%) of 3-methanesulfonyloxy-1-(4-phenoxybenzyl)piperidin-2-one as a pale yellow oil.

$^1$H-NMR (300 MHz, CDCl$_3$)

δ: 7.37–6.96 (9H, m), 5.06 (1H, dd, J=7.9, 5.7 Hz), 4.58 (1H, d, J=14.6 Hz), 4.52 (1H, d, J=14.4 Hz), 3.31 (3H, s), 3.29–3.20 (2H, m), 2.27–1.81 (4H, m).

(3) A mixture of 400 mg (1.1 mmol) of 3-methanesulfonyloxy-1-(4-phenoxybenzyl)piperidin-2-one, 146 mg (1.3 mmol) of potassium thioacetate and 4 ml of N,N-dimethylformamide was stirred at room temperature for 1 hour and then concentrated under reduced pressure, and the residue obtained was treated with ethyl acetate, washed twice with water, twice with a saturated aqueous solution of sodium hydrogen carbonate and then with saturated brine. The ethyl acetate layer was dried over anhydrous sodium sulfate and concentrated under reduced pressure, and the residue obtained was subjected to column chromatography on silica gel eluting with ethyl acetate: hexane (20:80) to obtain 328 mg (yield: 87%) of 3-acetylthio-1-(4-phenoxybenzyl)piperidin-2-one as a pale red to pale brown oil.

$^1$H-NMR (300 MHz, CDCl$_3$)

δ: 7.36–6.94 (9H, m), 4.60 (1H, d, J=14.5 Hz), 4.54 (1H, d, J=14.4 Hz), 4.29 (1H, dd, J=7.7, 5.5 Hz), 3.34–3.21 (2H, m), 2.38 (3H, s), 2.30–2.20 (1H, m), 2.00–1.81 (3H, m).

Example 47

3-Benzoylthio-1-(4-phenoxybenzyl)piperidin-2-one

A mixture of 200 mg (0.5 mmol) of 3-methanesulfonyloxy-1-(4-phenoxybenzyl)piperidin-2-one obtained in Example 46, 75 μl (0.6 mmol) of thiobenzoic acid, 87 mg (0.3 ml) of cesium carbonate and 1 ml of N,N-dimethylformamide was stirred at room temperature for 15 hours, treated with 6 μl (0.1 mmol) of thiobenzoic acid and 9 mg (0.03 mmol) of cesium carbonate, and stirred at room temperature for 1 hour. The mixture was concentrated under reduced pressure, and the residue obtained was treated with ethyl acetate, washed twice with water, twice with a saturated aqueous solution of sodium hydrogen carbonate and then with saturated brine. The ethyl acetate layer was dried over anhydrous sodium sulfate and concentrated under reduced pressure, and the residue obtained was subjected to column chromatography on silica gel eluting with ethyl acetate: hexane (8:92) to obtain 182 mg (yield: 82%) of 3-benzoylthio-1-(4-phenoxybenzyl)piperidin-2-one as a pale red oil.

$^1$H-NMR (300 MHz, CDCl$_3$)

δ: 7.99–7.96 (2H, m), 7.60–6.95 (12H, m), 4.64 (1H, d, J=14.5 Hz), 4.58 (1H, d, J=14.4 Hz), 4.51 (1H, dd, J=7.8, 5.8 Hz), 3.41–3.26 (2H, m), 2.40–2.30 (1H, m), 2.11–1.86 (3H, m).

Example 48

3-Mercapto-1-(4-phenoxybenzyl)piperidin-2-one 127 mg (0.04 mmol) of 3-acethylthio-1-(4-phenoxybenzyl)piperidin-2-one obtained in Example 46 was processed similarly to Example 29 to obtain 108 mg (yield: 96%) of 3-mercapto-1-(4-phenoxybenzyl)piperidin-2-one as a brown oil.

$^1$H-NMR (300 MHz, CDC$_{13}$)

δ: 7.37–6.94 (9H, m), 4.61 (1H, d, J=14.5 Hz), 4.50 (1H, d, J=14.5 Hz), 3.84–3.78 (1H, m), 3.34–3.20 (2H, m), 2.60 (1H, d, J=4.2 Hz), 2.28–1.70 (4H, m).

Example 49

S—[(3R)-5-oxo-1-(4-phenoxybenzyl)pyrrolidinyl] thiocarbamate 400 mg (1.34 mmol) of (R)-4-mercapto-1-(4-phenoxybenzyl)pyrrolidin-2-one obtained in Example 25 was dissolved in 10 ml of chloroform, and added dropwise to a solution of 118.7 μl (1.47 mmol) of N-chlorocarbonyl isocyanate in 2 ml of chloroform at a temperature of −18 to −12° C., and after completion of the addition the mixture was stirred at the same temperature for 30 minutes and then warmed to 0° C. over a period of 1 hour, and then stirred at room temperature for 12 hours. The reaction mixture was concentrated under reduced pressure, dissolved in ethyl acetate, washed with 6N hydrochloric acid and saturated brine, and then dried over anhydrous sodium sulfate. The mixture was concentrated under reduced pressure and purified by preparative thin layer chromatography (eluent: n-hexane: ethyl acetate (1:3)) to obtain 212 mg (yield: 46%) of the title compound as a white solid.

$^1$H-NMR (300 MHz, CDCl$_3$)

δ: 7.36–6.94 (9H, m), 5.59 (2H, br), 4.43 (2H, s), 4.08–4.03 (1H, m), 3.78 (1H, dd, J=10.7, 7.3 Hz), 3.27 (1H, dd, J=10.7, 4.6 Hz), 2.93 (1H, dd, J=17.4, 8.9 Hz), 2.47 (1H, dd, J=17.4, 5.7 Hz)

Example 50

S—[(3H)-5-oxo-1-(4-phenoxybenzyl)pyrrolidinyl] methylthiocarbamate 220 mg (0.74 mmol) of (R)-4-mercapto-1-(4-phenoxybenzyl)pyrrolidin-2-one obtained in Example 25 was dissolved in 2 ml of chloroform, and treated with 50 mg (0.88 mmol) of methyl isocyanate and 0.5 μl (catalytic amount) of triethylamine and then stirred under nitrogen atmosphere for 20 minutes. The reaction mixture was concentrated under reduced pressure, dissolved in chloroform, washed with water, and then dried over anhydrous sodium sulfate. The mixture was concentrated under reduced pressure and purified by preparative thin layer chromatography (eluent: n-hexane: ethyl acetate (1:2, 1:3)) and precipitated from n-hexane: ethyl acetate to obtain 198 mg (yield: 76%) of the title compound as a white powder.

Elemental analysis (%): C$_{19}$H$_{20}$N$_2$O$_3$S.0.5H$_2$O

Calcd.: C, 62.44;H, 5.79;N, 7.66

Found: C, 62.46;H, 5.87;N, 7.66

Example 51

S—[(3R)-5-oxo-1-(4-phenoxybenzyl)pyrrolidinyl] ethylthiocarbamate

Similarly to Example 50 and starting from 150 mg (0.501 mmol) of (R)-4-mercapto-1-(4-phenoxybenzyl)pyrrolidin-2-one obtained in Example 25, 87.2 μl (1.10 mmol) of ethyl isocyanate and 13.9 μl (0.102 mmol) of triethylamine, 122 mg (yield: 66%) of the title compound was obtained as a colorless needle.

Elemental analysis (%): C$_{20}$H$_{22}$N$_2$O$_3$S

Calcd.: C, 64.84;H, 5.99;N, 7.56

Found: C, 84.88;H, 6.04;N, 7.65

Example 52

S—[5-oxo-1-(4-phenoxybenzyl)-3-pyrrolidinyl] propylcarbamothioate

Similarly to Example 50 and starting from 100 mg (0.33 mmol) of 4-mercapto-1-(4-phenoxybenzyl)pyrrolidin-2-one obtained in Example 17, 34 μl (0.37 mmol) of propyl isocyanate and 47 μl (0.33 mmol) of triethylamine, 110 mg (yield: 87%) of the title compound was obtained as a colorless needle.

$^1$H-NMR (200 MHz, CDCl$_3$)

δ: 7.40–6.90 (9H, m), 5.45–5.30 (1H, m), 4.43 (2H, s), 4.15–4.00 (1H, m), 3.79 (1H, dd, J=7.4, 10.0 Hz), 3.27 (1H, dd, J=4.8, 10.0 Hz), 3.30–3.15 (2H, m), 2.92 (1H, dd, J=8.8, 16.0 Hz), 2.46 (1H, dd, J=6.0, 18.0 Hz), 1.65–1.45 (2H, m), 0.92 (3H, t, J=7.4 Hz)

Example 53

S—[5-oxo-1-(4-phenoxybenzyl)-3-pyrrolidinyl] phenylcarbamothioate

Similarly to Example 50 and starting from 100 mg (0.33 mmol) of 4-mercapto-1-(4-phenoxybenzyl)pyrrolidin-2-one obtained in Example 17, 36 μl (0.33 mmol) of phenyl isocyanate and 47 μl (0.33 mmol) of triethylamine, 120 mg (yield: 87%) of the title compound was obtained as a colorless needle.

$^1$H-NMR (200 MHz, CDC$_{13}$)

δ: 7.52–6.90 (15H, m), 4.45 (2H, s), 4.22–4.08 (1H, m), 3.85 (1H, dd, J=7.1, 12.0 Hz), 3.34 (1H, dd, J=4.2, 12.0 Hz), 2.98 (1H, dd, J=8.8, 18.0 Hz), 2.53 (1H, dd, J=5.2, 18.0 Hz)

Example 54

S—[(3R)-5-oxo-1-(4-phenoxybenzyl)pyrrolidinyl] benzylthiocarbamate 200 mg (0.67 mmol) of (R)-4-mercapto-1-(4-phenoxybenzyl)pyrrolidin-2-one obtained in Example 25 was dissolved in 2 ml of chloroform, treated with 99 μl (0.80 mmol) of benzyl isocyanate and 0.5 μl (catalytic amount) of triethylamine and then stirred under nitrogen atmosphere for 1 hour. The reaction mixture was concentrated under reduced pressure and purified by preparative thin layer chromatography (eluent: chloroform: methanol (20:1)) and precipitated from n-hexane: ethyl acetate to obtain 217 mg (yield: 75%) of the title compound as a white powder.

$^1$H-NMR (300 MHz, CDCl$_3$)

δ: 7.37–6.94 (14H, m), 5.71 (1H, br), 4.40 (4H, bs), 4.15–4.06 (1H, m), 3.79 (1H, dd, J=10.7, 7.3 Hz), 3.28 (1H, dd, J=10.7, 4.8 Hz), 2.92 (1H, dd, J=17.4, 8.9 Hz), 2.46 (1H, dd, J=17.4, 6.0 Hz)

Example 55

S—[(3R)-5-oxo-1-(4-phenoxybenzyl)pyrrolidinyl] acetylthiocarbamate 264 mg (1.76 mmol) of silver cyanate and 125 μl (1.76 mmol) of acetyl chloride were added to 4 ml of toluene, and the mixture was stirred at 70° C. for 30 minutes. The reaction mixture was cooled, and the supernatant was used to dissolve 220 mg (0.74 mmol) of (R)-4-mercapto-1-(4-phenoxybenzyl)pyrrolidin-2-one obtained in Example 25, to which 5.1 μl (catalytic amount) of triethylamine was added, and the mixture was stirred at room temperature for 20 minutes. The reaction mixture was concentrated under reduced pressure, dissolved in ethyl acetate, washed twice with water and then with saturated brine, and dried over anhydrous sodium sulfate. The reaction mixture was concentrated under reduced pressure and purified by preparative thin layer chromatography (eluent: n-hexane: ethyl acetate (1:2)) and precipitated from n-hexane: ethyl acetate to obtain 193 mg (yield: 68%) of the title compound as a white powder.

$^1$H-NMR (300 MHz, CDCl$_3$)

δ: 8.40 (1H, s), 7.37–6.95 (9H, m), 4.44 (2H, s), 4.40 (4H, bs), 4.12–4.02 (1H, m), 3.78 (1H, dd, J=10.7, 7.7 Hz), 3.26 (1H, dd, J=10.7, 5.0 Hz), 2.95 (1H, dd, J=17.5, 9.1 Hz), 2.50 (1H, dd, J=17.5, 6.2 Hz), 2.05 (3H, s)

Example 56

S—[(3R)-5-oxo-1-(4-phenoxybenzyl)pyrrolidinyl] benzoylthiocarbamate 220 mg (0.74 mmol) of (R)-4-mercapto-1-(4-phenoxybenzyl)pyrrolidin-2-one obtained in Example 25 was dissolved in 2 ml of chloroform, treated with 113 μl (0.81 mmol) of benzoyl isocyanate and 5.1 μl (catalytic amount) of triethylamine and then stirred under nitrogen atmosphere for 30 minutes. The reaction mixture was concentrated under reduced pressure, dissolved in ethyl acetate, washed twice with water and then with saturated brine, and dried over anhydrous sodium sulfate. The reaction mixture was concentrated under reduced pressure and purified by preparative thin layer chromatography (eluent: n-hexane: ethyl acetate (1:2)) to obtain 230 mg (yield: 70%) of the title compound as a colorless oil.

$^1$H-NMR (300 MHz, CDCl$_3$)

δ: 7.97–6.92 (14H, m), 4.47–4.32 (2H, m), 4.14–4.04 (1H, m), 3.79 (1H, dd, J=10.7, 7.8 Hz), 3.29 (1H, dd, J=10.7, 5.1 Hz), 2.93 (1H, dd, J=17.5, 9.0 Hz), 2.51 (1H, dd, J=17.5, 6.2 Hz).

Example 57

O-Ethyl S—[(3R)-5-oxo-1-(4-phenoxybenzyl) pyrrolidinyl]imidothiodicarbonate 220 mg (0.74 mmol) of (R)-4-mercapto-1-(4-phenoxybenzyl)pyrrolidin-2-one obtained in Example 25 was dissolved in 2 ml of chloroform, treated with 93 μl (0.81 mmol) of ethyl isocyanatoformate and 5.1 μl (catalytic amount) of triethylamine and then stirred under nitrogen atmosphere for 30 minutes. The reaction mixture was concentrated under reduced pressure and purified by preparative thin layer chromatography (eluent: n-hexane: ethyl acetate (1:2)) and precipitated from n-hexane: ethyl acetate to obtain 214 mg (yield: 70%) of the title compound as a white powder.

$^1$H-NMR (300 MHz, CDCl$_3$)

δ: 7.69 (1H, bs), 7.37–6.94 (9H, m), 4.43 (2H, s), 4.24 (2H, q, J=7.1 Hz), 4.07–4.03 (1H, m), 3.79 (1H, dd, J=10.7, 7.7 Hz), 3.25 (1H, dd, J=10.7, 5.1 Hz), 2.94 (1H, dd, J=17.5, 9.1 Hz), 2.50 (1H, dd, J=17.5, 6.3 Hz), 1.31 (3H, t, J=7.1 Hz)

Example 58

Ethyl [({[(3R)-5-oxo-1-(4-phenoxybenzyl) pyrrolidinyl]sulfanyl}carbonyl)amino]acetate Similarly to Example 50 and starting from 300 mg (1.00 mmol) of (R)-4-mercapto-1-(4-phenoxybenzyl)pyrrolidin-2-one obtained in Example 25, 246 μl (2.20 mmol) of ethyl isocyanatoacetate and 41.7 μl (0.300 mmol) of triethylamine, 417 mg (yield: 97%) of the title compound was obtained as a colorless oil.

Elemental analysis (%): C$_{22}$H$_{24}$N$_2$O$_5$S.0.44H$_2$O

Calcd.: C, 60.64;H, 5.74;N, 6.43

Found: C, 60.60;H, 5.70;N, 6.43

Example 59

[({[(3R)-5-Oxo-1-(4-phenoxybenzyl)pyrrolidinyl] sulfanyl}carbonyl)amino]acetic acid 225 mg (0.525 mmol) of ethyl [({[(3R)-5-oxo-1-(4-phenoxybenzyl)pyrrolidinyl]sulfanyl)carbonyl)amino]acetate obtained in Example 58 was dissolved in a mixture of 3 ml of acetic acid and 3 ml of conc. hydrochloric acid, and then heated at 100° C. for 25 minutes with stirring. The reaction mixture was poured into an iced water and extracted twice with ethyl acetate, and the ethyl acetate layer was washed three times with water and once with saturated brine, and then dried over anhydrous sodium sulfate. After concentrating under reduced pressure followed by column chromatography on silica gel, the fraction eluted with chloroform: methanol (95:5) was concentrated and precipitated from ether to obtain 123 mg (yield: 59%) of the title compound as a white powder.

Elemental analysis (%): C$_{20}$H$_{20}$N$_2$O$_5$S

Calcd.: C, 59.99;H, 5.03;N, 7.00

Found: C, 59.81;H, 4.92;N, 7.07

Example 60

Ethyl [({[(3R)-5-oxo-1-(4-phenoxybenzyl) pyrrolidinyl]sulfanylcarbonyl)amino]prop anoate 200 mg (0.67 mmol) of (R)-4-mercapto-1-(4-phenoxybenzyl)pyrrolidin-2-one obtained in Example 25 was dissolved in 2 ml of chloroform, treated with 106 μl (0.80 mmol) of ethyl 3-isocyanatopropionate and 0.5 μl (catalytic amount) of triethylamine and then stirred under nitrogen atmosphere for 30 minutes. The reaction mixture was concentrated under reduced pressure and purified by preparative thin layer chromatography (eluent: chloroform: methanol (20:1)) to obtain 243 mg (yield: 82%) of the title compound as a colorless oil.

$^1$H-NMR (300 MHz, CDCl$_3$)

δ: 7.37–6.94 (9H, m), 5.94 (1H, br), 4.43 (2H, s), 4.16 (2H, q, J=7.1 Hz), 4.09–4.02 (1H, m), 3.76 (1H, dd, J=10.6, 7.5 Hz), 3.53 (2H, br) 3.25 (1H, dd, J=10.6, 5.0 Hz), 2.91 (1H, dd, J=17.3, 8.9 Hz), 2.53 (2H, t, J=5.9 Hz), 2.45 (1H, dd, J=17.4, 6.2 Hz), 1.26 (3H, t, J=7.1 Hz)

Example 61

N-({[(3R)-5-oxo-1-(4-phenoxybenzyl)pyrrolidinyl] sulfanyl}carbonyl)-p-alanine 261 mg (0.59 mmol) of ethyl [({[(3R)-5-oxo-1-(4-phenoxybenzyl)pyrrolidinyl]sulfanyl)carbonyl)amino)prop anoate was dissolved in 3 ml of a (1:1) mixture of conc. hydrochloric acid and acetic acid, and stirred at 100° C. for 30 minutes. The reaction mixture was concentrated under reduced pressure, dissolved in ethyl acetate, washed with 1N hydrochloric acid and saturated brine, and dried over anhydrous sodium sulfate. The reaction mixture was concentrated under reduced pressure and purified by preparative thin layer chromatography (eluent: chloroform: methanol (10:1)) to obtain 170 mg (yield: 70%) of the title compound as a colorless oil.

$^1$H-NMR (300 MHz, DMSO-d$_6$)

δ: 8.31 (1H, br), 7.42–6.95 (9H, m), 4.39 (1H, d, J=15.1 Hz), 4.33 (1H, d, J=15.1 Hz), 3.98–3.90 (1H, m), 3.71 (1H, dd, J=10.4, 7.3 Hz), 3.26 (2H, t, J=6.5 Hz), 3.16 (1H, dd, J=10.4, 4.5 Hz), 2.83 (1H, dd, J=17.0, 8.6 Hz), 2.36 (2H, t, J=6.9 Hz), 2.27 (1H, dd, J=17.0, 5.6 Hz)

Example 62

S—[(3R)-5-oxo-1-(4-phenoxybenzyl)pyrrolidinyl] dimethylcarbamothioate 200 mg (0.67 mmol) of (R)-4-mercapto-1-(4-phenoxybenzyl)pyrrolidin-2-one obtained in Example 25 and 68 μl (0.73 mmol) of N,N-dimethylcarbonyl chloride were dissolved in 1 ml of chloroform, treated dropwise with a solution of 102 μl (0.73 mmol) of triethylamine in 1 ml of chloroform at 0° C., and after completion of the addition the mixture was stirred at room temperature for 1 hour. Subsequently, 27 mg (0.67 mmol) of 60% sodium hydride was added and the mixture was stirred at room temperature for 10 minutes, concentrated under reduced pressure, dissolved in ethyl acetate, washed twice with water and then with saturated brine, and dried over anhydrous sodium sulfate. The reaction mixture was concentrated under reduced pressure and purified by preparative thin layer chromatography (eluent: n-hexane: ethyl acetate (1:2)) to obtain 153 mg (yield: 62%) of the title compound as a pale yellow oil.
Elemental analysis (%): $C_{20}H_{22}N_2O_3S \cdot 0.1H_2O$
Calcd.: C, 64.52;H, 6.01;N, 7.52
Found: C, 64.38;H, 6.05;N, 7.41

Example 63

S—[(3R)-5-oxo-1-(4-phenoxybenzyl)pyrrolidinyl]4-morpholinecarbothioate

Similarly to Example 62 and starting from 150 mg (0.501 mmol) of (R)-4-mercapto-1-(4-phenoxybenzyl)pyrrolidin-2-one obtained in Example 25, 451 μl (3.85 mmol) of morpholinecarbonyl chloride and 140 mg (3.50 mmol) of 60% sodium hydride, 185 mg (yield: 90%) of the title compound was obtained as a colorless oil.
Elemental analysis (%): $C_{22}H_{24}N_2O_4S \cdot 0.3H_2O$
Calcd.: C, 63.23;H, 5.93;N, 6.70
Found: C, 63.09;H, 5.95;N, 6.66

Example 64

S—[(3R)-5-oxo-1-(4-phenoxybenzyl)pyrrolidinyl] propanethioate 200 mg (0.67 mmol) of (R)-4-mercapto-1-(4-phenoxybenzyl)pyrrolidin-2-one obtained in Example 25 and 64 μl (0.73 mmol) of propionyl chloride were dissolved in 2 ml of chloroform, treated dropwise with a solution of 102 μl (0.73 mmol) of triethylamine in 1 ml of chloroform at 0° C., and after completion of the addition the mixture was stirred at 0° C. for 1 hour. The mixture was concentrated under reduced pressure, dissolved in ethyl acetate, washed with water and saturated brine, and dried over anhydrous sodium sulfate. The reaction mixture was concentrated under reduced pressure and purified by preparative thin layer chromatography (eluent: n-hexane: ethyl acetate (1:1)) to obtain 228 mg (yield: 96%) of the title compound as a pale pinkish oil.
$^1$H-NMR (300 MHz, $CDCl_3$)
δ: 7.37–6.95 (9H, m), 4.46 (1H, d, J=14.7 Hz), 4.40 (1H, d, J=14.7 Hz), 4.10–4.01 (1H, m), 3.76 (1H, dd, J=10.7, 7.5 Hz), 3.17 (1H, dd, J=10.7, 5.0 Hz), 2.92 (1H, dd, J=17.4, 9.0 Hz), 2.55 (2H, t, J=7.5 Hz), 2.42 (1H, dd, J=17.4, 6.0 Hz), 1.16 (3H, t, J=7.5 Hz)

Example 65

S—[(3R)-5-oxo-1-(4-phenoxybenzyl)pyrrolidinyl] butanethioate 200 mg (0.67 mmol) of (R)-4-mercapto-1-(4-phenoxybenzyl)pyrrolidin-2-one obtained in Example 25 and 76 μl (0.73 mmol) of butyryl chloride were dissolved in 2 ml of chloroform, treated dropwise with a solution of 102 μl (0.73 mmol) of triethylamine in 1 ml of chloroform at 0° C., and after completion of the addition the mixture was stirred at 0° C. for 1 hour. The mixture was concentrated under reduced pressure, dissolved in ethyl acetate, washed with water and saturated brine, and dried over anhydrous sodium sulfate. The reaction mixture was concentrated under reduced pressure and purified by preparative thin layer chromatography (eluent: n-hexane: ethyl acetate (1:1)) to obtain 228 mg (yield: 92%) of the title compound as a colorless oil.
$^1$H-NMR (300 MHz, $CDCl_3$)
δ: 7.37–6.95 (9H, m), 4.47 (1H, d, J=14.7 Hz), 4.39 (1H, d, J=14.7 Hz), 4.10–4.01 (1H, m), 3.76 (1H, dd, J=10.7, 7.5 Hz), 3.16 (1H, dd, J=10.7, 4.9 Hz), 2.92 (1H, dd, J=17.4, 8.9 Hz), 2.51 (2H, t, J=7.4 Hz), 2.42 (1H, dd, J=17.4, 5.9 Hz), 1.73–1.60 (2H, m), 1.16 (3H, t, J=7.5 Hz)

Example 66

S—[5-oxo-1-(4-phenoxybenzyl)-3-pyrrolidinyl] pentanethioate

Similarly to Example 64 and starting from 100 mg (0.33 mmol) of 4-mercapto-1-(4-phenoxybenzyl)pyrrolidin-2-one obtained in Example 17, 48 mg (0.40 mmol) of valeryl chloride and 57 μl (0.40 mmol) of triethylamine, 78 mg (yield: 62%) of the title compound was obtained as a colorless oil.
$^1$H-NMR (200 MHz, $CDCl_3$)
δ: 7.40–6.90 (9H, m), 4.48 (1H, d, J=16.0 Hz), 4.40 (1H, d, J=14.0 Hz), 4.12–3.97 (1H, m), 3.77 (1H, dd, J=7.5, 10.0 Hz), 3.17 (1H, dd, J=4.9, 10.0 Hz), 2.93 (1H, dd, J=8.9, 16.0 Hz), 2.53 (2H, t, J=7.8 Hz), 2.43 (1H, dd, J=6.0, 18.0 Hz), 1.70–1.55 (2H, m), 1.42–1.24 (2H, m), 0.90 (3H, t, J=7.3 Hz)

Example 67

S—[(3R)-5-oxo-1-(4-phenoxybenzyl)pyrrolidinyl]2-methylpropanethioate 200 mg (0.67 mmol) of (R)-4-mercapto-1-(4-phenoxybenzyl)pyrrolidin-2-one obtained in Example 25 and 77 μl (0.73 mmol) of isobutyryl chloride were dissolved in 2 ml of chloroform, treated dropwise with a solution of 102 μl (0.73 mmol) of triethylamine in 1 ml of chloroform at 0° C., and after completion of the addition the mixture was stirred at 0° C. for 1 hour. The mixture was concentrated under reduced pressure, dissolved in ethyl acetate, washed with water and saturated brine, and dried over anhydrous sodium sulfate. The reaction mixture was concentrated under reduced pressure and purified by preparative thin layer chromatography (eluent: n-hexane: ethyl acetate (1:1)) to obtain 223 mg (yield: 91%) of the title compound as a colorless oil. $^1$H-NMR (300 MHz, $CDCl_3$)
δ: 7.06–6.95 (9H, m), 4.47 (1H, d, J=14.6 Hz), 4.39 (1H, d, J=14.7 Hz), 4.07–3.73 (1H, m), 3.76 (1H, dd, J=10.6, 7.4 Hz), 3.15 (1H, dd, J=10.6, 4.8 Hz), 2.92 (1H, dd, J=17.4, 8.9 Hz), 2.77–2.63 (1H, m), 2.42 (1H, dd, J=17.4, 5.8 Hz), 1.19–1.15 (6H, m)

Example 68

S—[5-oxo-1-(4-phenoxybenzyl)-3-pyrrolidinyl] 2-phenylethanethioate

Similarly to Example 64 and starting from 100 mg (0.33 mmol) of 4-mercapto-1-(4-phenoxybenzyl)pyrrolidin-2-one obtained in Example 17, 57 mg (0.37 mmol) of phenylacetyl chloride and 57 μl (0.40 mmol) of triethylamine, 61 mg (yield: 44%) of the title compound was obtained as a colorless oil.
$^1$H-NMR (200 MHz, $CDCl_3$)
δ: 7.40–6.90 (14H, m), 4.45 (1H, d, J=14.8 Hz), 4.36 (1H, d, J=14.7 Hz), 4.10–3.95 (1H, m), 3.79 (2H, s), 3.74 (1H, dd, J=7.5, 10.0 Hz), 3.14 (1H, dd, J=4.9, 10.0 Hz), 2.90 (1H, dd, J=9.0, 18.0 Hz), 2.40 (1H, dd, J=6.1, 18.0 Hz)

Example 69

S—[5-oxo-1-(4-phenoxybenzyl)-3-pyrrolidinyl]-(4-chlorophenyl)ethanethioate

Similarly to Example 64 and starting from 100 mg (0.33 mmol) of 4-mercapto-1-(4-phenoxybenzyl)pyrrolidin-2-one obtained in Example 17, 76 mg (0.40 mmol) of p-chlorophenylacetyl chloride and 57 μl (0.40 mmol) of triethylamine, 85 mg (yield: 57%) of the title compound was obtained as a colorless oil.
$^1$H-NMR (200 MHz, CDCl$_3$)
δ: 7.40–6.90 (13H, m), 4.45 (1H, d, J=14.7 Hz), 4.37 (1H, d, J=14.7 Hz), 4.10–3.95 (1H, m), 3.75 (2H, s), 3.74 (1H, dd, J=7.5, 10.0 Hz), 3.13 (1H, dd, J=4.9, 12.0 Hz), 2.90 (1H, dd, J=8.8, 18.0 Hz), 2.38 (1H, dd, J=5.9, 20.0 Hz)

Example 70

S—[5-oxo-1-(4-phenoxybenzyl)-3-pyrrolidinyl] 2,2-diphenylethanethioate

Similarly to Example 64 and starting from 50 mg (0.17 mmol) of 4-mercapto-1-(4-phenoxybenzyl)pyrrolidin-2-one obtained in Example 17, 58 mg (0.25 mmol) of diphenylacetyl chloride and 57 μl (0.40 mmol) of triethylamine, 57 mg (yield: 69%) of the title compound was obtained as a colorless oil.
$^1$H-NMR (200 MHz, CDCl$_3$)
δ: 7.40–6.90 (19H, m), 5.13 (1H, s), 4.45 (1H, d, J=14.5 Hz), 4.36 (1H, d, J=14.7 Hz), 4.14–4.00 (1H, m), 3.77 (1H, dd, J=7.4, 10.0 Hz), 3.16 (1H, dd, J=4.8, 12.0 Hz), 2.92 (1H, dd, J=8.9, 18.0 Hz), 2.41 (1H, dd, J=5.9, 18.0 Hz)

Example 71

Ethyl 3-oxo-3-{[(3R)-5-oxo-1-(4-phenoxybenzyl) pyrrolidinyl]sulfanyl)propanoate 200 mg (0.67 mmol) of (R)-4-mercapto-1-(4-phenoxybenzyl)pyrrolidin-2-one obtained in Example 25 and 94 μl (0.73 mmol) of ethyl-3-chloro-3-oxoropionate were dissolved in 1 ml of chloroform, treated dropwise with a solution of 102 μl (0.73 mmol) of triethylamine in 1 ml of chloroform at 0° C., and after completion of the addition the mixture was stirred at 0° C. for 1 hour. The mixture was concentrated under reduced pressure, dissolved in ethyl acetate, washed twice with water and then with saturated brine, and dried over anhydrous sodium sulfate. The reaction mixture was concentrated under reduced pressure and purified by preparative thin layer chromatography (eluent: n-hexane: ethyl acetate (1:2)) to obtain 175 mg (yield: 63%) of the title compound as a colorless oil.
$^1$H-NMR (300MHz, CDCl$_3$)
δ: 7.37–6.95 (9H, m), 4.43 (2H, s), 4.19 (2H, q, J=7.1 Hz), 4.14–4.09 (1H, m), 3.78 (1H, dd, J=10.7, 7.5 Hz), 3.55 (2H, s), 3.20 (1H, dd, J=10.7, 4.8 Hz), 2.94 (1H, dd, J=17.4, 8.9 Hz), 2.44 (1H, dd, J=17.4, 5.9 Hz), 1.27 (3H, t, J=7.1 Hz)

Example 72 t-Butyl 3-oxo-3-{[(3R)-5-oxo-1-(4-phenoxybenzyl) pyrrolidinyl]sulfanyl}propanoate 124 μl (0.73 mmol) of mono-t-butyl malonate was dissolved in 1 ml of acetonitrile, and 130 mg (0.73 mmol) of N,N-carbonyldiimidazole was added, and the mixture was stirred for 1 hour, and then a solution of 200 mg (0.67 mmol) of (R)-4-mercapto-1-(4-phenoxybenzyl)pyrrolidin-2-one obtained in Example 25 in 1 ml of acetonitrile was added and the mixture was stirred for 10 minutes. The reaction mixture was concentrated under reduced pressure, dissolved in ethyl acetate, washed twice with 0.1 N hydrochloric acid and then with saturated brine, and dried over anhydrous sodium sulfate. The reaction mixture was concentrated under reduced pressure and purified by preparative thin layer chromatography (eluent: n-hexane: ethyl acetate (1:2)) to obtain 180 mg (yield: 61%) of the title compound as a colorless oil.
$^1$H-NMR (300 MHz, CDCl$_3$)
δ: 7.37–6.95 (9H, m), 4.43 (2H, s), 4.14–4.06 (1H, m), 3.78 (1H, dd, J=10.7, 7.5 Hz), 3.47 (2H, s), 3.20 (1H, dd, J=10.7, 4.8 Hz), 2.93 (1H, dd, J=17.4, 9.0 Hz), 2.44 (1H, dd, J=17.4, 5.9 Hz), 1.53 (9H, s)

Example 73

3-Oxo-3-{[(3R)-5-oxo-1-(4-phenoxybenzyl) pyrrolidinyl]sulfanyl)propanoic acid 224 mg (0.51 mmol) of t-butyl 3-oxo-3-{[(3R)-5-oxo-1-(4-phenoxybenzyl)pyrrolidinyl]sulfanyl} propanoate obtained in Example 72 and 203 μl (1.28 mmol) of triethylsilane were dissolved in a mixture of 2 ml of acetic acid and 2 ml of chloroform, and stirred for 5 days. The reaction mixture was concentrated under reduced pressure, dissolved in ethyl acetate, washed with 1N hydrochloric acid and then with a mixture of 1 N hydrochloric and saturated brine, and dried over anhydrous sodium sulfate. The reaction mixture was concentrated under reduced pressure and precipitated from ethyl acetate to obtain 151 mg (yield: 77%) of the title compound as a white powder.
$^1$H-NMR (300 MHz, DMSO-d$_6$)
δ: 7.42–6.97 (9H, m), 4.40 (1H, d, J=15.1 Hz), 4.35 (1H, d, J=15.1 Hz), 4.11–4.02 (1H, m), 3.76 (1H, dd, J=10.6, 7.4 Hz), 3.66 (2H, s), 3.16 (1H, dd, J=10.6, 4.3 Hz), 2.90 (1H, dd, J=17.1, 8.8 Hz), 2.30 (1H, dd, J=17.1, 5.2 Hz)

Example 74

Ethyl 4-oxo-4-{[(3R)-5-oxo-1-(4-phenoxybenzyl) pyrrolidinyl]sulfanyl}butanoate

113 μl (0.88 mmol) of monoethyl succinate was dissolved in 1 ml of acetonitrile, and 130 mg (0.73 mmol) of N,N-carbonyldiimidazole was added, and the mixture was stirred for 30 minutes, and then a solution of 200 mg (0.67 mmol) of (R)-4-mercapto-1-(4-phenoxybenzyl)pyrrolidin-2-one obtained in Example 25 in 1 ml of acetonitrile was added and the mixture was stirred for 10 minutes. The reaction mixture was concentrated under reduced pressure, dissolved in ethyl acetate, washed twice with 1 N hydrochloric acid and then with saturated brine, and dried over anhydrous sodium sulfate. The reaction mixture was concentrated under reduced pressure and purified by preparative thin layer chromatography (eluent: n-hexane: ethyl acetate (1:2)) to obtain 236 mg (yield: 75%) of the title compound as a white solid.
$^1$H-NMR (300 MHz, CDCl$_3$)
δ: 7.37–6.95 (9H, m), 4.43 (2H, s), 4.11–4.04 (3H, m), 3.75 (1H, dd, J=10.6, 7.5 Hz), 3.17 (1H, dd, J=10.6, 5.0 Hz), 2.91 (1H, dd, J=17.4, 8.9 Hz), 2.86 (2H, t, J=7.1 Hz), 2.62 (2H, t, J=6.9 Hz), 2.42 (1H, dd, J=17.4, 6.0 Hz), 1.24 (3H, t, J=7.1 Hz), Example 75

4-Oxo-4-([(3R)-5-oxo-1-(4-phenoxybenzyl) pyrrolidinyl]sulfanyl}butanoic acid 200 mg (0.67 mmol) of (R)-4-mercapto-1-(4-phenoxybenzyl)pyrrolidin-2one obtained in Example 25 and 67 mg (0.67 mmol) of succinic anhydride were dissolved in 2 ml of THF, and 27 mg (0.67 mmol) of 60% sodium hydride was added, and the mixture was stirred at room temperature for 16 hours. The reaction mixture was concentrated under reduced pressure, dissolved in ethyl acetate, washed with 1 N hydrochloric acid and then with saturated brine, and dried over anhydrous sodium sulfate. The reaction mixture was concentrated under reduced pressure and purified by preparative thin layer chromatography (eluent: chloroform: methanol (5:1)) to obtain 163 mg (yield: 61%.) of the title compound as a pale brown oil.
Elemental analysis (9%): $C_{21}H_{21}NO_5S \cdot 0.1H_2O$
Calcd.: C, 62.85;H, 5.32;N, 3.49
Found: C, 62.80;H, 5.12;N, 3.52

Example 76

(3R)-5-Oxo-1-(4-phenoxybenzyl)pyrrolidinyl methyldithiocarbonate 220 mg (0.74 mmol) of (R)-4-mercapto-1-(4-phenoxybenzyl)pyrrolidin-2-one obtained in Example 25 was dissolved in 2 ml of chloroform, treated with 59 mg (0.81 mmol) of methyl isothiocyanate and 5.1 µl (catalytic amount) of triethylamine, and stirred under nitrogen atmosphere for 12 hours. The reaction mixture was concentrated under reduced pressure and purified by preparative thin layer chromatography (eluent: n-hexane:ethyl acetate (1:2)) to obtain 75 mg (yield: 27%) of the title compound as a colorless oil.
$^1$H-NMR (300 MHz, CDCl$_3$)
δ:8.30–7.98 (1H, m), 7.35–6.92 (9H, m), 4.56–4.49 (1H, m), 4.44 (1H, d, J=14.8 Hz), 4.36 (1H, d, J=14.7 Hz), 3.89 (1H, dd, J=11.1, 6.9 Hz), 3.37 (1H, dd, J=11.1, 3.0 Hz), 3.19 (3H, d, J=7.8 Hz), 3.02 (1H, dd, J=17.9, 8.9 Hz), 2.55 (1H, dd, J=17.7, 4.0 Hz)

Example 77

(3R)-5-Oxo-1-(4-phenoxybenzyl)pyrrolidinyl ethyldithiocarbonate 220 mg (0.74 mmol) of (R)-4-mercapto-1-(4-phenoxybenzyl)pyrrolidin-2-one obtained in Example 25 was dissolved in 2 ml of chloroform, treated with 71 µl (0.81 mmol) of ethyl isothiocyanate and a previously prepared solution of 5.1 µl (catalytic amount) of triethylamine and 2.1 µl (catalytic amount) of acetic acid in 0.1 ml of chloroform, and stirred under nitrogen atmosphere for 2 days. The reaction mixture was concentrated under reduced pressure, dissolved in ethyl acetate, washed with 0.1 N hydrochloric acid and then with saturated brine, and dried over anhydrous sodium sulfate. The reaction mixture was concentrated under reduced pressure and purified by preparative thin layer chromatography (eluent: n-hexane:ethyl acetate (1:2)) to obtain 211 mg (yield: 74%) of the title compound as a pale pinkish oil.
$^1$H-NMR (300 MHz, CDCl$_3$) δ: 7.61–6.91 (10H, m), 4.51–4.38 (3H, m), 3.91–3.84 (1H, m), 3.74–3.32 (3H, m), 3.06–2.97 (1H, m), 2.55–2.48 (1H, m), 1.26 (3H, t, J=7.2 Hz) Example 78 (4R)-4-[(Methoxycarbonyl) disulfanyl]-2-oxo-1-(4-phenoxybenzyl)pyrrolidine 50 mg (0.17 mmol) of (R)-4-mercapto-1-(4-phenoxybenzyl)pyrrolidin-2-one obtained in Example 25 was dissolved in 1 ml of methanol, and 17 µl (0.18 mmol) of methoxycarbonylsulfenyl chloride was added and the mixture was stirred at room temperature for 1 hour. The reaction mixture was concentrated under reduced pressure, dissolved in ethyl acetate, washed with water and saturated brine, and dried over anhydrous sodium sulfate. The reaction mixture was concentrated under reduced pressure to obtain 62 mg (yield: 95%) of the title compound as a pale brown oil.
Elemental analysis (%): $C_{19}H_{19}NO_4S_2$
Calcd.: C, 58.59;H, 4.92;N, 3.60
Found: C, 58.29;H, 4.95;N, 3.61

Example 79

(4R)-4-(Ethyldisulfanyl)-1-(4-phenoxybenzyl)-2-pyrrolidinone 220 mg (0.57 mmol) of (4R)-4-[(methoxycarbonyl) disulfanyl]-2-oxo-1-(4-phenoxybenzyl)pyrrolidine obtained in Example 78 was dissolved in a mixture of 1 ml of chloroform and 1 ml of methanol, treated with 209 µl (2.82 mmol) of ethanethiol and 0.4 µl (catalytic amount) of triethylamine, and stirred under nitrogen atmosphere at room temperature for 30 minutes. The reaction mixture was concentrated under reduced pressure, dissolved in ethyl acetate, washed with water and saturated brine, and dried over anhydrous sodium sulfate. The reaction mixture was concentrated under reduced pressure and purified by preparative thin layer chromatography (eluent: n-hexane: ethyl acetate (1:2)) to obtain 140 mg (yield: 69%) of the title compound as a colorless oil.
Elemental analysis (%): $C_{19}H_{21}NO_2S_2$
Calcd.: C, 63.48;H, 5.89;N, 3.90
Found: C, 63.31;H, 5.91;N, 4.09

Example 80

(4R)-4-(Hexyldisulfanyl)-1-(4-phenoxybenzyl)-2-pyrrolidinone 200 mg (0.51 mmol) of (4R)-4-[(methoxycarbonyl) disulfanyl]-2-oxo-1-(4-phenoxybenzyl)pyrrolidine obtained in Example 78 was dissolved in a mixture of 1 ml of chloroform and 1 ml of methanol, treated with 362 µl (2.57 mmol) of 1-hexanethiol and 0.4 µl (catalytic amount) of triethylamine, and stirred under nitrogen atmosphere at room temperature for 30 minutes. The reaction mixture was concentrated under reduced pressure, dissolved in ethyl acetate, washed with water, 0.1 N hydrochloric acid and saturated brine, and dried over anhydrous sodium sulfate. The reaction mixture was concentrated under reduced pressure and purified by preparative thin layer chromatography (eluent: n-hexane: ethyl acetate (1:1)) to obtain 157 mg (yield: 74t) of the title compound as a colorless oil.
$^1$H-NMR (300 MHz, CDCl$_3$)
δ: 7.37–6.96 (9H, m), 4.47 (1H, d, J=14.7 Hz), 4.41 (1H, d, J=14.7 Hz), 3.64–3.51 (2H, m), 3.33 (1H, dd, J=9.9, 3.5 Hz), 2.83 (1H, dd, J=17.4, 8.0 Hz), 2.65 (1H, t, J=7.3 Hz), 2.56 (1H, dd, J=17.5, 4.8 Hz), 1.68–1.57 (2H, m), 1.40–1.27 (6H, m), 0.88 (3H, t, J=6.7 Hz)

Example 81

(4R)-4-(t-Butyldisulfanyl)-1-(4-phenoxybenzyl)-2-pyrrolidinone 220 mg (0.57 mmol) of (4R)-4-[(methoxycarbonyl) disulfanyl]-2-oxo-1-(4-phenoxybenzyl)pyrrolidine obtained in Example 78 was dissolved in a mixture of 1 ml of chloroform and 1 ml of methanol, treated with 319 µl (2.83 mmol) of 2-methyl-2-propanethiol and 0.4 µl (catalytic amount) of triethylamine, and stirred under nitrogen atmosphere at room temperature for 30 minutes. The reaction mixture was concentrated under reduced pressure, dissolved in ethyl acetate, washed twice with water and saturated brine, and dried over anhydrous sodium sulfate. The reaction mixture was concentrated under reduced pressure and purified by preparative thin layer chromatography (eluent: n-hexane: ethyl acetate (1:2)) to obtain 183 mg (yield: 84%) of the title compound as a white solid.
Elemental analysis (%): $C_{21}H_{25}NO_2S_2$
Calcd.: C, 65.08;H, 6.50;N, 3.61
Found: C, 65.02;H, 6.26;N, 3.65

Example 82

Ethyl 2-{[(3R)-5-oxo-1-(4-phenoxybenzyl)-2-pyrrolidinyl]disulfanyl}acetate 220 mg (0.57 mmol) of (4R)-4-[(methoxycarbonyl)disulfanyl]-2-oxo-1-(4-phenoxybenzyl)pyrrolidine obtained in Example 78 was dissolved in a mixture of 1 ml of chloroform and 1 ml of methanol, treated with 68 μl (0.62 mmol) of ethyl 2-mercaptoacetate and 0.4 μl (catalytic amount) of triethylamine, and stirred at room temperature for 2 hours. The reaction mixture was concentrated under reduced so pressure, dissolved in ethyl acetate, filtered to remove insolubles, washed with water and saturated brine, and dried over anhydrous sodium sulfate. The reaction mixture was concentrated under reduced pressure and purified by preparative thin layer chromatography (eluent: n-hexane: ethyl acetate (1:2)) to obtain 51 mg (yield: 22%) of the title compound as a colorless oil.
Elemental analysis (%): $C_{21}H_{23}NO_4S_2$
Calcd.: C, 60.41;H, 5.55;N, 3.35
Found: C, 60.32;H, 5.53;N, 3.45

Example 83

2-{[(3R)-5-Oxo-1-(4-phenoxybenzyl)-2-pyrrolidinyl]disulfanyl}acetic acid 220 mg (0.57 mmol) of (4R)-4-[(methoxycarbonyl)disulfanyl]-2-oxo-1-(4-phenoxybenzyl)pyrrolidine obtained in Example 78 was dissolved in 2 ml of methanol, treated with 39 μl (0.57 mmol) of mercaptobutyric acid and 0.8 μl (catalytic amount) of triethylamine, and stirred at room temperature for 3 hours. The reaction mixture was concentrated under reduced pressure, dissolved in ethyl acetate, washed with 0.1 N hydrochloric acid, and dried over anhydrous sodium sulfate. The reaction mixture was concentrated under reduced pressure, purified by preparative thin layer chromatography (eluent: chloroform: methanol (5:1)) and precipitated from ethyl acetate to obtain 136 mg (yield: 62%) of the title compound as a white powder.
$^1$H-NMR (300 Mz, DMSO-$d_6$)
δ: 7.41–6.97 (9H, m), 4.43 (1H, d, J=14.8 Hz), 4.32 (1H, d, J=14.8 Hz), 3.86–3.16 (7H, m), 2.85 (1H, dd, J=17.4, 8.2 Hz), 2.31 (1H, t, dd, J=17.4, 3.7 Hz)

Example 84

Ethyl 3-{[(3R)-5-oxo-1-(4-phenoxybenzyl)-2-pyrrolidinyl]disulfanyl}propanoate 220 mg (0.57 mmol) of (4R)-4-[(methoxycarbonyl)disulfanyl]-2-oxo-1-(4-phenoxybenzyl)pyrrolidine obtained in Example 78 was dissolved in a mixture of 1 ml of chloroform and 1 ml of methanol, treated with 332 μl (2.57 mmol) of ethyl 3-mercaptopropionate and 0.4 [l (catalytic amount) of triethylamine, and stirred at room temperature for 30 minutes. The reaction mixture was concentrated under reduced pressure, dissolved in ethyl acetate, washed with 0.1 N hydrochloric acid and saturated brine, and dried over anhydrous sodium sulfate. The reaction mixture was concentrated under reduced pressure and purified by preparative thin layer chromatography (eluent: n-hexane: ethyl acetate (1:2)) to obtain 72 mg (yield: 33%) of the title compound as a colorless oil.
$^1$H-NMR (300 MHz, CDCl$_3$)
δ: 7.36–6.95 (9H, m), 4.47 (1H, d, J=14.7 Hz), 4.40 (1H, d, J=14.7 Hz), 4.14 (2H, q, J=7.1 Hz), 3.65–3.54 (2H, m), 3.36–3.30 (1H, m), 2.92–2.79 (3H, m), 2.68 (2H, t, J=7.0 Hz), 2.52 (1H, dd, J=17.5, 4.4 Hz), 1.26 (3H, t, J=7.0 Hz)

Example 85

3-{[(3R)-5-Oxo-1-(4-phenoxybenzyl)-2-pyrrolidinyl]disulfanyl}propanoic acid 200 mg (0.51 mmol) of (4R)-4-[(methoxycarbonyl)disulfanyl]-2-oxo-1-(4-phenoxybenzyl)pyrrolidine obtained in Example 78 was dissolved in 2 ml of methanol, treated with 45 μl (0.51 mmol) of 3-mercaptopropionic acid and 0.4 μl (catalytic amount) of triethylamine, and stirred at room temperature for 4 hours. The reaction mixture was concentrated under reduced pressure and purified by preparative thin layer chromatography (eluent: chloroform: methanol (10:1)) to obtain 188 mg (yield: 91%) of the title compound as a colorless oil.
$^1$H-NMR (300 MHz, DMSO-$d_6$)
δ: 7.41–6.95 (9H, m), 4.43 (1H, d, J=14.8 Hz), 4.31 (1H, d, J=14.9 Hz), 3.78–3.71 (1H, m), 3.65 (1H, dd, J=0.7, 6.7 Hz), 3.25 (1H, dd, J=10.7, 2.9 Hz), 2.89–2.78 (3H, m), 2.57 (2H, t, J=6.8 Hz), 2.31 (1H, dd, J=17.3, 3.8 Hz), Example 86

2-{[(3R)-5-Oxo-1-(4-phenoxybenzyl)-1-pyrrolidinyl]disulfanyl}propanoic acid 200 mg (0.67 mmol) of (R)-4-mercapto-1-(4-phenoxybenzyl)pyrrolidin-2-one obtained in Example 25 was dissolved in 3 ml of 95% ethanol, and 226 mg (0.67 mmol) of 0-carboxyphenyl 0-carboxybenzenethiol sulfonate was added, and the mixture was stirred at room temperature for 12 hours. The reaction mixture was concentrated under reduced pressure, dissolved in chloroform, filtered to remove insolubles, and purified by preparative thin layer chromatography (eluent: chloroform: methanol (8:1)) to obtain 185 mg (yield: 61%) of the title compound as a colorless oil.
Elemental analysis (%): $C_{24}H_{21}NO_4S_2 \cdot 0.25H_2O$
Calcd.: C, 63.20;H, 4.75;N, 3.07
Found: C, 63.05;H, 4.66;N, 2.97

Example 87

(4R)-4-[(2-Nitrophenyl)disulfanyl)-1-(4-phenoxybenzyl)-2-pyrrolidinone 200 mg (0.67 mmol) of (R)-4-mercapto-1-(4-phenoxybenzyl)pyrrolidin-2-one obtained in Example 25 was dissolved in 2 ml of acetic acid, and 133 mg (0.70 mmol) of 2-nitrobenzenesulfenyl chloride was added, and the mixture was stirred at room temperature for 15 minutes. The reaction mixture was concentrated under reduced pressure, dissolved in ethyl acetate, washed twice with water and then with saturated brine, and purified by preparative thin layer chromatography (eluent: n-hexane: ethyl acetate (1:2)) to obtain 272 mg (yield: 90%) of the title compound as a pale yellow oil.
Elemental analysis (%): $C_{23}H_{20}N_2O_4S_2$
Calcd.: C, 61.04;H, 4.45;N, 6.19
Found: C, 60.99;H, 4.51;N, 6.05

Example 88

(4-Amino-2-methyl-5-pyrimidinyl)methyl((Z)-4-hydroxy-1-methyl-2-[[(3R)-5-oxo-1-(4-phenoxybenzyl)pyrrolidinyl]disulfanyl)-1-butenyl)formamide 100 mg (0.26 nmmol) of (4R)-4-[(methoxycarbonyl)disulfanyl]-2-oxo-1-(4-phenoxybenzyl)pyrrolidine obtained in Example 78 was dissolved in 1 ml of ethanol, added to a mixture of 87 mg (0.26 mmol) of thiamine hydrochloride, 77 μl (0.77 mmol) of a 10 N aqueous solution of sodium hydroxide, 15 μl (0.26 mmol) of acetic acid and 1 ml of ethanol, and stirred at room temperature for 20 minutes. The reaction mixture was concentrated under reduced pressure, dissolved in ethyl acetate, washed with a saturated aqueous solution of sodium hydrogen carbonate and saturated brine, and dried over anhydrous sodium sulfate. The reaction mixture was concentrated under reduced pressure and purified by preparative thin layer chromatography (eluent: chloroform: methanol (10:1)) to obtain 68 mg (yield: 45%) of the title compound as a white foam.
Elemental analysis (%): $C_{29}H_{33}N_5O_4S_2O$
Calcd.: C, 59.16;H, 5.82;N, 11.89
Found: C, 59.14;H, 5.99;N, 11.97

Example 89

(4R)-4-(Methylsulfanyl)-1-(4-phenoxybenzyl)-2-pyrrolidinone 220 mg (0.74 mmol) of (R)-4-mercapto-1-(4-phenoxybenzyl)pyrrolidin-2-one obtained in Example 25 and 50 μl (0.81 mmol) of iodomethane were dissolved in 2 ml of THF, treated with 29 mg (0.74 mmol) of 60% sodium hydride, and stirred under nitrogen atmosphere at room temperature for 10 minutes. The reaction mixture was concentrated under reduced pressure, dissolved in ethyl acetate, washed with 0.1 N hydrochloric acid and saturated brine, and dried over anhydrous sodium sulfate. The reaction mixture was concentrated under reduced pressure and purified by preparative thin layer chromatography (eluent: n-hexane: ethyl acetate (1:2)) to obtain 180 mg (yield: 78%) of the title compound as a colorless oil.
Elemental analysis (%): $C_{18}H_{19}NO_2S$
Calcd.: C, 68.98;H, 6.11;N, 4.47
Found: C, 68.80;H, 6.00;N, 4.57

Example 90 (4R)-4-[(2-Hydroxyethyl)sulfanyl]-1-(4-phenoxybenzyl)-2-pyrrolidinone 200 mg (0.67 mmol) of (R)-4-mercapto-1-(4-phenoxybenzyl)pyrrolidin-2-one obtained in Example 25 and 47 μl (0.67 mmol) of 2-bromoethanol were dissolved in 2 ml of THF, treated with 27 mg (0.67 mmol) of 60% sodium hydride, and stirred at room temperature for 10 minutes. The reaction mixture was concentrated under reduced pressure, dissolved in ethyl acetate, washed with 1 N hydrochloric acid and saturated brine, and dried over anhydrous sodium sulfate. The reaction mixture was concentrated under reduced pressure and purified by preparative thin layer chromatography (eluent: chloroform: methanol (15:1)) to obtain 149 mg (yield: 65%) of the title compound as a pale brown oil.
Elemental analysis (%): $C_{19}H_{21}NO_3S$
Calcd.: C, 66.45;H, 6.16;N, 4.08
Found: C, 66.30;H, 6.08;N, 4.05

Example 91

2-{[(3R)-5-Oxo-1-(4-phenoxybenzyl)pyrrolidinyl]sulfanyl}acetic acid 199 mg (0.66 mmol) of (R)-4-mercapto-1-(4-phenoxybenzyl)pyrrolidin-2-one obtained in Example 25 and 47 mg (0.66 mmol) of bromoacetic acid were dissolved in 2 ml of THF, treated with 27 mg (1.33 mmol) of 60% sodium hydride, and stirred at room temperature for 10 minutes. The reaction mixture was concentrated under reduced pressure, dissolved in ethyl acetate, washed twice with 1 N hydrochloric acid and then with saturated brine, and dried over anhydrous sodium sulfate. The reaction mixture was concentrated under reduced pressure and purified by preparative thin layer chromatography (eluent: chloroform: methanol (1:3)) to obtain 138 mg (yield: 58%) of the title compound as a pale brown oil.
Elemental analysis (%): $C_{19}H_{19}NO_4S \cdot 0.8H_2O$
Calcd.: C, 61.37;H, 5.58;N, 3.76
Found: C, 61.15;H, 5.32;N, 3.95

Example 92

Ethyl 3-([[(3R)-5-oxo-1-(4-phenoxybenzyl)pyrrolidinyl]sulfanyl}propanoate

Similarly to Example 89 and starting from 150 mg (0.501 mmol) of (R)-4-mercapto-1-(4-phenoxybenzyl)pyrrolidin-2-one obtained in Example 25, 70.7 μl (0.551 mmol) of ethyl 3-bromopropionate and 20.0 mg (0.501 mmol) of 60% sodium hydride, 145 mg (yield: 72%) of the title compound was obtained as a colorless oil.
$^1$H-NMR (300 MHz, $CDCl_3$)
δ: 7.34 (2H, m), 7.20 (2H, d, J=8.3 Hz), 7.11 (1H, m), 7.01 (2H, m), 6.97 (2H, d, J=8.3 Hz,), 4.43 (2H, s), 4.15 (1H, q, J=7.2 Hz), 3.61 (1H, dd, J=10.2, 7.5 Hz), 3.49 (1H, m), 3.19 (1H, dd, J=10.2, 5.3 Hz), 2.86 (1H, dd, J=7.0, 8.3 Hz), 2.79 (2H, t, J=7.2 Hz), 2.57 (2H, t, J=7.2 Hz), 2.43 (1H, dd, J=17.0, 6.4 Hz), 1.26 (3H, t, J=7.2 Hz)

Example 93

3-{[(3R)-5-Oxo-1-(4-phenoxybenzyl)pyrrolidinyl]sulfanyl}propanoic acid

Similarly to Example 89 and starting from 150 mg (0.501 mmol) of (R)-4-mercapto-1-(4-phenoxybenzyl)pyrrolidin-2-one obtained in-Example 25, 76.6 μl (0.501 mmol) of 3-bromopropionic acid and 40.1 mg (1.00 mmol) of 60% sodium hydride, 71.5 mg (yield: 38%) of the title compound was obtained as a white powder.
$^1$H-NMR (300 MHz, $CDCl_1$)
δ: 7.34 (2H, m), 7.20 (2H, d, J=8.5 Hz), 7.11 (1H, m), 7.00 (2H, m), 6.96 (2H, d, J=8.5 Hz), 4.43 (2H, s), 3.62 (1H, dd, J=10.0, 7.7 Hz), 3.51 (1H, m), 3.19 (1H, dd, J=10.0, 5.1 Hz), 2.88 (1H, dd, J=17.3, 8.3 Hz), 2.79 (2H, t, J=7.1 Hz), 2.63 (2H, t, J=7.1 Hz), 2.47 (1H, dd, J=17.3, 6.0 Hz)

Example 94

4-[(4-Bromobenzyl)sulfanyl)-1-(4-phenoxybenzyl)-2-pyrrolidinone

Similarly to Example 89 and starting from 80 mg (0.27 mmol) of 4-mercapto-1-(4-phenoxybenzyl)pyrrolidin-2-one obtained in Example 17, 67 mg (0.27 mmol) of p-bromobenzyl bromide and 12 mg (0.30 mmol) of 60% sodium hydride, 110 mg (yield: 87.9%) of the title compound was obtained as a colorless oil.
$^1$H-NMR (200 MHz, $CDCl_1$)
δ: 7.45–6.90 (13H, m), 4.44 (1H, d, J=14.6 Hz), 4.35 (1H, d, J=14.7 Hz), 3.67 (1H, s), 3.46 (1H, dd, J=7.3, 8.0 Hz), 3.32–3.19 (1H, m), 3.10 (1H, dd, J=5.2, 10.0 Hz), 2.76 (1H, dd, J=8.4, 18.0 Hz), 2.39 (1H, dd, J=6.2, 22.0 Hz)

Example 95

Methyl 4-({[(3R)-5-oxo-1-(4-phenoxybenzyl)pyrrolidinyl]sulfanyl}methyl)benzoate 500 mg (1.67 mmol) of (R)-4-mercapto-1-(4-phenoxybenzyl)pyrrolidin-2-one obtained in Example 25 and 383 mg (1.67 mmol) of methyl 4-(bromomethyl) benzoate were dissolved in 5 ml of THF, treated with 67 mg (1.67 mmol) of 60% sodium hydride, and stirred under nitrogen atmosphere at room temperature for 10 minutes. The reaction mixture was concentrated under reduced pressure, dissolved in ethyl acetate, washed with water and saturated brine, and dried over anhydrous sodium sulfate. The reaction mixture was concentrated under reduced pressure and purified by column chromatography on silica gel, and the fraction eluted with n-hexane: ethyl acetate (2:1 to 1:1) was concentrated to obtain 645 mg (yield: 86%) of the title compound as a yellow oil.
Elemental analysis (e): $C_{26}H_{25}NO_4S$
Calcd.: C, 69.78;H, 5.63;N, 3.13
Found: C, 69.64;H, 5.72;N, 3.35

Example 96

4-({[(3R)-5-oxo-1-(4-phenoxybenzyl)pyrrolidinyl] sulfanyl}methyl)benzoic acid 250 mg (0.56 mmol) of methyl 4-(({[(3R)-5-oxo-1-(4-phenoxybenzyl)pyrrolidinyl]sulfanyl}methyl)benzoate obtained in Example 95 and 234 mg (5.59 mmol) of lithium hydroxide monohydrate was stirred at room temperature for 1 hour in a mixture of 2 ml of methanol, 1 ml of water and 1.5 ml of THF. The reaction mixture was treated with ethyl acetate, washed with 1 N hydrochloric acid and then with a mixture of 1 N hydrochloric acid and saturated brine, and dried over anhydrous sodium sulfate. The reaction mixture was concentrated under reduced pressure and purified by preparative thin layer chromatography (eluent: chloroform: methanol (8:1)) to obtain 178 mg (yield: 73%) of the title compound as a colorless glassy substance.
Elemental analysis (%): $C_{25}H_{23}NO_4S.0.1H_2O$
Calcd.: C, 68.97;H, 5.37;N, 3.21
Found: C, 68.89;H, 5.32;N, 3.35

Example 97

1-(4-phenoxybenzyl)-4-({[2-(phenylsulfonyl)ethyl] sulfanyl}-2-pyrrolidinone 150 mg (0.501 mmol) of (R)-4-mercapto-1-(4-phenoxybenzyl)pyrrolidin-2-one obtained in Example 25 was dissolved in 15 ml of THF, cooled on ice, combined under argon gas atmosphere with 168 mg (1.00 mmol) of phenylvinylsulfonic acid and 56.0 μl (0.400 mmol) of triethylamine, and stirred for 48 hours at room temperature. The reaction mixture was treated with ethyl acetate, washed with water and saturated brine, and dried over anhydrous sodium sulfate. The reaction mixture was concentrated under reduced pressure and subjected to column chromatography on silica gel, and the fraction eluted with hexane: ethyl acetate (20:80–10:90) was concentrated under reduced pressure and precipitated from diethyl ether to obtain 101 mg (yield: 43%) of the title compound as a white powder.
Elemental analysis (%): $C_{25}H_{25}NO_4S_2$
Calcd.: C, 64.21;H, 5.39;N, 3.00
Found: C, 64.18;H, 5.61;N, 2.99

Example 98

(4R)-4-[(Methoxymethyl)sulfanyl]-1-(4-phenoxybenzyl)-2-pyrrolidinone

Similarly to Example 64 and starting from 150 mg (0.501 mmol) of (R)-4-mercapto-1-(4-phenoxybenzyl)pyrrolidin-2-one obtained in Example 25, 190 pl (2.51 mmol) of chloromethylether and 349 μl (2.51 mmol) of triethylamine, 158 mg (yield: 92%) of the title compound was obtained as a colorless oil.
Elemental analysis (%): $Cl_{19}H_{21}NO_3S$
Calcd.: C, 66.45;H, 6.61;N, 4.08
Found: C, 66.53;H, 5.87;N, 4.41

Example 99

(4R)-4-[(3-Oxo-1,3-dihydro-2-benzofuran-1-yl) sulfanyl]-1-(4-phenoxybenzyl)-2-pyrrolidinone 180 mg (0.60 mmol) of (R)-4-mercapto-1-(4-phenoxybenzyl)pyrrolidin-2-one obtained in Example 25 and 99.3 mg (0.66 mmol) of O-formylbenzenebenzoic acid were dissolved in 2 ml of trifluoroacetic acid, and stirred at room temperature for 17 hours. The reaction mixture was concentrated under reduced pressure, dissolved in ethyl acetate, washed twice with an saturated aqueous solution of sodium hydrogen carbonate and then with saturated brine, and dried over anhydrous sodium sulfate. The reaction mixture was concentrated under reduced pressure and purified by preparative thin layer chromatography (eluent: n-hexane: ethyl acetate (1:1)) to obtain 224 mg (yield: 86%) of the title compound as a colorless oil.
Elemental analysis (%): $C_{25}H_{21}NO_4S$
Calcd.: C, 69.59;H, 4.91;N, 3.25
Found: C, 69.83;H, 4.82;N, 3.35

Example 100

N-({[(3R)-5-Oxo-1-(4-phenoxybenzyl)pyrrolidinyl] sulfanyl}methyl)acetamide 180 mg (0.60 mmol) of (R)-4-mercapto-1-(4-phenoxybenzyl)pyrrolidin-2-one obtained in Example 25 and 58.9 mg (0.66 mmol) of acetamidemethanol were dissolved in 1 ml of trifluoroacetic acid, and stirred at room temperature for 30 minutes. The reaction mixture was concentrated under reduced pressure, dissolved in ethyl acetate, washed twice with an saturated aqueous solution of sodium hydrogen carbonate and then with saturated brine, and dried over anhydrous sodium sulfate. The reaction mixture was concentrated under reduced pressure and purified by preparative thin layer chromatography (eluent: chloroform: methanol (9:1)) to obtain 167 mg (yield: 75%) of the title compound as a pale brown oil.
Elemental analysis (%): $C_{20}H_{22}N_2O_3S$
Calcd.: C, 64.84;H, 5.99;N, 7.56
Found: C, 64.89;H, 6.26;N, 7.76

Example 101

2,2-Dimethyl-N-({[(3R)-5-oxo-1-(4-phenoxybenzyl) pyrrolidinyl]sulfanyl}methyl)propanamide 220 mg (0.74 mmol) of (R)-4-mercapto-1-(4-phenoxybenzyl)pyrrolidin-2-one obtained in Example 25 and 108.1 mg (0.81 mmol) of N-hydroxyacetamidemethanol were dissolved in 2 ml of trifluoroacetic acid, and stirred at room temperature for 10 minutes. The reaction mixture was concentrated under reduced pressure, dissolved in ethyl acetate, washed twice with an saturated aqueous solution of sodium hydrogen carbonate and then with saturated brine, and dried over anhydrous sodium sulfate. The reaction mixture was concentrated under reduced pressure and purified by preparative thin layer chromatography (eluent: n-hexane: ethyl acetate (1:1)) to obtain 209 mg (yield: 69%) of the title compound as a pale brown oil.

Elemental analysis (%): $C_{23}H_{28}N_2O_3S \cdot 0.1H_2O$
Calcd.: C, 66.67;H, 6.85;N, 6.76
Found: C, 66.55;H, 6.94;N, 6.67

Example 102

N-({[(3R)-5-oxo-1-(4-phenoxybenzyl)pyrrolidinyl]sulfanyl}methyl)benzamide 220 mg (0.74 mmol) of (R)-4-mercapto-1-(4-phenoxybenzyl)pyrrolidin-2-one obtained in Example 25 and 116.7 mg (0.77 mmol) of N-hydroxybenzamidemethanol were dissolved in 2 ml of trifluoroacetic acid, and stirred at room temperature for 10 minutes. The reaction mixture was concentrated under reduced pressure, purified by preparative thin layer chromatography (eluent: n-hexane: ethyl acetate (1:3)) and precipitated from ethyl acetate to obtain 172 mg (yield: 54%) of the title compound as a white powder.
Elemental analysis (%): $C_{25}H_{24}N_2O_3S \cdot 0.1H_2O$
Calcd.: C, 69.13;H, 5.61;N, 6.44
Found: C, 69.11;H, 5.61;N, 6.34

Example 103

Ethyl {[(3R)-5-oxo-1-(4-phenoxybenzyl)pyrrolidinyl]sulfanyl}methylcarbamate 200 mg (0.67 mmol) of (R)-4-mercapto-1-(4-phenoxybenzyl)pyrrolidin-2-one obtained in Example 25 and 88 mg (0.73 mmol) of N-(hydroxymethyl)urethane were dissolved in 2 ml of trifluoroacetic acid, and stirred at room temperature for 10 minutes. The reaction mixture was concentrated under reduced pressure, dissolved in ethyl acetate, washed with water and saturated brine, and dried over anhydrous sodium sulfate. The reaction mixture was concentrated under reduced pressure and purified by preparative thin layer chromatography (eluent: n-hexane: ethyl acetate (1:2)) to obtain 177 mg (yield: 66%) of the title compound as a pale yellow oil.
Elemental analysis (%): $C_{21}H_{24}N_2O_4S \cdot 0.1H_2O$
Calcd.: C, 62.69;H, 6.06;N, 6.96
Found: C, 62.45;H, 6.07;N, 6.91

Example 104

2-({[(3R)-5-oxo-1-(4-phenoxybenzyl)pyrrolidinyl]sulfanyl}methyl)-1H-isoindole-1,3-(2H)-dione 220 mg (0.74 mmol) of (R)-4-mercapto-1-(4-phenoxybenzyl)pyrrolidin-2-one obtained in Example 25 and 176 mg (0.74 mmol) of N-(bromomethyl)phthalimide were dissolved in 2 ml of THF, treated with 29 mg (0.74 mmol) of 60% sodium hydride and stirred at room temperature under nitrogen atmosphere for 50 minutes. The reaction mixture was concentrated under reduced pressure, dissolved in ethyl acetate, washed twice with 0.1 N hydrochloric acid and then with saturated brine, and dried over anhydrous sodium sulfate. The reaction mixture was concentrated under reduced pressure and purified by preparative thin layer chromatography (eluent: n-hexane: ethyl acetate (1:2)) to obtain 253 mg (yield: 75%) of the title compound as a colorless oil.
Elemental analysis (%): $C_{26}H_{22}N_2O_4S \cdot 0.1H_2O$
Calcd.: C, 67.83;H, 4.86;N, 6.08
Found: C, 67.74;H, 4.97;N, 6.05

Example 105

3-{[(3R)-5-Oxo-1-(4-phenoxybenzyl)pyrrolidinyl]sulfanyl}-2,5-pyrrolidinedione 150 mg (0.50 mmol) of (R)-4-mercapto-1-(4-phenoxybenzyl)pyrrolidin-2-one obtained in Example 25 was dissolved in 1.5 ml of chloroform, treated with 54 mg (0.55 mmol) of maleimide and 7 µl (catalytic amount) of triethylamine, and stirred at room temperature for 2 hours. The reaction mixture was concentrated under reduced pressure, dissolved in ethyl acetate, washed twice with water and then with saturated brine, and dried over anhydrous sodium sulfate. The reaction mixture was concentrated under reduced pressure and purified by preparative thin layer chromatography (eluent: chloroform: methanol (8:1)) to obtain 165 mg (yield: 83%) of the title compound as a milky white powder.
Elemental analysis (e): $C_{21}H_{20}N_2O_4S \cdot 0.2H_2O$
Calcd.: C, 63.04;H, 5.13;N, 7.00
Found: C, 63.00;H, 4.99;N, 6.94

Example 106

1-Methyl-3-f[(3R)-5-oxo-1-(4-phenoxybenzyl)pyrrolidinyl]sulfanyl}-2,5-pyrrolidinedione 150 mg (0.50 mmol) of (R)-4-mercapto-1-(4-phenoxybenzyl)pyrrolidin-2-one obtained in Example 25 was dissolved in 1.5 ml of chloroform, treated with 61 mg (0.55 mmol) of N-methylmaleimide and 7 µl (catalytic amount) of triethylamine, and stirred at room temperature for 2 hours. The reaction mixture was concentrated under reduced pressure, dissolved in ethyl acetate, washed three times with water and then with saturated brine, and dried over anhydrous sodium sulfate. The reaction mixture was concentrated under reduced pressure and purified by preparative thin layer chromatography (eluent: chloroform: methanol (15:1)) to obtain 155 mg (yield: 75%) of the title compound as a pale yellow oil.
Elemental analysis (%): $C_{22}H_{22}N_2O_4S \cdot 0.3H_2O$
Calcd.: C, 63.53;H, 5.47;N, 6.73
Found: C, 63.28;H, 5.40;N, 6.50

Example 107

O-Ethyl S—[(3R)-5-oxo-1-(4-phenoxybenzyl)pyrrolidinyl]carbanothioate 180 mg (0.60 mmol) of (R)-4-mercapto-1-(4-phenoxybenzyl)pyrrolidin-2-one obtained in Example 25 was dissolved in 1 ml of chloroform, and 63 µl (0.66 mmol) of ethyl chloroformate at 0° C. was added and then a solution of 92 µl (0.66 mmol) of triethylamine in 1 ml of chloroform was added dropwise, and after completion of the addition the mixture was stirred at 0° C. for 1 hour. The reaction mixture was concentrated under reduced pressure, dissolved in ethyl acetate, washed twice with water and then with saturated brine, and dried over anhydrous sodium sulfate. The reaction mixture was concentrated under reduced pressure and purified by preparative thin layer chromatography (eluent: n-hexane: ethyl acetate (1:2)) to obtain 184 mg (yield: 83%) of the title compound as a pale yellow oil.
Elemental analysis (%): $C_{20}H_{21}NO_4S \cdot 0.1H_2O$
Calcd.: C, 64.35;H, 5.72;N, 3.75
Found: C, 64.15;H, 5.71;N, 3.85

Example 108

S—[6-Oxo-1-(4-phenoxybenzyl)-3-piperidinyl]ethanethioate 179 mg (0.77 mmol) of 5-{[tert-butyl(dimethyl)silyl]oxy)-2-piperidinone synthesized by a method known in a literature (Arch. Pharm. (Weinheim), 316, pp719–723, 1983), 34 mg (0.86 mmol) of 60% sodium hydride and 149 µl (0.82 mmol) of 4-phenoxybenzyl chloride were stirred in 2 ml of THF at room temperature for 16 hours. The reaction mixture was concentrated under reduced pressure, treated with ethyl acetate, washed twice with water and then with saturated brine, and dried over anhydrous sodium sulfate. The reaction mixture was concentrated under reduced pressure to obtain 5-{[tert-butyl(dimethyl)silyl]oxy}-1-(4-phenoxybenzyl)-2-piperidinone which was then dissolved in 1 ml of THF, treated with 1.74 ml (1.74 mmol) of a 1M solution of tetrabutylammonium fluoride in THF and stirred at room temperature for 30 minutes. The reaction mixture was concentrated under reduced pressure and purified by preparative thin layer chromatography (eluent: methanol: ethyl acetate (1:9)) (yield: 83% in 2 steps) to obtain 187 mg (0.628 mmol) of 5-hydroxy-1-(4-phenoxybenzyl)-2-piperidinone, which was stirred together with 131 µl (0.94 mmol) of triethylamine and 73 µl (0.94 mmol) of methanesulfonyl chloride in 2 ml of chloroform at room temperature for 15 minutes. The reaction mixture was concentrated under reduced pressure, treated with ethyl acetate, washed twice with water and then with saturated brine, and dried over anhydrous sodium sulfate to obtain (yield: 87%) 205 mg (0.55 mmol) of 6-oxo-1-(4-phenoxybenzyl)-3-piperidinyl methanesulfonate which was then dissolved in 2 ml of DMF, treated with 106 mg (0.93 mmol) of potassium thioacetate, and stirred at 70° C. for 12 hours. The reaction mixture was treated with ethyl acetate, washed 5 times with water and then with saturated brine, and dried over anhydrous sodium sulfate. The reaction mixture was concentrated under reduced pressure and purified by preparative thin layer chromatography (eluent: n-hexane: ethyl acetate (2:1)) to obtain 97 mg (yield: 50%) of the title compound as a pale yellow oil.
Elemental analysis (%): $C_{20}H_{22}NO_3S$
Calcd.: C, 67.58;H, 5.95;N, 3.94
Found: C, 67.33;H, 5.90;N, 3.80

Example 109

1-(4-Phenoxybenzyl)-5-sulfanyl-2-piperidinone 20 mg (0.056 mmol) of S—[6-oxo-1-(4-phenoxybenzyl)-3-piperidinyl]ethanethioate obtained in Example 108 was dissolved in 0.2 ml of ethanol, and 80 µl (1.13 mmol) of acetyl chloride was added slowly. Thereafter, the mixture was stirred at 50° C. for 1 hour, concentrated under reduced pressure, dissolved in ethyl acetate, washed with saturated brine and dried over anhydrous sodium sulfate. The reaction mixture was concentrated under reduced pressure and purified by preparative thin layer chromatography (eluent: n-hexane: ethyl acetate (2:3)) to obtain 14 mg (yield: 78%) of the title compound as a colorless oil.
$^1$H-NMR (300 MHz, $CDCl_3$)
δ: 7.36–6.95 (9H, m), 4.59 (1H, d, J=14.6 Hz), 4.50 (1H, d, J=14.6 Hz), 3.51–3.43 (1H, m), 3.25–3.13 (2H, m), 2.71–2.45 (2H, m), 2.25–2.16 (1H, m), 1.90–1.77 (1H, m), 1.62–1.59 (1H, m)

Example 110

S—[2-Oxo-1-(4-phenoxybenzyl)-4-piperidinyl] ethanethioate

Using alanine ethyl ester instead of glycine ethyl ester and by a method similar to that in Example 15, S—[2-oxo-1-(4-phenoxybenzyl)-4-piperidinyl]ethanethioate was obtained.
$^1$H-NMR (200 MHz, $CDCl_3$)
d: 7.40–6.90 (9H, m), 4.62 (1H, d, J=14.7 Hz), 4.52 (1H, d, J=14.5 Hz), 3.92–3.78 (1H, m), 3.32 (1H, d, J=5.2 Hz), 3.29 (1H, d, J=5.3 Hz), 2.87 (1H, dd, J=5.7, 16.0 Hz), 2.50 (1H, dd, J=9.1, 18.0 Hz), 2.33 (3H, s), 2.25–2.05 (1H, m), 1.95–1.76 (1H, m)

Example 111

1-(4-Phenoxybenzyl)-4-sulfanyl-2-piperidinone

From 20 mg (0.054 mmol) of S—[2-oxo-1-(4-phenoxybenzyl)-4-piperidinyl]ethanethioate obtained in Example 110 and by a method similar to that in Example 184, 14 mg (yield: 82.6%) of 1-(4-phenoxybenzyl)-4-sulfanyl-2-piperidinone was obtained as a colorless oil.
$^1$H-NMR (200 MHz, $CDCl_3$)
d: 7.40–6.90 (9H, M), 4.66 (1H, d, J=14.4 Hz), 4.48 (1H, d, J=14.6 Hz), 3.45–3.20 (3H, m), 2.92 (1H, dd, J=5.3, 18.0 Hz), 2.48 (1H, dd, J=9.1, 18.0 Hz), 2.25–2.10 (1H, m), 1.90–1.70 (1H, m), 1.67 (1H, d, J=6.5 Hz)

Example 112

4-Acetylthio-1-[4-(2'-fluorophenoxy)benzyl] pyrrolidin-2-one

By a method similar to that in Example 30 and starting from 1.67 g (8.1 mmol) of 4-(2'-fluorophenoxy)benzyl chloride prepared from 4-fluorobenzaldehyde and 2-fluorophenol and 1.70 g (9.8 mmol) of 4-trimethylsilyloxypyrrolidin-2-one, 396 mg (yield: 17%) of 4-acetylthio-1-[4-(2'-fluorophenoxy)benzyl]pyrrolidin-2-one was obtained as a tan oil.
Elemental analysis (%): $C_{19}H_{18}NO_3SF$
Calcd.: C, 63.49;H, 5.05;N, 3.90;S, 8.92
Found: C, 63.24;H, 5.11;N, 3.85;S, 9.01

Example 113

4-Mercapto-1-[4-(2'-fluorophenoxy)benzyl) pyrrolidin-2-one

By a method similar to that in Example 31 and starting from 112 mg (0.30 mmol) of 4-acetylthio-1-[4-(2'-fluorophenoxy)benzyl]pyrrolidin-2-one obtained in Example 112, 97.0 mg (yield: 98%) of 4-mercapto-1-[4-(2'-fluorophenoxy)benzyl]pyrrolidin-2-one was obtained as a colorless oil.
$^1$H-NMR (300 MHz, $CDCl_3$)
δ: 7.20 (2H, d, J=8.5 Hz), 7.17–7.03 (4H, m), 6.94 (2H, d, J=8.5 Hz), 4.47 (1H, d, J=14.7 Hz), 4.40 (1H, d, J=14.7 Hz), 3.64 (1H, dd, J=10.0, 7.2 Hz), 3.53 (1H, m), 3.16 (1H, dd, J=10.0, 5.0 Hz), 2.91 (1H, dd, J=17.1, 8.1 Hz), 2.42 (1H, dd, J=17.1, 6.1 Hz), 1.86 (1H, d, J=6.7 Hz)

Example 114

4-Acetylthio-1-[4-(3$^1$-fluorophenoxy)benzyl] pyrrolidin-2-one

By a method similar to that in Example 30 and starting from 1.73 g (7.3 mmol) of 4-(3'-fluorophenoxy)benzyl chloride prepared from 4-fluorobenzaldehyde and 3-fluorophenol and 1.90 g (11 mmol) of 4-trimethylsilyloxypyrrolidin-2-one, 664 mg (yield: 25%) of 4-acetylthio-1-[4-(3'-fluorophenoxy)benzyl]pyrrolidin-2-one was obtained as a tan oil.

Elemental analysis (%): $C_{19}H_{18}NO_3SF$
Calcd.: C, 63.49;H, 5.05;N, 3.90;S, 8.92
Found: C, 63.19;H, 5.08;N, 3.79;S, 9.00

Example 115

4-Mercapto-1-[4-(3'-fluorophenoxy)benzyl]pyrrolidin-2-one

By a method similar to that in Example 31 and starting from 205 mg (0.60 mmol) of 4-acetylthio-1-[4-(3'-fluorophenoxy)benzyl]pyrrolidin-2-one obtained in Example 112, 143 mg (yield: 75%) of 4-mercapto-1-[4-(3'-fluorophenoxy)benzyl]pyrrolidin-2-one was obtained as a colorless oil.
$^1$H-NMR (300 MHz, CDCl$_3$)
δ: 7.28 (1H, m), 7.24 (2H, d, J=8.5 Hz), 7.00 (2H, d, J=8.5 Hz), 6.79 (2H, ddd, J=11.4, 8.3, 2.5 Hz), 6.69 (1H, ddd, J=10.2, 2.3, 2.3 Hz), 4.49 (1H, d, J=14.8 Hz), 4.42 (1H, d, J=14.8 Hz), 3.67 (1H, dd, J=10.1, 7.2 Hz), 3.55 (1H, m), 3.18 (1H, dd, J=10.1, 5.0 Hz), 2.92 (1H, dd, J=17.1, 8.1 Hz), 2.43 (1H, dd, J=17.1, 6.1 Hz), 1.88 (1H, d, J=6.7 Hz)

Example 116

(S)-4-Acethylthio-1-[4-(4'-fluorophenoxy)benzyl]pyrrolidin-2-one

4-Acetylthio-1-(4-(4'-fluorophenoxy)benzyl)pyrrolidin-2-one synthesized in Example 30 was resolved by HPLC using a chiral column (DAICEL, CHIRALCEL OD 20×250 mm) (mobile phase=hexane: ethanol (90:10), flow rate=10 ml/min, Detection at 254 nm) to obtain (S)-4-acetylthio-1-[4-(4'-fluorophenoxy)benzyl]pyrrolidin-2-one.
$^1$H—NR (300 MHz, CDCl$_3$)
δ: 7.18 (2H, d, J=8.5 Hz), 7.04 (2H, dd, J=9.3, 8.0 Hz), 6.97 (2H, dd, J=9.3, 4.7 Hz), 6.92 (2H, d, J=8.5 Hz), 4.45 (1H, d, J=15.2 Hz), 4.39 (1H, d, J=15.2 Hz), 4.05 (1H, m), 3.75 (1H, dd, J=10.6, 7.6 Hz), 3.17 (1H, dd, J=10.6, 5.0 Hz), 2.91 (1H, dd, J=17.4, 9.0 Hz), 2.42 (1H, dd, J=17.4, 6.1 Hz), 2.32 (3H, s)

Example 117

(R)-4-Acethylthio-1-[4-(4'-fluorophenoxy)benzyl)pyrrolidin-2-one

By a method similar to that in Example 116, 4-acetylthio-1-(4-(4'-fluorophenoxy)benzyl)pyrrolidin-2-one synthesized in Example 30 was resolved by HPLC using a chiral column to obtain (R)-4-acetylthio-1-[4-(4'-fluorophenoxy)benzyl]pyrrolidin-2-one.
$^1$H-NMR (300 MHz, CDCl$_3$)
δ: 7.18 (2H, d, J=8.5 Hz), 7.04 (2H, dd, J=9.3, 8.0 Hz), 6.97 (2H, dd, J=9.3, 4.7 Hz), 6.92 (2H, d, J=8.5 Hz), 4.45 (1H, d, J=15.2 Hz), 4.39 (1H, d, J=15.2 Hz), 4.05 (1H, m), 3.75 (1H, dd, J=10.6, 7.6 Hz), 3.17 (1H, dd, J=10.6, 5.0 Hz), 2.91 (1H, dd, J=17.4, 9.0 Hz), 2.42 (1H, dd, J=17.4, 6.2 Hz), 2.32 (3H, s)

Example 118

(R)-4-Mercapto-1-[4-(4'-fluorophenoxy)benzyl]pyrrolidin-2-one

By a method similar to that in Example 31 and starting from (R)-4-acethylthio-1-[4-(4'-fluorophenoxy)benzyl]pyrrolidin-2-one obtained in Example 117, (R)-4-mercapto-1-[4-(4'-fluorophenoxy)benzyl]pyrrolidin-2-one was obtained.
$^1$H-NMR (300 MHz, CDCl$_3$)
δ: 7.22–6.91 (8H, m), 4.47 (1H, d, J=14.7 Hz), 4.39 (1H, d, J=14.7 Hz), 3.64 (1H, dd, J=10.0, 7.2 Hz), 3.59–3.48 (1H, m), 3.16 (1H, dd, J=10.0, 5.0 Hz), 2.91 (1H, dd J=17.1, 8.1 Hz), 2.42 (1H, dd, J=17.0, 6.1 Hz), 1.86 (1H, d, J=6.7 Hz)

Example 119

4-Acetylthio-1-[4-(2', 4'-difluorophenoxy)benzyl]pyrrolidin-2-one

By a method similar to that in Example 30 and starting from 1.83 g (7.2 mmol) of 4-(2, 4'-difluorophenoxy)benzyl chloride prepared from 4-fluorobenzaldehyde and 2,4-difluorophenol and 1.50 g (8.6 mmol) of 4-trimethylsilyloxypyrrolidin-2-one, 288 mg (yield: 10%) of 4-acetylthio-1-[4-(2', 41-difluorophenoxy)benzyl]pyrrolidin-2-one was obtained as a white powder.
Elemental analysis (%): $C_{19}H_{17}NO_3SF_2$
Calcd.: C, 60.47;H, 4.54;N, 3.71;S, 8.50
Found: C, 60.69;H, 4.64;N, 3.81;S, 8.49

Example 120

4-Mercapto-1-[4-(2', 4'-difluorophenoxy)benzyl]pyrrolidin-2-one

By a method similar to that in Example 31 and starting from 10 mg (0.26 mmol) of 4-acetylthio-1-[4-(2', 4'-difluorophenoxy)benzyl]pyrrolidin-2-one obtained in Example 119, 60.0 mg (yield: 69%) of 4-mercapto-1-[4-(2', 4'-difluorophenoxy)benzyl]pyrrolidin-2-one was obtained as a white powder.
$^1$H-NMR (300 MHz, CDCl$_3$)
δ: 7.19 (2H, d, J=8.5 Hz), 7.06 (1H, ddd, J=14.5, 9.0, 5.5 Hz), 7.00–6.88 (2H, m), 6.89 (2H d, J=8.5 Hz), 4.46 (1H, d, J=14.7 Hz), 4.38 (1H, d, J=14.7 Hz), 3.64 (1H, dd, J=10.0, 7.2 Hz), 3.53 (1H, m), 3.15 (1H, dd, J=10.0, 5.0 Hz), 2.90 (1H, dd, J=17.1, 8.1 Hz), 2.41 (1H, dd, J=17.1, 6.1 Hz), 1.85 (1H, d, J=6.7 Hz)

Example 121

4-Acetylthio-1-[4-(3', 4'-difluorophenoxy)benzyl]pyrrolidin-2-one

By a method similar to that in Example 30 and starting from 1.90 g (7.5 mmol) of 4-(3', 4'-difluorophenoxy)benzyl chloride prepared from 4-fluorobenzaldehyde and 3,4-difluorophenol and 1.60 g (9.0 mmol) of 4-trimethylsilyloxypyrrolidin-2-one, 506 mg (yield: 19%) of 4-acetylthio-1-[4-(3', 4'-difluorophenoxy)benzyl]pyrrolidin-2-one was obtained as a pale tan powder.
Elemental analysis (%): $C_{19}H_{17}NO_3SF_2$
Calcd.: C, 60.47;H, 4.54;N, 3.71;S, 8.50
Found: C, 60.45;H, 4.51;N, 3.78;S, 8.48

Example 122

4-Mercapto-1-[4-(3', 4'-difluorophenoxy)benzyl)pyrrolidin-2-one

By a method similar to that in Example 31 and starting from 100 mg (0.26,mmol) of 4-acetylthio-1-[4-(3', 4'-difluorophenoxy)benzyl]pyrrolidin-2-one obtained in Example 121, 55.0 mg (yield: 63%) of 4-mercapto-1-[4-(3', 4'-difluorophenoxy)benzyl]pyrrolidin-2-one was obtained as a white powder.

¹H-NMR (300 MHz, CDCl₃)
δ: 7.24 (2H, d, J=8.5 Hz), 7.12 (1H, dd, J=18.8, 9.1 Hz), 6.96 (2H, d, J=8.5 Hz), 6.83 (1H, ddd, J=11.2, 6.6, 2.9 Hz), 6.72 (1H, m), 4.49 (1H, d, J=14.8 Hz), 4.40 (1H, d, J=14.8 Hz), 3.67 (1H, dd, J=10.0, 7.2 Hz), 3.55 (11H, m), 3.17 (1H, dd, J=10.0, 5.0 Hz), 2.92 (1H, dd, J=17.1, 8.1 Hz), 2.43 (1H, dd, J=17.1, 6.1 Hz), 1.87 (1H, d, J=6.7 Hz)

Example 123

(R)-4-Acethylthio-1-[4-(4'-methylphenoxy)benzyl]pyrrolidin-2-one (1) 5.00 g (24 mmol) of 4-(4'-methylphenoxy)benzaldehyde prepared from 4-fluorobenzaldehyde and 4-cresol similarly to Example 30 was dissolved in 60 ml of ethanol and 30 ml of water, treated with 3.90 g (47 mmol) of sodium acetate and 2.10 g (31 mmol) of hydroxyammonium chloride, and heated under reflux for 2 hours. The reaction mixture was concentrated under reduced pressure, treated with water and extracted twice with ethyl acetate, and the organic layer obtained was washed with water and saturated brine, and dried over anhydrous sodium sulfate. The mixture was concentrated under reduced pressure, and the residue was solidified with hexane-ethyl acetate. The powder thus obtained was dissolved in 100 ml of methanol, and 250 mg of 10% Pd/C was added, and the mixture was stirred at room temperature under hydrogen atmosphere. The reaction mixture was filtered, concentrated under reduced pressure, treated with water and extracted twice with ethyl acetate, and the organic layer obtained was washed with saturated sodium bicarbonate and saturated brine and dried over anhydrous sodium sulfate. After filtration, a 4N solution of hydrochloric acid in ethyl acetate was added to obtain 4.50 g (yield: 76%) of 4-(4'-methylphenoxy)benzylamine hydrochloride as a white powder.

¹H-NMR (300 MHz, CD₃OD)
δ: 8.23 (2H, brs), 7.46 (2H, d, J=8.6 Hz), 7.22 (2H, d, J=8.3 Hz), 7.00 (2H, d, J=8.6 Hz), 6.91 (2H, d, J=8.3 Hz), 4.11 (0.5H, brs), 3.99 (1.5H, brs), 2.33 (3H, s), (2) 4.50 g (18 mmol) of 4-(4'-methylphenoxy)benzylamine hydrochloride was dissolved in a solvent mixture of 25 ml of tetrahydrofuran and 50 ml of acetonitrile, treated with 2.8 ml (20 mmol) of triethylamine, and stirred at room temperature for 40 minutes. To 4.00 g (25 mmol) of (S)—O-acetylmalic anhydride (TOKYO KASEI) was added, and the mixture was stirred at room temperature for 4.5 hours. The reaction mixture was concentrated under reduced pressure, dissolved in 50 ml of acetyl chloride, and heated under reflux for 3 hours. The mixture was concentrated under reduced pressure, treated with ethyl acetate, washed with saturated sodium bicarbonate and saturated brine, and dried over anhydrous sodium sulfate. The mixture was concentrated under reduced pressure, and the residue was subjected to column chromatography on silica gel eluting with hexane: ethyl acetate (80:20–75:25) to obtain 3.80 g (yield: 60%) of (S)-3-acetoxy-1-[4-(4'-methylphenoxy)benzyl]pyrrolidine-2,5-dione as a yellow oil.

¹H-NMR (300 MHz, CDCl₃)
δ: 7.34 (2H, d, J=8.6 Hz), 7.14 (2H, d, J=8.2 Hz), 6.91 (2H, d, J=8.6 Hz), 6.90 (2H, d, J=8.2 Hz), 5.45 (1H, dd, J=8.7, 4.8 Hz), 4.68 (1H, d, J=13.2 Hz), 4.63 (1H, d, J=13.2 Hz), 3.16 (1H, dd, J=18.3, 8.7 Hz), 2.67 (1H, dd, J=18.3, 4.8 Hz), 2.33 (3H, s), 2.16 (3H, s)

(3) 3.60 g (10 mmol) of (S)-3-acetoxy-1-[4-(4'-methylphenoxy)benzyl]pyrrolidine-2,5-dione was dissolved in a solvent mixture of 40 ml of tetrahydrofuran and 20 ml of ethanol, and stirred at −18 to −13° C. When the temperature became the lowest, 386 mg (10 mmol) of sodium borohydride was added, and the mixture was stirred at −18 to −13° C. for 8 hours. After the reaction and when the temperature became the lowest, saturated sodium bicarbonate and saturated brine were added, and the mixture was extracted three times with ethyl acetate, and the organic layer obtained was washed with saturated brine and dried over anhydrous sodium sulfate. The mixture was concentrated under reduced pressure, and the residue was treated with 50 ml of trifluoroacetic acid and 1.6 ml (10 mmol) of triethylsilane, and stirred at room temperature for 35 minutes. 2.8 ml (20 mmol) of triethylamine was added, and the mixture was stirred at room temperature for 40 minutes. The residue obtained by concentrating under reduced pressure after completion of the reaction was added to a solution of 30 ml of ethanol with 15 ml (0.20 mol) of acetyl chloride, and heated at 50° C. with stirring for 2 hours. The mixture was concentrated under reduced pressure, and the residue was subjected to column chromatography on silica gel eluting with hexane:acetone (50:50) to obtain 2.20 g (yield: 73%) of (S)-4-hydroxy-1-[4-(4'-methylphenoxy)benzyl]pyrrolidin-2-one as a white powder.

¹H-NMR (300 MHz, CDCl₃)
δ: 7.18 (2H, d, J=8.5 Hz), 7.14 (2H, d, J=8.3 Hz), 6.93 (2H, d, J=8.5 Hz), 6.90 (2H, d, J=8.3 Hz), 4.49 (1H, m), 4.44 (2H, s), 3.52 (1H, dd, J=10.9, 5.6 Hz), 3.20 (1H, dd, J=10.9, 1.9 Hz), 2.74 (1H, dd, J=17.4, 6.6 Hz), 2.44 (1H, dd, J=17.4, 2.3 Hz), 2.35 (1H, brs), 2.33 (3H, s)

(4) 2.00 g (6.7 mmol) of (S)-4-hydroxy-1-[4-(4'-methylphenoxy)benzyl]pyrrolidin-2-one was dissolved in 15 ml of chloroform, and 0.73 ml (9.4 mmol) of methanesulfonyl chloride was added and the mixture was stirred with cooling on ice. To this mixture, a solution of 1.3 ml (9.4 mmol) of triethylamine in 5 ml of chloroform was added dropwise over a period of 10 minutes, and the mixture was stirred further for 3 hours with cooling on ice. The mixture was concentrated under reduced pressure, treated with ethyl acetate, washed three times with water and then with saturated brine, and dried over anhydrous sodium sulfate. The mixture was concentrated under reduced pressure, and the residue was washed with ethyl acetate-hexane to obtain 2.40 g (yield: 95%) of (S)-4-methanesulfonyloxy-1-[4-(4'-methylphenoxy)benzyl]pyrrolidin-2-one as a white powder.

¹H-NMR (300 MHz, CDCl₃)
δ: 7.18 (2H, d, J=8.6 Hz), 7.15 (2H, d, J=8.6 Hz), 6.94 (2H, d, J=8.3 Hz), 6.91 (2H, d, J=8.3 Hz), 5.29 (1H, m), 4.49 (1H, d, J=15.0 Hz), 4.42 (1H, d, J=15.0 Hz), 3.66 (1H, dd, J=12.0, 5.7 Hz), 3.52 (1H, dd, J=12.0, 2.0 Hz), 3.02 (3H, s), 2.87 (1H, dd, J=17.9, 6.8 Hz), 2.71 (1H, dd, J=17.9, 2.5 Hz), 2.34 (3H, s)

(5) 1.30 g (8.30 mmol) of cesium carbonate was dispersed in 10 ml of N,N-dimethylformamide, and 2.1 ml (30 mmol) of thioacetic acid was added, and the mixture was stirred at room temperature for several minutes. Thereafter, the mixture was deaerated under reduced pressure to obtain a solution of cesium thioacetate. 2.20 g (5.9 mmol) of (S)-4-methanesulfonyloxy-1-[4-(4'-methylphenoxy)benzyl]pyrrolidin-2-one was dissolved in 10 ml of N,N-dimethylformamide to which the solution of cesium thioacetate prepared above was added, and the mixture was further deaerated under reduced pressure. This solution was stirred under nitrogen atmosphere at room temperature for 61 hours. This reaction mixture was treated with water and extracted three times with ethyl acetate, and the organic layer obtained was washed three times with water and then with saturated brine, and dried over anhydrous sodium sulfate. The mixture was concentrated under reduced pressure, and the residue was subjected to column chromatography on silica gel eluting with hexane: ethyl acetate (80:20–70:30) and the effluent was treated with an activated charcoal to obtain 1.70 g (yield: 81%) of (R)-4-acethylthio-1-[4-(4'-methylphenoxy)benzyl]pyrrolidin-2-one as a pale red oil.

$^1$H-NMR (300 MHz, CDCl$_3$)

δ: 7.17 (2H, d, J=8.4 Hz), 7.13 (2H, d, J=8.3 Hz), 6.93 (2H, d, J=8.4 Hz), 6.91 (2H, d, J=8.3 Hz), 4.45 (1H, d, J=14.7 Hz), 4.38 (1H, d, J=14.7 Hz), 4.05 (1H, m), 3.75 (1H, dd, J=10.7, 7.6 Hz), 3.16 (1H, dd, J=10.7, 5.0 Hz), 2.91 (1H, dd, J=17.4, 9.0 Hz), 2.41 (1H, dd, J=17.4, 6.0 Hz), 2.34 (3H, s), 2.32 (3H, s)

Example 124

(R)-4-Acethylthio-1-[4-(4'-ethylphenoxy)benzyl]pyrrolidin-2-one

By a method similar to that in Example 123 and starting from 4-(4'-methylphenoxy)benzylamine, which was prepared from 4-fluorobenzaldehyde and 4-ethylphenol, and (S)—O—acetylmalic anhydride, (R)-4-acethylthio-1-[4-(4'-ethylphenoxy)benzyl]pyrrolidin-2-one was obtained as a pale red oil.

$^1$H-NMR (300 MHz, CDCl$_3$)

δ: 7.17 (4H, d, J=8.5 Hz), 6.92 (2H, d, J=8.6 Hz), 6.92 (2H, d, J=8.5 Hz), 4.46 (1H, d, J=14.7 Hz), 4.39 (1H, d, J=14.7 Hz), 4.05 (1H, m), 3.75 (1H, dd, J=10.6, 7.5 Hz), 3.16 (1H, dd, J=10.6, 5.0 Hz), 2.91 (1H, dd, J=17.4, 8.9 Hz), 2.63 (2H, q, J=7.6 Hz), 2.42 (1H, dd, J=17.4, 6.0 Hz), 2.31 (3H, s), 1.24 (3H, t, J=7.6 Hz)

Example 125

(R)-4-Acethylthio-1-[4-(4-chlorophenoxy)benzyl]pyrrolidin-2-one (1) Starting from 30.0 g (233 mmol) of 4-chlorophenol, 28.9 g (233 mmol) of 4-fluorobenzaldehyde and 32.2 g (233 mmol) of potassium carbonate, 51.8 g (yield: 96%) of 4-(4-chlorophenoxy)benzaldehyde was obtained as pale yellow prisms.

$^1$H-NMR (300 MHz, CDCl$_3$)

δ: 9.93 (1H, s), 7.86 (2H, d, J=8.7 Hz), 7.38 (2H, d, J=9.0 Hz), 7.04 (4H, m)

(2) Starting from 46.5 g (200 nmmol) of 4-(4-chlorophenoxy)benzaldehyde, 17.4 g (250 mmol) of hydroxylamine hydrochloride and 25.2 g (300 mmol) of sodium hydrogen carbonate, 47.9 g (yield: 97%) of 4-(4-chlorophenoxy)benzaldehyde oxime was obtained as a white powder.

$^1$H-NMR (300 MHz, CDCl3)

δ: 8.11 (1H, s), 7.55 (2H, d, J=8.7 Hz), 7.32 (2H, d, J=9.1 Hz), 6.98 (4H, m)

(3) 800 ml of diethyl ether was treated with 22.8 g (600 mmol) of lithium aluminum hydride, and a solution of 46.9 g (189 mmol) of 4-(4-chlorophenoxy)benzaldehyde oxime in 200 ml of diethyl ether was added dropwise over a period of 1 hour with stirring. The reaction mixture was treated with water with cooling on ice and filtered through Celite, and the precipitate was washed with ethyl acetate, and the organic phase was washed with water and saturated brine, and dried over anhydrous sodium sulfate. The mixture was concentrated under reduced pressure, dissolved in ethyl acetate, treated with 80 ml of 4N hydrochloric acid/ethyl acetate and then allowed to stand. The precipitate was collected by filtration, washed several times with diethyl ether and dried to obtain 43.7 g (yield: 86%) of 4-(4-chlorophenoxy)benzylamine hydrochloride as a white powder.

$^1$H-NMR (300 MHz, DMSO-d$_6$)

δ: 8.42 (2H, brs), 7.53 (2H, d, J=8.3 Hz), 7.46 (2H, d, J=8.9 Hz), 7.08 (2H, d, J=8.3 Hz), 7.02 (2H, d, J=8.9 Hz), 4.00 (2H, s)

(4) Similarly to Example 123 and starting from 30.0 g (111 mmol) of 4-(4-chlorophenoxy)benzylamine hydrochloride, 15.5 ml (111 mmol) of triethylamine and 20.2 g (128 mmol) of (S)—O-acetylmalic anhydride, 39.4 g (yield: 95%) of (S)-3-acetoxy-1-[4-(4-chlorophenoxy)benzyl]succinimide was obtained as a colorless oil.

$^1$H-NMR (300 MHz, CDCl$_3$)

δ: 7.36 (2H, d, J=8.7 Hz), 7.28 (2H, d, J=9.0 Hz), 6.93 (4H, m), 5.45 (1H, dd, J=8.9, 4.9 Hz), 4.70 (1H, d, J=14.3 Hz), 4.64 (1H, d, J=14.3 Hz), 3.17 (1H, dd, J=18.5, 8.9 Hz), 2.68 (1H, dd, J=18.5, 4.9 Hz), 2.16 (3H, s)

(5) 39.0 g (104 mmol) of (S)-3-acetoxy-1-[4-(4-chlorophenoxy)benzyl]succinimide, 3.93 g (104 mmol) of sodium borohydride and 16.6 ml (104 mmol) of triethylsilane were subjected respectively to a reduction, followed by hydrolysis to obtain 14.8 g (yield: 45%) of (S)-4-hydroxy-1-[4-(4-chlorophenoxy)benzyl]pyrrolidin-2-one as a pale yellow oil.

Elemental analysis (%): C$_{17}$H$_{16}$NO$_3$Cl.0.3H$_2$O

Calcd.: C, 63.18;H, 5.18;N, 4.33

Found: C, 63.13;H, 5.06;N, 4.34

(6) Starting from 14.5 g (45.6 mmol) of (S)-4-hydroxy-1-[4-(4-chlorophenoxy)benzyl]pyrrolidin-2-one, 4.94 ml (63.8 mmol) of methanesulfonyl chloride and 8.90 ml (63.8 mmol) of triethylamine, 14.6 g (yield: 81%) of (S)-4-methanesulfonyloxy-1-[4-(4-chlorophenoxy)benzyl]pyrrolidin-2-one was obtained as a white powder.

Elemental analysis (%): C$_{18}$H$_{18}$NO$_5$SCl.0.2H$_2$O

Calcd.: C, 54.12;H, 4.64;N, 3.51

Found: C, 54.09;H, 4.59;N, 3.43

(7) Starting from 14.0 g (35.4 mmol) of (S)-4-methanesulfonyloxy-1-[4-(4-chlorophenoxy)benzyl]pyrrolidin-2-one, 12.7 ml (177 mmol) of thioacetic acid and 8.07 g (24.8 mmol) of cesium carbonate, 11.7 g (yield: 88%) of (R)-4-acetylthio-1-[4-(4-chlorophenoxy)benzyl]pyrrolidin-2-one was obtained as a tan oil.

Elemental analysis (%): C$_{19}$H$_{18}$NO$_3$SCl.0.25H$_2$O

Calcd.: C, 59.99;H, 4.90;N, 3.68

Found: C, 59.96;H, 4.78;N, 3.67

Example 126

(R)-4-Mercapto-1-[4-(4-chlorophenoxy)benzyl]pyrrolidin-2-one

To 23 ml of ethanol with cooling on ice, 8.55 ml (120 mmol) of acetyl chloride was added dropwise over a period of 30 minutes with stirring. In this solution, 2.26 g (6.01 mmol) of (R)-4-acetylthio-1-[4-(4-chlorophenoxy)benzyl]pyrrolidin-2-one obtained in Example 125 was dissolved and heated at 50° C. for 1.5 hours with stirring. The reaction mixture was concentrated under reduced pressure, treated with ethyl acetate, washed with water and saturated brine and dried over anhydrous sodium sulfate. The mixture was concentrated under reduced pressure, and the residue was subjected to column chromatography on silica gel, and the fraction eluted with hexane: ethyl acetate (40:60) was concentrated under reduced pressure to obtain 1.29 g (yield: 64%) of (R)-4-mercapto-1-[4-(4-chlorophenoxy)benzyl]pyrrolidin-2-one as a pale red oil.

Elemental analysis (%): $C_{17}H_{16}NO_2SCl.0.2H_2O$
Calcd.: C, 60.51;H, 4.90;N, 4.15
Found: C, 60.41;H, 4.96;N, 4.12

Example 127

(R)-4-Acetylthio-1-[4-(4'-methylphenoxy)benzyl] pyrrolidin-2-one

By a method similar to that in Example 30 and starting from 1.97 g (8.9 mmol) of 4-(4'-methylphenoxy)benzyl chloride prepared from 4-fluorobenzaldehyde and 4-cresol and 1.50 g (8.9 mmol) of 4-trimethylsilyloxypyrrolidin-2-one, 397 mg (yield: 12%) of 4-acetylthio-1-[4-(4'-methylphenoxy)benzyl]pyrrolidin-2-one was obtained as a white powder.
Elemental analysis (%): $C_{20}H_{21}NO_3S$
Calcd.: C, 67.58;H, 5.95;N, 3.94;S, 9.02
Found: C, 67.53;H, 5.94;N, 4.15;S, 9.05

Example 128

4-Mercapto-1-[4-(4'-methylphenoxy)benzyl] pyrrolidin-2-one

By a method similar to that in Example 31 and starting from 103 mg (0.30 mmol) of 4-acetylthio-1-[4-(4'-methylphenoxy)benzyl]pyrrolidin-2-one obtained in Example 127, 87 mg (yield: 96%) of 4-mercapto-1-[4-(4'-methylphenoxy)benzyl]pyrrolidin-2-one was obtained as a colorless oil.
$^1$H-NMR (300 MHz, $CDCl_3$)
δ:7.18 (2H, d, J=8.5 Hz), 7.14 (2H, d, J=8.4 Hz), 6.93 (2H, d, J=8.5 Hz), 6.91 (2H, d, J=8.4 Hz), 4.46 (1H, d, J=14.7 Hz), 4.39 (1H, d, J=14.7 Hz), 3.64 (1H, dd, J=10.0, 7.3 Hz), 3.53 (1H, m), 3.16 (1H, dd, J=10.0, 5.1 Hz), 2.91 (1H, dd, J=17.1, 8.1 Hz), 2.42 (1H, dd, J=17.1, 6.2 Hz), 2.34 (3H, s) 1.86 (1H, d, J=6.7 Hz)

Example 129

4-Acetylthio-1-[4-(4'-(trifluoromethyl)phenoxy) benzyl]pyrrolidin-2-one

By a method similar to that in Example 30 and starting from 382 mg (1.3 mmol) of 4-(4'-(trifluoromethyl)phenoxy) benzyl chloride prepared from 4-fluorobenzaldehyde and 4-(trifluoromethyl)phenol and 338 mg (2.0 mmol) of 4-trimethylsilyloxypyrrolidin-2-one, 95.0 mg (yield: 18%) of 4-acetylthio-1-{4-[4'-(trifluoromethyl)phenoxy] benzyl}pyrrolidin-2-one was obtained as a colorless oil.
$^1$H-NMR (300 MHz, $CDCl_3$)
δ:7.58 (2H, d, J=8.7 Hz), 7.25 (2H, d, J=8.5 Hz), 7.05 (2H, d, J=8.7 Hz), 7.02 (2H, d, J=8.5 Hz), 4.49 (1H, d, J=15.0 Hz), 4.42 (1H, d, J=15.0 Hz), 4.07 (1 H, m), 3.78 (1H, dd, J=10.6, 7.5 Hz), 3.19 (1H, dd, J=10.6, 5.0 Hz), 2.93 (1H, dd, J=17.5, 9.0 Hz), 2.44 (1H, dd, J=17.4, 6.0 Hz), 2.33 (3H, s)

Example 130

4-Mercapto-1-{4-[4'-(trifluoromethyl)phenoxy] benzyl}pyrrolidin-2-one

By a method similar to that in Example 31 and starting from 58.0 mg (0.14 mmol) of 4-acetylthio-1-{4-[4'-(trifluoromethyl)phenoxy]benzyl)pyrrolidin-2-one obtained in Example 129, 46.0 mg (yield: 89%) of 4-mercapto-1-{4-[4'-(trifluoromethyl)phenoxy]benzyl)pyrrolidin-2-one was obtained as a colorless oil.

$^1$H-NMR (300 MHz, $CDCl_3$)
δ:7.58 (2H d, J=8.7 Hz), 7.27 (2H, d, J=8.7 Hz), 7.04 (2H, d, J=8.4 Hz), 7.02 (2H, d, J=8.4 Hz), 4.52 (1H, d, J=14.8 Hz), 4.42 (1H, d, J=14.8 Hz), 3.68 (1H, dd, J=10.0, 7.2 Hz), 3.56 (1H, m), 3.19 (1H, dd, J=10.0, 5.0 Hz), 2.94 (1H, dd, J=17.1, 8.1 Hz), 2.43 (1H, dd, J=17.1, 6.1 Hz), 1.87 (1H, d, J=6.7 Hz)

Example 131

4-Acetylthio-1-[4-(4'-ethoxycarbonylphenoxy) benzyl]pyrrolidin-2-one

By a method similar to that in Example 30 and starting from ethyl 4-(4'-chloromethylphenoxy)benzoate prepared from 4-fluorobenzaldehyde and ethyl 4-hydroxybenzoate and 4-trimethylsilyloxypyrrolidin-2-one, 4'-acetylthio-1-[4-(4'-ethoxycarbonylphenoxy)benzyl]pyrrolidin-2-one was obtained as a colorless oil (yield: 17%).
$^1$H-NMR (300 MHz, $CDCl_3$)
δ:8.02 (2H, d, J=8.8 Hz), 7.24 (2H, d, J=8.6 Hz), 7.02 (2H, d, J=8.6 Hz), 6.98 (2H, d, J=8.8 Hz), 4.49 (1H, d, J=14.9 Hz), 4.42 (1H, d, J=14.9 Hz), 4.56 (2H, q, J=7.1 Hz), 4.07 (1H, m), 3.78 (1H, dd, J=10.6, 7.5 Hz), 3.19 (1H, dd, J=10.6, 4.9 Hz), 2.93 (1H, dd, J=17.4, 8.9 Hz), 2.44 (1H, dd, J=17.4, 6.0 Hz), 2.32 (3H, s), 1.39 (3H, t, J=7.1 Hz)

Example 132

4-Mercapto-1-[4-(4'-ethoxycarbonylphenoxy) benzyl]pyrrolidin-2-one

By a method similar to that in Example 31 and starting from 108 mg (0.26 mmol) of 4-acetylthio-1-[4-(4'-ethoxycarbonylphenoxy)benzyl]pyrrolidin-2-one obtained in Example 131, 100 mg of 4-mercapto-1-[4-(4'-ethoxycarbonylphnoxy)benzyl]pyrrolidin-2-one was obtained almost quantitatively as a pale yellow oil.
$^1$H-NMR (300 MHz, $CDCl_3$)
δ:8.01 (2H, d, J=8.8 Hz), 7.27 (2H, d, J=8.5 Hz), 7.02 (2H, d, J=8.5 Hz), 6.98 (2H, d, J=8.8 Hz), 4.51 (1H, d, J=14.8 Hz), 4.42 (1H, d, J=14.8 Hz), 4.36 (2H, q, J=7.1 Hz), 3.68 (1H, dd, J=10.1, 7.2 Hz), 3.56 (1H, m), 3.19 (1H, dd, J=10.1, 5.0 Hz), 2.93 (1H, dd, J=17.1, 8.1 Hz), 2.43 (1H, dd, J=17.1, 6.0 Hz), 1.88 (1H, d, J=6.7 Hz), 1.48 (3H, t, J=7.1 Hz)

Example 133

4-Acetylthio-1-[4-(4'-carboxyphenoxy)benzyl] pyrrolidin-2-one (1) By a method similar to that in Example 30 and starting from 6.20 g (18 mmol) of benzyl 4-(4'-chloromethylphenoxy)benzoate prepared from 4-fluorobenzaldehyde and benzyl 4-hydroxybenzoate and 3.00 g (18 nmmol) of 4-trimethylsilyloxypyrrolidin-2-one, 471 mg (yield: 5%) of 4-methanesulfonyloxy-1-[4-(4'-benzyloxycarbonylphenoxy)benzyl]pyrrolidin-2-one was obtained as a tan oil.
$^1$H-NMR (300 MHz, $CDCl_3$)
δ:8.05 (2H, d, J=8.8 Hz), 7.48–7.32 (5H, m), 7.25 (2H, d, J=8.5 Hz), 7.03 (2H, d, J=8.5 Hz), 6.98 (2H, d, J=8.8 Hz), 5.35 (2H, s), 5.30 (1H, m), 4.50 (2H s), 3.69 (1H, dd, J=12.0, 5.6 Hz), 3.55 (1H, dd, J=12.0, 1.9 Hz), 3.03 (3H, s), 2.89 (1H, dd, J=17.9, 6.8 Hz), 2.72 (1H, dd, J=17.9, 2.4 Hz)

(2) 471 mg (1.1 mmol) of 4-methanesulfonyloxy-1-[4-(4'-benzyloxycarbonylphenoxy)benzyl]pyrrolidin-2-one was dissolved in 20 ml of tetrahydrofuran, 24.0 mg of 10% Pd/C was added, and the mixture was stirred under hydrogen atmosphere at room temperature for 2.5 hours. The reaction mixture was filtered and concentrated under reduced pressure, and the residue was precipitated from hexane-ethyl acetate to obtain 240 mg (yield: 59%) of 4-methanesulfonyloxy-1-[4-(4'-carboxylphenoxy)benzyl]pyrrolidin-2-one as a white powder.

$^1$H—NMC (300 MHz, CDCl$_3$)

δ:8.08 (2H, d, J=8.7 Hz), 7.27 (2H, d, J=8.6 Hz), 7.06 (2H, d, J=8.6 Hz), 7.01 (2H, d, J=8.7 Hz), 5.31 (1H, m), 4.51 (2H, s), 3.71 (1H, dd, J=12.0, 5.6 Hz), 3.57 (1H, dd, J=12.0, 2.0 Hz), 3.04 (3H, s), 2.91 (1H, dd, J=18.0, 6.9 Hz), 2.74 (1H, dd, J=18.0, 2.2 Hz)

(3) 240 mg (0.59 mmol) of 4-methanesulfonyloxy-1-[4-(4'-carboxylphenoxy)benzyl]pyrrolidin-2-one was dissolved in 20 ml of ethanol, and 822 mg (3.0 mmol) of potassium thioacetate was added, and the mixture was heated under reflux for 2 hours. The reaction mixture was concentrated under reduced pressure, treated with 5% aqueous sodium hydrogen sulfate and extracted twice with ethyl acetate, and the organic layer obtained was washed with water and saturated brine, and dried over anhydrous sodium sulfate. The mixture was concentrated under reduced pressure, and the residue was subjected to column chromatography on silica gel eluting with chloroform: methanol (98:1) and then again to column chromatography on silica gel eluting with hexane: ethyl acetate (40:60) to obtain 103 mg (yield: 45%) of 4-acetylthio-1-[4-(4'-carboxylphenoxy)benzyl]pyrrolidin-2-one as a pale yellow powder.

$^1$H-NMR (300 MHz, CDCl$_3$)

δ:8.07 (2H, d, J=8.8 Hz), 7.26 (2H, d, J=8.4 Hz), 7.04 (2H, d, J=8.4 Hz), 7.01 (2H, d, J=8.8 Hz), 4.51 (1H, d, J=14.8 Hz), 4.43 (1H, d, J=14.8 Hz), 4.07 (1H, m), 3.79 (1H, dd, J=10.6, 7.5 Hz), 3.20 (1H, dd, J=10.6, 5.0 Hz), 2.94 (1H, dd, J=17.4, 9.0 Hz), 2.44 (1H, dd, J=17.4, 6.0 Hz), 2.33 (3H, s)

Example 134

4-Acetylthio-1-[4-(4'-aminocarbonylphenoxy)benzyl]pyrrolidin-2-one (1) 310 mg (0.76 mmol) of 4-methanesulfonyloxy-1-[4-(4'-carboxylphenoxy)benzyl]pyrrolidin-2-one prepared by a method similar to that in Example 133 was dissolved in 5 ml of thionyl chloride, and stirred at room temperature for 1.5 hours. The reaction mixture was concentrated under reduced pressure, treated with 5 ml of tetrahydrofuran and 1 ml of conc. aqueous ammonia, and stirred at room temperature for 1.5 hours. The reaction mixture was concentrated under reduced pressure, treated with dilute hydrochloric acid and extracted twice with ethyl acetate, and the organic layer obtained was washed with water and saturated brine, and dried over anhydrous sodium sulfate. The reaction mixture was concentrated under reduced pressure, and the residue was precipitated from hexane-ethyl acetate to obtain 147 mg (yield: 48%) of 4-methanesulfonyloxy-1-[4-(4'-aminocarbonylphenoxy)benzyl]pyrrolidin-2-one as a white powder.

$^1$H-NMR (300 MHz, DMSO-d$_6$)

δ:7.87 (2H, d, J=8.2 Hz), 7.27 (2H, d, J=8.2 Hz), 7.04 (2H, d, J=8.5 Hz), 6.98 (2H, d, J=8.5 Hz), 5.29 (1H, m), 4.53 (1H, brs), 4.41 (2H, s), 3.97 (1H, brs), 3.69 (1H, dd, J=11.5, 5.4 Hz), 3.41 (1H, d, J=11.5 Hz), 3.30 (1H, m), 3.21 (3H, s), 2.91 (1H, dd, J=17.9, 6.9 Hz)

(2) 147 mg (0.36 mmol) of 4-methanesulfonyloxy-1-[4-(4'-aminocarbonylphenoxy)benzyl]pyrrolidin-2-one was dissolved in 20 ml of ethanol, treated with 123 mg (1.1 mmol) of potassium thioacetate, and heated under reflux for 1.5 hours. The reaction mixture was concentrated under reduced pressure, treated with water and extracted twice with ethyl acetate, and the organic layer obtained was washed with water and saturated brine, and dried over anhydrous sodium sulfate. The mixture was concentrated under reduced pressure, and the residue was subjected to column chromatography on silica gel eluting with chloroform: methanol (98:2–95:5) to obtain 62.0 mg (yield: 45%) of 4-acethylthio-1-[4-(4'-aminocarbonylphenoxy)benzyl]pyrrolidin-2-one as a white powder.

$^1$H-NMR (300 MHz, CDCl$_3$)

δ:7.80 (2H, d, J=8.7 Hz), 7.24 (2H, d, J=8.5 Hz), 7.01 (2H, d, J=8.7 Hz), 7.01 (2H, d, J=8.5 Hz), 5.90 (2H, brs), 4.49 (1H, d, J=14.9 Hz), 4.42 (1H, d, J=14.9 Hz), 4.07 (1H, m), 3.78 (1H, dd, J=10.6, 7.5 Hz), 3.20 (1H, dd, J=10.6, 4.9 Hz), 2.93 (1H, dd, J=17.4, 9.0 Hz), 2.43 (1H, dd, J=17.4, 6.0 Hz), 2.33 (3H, s)

Example 135

4-Mercapto-1-[4-(4'-aminocarbonylphenoxy)benzyl]pyrrolidin-2-one

By a method similar to that in Example 31 and starting from 23.0 mg (0.060 mmol) of 4-acetylthio-1-[4-(4'-carboxamidephenoxy)benzyl]pyrrolidin-2-one obtained in Example 134, 22.0 mg of 4-mercapto-1-[4-(4'-aminocarbonylphenoxy)benzyl]pyrrolidin-2-one was obtained almost quantitatively as a colorless oil.

$^1$H-NMR (300 MHz, CDCl$_3$)

δ:7.79 (2H, d, J=8.7 Hz), 7.27 (2H, d, J=8.6 Hz), 7.02 (2H, d, J=8.6 Hz), 7.02 (2H, d, J=8.7 Hz), 5.90–5.60 (2H, brd), 4.51 (1H, d, J=14.8 Hz), 4.42 (1H, d, J=14.8 Hz), 3.68 (1H, dd, J=10.0, 7.3 Hz), 3.57 (1H, m), 3.19 (1H, dd, J=10.0, 5.0 Hz), 2.93 (1H, dd, J=17.1, 8.1 Hz), 2.43 (1H, dd, J=17.1, 6.0 Hz), 1.88 (1H, d, J=6.7 Hz)

Example 136

4-Acetylthio-1-[4-(4'-hydroxyphenoxy)benzyl]pyrrolidin-2-one (1) 1.16 g (3.1 mmol) of 4-methanesulfonyloxy-1-[4-(4'-methoxyphenoxy)benzyl]pyrrolidin-2-one prepared by a method similar to that in Example 36 was dissolved in 25 ml of chloroform, and treated with 4 ml of boron tribromide (3M dichloromethane solution) and then stirred at room temperature for 1 hour. The reaction mixture was concentrated under reduced pressure, treated with ethyl acetate, washed with water and saturated brine, and dried over anhydrous sodium sulfate. The mixture was concentrated under reduced pressure and the residue was subjected to column chromatography on silica gel eluting with ethyl acetate to obtain 933 mg (yield: 80%) of 4-methanesulfonyloxy-1-[4-(4'-hydroxyphenoxy)benzyl]pyrrolidin-2-one as a gray powder.

$^1$H-NMR (300 MHz, CDCl$_3$)

δ:7.15 (2H, d, J=8.5 Hz), 6.91 (2H, d, J=9.0 Hz), 6.88 (2H, d, J=8.5 Hz), 6.82 (2H, d, J=9.0 Hz), 5.35 (1H, s), 5.28 (1H, m), 4.49 (1H, d, J=14.7 Hz), 4.41 (1H, d, J=14.7 Hz), 3.66 (1H, dd, J=12.0, 5.6 Hz), 3.52 (1H, dd, J=12.0, 1.8 Hz), 3.02 (3H, s), 2.88 (1H, dd, J=18.0, 6.8 Hz), 2.72 (1H, dd, J=18.0, 2.4 Hz)

(2) 933 mg (2.5 mmol) of 4-methanesulfonyloxy-1-[4-(4'-hydroxyphenoxy)benzyl]pyrrolidin-2-one was dissolved in 50 ml of ethanol, treated with 1.40 g (13 mmol) of potassium thioacetate, and heated under reflux for 2 hours.

The reaction mixture was concentrated under reduced pressure, treated with water and extracted twice with ethyl acetate, and the organic layer obtained was washed with water and saturated brine, and dried over anhydrous sodium sulfate. The mixture was concentrated under reduced pressure, and the residue was subjected to column chromatography on silica gel eluting with hexane: ethyl acetate (50:50) and then again to column chromatography on silica gel eluting with chloroform to obtain 434 mg (yield: 49%) of 4-acetylthio-1-[4-(4'-hydroxyphenoxy)benzyl]pyrrolidin-2-one as a colorless oil.
Elemental analysis (%): $C_{19}H_{19}NO_4S$
Calcd.: C, 63.85;H, 5.36;N, 3.92;S, 8.97
Found: C, 63.66;H, 5.16;N, 4.05;S, 8.86

Example 137

4-Mercapto-1-[4-(4'-hydroxyphenoxy)benzyl]pyrrolidin-2-one

By a method similar to that in Example 31 and starting from 58.0 mg (0.16 mmol) of 4-acetylthio-1-[4-(4'-hydroxyphenoxy)benzyl]pyrrolidin-2-one obtained in Example 136, 35.0 mg (yield: 68%) of 4-mercapto-1-[4-(4'-hydroxyphenoxy)benzyl]pyrrolidin-2-one was obtained as a white powder.
$^1$H-NMR (300 MHz, CDCl$_3$)
δ:8.42 (1H, s), 7.09 (2H, d, J=8.5 Hz), 6.81 (2H, d, J=8.5 Hz), 6.79 (4H, d, J=4.7 Hz), 4.37 (1H, d, J=14.7 Hz), 4.31 (1H, d, J=14.7 Hz), 3.58 (1H, dd, J=10.0, 7.2 Hz), 3.47 (1H, m), 3.09 (1H, dd, J=10.0, 5.0 Hz), 2.84 (1H, dd, J=17.0, 8.1 Hz), 2.34 (1H, dd, J=17.0, 6.1 Hz), 1.83 (1H, d, J=6.7 Hz)

Example 138

4-Acetylthio-1-[4-(4'-ethoxyphenoxy)benzyl]pyrrolidin-2-one

By a method similar to that in Example 30 and starting from 1.83 g (7.0 mmol) of 4-(4'-ethoxyphenoxy)benzyl chloride prepared from 4-fluorobenzaldehyde and 4-ethoxyphenol and 1.20 g (7.0 mmol) of 4-trimethylsilyloxypyrrolidin-2-one, 667 mg (yield: 25%) of 4-acetylthio-1-{4-[4'-ethoxyphenoxy)benzyl]pyrrolidin-2-one was obtained as a yellow oil.
Elemental analysis (%): $C_{21}H_{23}NO_4S$
Calcd.: C, 65.43;H, 6.01;N, 3.63;S, 8.32
Found: C, 65.61;H, 5.93;N, 3.75;S, 8.29

Example 139

4-Mercapto-1-[4-(4'-ethoxyphenoxy)benzyl]pyrrolidin-2-one

By a method similar to that in Example 31 and starting from 192 mg (0.50 mmol) of 4-acetylthio-1-[4-(4'-ethoxyphenoxxy)benzyl]pyrrolidin-2-one obtained in Example 138, 128 mg (yield: 75%) of 4-mercapto-1-[4-(4'-ethoxyphenoxy)benzyl]pyrrolidin-2-one was obtained as a colorless oil.
$^1$H-NMR (300 MHz, CDCl$_3$)
δ: 7.17 (2H, d, J=8.6 Hz), 6.96 (2H, d, J=9.1 Hz), 6.89 (2H, d, J=8.6 Hz), 6.87 (2H, d, J=9.1 Hz), 4.45 (1H, d, J=14.7 Hz), 4.38 (1H, d, J=14.7 Hz), 4.02 (2H, q, J=7.0 Hz), 3.63 (1H, dd, J=10.0, 7.2 Hz), 3.52 (1H, m), 3.15 (1H, dd, J=10.0, 5.1 Hz), 2.91 (1H, dd, J=17.0, 8.2 Hz), 2.42 (1H, dd, J=17.0, 6.2 Hz), 1.86 (1H d, J=6.8 Hz), 1.42 (3H, t, J=7.0 Hz)

Example 140

4-Acetylthio-1-{4-[4'-(trifluoromethoxy)phenoxy]benzyl}pyrrolidin-2-one

By a method similar to that in Example 30 and starting from 1.85 g (6.1 mmol) of 4-[4'-(trifluoromethoxy)phenoxy]benzyl chloride prepared from 4-fluorobenzaldehyde and 4-(trifluoromethoxy)phenol and 1.60 g (9.2 mmol) of 4-trimethylsilyloxypyrrolidin-2-one, 639 mg (yield: 25%) of 4-acetylthio-1-{4-[4'-(trifluoromethoxy)phenoxy]benzyl}pyrrolidin-2-one was obtained as a white powder.
Elemental analysis (%): $C_{20}H_{18}NO_4SF_3$
Calcd.: C, 56.46;H, 4.26;N, 3.29;S, 7.54
Found: C, 56.57;H, 4.26;N, 3.47;S, 7.51

Example 141

4-Mercapto-1-{4-[4'-(trifluoromethoxy)phenoxy]benzyl}pyrrolidin-2-one

By a method similar to that in Example 31 and starting from 160 mg (0.40 mmol) of 4-acetylthio-1-{4-[4'-(trifluoromethoxy)phenoxy]benzyl}pyrrolidin-2-one obtained in Example 140, 102 mg (yield: 71%) of 4-mercapto-1-{4-[4'-(trifluoromethoxy)phenoxy]benzyl}pyrrolidin-2-one was obtained as a colorless oil.
$^1$H-NMR (300 MHz, CDCl$_3$)
δ:7.23 (2H, d, J=8.5 Hz), 7.19 (2H, d, J=8.5 Hz), 7.00 (2H, d, J=8.5 Hz), 6.97 (2H, d, J=8.5 Hz), 4.49 (1H, d, J=14.8 Hz), 4.40 (1H, d, J=14.8 Hz), 3.66 (1H, dd, J=10.0, 7.2 Hz), 3.55 (1H, m), 3.17 (1H, dd, J=10.0, 5.0 Hz), 2.92 (1H, dd, J=17.1, 8.1 Hz), 2.43 (l1H, dd, J=17.1, 6.1 Hz), 1.87 (1H, d, J=6.7 Hz)

Example 142

4-Acetylthio-1-[4-(4'-nitrophenoxy)benzyl]pyrrolidin-2-one

By a method similar to that in Example 30 and starting from 4-(4'-nitrophenoxy)benzyl chloride prepared from 4-hydroxybenzaldehyde and p-dinitrobenzene and 4-trimethylsilyloxypyrrolidin-2-one, 4-acetylthio-1-(4-[4'-nitrophenoxy)benzyl]pyrrolidin-2-one was obtained as a yellow oil (yield: 8%).
$^1$H-NMR (300 MHz, CDCl$_3$)
δ:8.21 (2H, d, J=9.2 Hz), 7.30 (2H, d, J=8.5 Hz), 7.06 (2H, d, J=8.5 Hz), 7.02 (2H, d, J=9.2 Hz), 4.48 (2H, s), 4.08 (1H, m), 3.80 (1H, dd, J=10.6, 7.6 Hz), 3.21 (1H, dd, J=10.6, 5.0 Hz), 2.93 (1H, dd, J=17.4, 9.0 Hz), 2.45 (1H, dd, J=17.4, 6.1 Hz), 2.34 (3H, s)

Example 143

4-Mercapto-1-[4-(4'-nitrophenoxy)benzyl]pyrrolidin-2-one

By a method similar to that in Example 31 and starting from 52.0 mg (0.13 mmol) of 4-acetylthio-1-[4-(4'-nitrophenoxy)benzyl)pyrrolidin-2-one obtained in Example 142, 34.0 mg (yield: 73%) of 4-mercapto-1-[4-(4'-nitrophenoxy)benzyl]pyrrolidin-2-one was obtained as a yellow oil.
$^1$H-NMR (300 MHz, CDCl$_3$)
δ:8.21 (2H, d, J=9.2 Hz), 7.32 (2H, d, J=8.5 Hz), 7.06 (2H, d, J=8.5 Hz), 7.01 (2H, d, J=9.2 Hz), 4.54 (1H, d, J=14.9 Hz), 4.42 (1H, d, J=14.9 Hz), 3.69 (1H, dd, J=10.0, 7.2 Hz), 3.58 (1H, m), 3.20 (1H, dd, J=10.0, 5.0 Hz), 2.94 (1H, dd, J=17.1, 8.1 Hz), 2.44 (1H, dd, J=17.1, 6.0 Hz), 1.89 (1H, d, J=6.6 Hz)

Example 144

4-Acetylthio-1-[4-(4'-acetoaminophenoxy)benzyl]pyrrolidin-2-one (1) 1.86 g (5.7 mmol) of 4-hydroxy-1-[4-(4'-nitrophenoxy)benzyl]pyrrolidin-2-one prepared by a method similar to that in Example 142 was dissolved in 40 ml of pyridine, treated with 10 ml of acetic anhydride, and stirred at room temperature for 14 hours. The reaction mixture was concentrated under reduced pressure, treated with water and extracted twice with ethyl acetate, and the organic layer obtained was washed with water and saturated brine, and dried over anhydrous sodium sulfate. After concentrating under reduced pressure, the residue was precipitated from hexane-ethyl acetate to obtain 1.80 g (yield: 85%) of 4-acetoxy-1-[4-(4'-nitrophenoxy)benzyl]pyrrolidin-2-one as a tan powder.

$^1$H-NMR (300 MHz, CDCl$_3$)

δ:8.22 (2H, d, J=9.2 Hz), 7.29 (2H, d, J=8.5 Hz), 7.07 (2H, d, J=8.5 Hz), 7.02 (2H, d, J=9.2 Hz), 5.29 (1H, m), 4.51 (2H, s), 3.68 (1H, dd, J=11.5, 6.0 Hz), 3.28 (1H, dd, J=11.5, 2.0 Hz), 2.85 (1H, dd, J=17.9, 7.2 Hz), 2.57 (1H, dd, J=17.9, 2.5 Hz), 2.06 (3H, s)

(2) 1.80 g (4.9 mmol) of 4-acetoxy-1-[4-(4'-nitrophenoxy)benzyl]pyrrolidin-2-one was dissolved in a solvent mixture of 100 ml of methanol and 10 ml of tetrahydrofuran, treated with 10% Pd/C and stirred under hydrogen atmosphere at room temperature for 4.5 hours. The reaction mixture was filtered, concentrated under reduced pressure and treated with a 4N solution of hydrochloric acid in ethyl acetate to obtain 1.67 g (yield: 90%) of 4-acetoxy-1-[4-(4'-aminophenoxy)benzyl]pyrrolidin-2-one hydrochloride as a white powder.

$^1$H-NMR (300 MHz, CD$_3$OD)

δ:7.35 (2H, d, J=8.9 Hz), 7.30 (2H, d, J=8.6 Hz), 7.11 (2H, d, J=8.9 Hz), 7.02 (2H, d, J=8.6 Hz), 5.27 (1H, m), 4.52 (1H, d, J=14.9 Hz), 4.44 (1H, d, J=14.9 Hz), 3.73 (1H, dd, J=11.7, 5.7 Hz), 3.33 (1H, dd, J=11.7, 1.5 Hz), 2.90 (1H, dd, J=18.0, 7.1 Hz), 2.47 (1H, dd, J=18.0, 1.8 Hz), 2.02 (3H, s)

(3) 324 mg (0.86 mmol) of 4-acetoxy-1-[4-(4'-aminophenoxy)benzyl]pyrrolidin-2-one hydrochloride was dissolved in 10 ml of chloroform, treated with 360 μl (2.6 mmol) of triethylamine and 122 μl (1.7 mmol) of acetyl chloride, and stirred at room temperature for 14 hours. The reaction mixture was concentrated under reduced pressure, treated with ethyl acetate, washed with water and saturated brine, and dried over anhydrous sodium sulfate. The mixture was concentrated under reduced pressure, and the residue was subjected to column chromatography on silica gel eluting with ethyl acetate to obtain 265 mg (yield: 81%) of 4-acetoxy-1-[4-(4'-acetoaminophenoxy)benzyl]pyrrolidin-2-one as a white powder.

$^1$H-NMR (300 MHz, CDCl$_3$)

δ:7.46 (2H, d, J=8.9 Hz), 7.25 (1H, brs), 7.17 (2H, d, J=8.5 Hz), 6.97 (2H, d, J=8.9 Hz), 6.93 (2H, d, J=8.5 Hz), 5.25 (1H, m), 4.48 (1H, d, J=15.7 Hz), 4.42 (1H, d, J=15.7 Hz), 3.63 (1H, dd, J=11.6, 6.0 Hz), 3.24 (1H, dd, J=11.6, 1.9 Hz), 2.82 (1H, dd, J=17.8, 7.2 Hz), 2.53 (1H, dd, J=17.8, 2.4 Hz), 2.18 (3H, s), 2.04 (3H, s)

(4) 265 mg (0.69 mmol) of 4-acetoxy-1-[4-(4'-acetoaminophenoxy)benzyl]pyrrolidin-2-one was dissolved in 10 ml of ethanol and 1 ml of chloroform, treated with 330 mg (3.5 mmol) of guanidine hydrochloride and 481 μl (3.5 mmol) of triethylamine, and stirred at room temperature for 5 days. The reaction mixture was concentrated under reduced pressure, treated with ethyl acetate, washed with water and saturated brine, and dried over anhydrous sodium sulfate. After concentrating under reduced pressure, the residue was precipitated from hexane-ethyl acetate to obtain 200 mg (yield: 85%) of 4-hydroxy-1-[4-(4'-acetoaminophenoxy)benzyl]pyrrolidin-2-one as a white powder.

$^1$H-NMR (300 MHz, CDCl$_3$)

δ:7.45 (2H, d, J=8.9 Hz), 7.19 (2H, d, J=8.5 Hz), 7.15 (1H, brs), 6.96 (2H, d, J=8.9 Hz), 6.92 (2H, d, J=8.5 Hz), 4.51 (1H, m), 4.47 (1H, d, J=14.9 Hz), 4.40 (1H, d, J=14.9 Hz), 3.53 (1H, dd, J=10.9, 5.6 Hz), 3.21 (1H, dd, J=10.9, 1.8 Hz), 2.75 (1H, dd, J=17.4, 6.6 Hz), 2.44 (1H, dd, J=17.4, 2.3 Hz), 2.12 (3H, s), 2.09 (1H, brs)

(5) Then by a method similar to that in Example 30 and starting from 159 mg (0.47 mmol) of 4-hydroxy-1-[4-(4'-acetoaminophenoxy)benzyl]pyrrolidin-2-one, 190 mg (yield:46%) of 4-acetylthio-1-[4-(4'-acetoaminophenoxy)benzyl]pyrrolidin-2-one as a yellow oil.

$^1$H-NMR (300 MHz, CDCl$_3$)

δ:7.46 (2H, d, J=8.9 Hz), 7.17 (2H, d, J=8.5 Hz), 7.14 (1H, brs), 6.98 (2H, d, J=8.9 Hz), 6.93 (2H, d, J=8.5 Hz), 4.46 (1H, d, J=14.7 Hz), 4.39 (1H, d, J=14.7 Hz), 4.06 (1H, m), 3.75 (1H, dd, J=10.7, 7.6 Hz), 3.18 (1H, dd, J=10.7, 4.9 Hz), 2.92 (1H, dd, J=17.4, 8.9 Hz), 2.42 (1H, dd, J=17.4, 6.0 Hz), 2.32 (3H, s), 2.18 (3H, s)

Example 145

4-Mercapto-1-[4-(4'-acetoaminophenoxy)benzyl]pyrrolidin-2-one

By a method similar to that in Example 31 and starting from 23.0 mg (0.060 mmol) of 4-acetylthio-1-[4-(4'-acetoaminophenoxy)benzyl]pyrrolidin-2-one obtained in Example 144, 22.0 mg 4-mercapto-1-[4-(4'-acetoaminophenoxy)benzyl]pyrrolidin-2-one was obtained almost quantitatively as a colorless oil.

$^1$H-NMR (300 MHz, CD$_3$OD)

δ:7.52 (2H, d, J=9.0 Hz), 7.25 (2H, d, J=8.5 Hz), 6.94 (2H, d, J=9.0 Hz), 6.94 (2H, d, J=8.5 Hz), 4.48 (1H, d, J=14.9 Hz), 4.37 (1H, d, J=14.9 Hz), 3.73 (1H, dd, J=10.4, 7.2 Hz), 3.59 (1H, m), 3.18 (1H, dd, J=10.4, 4.6 Hz), 2.92 (1H, dd, J=17.1, 8.1 Hz), 2.35 (1H, dd, J=17.1, 5.4 Hz), 2.11 (3H, s), 1.29 (1H, brs)

Example 146

4-Acetylthio-1-[4-(4'-methylsulfonylaminophenoxy)benzyl]pyrrolidin-2-one (1) 300 mg (0.80 mmol) of 4-hydroxy-1-[4-(4'-aminophenoxy)benzyl]pyrrolidin-2-one hydrochloride obtained in Example 144 was dissolved in 20 ml of chloroform, treated with 335 μl (2.4 mmol) of triethylamine and 93.0 μl (1.2 mmol) of methanesulfonyl chloride, and stirred at room temperature for 17 hours. The reaction mixture was concentrated under reduced pressure, treated with ethyl acetate, washed with water and saturated brine, and dried over anhydrous sodium sulfate. After concentrating under reduced pressure, the residue was subjected to column chromatography on silica gel eluting with ethyl acetate to obtain 285 mg (yield: 85%) of 4-acetoxy-1-[4-(4'-ethylsulfonylaminophenoxy)benzyl]pyrrolidin-2-one as a pale tan oil. $^1$H-NMR (300 MHz, CDCl$_3$)

δ:7.23 (2H, d, J=8.8 Hz), 7.21 (2H, d, J=8.2 Hz), 6.99 (2H, d, J=8.8 Hz), 6.96 (2H, d, J=8.2 Hz), 6.55 (1H, brs), 5.27 (1H, m), 4.46 (2H, s), 3.64 (1H, dd, J=11.5, 6.0 Hz), 3.25 (1H, dd, J=11.5, 2.0 Hz), 3.01 (3H, s), 2.83 (1H, dd, J=17.8, 7.2 Hz), 2.55 (1H, dd, J=17.8, 2.5 Hz), 2.05 (3H, s)

(2) Then by a method similar to that in Example 144 and starting from 285 mg (0.50 mmol) of 4-acetoxy-1-[4-(4'-methylsulfonylaminophenoxy)benzyl]pyrrolidin-2-one, 59.0 mg (yield: 20%) of 4-acetylthio-1-[4-(4'-methylsulfonylaminophenoxy)benzyl]pyrrolidin-2-one as a white powder.
H-NMR (300 MHz, CDCl$_3$)
δ:7.22 (2H, d, J=8.8 Hz), 7.21 (2H, d, J=8.6 Hz), 6.99 (2H, d, J=8.8 Hz), 6.96 (2H, d, J=8.6 Hz), 6.27 (1H, brs), 4.44 (2H, s), 4.06 (1H, m), 3.76 (1H, dd, J=10.7, 7.7 Hz), 3.18 (1H, dd, J=10.7, 5.0 Hz), 3.01 (3H, s), 2.92 (1H, dd, J=17.4, 9.0 Hz), 2.42 (1H, dd, J=17.4, 6.0 Hz), 2.32 (3H, s)

Example 147

4-Mercapto-1-[4-(4'-methylsulfonylaminophenoxy) benzyl]pyrrolidin-2-one

By a method similar to that in Example 31 and starting from 38.0 mg (0.090 mmol) of 4-acetylthio-1-[4-(4'-methylsulfonylaminophenoxy)benzyl]pyrrolidin-2-one obtained in Example 146, 28.0 mg (yield: 79%) of 4-mercapto-1-[4-(4'-methylsulfonylaminophenoxy)benzyl]pyrrolidin-2-one was obtained as a white powder.
$^1$H-NMR (300 MHz, CDCl$_3$)
δ: 7.22 (2H, d, J=8.7 Hz), 7.21 (2H, d, J=9.0 Hz), 6.99 (2H, d, J=9.0 Hz), 6.96 (2H, d, J=8.7 Hz), 6.33 (1H, s), 4.49 (1H, d, J=14.7 Hz), 4.40 (1H, d, J=14.7 Hz), 3.66 (1H, dd, J=10.0, 7.2 Hz), 3.55 (1H, m), 3.17 (1H, dd, J=10.0, 5.0 Hz), 3.00 (3H, s), 2.92 (1H, dd, J=17.1, 8.1 Hz), 2.42 (1H, dd, J=17.1, 6.0 Hz), 1.87 (1H, d, J=6.7 Hz)

Example 148

4-Acetylthio-1-[4-(4'-ethylaminocarbonylaminophenoxy)benzyl] pyrrolidin-2-one (1) 300 mg (0.80 mmol) of 4-hydroxy-1-[4-(4'-aminophenoxy)benzyl]pyrrolidin-2-one hydrochloride obtained in Example 144 was dissolved in 10 ml of chloroform, treated with 233 μl (1.6 mmol) of triethylamine and 317 μl (3.2 mmol) of ethyl cyanate, and stirred at room temperature for 14 hours. The reaction mixture was concentrated under reduced pressure, treated with ethyl acetate, washed with water and saturated brine, and dried over anhydrous sodium sulfate. After concentrating under reduced pressure, the residue was subjected to column chromatography on silica gel eluting with hexane-ethyl acetate (30:70–0:100) to obtain 278 mg (yield: 85%) of 4-acetoxy-1-[4-(4'-ethylaminocarbonylaminophenoxy) benzyl]pyrrolidin-2-one as a white powder.
$^1$H-NMR (300 MHz, CDCl$_3$)
δ:7.26 (2H, d, J=8.7 Hz), 7.17 (2H, d, J=8.4 Hz), 6.93 (2H, d, J=8.7 Hz), 6.92 (2H, d, J=8.4 Hz), 6.66 (1H, s), 5.26 (1H, m), 4.91 (1H, brs), 4.45 (2H, s), 3.64 (1H, dd, J=11.6, 6.0 Hz), 3.27 (3H, m), 2.82 (1H, dd, J=17.8, 7.2 Hz), 2.54 (1H, dd, J=17.8, 2.3 Hz), 2.04 (3H, s), 1.16 (3H, t, J=7.0 Hz)

(2) Then by a method similar to that in Example 30 and starting from 278 mg (0.68 mmol) of 4-acetoxy-1-[4-(4'-ethylaminocarbonylaminophenoxy)benzyl]pyrrolidin-2-one, 107 mg (yield: 37%) of 4-acetylthio-1-[4-(4'-ethylaminocarbonylaminophenoxy)benzyl]pyrrolidin-2-one was obtained as a white powder.
$^1$H-NMR (300 MHz, CDCl$_3$)
δ:7.26 (2H, d, J=8.8 Hz), 7.18 (2H, d, J=8.5 Hz), 6.97 (2H, d, J=8.8 Hz), 6.94 (2H, d, J=8.5 Hz), 6.29 (1H, brs), 4.66 (1H, brt), 4.46 (1H, d, J=14.8 Hz), 4.39 (1H, d, J=14.8 Hz), 4.06 (1H, m), 3.76 (1H, dd, J=10.6, 7.5 Hz), 3.30 (2H, m), 3.17 (1H, dd, J=10.6, 5.0 Hz), 2.92 (1H, dd, J=17.4, 8.9 Hz), 2.42 (1H, dd, J=17.4, 6.0 Hz), 2.32 (3H, s), 1.16 (3H, t, J=7.2 Hz)

Example 149

4-Mercapto-1-[4-(4'-ethylaminocarbonylaminophenoxy)benzyl] pyrrolidin-2-one

By a method similar to that in Example 31 and starting from 27.0 mg (0.060 mmol) of 4-acetylthio-1-[4-(4'-ethylaminocarbonylaminophenoxy)benzyl]pyrrolidin-2-one obtained in Example 148, 6.00 mg (yield: 26%) of 4-mercapto-1-[4-(4'-ethylaminocarbonylaminophenoxy) benzyl]pyrrolidin-2-one was obtained as a pale tan oil.
$^1$H-NMR (300 MHz, CDCl$_3$)
δ:7.26 (2H, d, J=8.7 Hz), 7.18 (2H, d, J=8.5 Hz), 6.95 (2H, d, J=8.7 Hz), 6.93 (2H, d, J=8.5 Hz), 6.47 (1H, s), 4.78 (1H, t, J=5.7 Hz), 4.46 (1H, d, J=14.8 Hz), 4.39 (1H, d, J=14.8 Hz), 3.66 (1H, dd, J=10.1, 7.3 Hz), 3.54 (1H, m), 3.29 (2H, qd, J=7.1 5.7 Hz), 3.17 (1H, dd, J=10.1, 5.0 Hz), 2.91 (1H, dd, J=17.1, 8.1 Hz), 2.42 (1H, dd, J=17.1, 6.1 Hz), 1.87 (1H, d, J=6.7 Hz), 1.15 (3H, t, J=7.1 Hz)

Example 150

4-Acetylthio-1-(2-nitro-4-phenoxybenzyl)pyrrolidin-2-one (1) 5.00 g (27 mmol) of 4-chloro-2-nitrobenzaldehyde was dissolved in 50 ml of pyridine, treated with 3.80 g (40 mmol) of phenol and 7.40 g (54 mmol) of potassium carbonate, and heated at 100° C. for 2.5 hours. Then 5.30 g (67 mmol) of copper (II) oxide was added and the mixture was heated at 120° C. for 15.5 hours. The reaction mixture was concentrated under reduced pressure, treated with ethyl acetate, and filtered to remove in solubles. The filtrate was washed with saturated aqueous sodium carbonate, water and saturated brine, and dried over anhydrous sodium sulfate. After concentrating under reduced pressure, the residue was subjected to column chromatography on silica gel eluting with hexane-ethyl acetate (97:3) to obtain 4.80 g (yield:73%) of 2-nitro-4-phenoxybenzaldehyde as a yellow oil.
$^1$H-NMR (300 MHz, CDCl$_3$)
δ: 10.48 (1H, s), 7.88 (1H, d, J=8.4 Hz), 7.45 (1H, d, J=7.5 Hz), 7.43 (1H, d, J=7.5 Hz), 7.25 (1H, dd, J=7.4, 7.4 Hz), 7.14 (1H, dd, J=8.4, 1.8 Hz), 7.10 (2H, d, J=8.7 Hz), 7.10 (2H, d, J=8.7 Hz), 6.89 (1H, d, J=1.8 Hz)

(2) Then by a method similar to that in Example 30 and starting from 2-nitro-4-phenoxybenzyl chloride, 4-acetylthio-1-(2-nitro-4-phenoxybenzyl)pyrrolidin-2-one was obtained as a colorless oil (yield: 11%).
$^1$H-NMR (300 MHz, CDCl3)
δ: 7.39 (1H, d, J=8.2 Hz), 7.35 (1H, d, J=7.8 Hz), 7.27 (1H, d, J=7.5 Hz) 7.5 Hz), 7.15 (1H, ddd, J=7.5, 7.5, 0.5 Hz), 7.08 (1H, dd, J=8.2, 2.0 Hz), 6.96 (2H, dd, J=7.8, 0.5 Hz), 6.84 (1H, d, J=2.0 Hz), 4.51 (2H, s), 4.02 (1H, m), 3.81 (1H, dd, J=10.7, 7.6 Hz), 3.23 (1H, dd, J=10.7, 4.9 Hz), 2.83 (1H, dd, J=17.4, 8.9 Hz), 2.34 (1H, dd, J=17.4, 6.0 Hz), 2.32 (3H, s)

Example 151

4-Acetylthio-1-(3-nitro-4-phenoxybenzyl)pyrrolidin-2-one (1) 1.90 g (40 mmol) of sodium hydride (60% in oil) was dispersed in 20 ml of N,N-dimethylformamide, and stirred at room temperature for 10 minutes. A solution of 3.80 g (40 mmol) of phenol in 20 ml of N,N-dimethylformamide was added, and the mixture was stirred at room temperature further for 10 minutes. To this solution, 7.40 g (40 mmol) of 4-chloro-3-nitrobenzaldehyde was added, and the mixture was stirred at room temperature for 10 minutes and then at 120° C. for 1 hour with heating. The reaction mixture was treated with ethyl acetate, washed with water and saturated brine, and then dried over anhydrous sodium sulfate. After concentrating under reduced pressure, the residue was subjected to column chromatography on silica gel eluting with hexane-ethyl acetate (90:10) to obtain 6.50 g (yield: 67%) of 3-nitro-4-phenoxybenzaldehyde as a yellow oil.

$^1$H-NMR (300 MHz, CDCl$_3$)

δ: 9.97 (1H, s), 8.44 (1H, d, J=2.1 Hz), 7.97 (1H, dd, J=8.8, 2.1 Hz), 7.48 (2H, d, J=7.7 Hz), 7.45 (1H, d, J=7.4 Hz), 7.30 (1H, dd, J=7.4, 7.4 Hz), 7.14 (1H, d, J=7.7 Hz), 7.05 (1H, d, J=8.8 Hz)

(2) Then by a method similar to that in Example 30 and starting from 1.04 g (3.9 mmol) of 3-nitro-4-phenoxybenzyl chloride, 344 mg (yield: 20%) of 4-acetylthio-1-(3-nitro-4-phenoxybenzyl)pyrrolidin-2-one was obtained as a pale yellow oil.

$^1$H-NMR (300 MHz, CDCl$_3$)

δ: 7.82 (1H, d, J=2.1 Hz), 7.41 (1H, d, J=8.6 Hz), 7.38 (2H, d, J=7.9 Hz), 7.20 (1H, dd, J=7.4, 7.4 Hz), 7.06 (2H, d, J=7.9 Hz), 6.98 (1H, d, J=8.6 Hz), 4.55 (1H, d, J=15.1 Hz), 4.40 (1H, d, J=15.1 Hz), 4.08 (1H, m), 3.81 (1H, dd, J=10.5, 7.4 Hz), 3.22 (1H, dd, J=10.5, 4.7 Hz), 2.93 (1H, dd, J=17.5, 8.9 Hz), 2.44 (1H, dd, J=17.5, 5.7 Hz), 2.34 (3H, s)

Example 152

4-Acetylthio-1-(3-methylsulfonylamino-4-phenoxybenzyl)pyrrolidin-2-one

3-Nitro-4-phenoxybenzaldehyde synthesized in Example 151 was processed similarly to Example 146 to obtain 4-acetylthio-1-(3-methylsulfonylamino-4-phenoxybenzyl) pyrrolidin-2-one as a colorless oil (yield:5%).

$^1$H-NMR (300 MHz, CDCl$_3$)

δ:7.49 (1H, d, J=1.9 Hz), 7.40 (1H, d, J=7.9 Hz), 7.36 (1H, d, J=8.1 Hz), 7.19 (1H, dd, J=7.9, 7.9 Hz), 7.00 (2H, d, J=8.1 Hz), 6.97 (1H, dd, J=8.3, 1.9 Hz), 6.85 (1H, d, J=8.3 Hz), 6.85 (1H, brs), 4.44 (2H, s), 4.07 (1H, m), 3.79 (1H, dd, J=10.6, 7.5 Hz), 3.22 (1H, dd, J=10.6, 5.0 Hz), 3.01 (3H, s), 2.92 (1H, dd, J=17.4, 9.0 Hz), 2.43 (1H, dd, J=17.4, 6.1 Hz), 2.33 (3H, s)

Example 153

4-Mercapto-1-(3-methylsulfonylamino-4-phenoxybenzyl)pyrrolidin-2-one

By a method similar to that in Example 31 and starting from 39.0 mg (0.090 mmol) of 4-acetylthio-1-(3-methylsulfonylamino-4-phenoxybenzyl)pyrrolidin-2-one obtained in Example 152, 34.0 mg (yield: 97%) of 4-mercapto-1-(3-methylsulfonylamino-4-phenoxybenzyl) pyrrolidin-2-one was obtained as a colorless oil.

$^1$H-NMR (300 MHz, CDCl$_3$)

δ:7.50 (1H, d, J=2.0 Hz), 7.39 (1H, d, J=7.5 Hz), 7.36 (1H, d, J=8.1 Hz), 7.18 (1H, dd, J=7.5, 7.5 Hz), 6.99 (3H, m), 6.86 (1H, d, J=8.3 Hz), 6.85 (1H, brs), 4.51 (1H, d, J=15.0 Hz), 4.40 (1H, d, J=15.0 Hz), 3.71 (1H, dd, J=10.1, 7.2 Hz), 3.57 (1H, m), 3.22 (1H, dd, J=10.1, 5.0 Hz), 3.01 (3H, s), 2.93 (1H, dd, J=17.2, 8.2 Hz), 2.43 (1H, dd, J=17.2, 6.0 Hz), 1.91 (1H, d, J=6.9 Hz) Example 154

4-Acetylthio-1-(4-phenylthiobenzyl)pyrrolidin-2-one

By a method similar to that in Example 30 and starting from 1.61 g (6.9 mmol) of 4-phenylthiobenzyl chloride prepared from 4-fluorobenzaldehyde and thiophenol and 1.80 g (10 mmol) of 4-trimethylsilyloxypyrrolidin-2-one, 716 mg (yield: 29%) of 4-acetylthio-1-(4-phenylthiobenzyl) pyrrolidin-2-one was obtained as a tan oil.

Elemental analysis (%): C$_{19}$H$_{19}$NO$_2$S$_2$

Calcd.: C, 63.83;H, 5.36;N, 3.92;S, 17.94

Found: C, 63.86;H, 5.11;N, 3.99;S, 17.77

Example 155

4-Mercapto-1-(4-phenylthiobenzyl)pyrrolidin-2-one

By a method similar to that in Example 31 and starting from 130 mg (0.36 mmol) of 4-acetylthio-1-(4-phenylthiobenzyl)pyrrolidin-2-one obtained in Example 154, 69.0 mg (yield: 61%) of 4-mercapto-1-(4-phenylthiobenzyl)pyrrolidin-2-one was obtained as a colorless oil.

$^1$H-NMR (300 MHz, CDCl$_3$)

δ:7.38–7.26 (7H, m), 7.17 (2H, d, J=8.33 Hz), 4.47 (1H, d, J=14.9 Hz), 4.40 (1H, d, J=14.9 Hz), 3.64 (1H, dd, J=10.0, 7.2 Hz), 3.54 (1H, m), 3.16 (1H, dd, J=10.0, 5.0 Hz), 2.92 (1H, dd, J=17.1, 8.1 Hz), 2.42 (1H, dd, J=17.1, 6.1 Hz), 1.86 (1H, d, J=6.7 Hz),

Example 156

4-Acetylthio-1-[4-(2'-pyridyloxy)benzyl]pyrrolidin-2-one

By a method similar to that in Example 30 and starting from 420 mg (1.9 mmol) of 4-(2'-pyridyloxy)benzyl chloride prepared from 4-fluorobenzaldehyde and 2-hydroxypyridine and 494 mg (2.9 mmol) of 4-trimethylsilyloxypyrrolidin-2-one, 47.0 mg (yield: 7%) of 4-acetylthio-1-[4-(2'-pyridyloxy)benzyl]pyrrolidin-2-one was obtained as a pale yellow powder.

$^1$H-NMR (300 MHz, CDCl$_3$)

δ:8.20 (1H, dd, J=5.0, 1.9 Hz), 7.70 (1H, ddd, J=8.8, 6.9, 1.9 Hz), 7.26 (2H, d, J=8.5 Hz), 7.11 (2H, d, J=8.5 Hz), 7.00 (1H, dd, J=6.9, 5.0 Hz), 6.92 (1H, d, J=8.8 Hz), 4.50 (1H, d, J=14.7 Hz), 4.42 (1H, d, J=14.7 Hz), 4.07 (1H, m), 3.78 (1H, dd, J=10.6, 7.6 Hz), 3.21.(1H, dd, J=10.6, 5.0 Hz), 2.93 (1H, dd, J=17.4, 9.0 Hz), 2.43 (1H, dd, J=17.4, 6.0 Hz), 2.32 (3H, s)

Example 157

4-Acetylthio-1-[4-(3'-thienyloxy)benzyl]pyrrolidin-2-one (1) 7.50 g (61 mmol) of 4-hydroxybenzaldehyde, 10.0 g (61 mmol) of 3-bromothiophene, 3.40 g (25 mmol) of potassium carbonate and 500 mg of copper turnings were treated and heated as neat at 140° C. for 44 hours. The reaction mixture was poured into an aqueous solution of sodium hydroxide and extracted three times with ethyl acetate, and the organic layer obtained was washed with a saturated aqueous solution of sodium carbonate, water and saturated brine, and then dried over anhydrous sodium sulfate. After concentrating under reduced pressure, the residue was subjected to column chromatography on silica gel eluting with hexane-ethyl acetate (70:30) to obtain 1.70 g (yield: 14%) of 4-(3'-thienyloxy)benzaldehyde as a yellow oil.

¹H,—NMR (300 MHz, CDCl₃)
δ:9.93 (1H, s), 7.85 (2H, d, J=8.6 Hz), 7.33 (1H, dd, J=5.1, 3.3 Hz), 7.11 (2H, d, J=8.6 Hz), 6.87 (1H dd, J=5.1, 1.4 Hz), 6.84 (1H, dd, J=3.3, 1.4 Hz)

(2) Then by a method similar to that in Example 30 and starting from 1.30 g (5.8 mmol) of 4-(3'-thienyloxy)benzyl chloride and 1.20 g (7.0 mmol) of 4-trimethylsilyloxypyrrolidin-2-one, 521 mg (yield: 26%) of 4-acetylthio-1-[4-(3'-thienyloxy)benzyl]pyrrolidin-2-one was obtained as a tan oil.

¹H-NMR (300 MHz, CDCl₃)
δ:7.26 (1H, dd, J=5.2, 3.3 Hz), 7.18 (2H, d, J=8.6 Hz), 7.00 (2H, d, J=8.6 Hz), 6.85 (1H, dd, J=5.2, 1.5 Hz), 6.62 (1H dd, J=3.3, 1.5 Hz), 4.46 (1H d, J=14.7 Hz), 4.39 (1H, d, J=14.7 Hz), 4.05 (1H, m), 3.75 (1H, dd, J=10.6, 7.6 Hz), 3.16 (1H, dd, J=10.6, 5.0 Hz), 2.92 (1H, dd, J=17.4, 9.0 Hz), 2.42 (1H, dd, J=17.4, 6.0 Hz), 2.32 (3H, s)

Example 158

4-Mercapto-1-[4-(3'-thienyloxy)benzyl]pyrrolidin-2-one

By a method similar to that in Example 31 and starting from 100 mg (0.30 mmol) of 4-acetylthio-1-[4-(3'-thienyloxy)benzyl]pyrrolidin-2-one obtained in Example 157, 74.0 mg (yield: 81%) of 4-mercapto-1-[4-(3'-thienyloxy)benzyl]pyrrolidin-2-one was obtained as a colorless oil.

¹H-NMR (300 MHz, CDCl₃)
δ:7.27 (1H, dd, J=5.2, 3.2 Hz), 7.20 (2H, d, J=8.6 Hz), 7.01 (2H, d, J=8.6 Hz), 6.84 (1H, dd, J=5.2, 1.5 Hz), 6.63 (1H, dd, J=3.2, 1.5 Hz), 4.47 (1H, d, J=14.7 Hz), 4.40 (1H, d, J=14.7 Hz), 3.65 (1H, dd, J=10.0, 7.2 Hz), 3.54 (1H, m), 3.16 (1H, dd, J=10.0, 5.0 Hz), 2.92 (1H, dd, J=17.1, 8.1 Hz), 2.42 (1H, dd, J=17.1, 6.1 Hz), 1.86 (1H, d, J=6.7 Hz)

Example 159

4-Acetylthio-1-(4-benzylbenzyl)pyrrolidin-2-one (1) 5.07 g (22.4 mmol) of 4-benzoylbenzoic acid was dissolved in 50 ml of N,N-dimethylformamide, treated with 3.10 g (22.4 mmol) of potassium carbonate and 2.79 ml (44.8 mmol) of methyl iodide and then stirred at room temperature for 14 hours. The reaction mixture was concentrated under reduced pressure, treated with ethyl acetate, washed with water and saturated brine, and then dried over anhydrous sodium sulfate. After concentrating under reduced pressure, the residue was crystallized from hexane-ethyl acetate to obtain 4.28 g (yield: 80%) of methyl 4-benzoylbenzoate as a colorless needle.

¹H-NMR (300 MHz, CDCl₃)
δ:8.15 (2H, d, J=8.3 Hz), 7.84 (2H, d, J=8.3 Hz), 7.81 (2H, m), 7.62 (1H, m), 7.50 (2H, m), 3.97 (3H, s)

(2) To a mixture of 24 ml of chloroform and 40 ml of trifluoroacetic acid, 1.89 g (49.9 mmol) of sodium borohydride was added and then 2.00 g (8.32 mmol) of methyl 4-benzoylbenzoate was added, and the mixture was stirred at room temperature for 5 hours, and 945 mg (25.0 mmol) of sodium borohydride was further added and stirred for 16 hours. The reaction mixture was concentrated under reduced pressure, treated with ethyl acetate, washed with saturated aqueous sodium hydrogen carbonate, water and saturated brine, and then dried over anhydrous sodium sulfate. After concentrating under reduced pressure, the residue was subjected to column chromatography on silica gel, and the fraction eluted with hexane: ethyl acetate (100:0–90:10) was concentrated under reduced pressure to obtain 1.81 g (yield: 96%) of methyl 4-benzylbenzoate as a colorless oil.

¹H-NMR (300 MHz, CDCl₃)
δ:7.95 (2H, d, J=8.3 Hz), 7.15–7.33 (7H, m), 4.03 (2H, s), 3.89 (3H, s)

(3) 1.76 g (7.78 mmol) of methyl 4-benzylbenzoate was dissolved in 40 ml of diethyl ether, treated with 591 mg (15.6 mmol) of lithium aluminum hydride and stirred at room temperature for 1 hour. The reaction mixture was treated with water with cooling on ice and extracted three times with ethyl acetate, and the ethyl acetate layer was washed twice with water and once with saturated brine, and dried over anhydrous sodium sulfate. The mixture was concentrated under reduced pressure to obtain 1.57 g (quantitative yield) of 4-benzylbenzylalcohol as a colorless oil.

¹H-NMR (300 MHz, CDCl₃)
δ:7.28 (4H, m), 7.19 (5H, m), 4.65 (2H, s), 3.98 (2H, s)

(4) 1.52 g (7.67 mmol) of 4-benzylbenzylalcohol was dissolved in chloroform, and 620 μl (7.67 mmol) of pyridine was added with cooling on ice, and a solution of 615 μl (8.44 mmol) of thionyl chloride in 5 ml of chloroform was added dropwise over a period of 30 minutes, and then the mixture was stirred at room temperature for 1 hour. The reaction mixture was concentrated under reduced pressure, treated with ethyl acetate, washed with water and saturated brine, and dried over anhydrous sodium sulfate. The mixture was concentrated under reduced pressure to obtain 1.68 g (quantitative yield) of 4-benzylbenzyl chloride as a colorless oil.

¹H-NMR (300 MHz, CDCl₃)
δ:7.29 (4H, m), 7.19 (5H, m), 4.56 (2H, s), 3.98 (2H, s)

(5) Similarly to Example 30 and starting from 1.60 g (7.38 mmol) of 4-benzylbenzyl chloride, 1.28 g (7.38 mmol) of 4-trimethylsilyloxypyrrolidin-2-one and 414 mg (7.38 mmol) of powdered potassium hydroxide, 510 mg (yield: 25%) of 4-hydroxy-1-(4-benzylbenzyl)pyrrolidin-2-one was obtained as a white powder.

¹H-NMR (300 MHz, CDCl₃)
δ:7.28 (2H, m), 7.13–7.23 (7H, m), 4.47 (1H, m), 4.44 (2H, s), 3.95 (2H, s), 3.49 (1H, dd, J=10.9, 5.7 Hz), 3.18 (1H, dd, J=10.9, 1.9 Hz), 2.73 (1H, dd, J=17.3, 6.4 Hz), 2.42 (1H, dd, J=17.3, 2.3 Hz), 2.14 (1H, brs)

(6) Starting from 460 mg (1.63 mmol) of 4-hydroxy-1-(4-benzylbenzyl)pyrrolidin-2-one, 454 μl (3.26 mmol) of triethylamine and 252 μl (3.26 mmol) of methanesulfonyl chloride, 534 mg (yield: 91%) of 4-methanesulfonyloxy-1-(4-benzylbenzyl)pyrrolidin-2-one was obtained as a white powder.

¹H-NMR (300 MHz, CDCl₃)
δ: 7.29 (2H, m), 7.13–7.23 (7H, m), 5.26 (1H, m), 4.48 (1H, d, J=14.9 Hz), 4.43 (1H, d, J=14.9 Hz), 3.96 (2H, s), 3.63 (1H, dd, J=11.7, 5.7 Hz), 3.49 (1H, dd, J=11.7, 2.1 H, z), 2.95 (3H, s), 2.86 (1H, dd, J=18.1, 6.8 Hz), 2.70 (1H, dd, J=18.1, 2.6 Hz)

(7) Starting from 500 mg (1.39 mmol) of 4-methanesulfonyloxy-1-(4-benzylbenzyl)pyrrolidin-2-one and 318 mg (2.78 mmol) of potassium thioacetate, 331 mg (yield: 70%) of 4-acetylthio-1-(4-benzylbenzyl)pyrrolidin-2-one was obtained as a white powder.

¹H-NMR (300 MHz, CDCl₃)
δ:7.29 (2H, m), 7.13–7.23 (7H, m), 4.42 (2H, s), 4.04 (1H, m), 3.96 (2H s), 3.72 (1H, dd, J=10.9, 7.5 Hz), 3.15 (1H, dd, J=10.9, 5.1 Hz), 2.91 (1H, dd, J=17.3, 9.1 Hz), 2.41 (1H, dd, J=17.3, 6.0 Hz), 2.30 (3H, s)

Example 160

4-Mercapto-1-(4-benzylbenzyl)pyrrolidin-2-one 200 mg (0.589 mmol) of 4-acetylthio-1-(4-benzylbenzyl)pyrrolidin-2-one obtained in Example 159 was processed similarly to Example 31 to obtain 147 mg (yield:84%) of 4-mercapto-1-(4-benzylbenzyl)pyrrolidin-2-one as a white powder.

$^1$H-NMR (300 MHz, CDCl$_3$)

δ:7.29 (2H, m), 7.13–7.23 (7H, m), 4.43 (2H, s), 3.97 (2H, s), 3.62 (1H, dd, J=9.8, 7.2 Hz), 3.51 (1H, m), 3.14 (1H, dd, J=9.8, 5.1 Hz), 2.90 (1H, dd, J=17.0, 8.3 Hz), 2.41 (1H, dd, J=17.0, 6.2 Hz), 1.85 (1H, d, J=6.8 Hz)

Example 161

4-Acetylthio-1-(4-benzoylbenzyl)pyrrolidin-2-one (1) 2.00 g (8.32 mmol) of methyl 4-benzoylbenzoate obtained in Example 159 was dissolved in 25 ml of nitromethane, treated with 9.10 ml (83.2 mmol) of trimethyl o-formate, 3.37 ml (83.2 mmol) of absolute methanol and 147 µl (1.66 mmol) of trifluoromethanesulfonic acid, heated under reflux for 4 hours with stirring, treated further with 9.10 ml (83.2 mmol) of trimethyl orthoformate, and 3.37 ml (83.2 mmol) of absolute methanol, and heated under reflux for 16 hours with stirring. The reaction mixture was treated with saturated aqueous sodium hydrogen carbonate and extracted twice with ethyl acetate, and the ethyl acetate layer was washed twice with water and once with saturated brine, and dried over anhydrous sodium sulfate. After concentrating under reduced pressure, the residue was subjected to column chromatography on silica gel eluting with hexane: ethyl acetate (95:5) to obtain 4-methoxycarbonylbenzophenone dimethylacetal, and 680 mg of the starting methyl ester was recovered using hexane: ethyl acetate (90:10).The starting material recovered was subjected to the reaction again and combined with 4-methoxycarbonylbenzophenone dimethylacetal to obtain 2.32 g (yield: 97%) as a colorless oil.

$^1$H-NMR (300 MHz, CDCl$_3$)

δ:7.96 (2H, d, J=8.7 Hz), 7.58 (2H, d, J=8.7 Hz), 7.48 (2H, m), 7.19–7.33 (3H, m), 3.88 (3H, s), 3.13 (6H, s)

(2) Starting from 2.27 g (7.93 mmol) of 4-methoxycarbonylbenzophenone dimethylacetal and 602 mg (15.9 mmol) of lithium aluminum hydride and similarly to Example 159, 2.05 g (quantitative yield) of 4-hydroxymethylbenzophenone dimethylacetal as a colorless oil.

$^1$H-NMR (300 MHz, CDCl$_3$)

δ: 7.50 (4H, m), 7.29 (4H, m), 7.21 (1H, m), 4.65 (2H, s), 3.13 (6H, s)

(3) 2.00 g (7.74 mmol) of 4-hydroxymethylbenzophenone dimethylacetal, 626 µl (7.74 mmol) of pyridine and 621 µl (8.51 mmol) of thionyl chloride were processed similarly to Example 159, 930 mg (yield: 52%) of 4-benzoylbenzyl chloride was obtained as a colorless oil.

$^1$H-NMR (300 MHz, CDCl$_3$)

δ:7.81 (4H, m), 7.59 (1H, m), 7.51 (4H, m), 4.65 (2H, s)

(4) Starting from 900 mg (3.90 mmol) of 4-benzoylbenzyl chloride, 535 mg (3.90 mmol) of 4-trimethylsilyloxypyrrolidin-2-on and 219 mg (3.90 mmol) of powdered potassium hydroxide, 200 mg (yield: 17%) of 4-hydroxy-1-(4-benzoylbenzyl)pyrrolidin-2-one was obtained as a tan powder.

$^1$H-NMR (300 MHz, CDCl$_3$)

δ:7.79 (4H, m), 7.60 (1H, m), 7.48 (2H, m), 7.36 (2H, d, J=8.3 Hz), 4.64 (1H, d, J=15.3 Hz), 4.55 (1H, m), 4.51 (1H, d, J=15.3 Hz), 3.57 (1H, dd, J=10.9, 5.7 Hz), 3.24 (1H, dd, J=10.9, 2.1 Hz), 2.78 (1H, dd, J=17.3, 6.4 Hz), 2.47 (1H, dd, J=17.3, 2.3 Hz), 1.99 (1H, brs)

(5) Starting from 180 mg (0.609 mmol) of 4-hydroxy-1-(4-benzoylbenzyl)pyrrolidin-2-one, 170 µl (1.22 mmol) of triethylamine and 94.3 µl (1.22 mmol) of methanesulfonyl chloride, 249 mg (quantitative yield) of 4-methanesulfonyloxy-1-(4-benzoylbenzyl)pyrrolidin-2-one was obtained as a colorless oil.

$^1$H-NMR (300 MHz, CDCl$_3$)

δ:7.79 (4H, m), 7.61 (1H, m), 7.49 (2H, m), 7.35 (2H, d, J=7.9 Hz), 5.32 (1H, m), 4.61 (1H, d, J=15.1 Hz), 4.55 (1H, d, J=15.1 Hz), 3.71 (1H, dd, J=11.9, 5.9 Hz), 3.57 (1H, dd, J=11.9, 1.9 Hz), 3.04 (3H, s), 2.91 (1H, dd, J=18.1, 6.8 Hz), 2.75 (1H, dd, J=18.1, 2.5 Hz)

(6) Starting from 227 mg (0.609 mmol) of 4-methanesulfonyloxy-1-(4-benzoylbenzyl)pyrrolidin-2-one and 140 mg (1.23 mmol) of potassium thioacetate, 138 mg (yield: 64%) of 4-acetylthio-1-(4-benzoylbenzyl) pyrrolidin-2-one was obtained as a colorless oil.

$^1$H-NMR (300 MHz, CDCl$_3$)

δ:7.80 (4H, m), 7.61 (1H, m), 7.49 (2H, m), 7.35 (2H, d, J=8.3 Hz), 4.61 (1H, d, J=15.1 Hz), 4.48 (1H, d, J=15.1 Hz), 4.09 (1H, m), 3.80 (1H, dd, J=10.6, 7.5 Hz), 3.21 (1H, dd, J=10.6, 4.9 Hz), 2.96 (1H, dd, J=17.5, 9.9 Hz), 2.46 (1H, dd, J=17.5, 5.9 Hz), 2.32 (3H, s)

Example 162

4-Mercapto-1-(4-benzoylbenzyl)pyrrolidin-2-one 108 mg (0.306 mmol) of 4-acetylthio-1-(4-benzoylbenzyl)pyrrolidin-2-one obtained in Example 161 was processed similarly to Example 31 to obtain 77.2 mg (yield: 81%) of 4-mercapto-1-(4-benzoylbenzyl)pyrrolidin-2-one as a colorless oil.

$^1$H-NMR (300 MHz, CDCl$_3$)

δ:7.80 (4H, m), 7.60 (1H, m), 7.49 (2H, m), 7.37 (2H, d, J=8.3 Hz), 4.61 (1H, d J=15.1 Hz), 4.51 (1H, d, J=15.1 Hz), 3.69 (1H, dd, J=10.0, 7.2 Hz), 3.59 (1H, m), 3.20 (1H, dd, J=10.0, 4.9 Hz), 2.95 (1H, dd, J=17.2, 8.1 Hz), 2.45 (1H, dd, J=17.2, 6.9 Hz), 1.90 (1H d, J=6.4 Hz)

Example 163

4-Acetylthio-1-(4-phenoxymethylbenzyl)pyrrolidin-2-one (1) 5.00 g (30.1 mmol) of methyl 4-hydroxymethylbenzoate was dissolved in 75 ml of chloroform, and 2.43 ml (30.1 mmol) of pyridine was added with cooling on ice, and then a solution of 2.42 ml (33.1 mmol) of thionyl chloride in 10 ml of chloroform was added dropwise over a period of 30 minutes, and then the mixture was stirred with cooling on ice for 30 minutes and 2 hours at room temperature. The reaction mixture was concentrated under reduced pressure, treated with ethyl acetate, washed twice with water and once with saturated brine, and dried over anhydrous sodium sulfate. After concentrating under reduced pressure, the residue was dissolved in 75 ml of N,N-dimethylformamide, treated with 2.83 g (30.1 mmol) of phenol and 4.16 g (30.1 mmol) of potassium carbonate, and stirred at room temperature for 40 hours. The reaction mixture was concentrated under reduced pressure, treated with ethyl acetate, washed twice with water and once with saturated brine, and dried over anhydrous sodium sulfate. After concentrating under reduced pressure, the residue was subjected to column chromatography on silica gel, and the fraction eluted with hexane: ethyl acetate (95:5) was concentrated under reduced pressure, and crystallized from hexane-ethyl acetate to obtain 5.35 g (yield: 73%) of methyl 4-phenoxymethylbenzoate as a colorless needle.

$^1$H-NMR (300 MHz, CDCl$_3$)

δ:8.06 (2H, d, J=8.3 Hz), 7.51 (2H, d, J=8.3 Hz), 7.30 (2H, m), 6.96 (3H, m), 5.13 (2H, s), 3.92 (3H, s)

(2) Starting from 5.35 g (22.1 mmol) of methyl 4-phenoxymethylbenzoate and 839 mg (22.1 mmol) of lithium aluminum hydride and similarly to Example 159, 4.22 g (yield: 89%) of 4-phenoxymethylbenzylalcohol was obtained as a white powder.
$^1$H-NMR (300 MHz, CDCl$_3$)
δ:7.41 (4H, m), 7.29 (2H, m), 6.96 (3H, m), 5.07 (2H, s), 4.70 (2H, s)

(3) 2.00 g (9.33 mmol) of 4-phenoxymethylbenzylalcohol, 755 μl (9.33 mmol) of pyridine and 749 μl (10.3 mmol) of thionyl chloride were processed similarly to Example 159 to obtain 2.20 g (quantitative yield) of 4-phenoxymethylbenzyl chloride as a colorless oil.
$^1$H-NMR (300 MHz, CDCl$_3$)
δ:7.42 (4H, m), 7.29 (2H, m), 6.97 (3H, m), 5.07 (2H, s), 4.60 (2H, s)

(4) Similarly to Example 30 and starting from 1.40 g (6.00 mmol) of 4-phenoxymethylbenzyl chloride, 1.04 g (6.00 mmol) of 4-trimethylsilyloxypyrrolidin-2-one and 396 mg (7.06 mmol) of powdered potassium hydroxide, 710 mg (yield: 40%) of 4-hydroxy-1-(4-phenoxymethylbenzyl)pyrrolidin-2-one was obtained as a white powder.
Elemental analysis (%): C$_{18}$H$_{19}$NO$_3$
Calcd.: C, 72.712;H, 6.44;N, 4.71
Found: C, 72.46;H, 6.45;N, 4.54

(5) Starting from 650 mg (2.19 mmol) of 4-hydroxy-1-(4-phenoxymethylbenzyl)pyrrolidin-2-one, 610 μl (4.38 mmol) of triethylamine and 339 μl (4.38 mmol) of methanesulfonyl chloride, 760 mg (yield: 92%) of 4-methanesulfonyloxy-1-(4-phenoxymethylbenzyl)pyrrolidin-2-one was obtained as a white powder.
Elemental analysis (%): C$_{19}$H$_{21}$NO$_5$S.0.1H$_2$O
Calcd.: C, 60.49;H, 5.66;N, 3.71
Found: C, 60.46;H, 5.84;N, 3.61

(6) Starting from 710 mg (1.89 mmol) of 4-methanesulfonyloxy-1-(4-phenoxymethylbenzyl)pyrrolidin-2-one and 432 mg (3.78 mmol) of potassium thioacetate, 464 mg (yield: 69%) of 4-acetylthio-1-(4-phenoxymethylbenzyl)pyrrolidin-2-one was obtained as a white powder.
$^1$H-NMR (300 MHz, CDCl$_3$)
δ: 7.42 (2H, d, J=7.9 Hz), 7.23–7.34 (4H, m), 6.97 (3H, m), 5.05 (2H, s), 4.51 (1H, d, J=14.7 Hz), 4.42 (1H, d, J=14.7 Hz), 4.05 (1H, m), 3.75 (1H, dd, J=10.6, 7.5 Hz), 3.17 (1H, dd, J=10.6, 4.9 Hz), 2.93 (1H, dd, J=17.3, 8.9 Hz), 2.43 (1H, dd, J=17.3, 6.0 Hz), 2.31 (3H, s)

Example 164

4-Mercapto-1-(4-phenoxymethylbenzyl)pyrrolidin-2-one 230 mg (0.647 mmol) of 4-acetylthio-1-(4-phenoxymethylbenzyl)pyrrolidin-2-one obtained in Example 163 was dissolved in 23 ml of methanol, treated with 132 μl (0.647 mmol) of a 28% solution of sodium methoxide in methanol, and stirred at room temperature for 0.5 hour. The reaction mixture was adjusted at pH 2.0, concentrated under reduced pressure, treated with ethyl acetate, washed twice with water and once with saturated brine, and dried over anhydrous sodium sulfate. After concentrating under reduced pressure, the mixture was precipitated from hexane-ethyl acetate to obtain 156 mg (yield: 77%) of 4-mercapto-1-(4-phenoxymethylbenzyl)pyrrolidin-2-one as a white powder.
$^1$H-NMR (300 MHz, CDCl$_3$)
δ:7.42 (2H, d, J=7.9 Hz), 7.24–7.33 (4H, m), 6.97 (3H, m), 5.05 (2H, s), 4.50 (1H, (d, J=14.9 Hz), 4.45 (1H, d, J=14.9 Hz), 3.64 (1H, dd, J=10.2, 7.2 Hz), 3.53 (1H, m), 3.16 (1H, dd, J=10.2, 5.1 Hz), 2.92 (1H, dd, J=17.2, 8.1 Hz), 2.43 (1H, dd, J=17.2, 6.2 Hz), 1.86 (1H, d, J=6.8 Hz)

Example 165

4-Acetylthio-1-(4-benzyloxybenzyl)pyrrolidin-2-one (1) 4.96 g (40.0 mmol) of 4-hydroxybenzylalcohol was dissolved in 100 ml of N,N-dimethylformamide, treated with 5.52 g (40.0 mmol) of potassium carbonate and 4.76 ml (40.0 mmol) of benzyl bromide, and stirred at room temperature for 14 hours. The reaction mixture was concentrated under reduced pressure, treated with in ethyl acetate, washed twice with water and once with saturated brine, and dried over anhydrous sodium sulfate. After concentrating under reduced pressure, the residue was subjected to column chromatography on silica gel, and the fraction eluted with hexane: ethyl acetate (60:40) was collected and concentrated under reduced pressure and precipitated from hexane-ethyl acetate to obtain 3.92 g (yield: 46%) of 4-benzyloxybenzylalcohol as a white powder.
$^1$H-NMR (300 MHz, CDCl$_3$)
δ:7.26–7.46 (7H, m), 6.97 (2H, d, J=8.3 Hz), 5.07 (2H, s), 4.62 (2H, s)

(2) 2.00 g (9.33 mmol) of 4-benzyloxybenzylalcohol, 755 μl (9.33 mmol) of pyridine and 749 μl (10.3 mmol) of thionyl chloride were processed similarly to Example 159, 2.17 g (quantitative yield) of 4-benzyloxybenzyl chloride was obtained as a colorless oil.
$^1$H-NMR (300 MHz, CDCl$_3$)
δ: 7.28–7.45 (7H, m), 6.95 (2H, d, J=8.3 Hz), 5.07 (2H, s), 4.56 (2H, s)

(3) Similarly to Example 30 and starting from 1.40 g (6.00 mmol) of 4-benzyloxybenzyl chloride, 1.04 g (6.00 mmol) of 4-trimethylsilyloxypyrrolidin-2-one and 396 mg (7.06 mmol) of powdered potassium hydroxide, 420 mg (yield: 24%) of 4-hydroxy-1-(4-benzyloxybenzyl)pyrrolidin-2-one was obtained as a white powder.
Elemental analysis (%): C$_{18}$H$_{19}$NO$_3$.0.1H$_2$O
Calcd.: C, 72.27;H, 6.47;N, 4.68
Found: C, 72.22;H, 6.23;N, 4.54

(4) Starting from 370 mg (1.24 mmol) of 4-hydroxy-1-(4-benzyloxybenzyl)pyrrolidin-2-one, 346 μl (2.48 mmol) of triethylamine and 192 μl (2.48 mmol) of methanesulfonyl chloride, 348 mg (yield: 75%) of 4-methanesulfonyloxy-1-(4-benzyloxybenzyl)pyrrolidin-2-one was obtained as a white powder.
Elemental analysis (%): C$_{19}$H$_{21}$NO$_5$S
Calcd.: C, 60.78;H, 5.64;N, 3.73
Found: C, 60.58;H, 5.77;N, 3.58

(5) Starting from 298 mg (0.794 mmol) of 4-methanesulfonyloxy-1-(4-benzyloxybenzyl)pyrrolidin-2-one and 181 mg (1.59 mmol) of potassium thioacetate, 171 mg (yield: 61%) of 4-acetylthio-1-(4-benzyloxybenzyl)pyrrolidin-2-one as a white powder.
$^1$H-NMR (300 MHz, CDCl$_3$)
δ:7.29–7.46 (5H, m), 7.15 (2H, d, J=8.5 Hz), 6.94 (2H, d, J=8.5 Hz), 5.05 (2H, s) 4.42 (1H, d, J=14.5 Hz), 4.36 (1H, d, J=14.5 Hz), 4.03 (1H, m), 3.72 (1H, dd, J=10.6, 7.5 Hz), 3.14 (1H, dd, J=10.6, 4.9 Hz), 2.91 (1H, dd, J=17.3, 9.0 Hz), 2.41 (1H, dd, J=17.3, 6.0 Hz), 2.30 (3H, s)

Example 166

4-Mercapto-1-(4-benzyloxybenzyl)pyrrolidin-2-one 100 mg (0.281 mmol) of 4-acetylthio-1-(4-benzyloxybenzyl)pyrrolidin-2-one obtained in Example 165 was processed similarly to Example 164 to obtain 46.1 mg (yield: 52%) of 4-mercapto-1-(4-benzyloxybenzyl) pyrrolidin-2-one as a white powder.

$^1$H-NMR (300 MHz, CDCl$_3$)

δ: 7.29–7.46 (5H, m), 7.17 (2H, d, J=8.5 Hz), 6.94 (2H, d, J=8.5 Hz), 5.05 (2H, s), 4.43 (1H, d, J=14.5 Hz), 4.38 (1H, d, J=14.5 Hz), 3.62 (1H dd, J=10.0, 7.4 Hz), 3.51 (1H, m), 3.13 (1H, dd, J=10.2, 5.1 Hz), 2.91 (1H, dd, J=17.2, 8.1 Hz), 2.41 (1H, dd, J=17.2, 6.2 Hz), 1.84 (1H, d, J=6.8 Hz)

Example 167

4-Acetylthio-1-(4-phenethylbenzyl)pyrrolidin-2-one (1) 4.75 g (22.8 mmol) of trans-4-stilbenecarboxaldehyde was dissolved in a solvent mixture of 100 ml of methanol and 100 ml of tetrahydrofuran, treated with 450 mg of 10% Pd/C, and stirred under hydrogen atmosphere at room temperature for 3 hours. The catalyst was filtered off, and the mixture was concentrated under reduced pressure, dissolved in 40 ml of methanol, treated with 431 mg (11.4 mmol) of sodium borohydride, and stirred at room temperature for 0.5 hour. The reaction mixture was adjusted at pH 3.0, concentrated under reduced pressure and extracted twice with ethyl acetate, and the ethyl acetate layer was washed twice with water and once with saturated brine, and dried over anhydrous sodium sulfate. After concentrating under reduced pressure, the residue was subjected to column chromatography on silica gel, and the fraction eluted with hexane: ethyl acetate (70:30) was collected and concentrated under reduced pressure to obtain 4.34 g (yield: 90%) of 4-phenethylbenzylalcohol as a white powder.

$^1$H-NMR (300 MHz, CDCl3)

δ:7.24–7.31 (4H, m), 7.19 (5H, m), 4.66 (2H, s), 2.92 (4H, s)

(2) 2.00 g (9.42 mmol) of 4-phenethylbenzylalchol, 762 μl (9.42 mmol) of pyridine and 759 μl (10.4 mmol) of thionyl chloride were processed similarly to Example 159, 2.24 g (quantitative yield) of 4-phenethylbenzyl chloride was obtained as a colorless oil.

$^1$H-NMR (300 MHz, CDCl$_3$)

δ:7.28 (4H, m), 7.18 (5H, m), 4.57 (2H, s), 2.91 (4H, s)

(3) Similarly to Example 30 and starting from 1.38 g (6.00 mmol) of 4-phenethylbenzyl chloride, 1.04 g (6.00 mmol) of 4-trimethylsilyloxypyrrolidin-2-one and 396 mg (7.06 mmol) of powdered potassium hydroxide, 730 mg (yield: 41%) of 4-hydroxy-1-(4-phenethylbenzyl)pyrrolidin-2-one was obtained as a white powder.

Elemental analysis (%): C$_{19}$H$_{21}$NO$_2$

Calcd.: C, 77.26;H, 7.17;N, 4.74

Found: C, 77.30;H, 7.05;N, 4.65

(4) Starting from 600 mg (2.03 mmol) of 4-hydroxy-1-(4-phenethylbenzyl)pyrrolidin-2-one, 566 μl (4.06 mmol) of triethylamine and 314 μl (4.06 mmol) of methanesulfonyl chloride, 542 mg (yield: 72%) of 4-methanesulfonyloxy-1-(4-phenethylbenzyl)pyrrolidin-2-one was obtained as a white powder.

Elemental analysis (%): C$_{20}$H$_{23}$NO$_4$S

Calcd.: C, 64.32;H, 6.21;N, 3.75

Found: C, 64.38;H, 6.12;N, 3.77

(5) Starting from 500 mg (1.34 mmol) of 4-methanesulfonyloxy-1-(4-phenethylbenzyl)pyrrolidin-2-one and 306 mg (2.68 mmol) of potassium thioacetate, 339 mg (yield: 72%) of 4-acetylthio-1-(4-phenethylbenzyl) pyrrolidin-2-one was obtained as a white powder.

Elemental analysis (%): C$_{21}$H$_{23}$NO$_2$S

Calcd.: C, 71.35;H, 6.56;N, 3.96

Found: C, 71.53;H, 6.37;N, 3.95

Example 168

4-Mercapto-1-(4-phenethylbenzyl)pyrrolidin-2-one 200 mg (0.566 mmol) of 4-acetylthio-1-(4-phenethylbenzyl)pyrrolidin-2-one obtained in Example 167 was processed similarly to Example 31 to obtain 154 mg (yield: 87%) of 4-mercapto-1-(4-phenethylbenzyl) pyrrolidin-2-one as a white powder.

$^1$H-NMR (300 MHz, CDCl$_3$)

δ:7.24–7.31 (3H, m), 7.13–7.23 (6H, m), 4.47 (1H, d, J=14.7 Hz), 4.40 (1H, d, J=14.7 Hz), 3.62 (1H, dd, J=9.8, 7.2 Hz), 3.52 (1H, m), 3.14 (1H, dd, J=9.8, 4.9 Hz), 2.92 (1H, dd, J=17.0, 8.3 Hz), 2.91 (4H, s), 2.42 (1H, dd, J=17.0, 6.2 Hz), 1.85 (1H, d, J=6.8 Hz)

Example 169

S—[5-Oxo-1-(4-phenoxyphenethyl)-3-pyrrolidinyl] ethanethioate 1.3 ml (6.64 mmol) of 4-phenoxyphenethylamine was added to a solution of 1.0 g (6.32 mmol) of O-acetylmalic anhydride in 6.5 ml of THF and the mixture was stirred for 1.3 hours. The reaction mixture was concentrated under reduced pressure, dissolved in 5 ml of acetyl chloride, and stirred at 60° C. for 12 hours. The reaction mixture was concentrated under reduced pressure, dissolved in ethyl acetate, washed with water, and then twice with a saturated aqueous solution of sodium hydrogen carbonate and then with saturated brine, and dried over anhydrous sodium sulfate. After concentrating under reduced pressure, the residue was precipitated from ethyl acetate (yield: 75%) to obtain 1.3 g (3.68 mmol) of 2,5-dioxo-1-(4-phenoxyphenethyl)-3-pyrrolidinyl acetate, which was then dissolved in a solvent mixture of 6.5 ml of ethanol and 13 ml of THF, and treated with 696 mg (18.40 mmol) of sodium borohydride at −18° C. and stirred at −18 to −9° C. for 5 hours. The reaction mixture was partitioned between a saturated aqueous solution of sodium hydrogen carbonate and ethyl acetate, and the ethyl acetate layer was washed with saturated brine, and dried over anhydrous sodium sulfate. After concentrating under reduced pressure, the residue was dissolved in 13 ml of trifluoroacetic acid, treated with 705 μl (4.42 mmol) of triethylsilane, and stirred at room temperature for 30 minutes. The reaction mixture was concentrated under reduced pressure, dissolved in ethyl acetate, washed twice with a saturated aqueous solution of sodium hydrogen carbonate and then with saturated brine, and dried over anhydrous sodium sulfate. After concentrating under reduced pressure, the residue was purified by column chromatography on silica gel, and the fraction eluted with n-hexane: ethyl acetate (3:2 to 1:1) was concentrated to obtain (2 steps, yield: 71%) 1.48 g (4.36 mmol) of 5-oxo-1-(4-phenoxyphenethyl)-3-pyrrolidinyl acetate, which was then dissolved in a solution prepared by adding 62 ml (87 mmol) of acetyl chloride dropwise to 10 ml of ethanol, and stirred at 50° C. for 1.5 hours. The reaction mixture was concentrated under reduced pressure and precipitated from ethyl acetate to obtain (yield: 80%) 995 mg (3.35 mmol) of 4-hydroxy-1-(4-phenoxyphenethyl)-2-pyrrolidinone, which was then dissolved in 10 ml of chloroform together with 363 μl (4.69 mmol) of methanesulfonyl chloride, and then treated dropwise with a solution of 654 μl (4.69 mmol) of triethylamine in 5 ml of chloroform at 0° C. over a period of 5 minutes. After completion of the addition, the mixture was stirred at 0° C. for 10 minutes. The reaction mixture was concentrated under reduced pressure, dissolved in ethyl acetate, washed twice with water and then with saturated brine, and dried over anhydrous sodium sulfate. The mixture was concentrated under reduced pressure to obtain 500 mg (1.33 mmol) of 5-oxo-1-(4-phenoxyphenethyl)-3-pyrrolidinyl methanesulfonate, which was then dissolved in a solvent mixture of 10 ml of DMF and 10 ml of ethanol, treated with 304 mg (2.66 mmol) of potassium thioacetate, and stirred at 90° C. for 4 hours. After a half of the solvent was distilled off, the reaction mixture was treated with ethyl acetate, washed 5 times with water and then with saturated brine, and dried over anhydrous sodium sulfate. After concentrating under reduced pressure, the residue was purified by column chromatography on silica gel, and the fraction eluted with n-hexane: ethyl acetate (2:1) was concentrated to obtain 404 mg (yield: 85%) of the title compound as a brown oil.
Elemental analysis (%): $C_{20}H_{21}NO_3S \cdot 0.25H_2O$
Calcd.: C, 66.73;H, 6.02;N, 3.89
Found: C, 66.79;H, 5.98;N, 3.76

Example 170

1-(4-Phenoxyphenethyl)-4-sulfanyl-2-pyrrolidinone 91 mg (0.26 mmol) of S-[5-oxo-1-(4-phenoxyphenethyl)-3-pyrrolidinyl]ethanethioate obtained in Example 169 was dissolved in a mixture of 1 ml of ethanol and 365 μl (5.14 mmol) of acetyl chloride, and stirred at 50° C. for 1.5 hours, and the reaction mixture was concentrated under reduced pressure, and purified by preparative thin layer chromatography (eluent: n-hexane: ethyl acetate (1:2)) to obtain 64 mg (yield: 70%) of the title compound as a colorless oil.
$^1$H-NMR (300 MHz, CDCl$_3$)
δ:7.35–6.93 (9H, m), 3.65–3.41 (4H, m), 3.16 (1H, dd, J=10.0, 5.1 Hz), 2.85–2.78 (3H, m), 2.32 (1H, dd, J=16.9, 6.2 Hz), 1.84 (1H, d, J=7.0 Hz)

Example 171

4-Acetylthio-1-(4-phenylsulfinylbenzyl)pyrrolidin-2-one (1) 324 mg (1.08 mmol) of 4-hydroxy-1-(4-phenylthiobenzyl)pyrrolidin-2-one obtained in Example 154 was dissolved in a mixture of 7 ml of acetic acid and 2 ml of 30% aqueous hydrogen peroxide, and stirred at room temperature for 1 hour. The reaction mixture was treated with ethyl acetate, washed twice with water and then with saturated brine, and dried over anhydrous sodium sulfate. After concentrating under reduced pressure, the residue was subjected to column chromatography on silica gel, and the fraction eluted with hexane: acetone (30:70–0:100) was concentrated under reducedpressureto obtain 239mg (yield: 70%) of 4-hydroxy-1-(4-phenylsulfinylbenzyl)pyrrolidin-2-one as a colorless oil.
$^1$H-NMR (300 MHz, CDCl$_3$)
δ:7.62 (4H, m), 7.46 (3H, m), 7.34 (2H, d, J=8.3 Hz), 4.57 (1H, d, J=15.3 Hz), 4.50 (1H, m), 4.40 (1H, d, J=15.3 Hz), 3.50 (1H, dd, J=10.9, 5.7 Hz), 3.18 (1H, dd, J=10.9, 1.7 Hz), 2.71 (1H, dd, J=17.3, 6.4 Hz), 2.42 (1H, dd, J=17.3, 2.5 Hz)
(2) Starting from 215 mg (0.682 mmol) of 4-hydroxy-1-(4-phenylsulfinylbenzyl)pyrrolidin-2-one, 286 μl (2.04 mmol) of triethylamine and 158 μl (2.04 mmol) of methanesulfonyl chloride, 198 mg (yield: 74%) of 4-methanesulfonyloxy-1-(4-phenylsulfinylbenzyl)pyrrolidin-2-one was obtained as a colorless oil.
$^1$H-NMR (300 MHz, CDCl$_3$)
δ:7.64 (4H, m), 7.47 (3H, m), 7.33 (2H, d, J=8.3 Hz), 5.28 (1H, m), 4.53 (1H, d, J=17.2 Hz), 4.48 (1H, d, J=17.2 Hz), 3.64 (1H, dd, J=12.1, 5.5 Hz), 3.50 (1H, br, d, J=12.1 Hz), 3.00 (3H, s), 2.87 (1H, dd, J=18.1, 6.9 Hz), 2.71 (1H, dd, J=18.1, 2.3 Hz)
(3) Starting from 180 mg (0.457 mmol) of 4-methanesulfonyloxy-1-(4-phenylsulfinylbenzyl)pyrrolidin-2-one and 104 mg (0.915 mmol) of potassium thioacetate, 129 mg (yield: 76%) of 4-acetylthio-1-(4-phenylsulfinylbenzyl)pyrrolidin-2-one was obtained as a colorless oil.
Elemental analysis (%): $C_{19}H_{19}NO_3S_2$
Calcd.: C, 61.10;H, 5.13;N, 3.75
Found: C, 61.05;H, 5.22;N, 3.83

Example 172

4-Mercapto-1-(4-phenylsulfinylbenzyl)pyrrolidin-2-one

Starting from 60.0 mg (0.161 mmol) of 4-acetylthio-1-(4-phenylsulfinylbenzyl)pyrrolidin-2-one obtained in Example 171 and 229 μl (3.22 mmol) of acetyl chloride and similarly to Example 126, 17.9 mg (yield: 34%) of 4-mercapto-1-(4-phenylsulfinylbenzyl)pyrrolidin-2-one was obtained as a colorless oil.
$^1$H-NMR (300 MHz, CDCl$_3$)
δ:7.64 (4H, m), 7.47 (3H, m), 7.35 (2H, d, J=7.9 Hz), 4.51 (1H, d, J=15.1 Hz), 4.43 (1H, d, J=15.1 Hz), 3.63 (1H, dd, J=9.6, 7.5 Hz), 3.55 (1H, m), 3.14 (1H, dd, J=9.6, 4.5 Hz), 2.91 (1H, dd, J=17.2, 8.1 Hz), 2.41 (1H, dd, J=17.2, 5.9 Hz), 1.86 (1H, d, J=6.8 Hz)

Example 173

4-Acetylthio-1-(4-phenylsulfonylbenzyl)pyrrolidin-2-one (1) 280 mg (0.935 mmol) of 4-hydroxy-1-(4-phenylthiobenzyl)pyrrolidin-2-one obtained in Example 154 was dissolved in a mixture of 7 ml of acetic acid and 2 ml of 30% aqueous hydrogen peroxide, and stirred at 70° C. for 1 hour. The reaction mixture was treated with ethylacetate, washed twice with water and then with saturated brine, and dried over anhydrous sodium sulfate. After concentrating under reduced pressure, toluene was added and then the mixture was concentrated under reduced pressure again into dryness, and precipitated from ethyl acetate to obtain 310 mg (quantitative amount) of 4-hydroxy-1-(4-phenylsulfonylbenzyl)pyrrolidin-2-one as a white powder.
Elemental analysis (%): $C_{17}H_{17}NO_4S$
Calcd.: C, 61.61;H, 5.17;N, 4.23
Found: C, 61.31;H, 4.95;N, 4.21
(2) Starting from 310 mg (0.935 mmol) of 4-hydroxy-1-(4-phenylsulfonylbenzyl)pyrrolidin-2-one, 430 μl (3.10 mmol) of triethylamine and 240 μl (3.10 mmol) of methanesulfonyl chloride, 359 mg (yield: 94%) of 4-methanesulfonyloxy-1-(4-phenylsulfonylbenzyl)pyrrolidin-2-one was obtained as a colorless oil.
Elemental analysis (%): $C_{18}H_{19}NO_6S_2$
Calcd.: C, 52.80;H, 4.68;N, 3.42
Found: C, 52.82;H, 4.57;N, 3.47
(3) Starting from 280 mg (0.684 mmol) of 4-methanesulfonyloxy-1-(4-phenylsulfonylbenzyl)pyrrolidin-2-one and 156 mg (1.37 mmol) of potassium thioacetate, 175 mg (yield: 66%) of 4-acetylthio-1-(4-phenylsulfonylbenzyl)pyrrolidin-2-one was obtained as a white powder.
Elemental analysis (%): $C_{19}H_{19}NO_4S_2$
Calcd.: C, 58.59;H, 4.92;N, 3.60
Found: C, 58.59;H, 4.85;N, 3.68

Example 174

4-Mercapto-1-(4-phenylsulfonylbenzyl)pyrrolidin-2-one

Starting from 90.0 mg (0.231 mmol) of 4-acetylthio-1-(4-phenylsulfonylbenzyl)pyrrolidin-2-one obtained in Example 173 and 365 μl (5.14 mmol) of acetyl chloride and similarly to Example 126, 61.2 mg (yield: 76%) of 4-mercapto-1-(4-phenylsulfonylbenzyl)pyrrolidin-2-one was obtained as a white powder.
Elemental analysis (%): $C_{17}H_{17}NO_3S_2$
Calcd.: C, 58.77;H, 4.93;N, 4.03
Found: C, 58.79;H, 4.93;N, 4.03

Example 175

(4S,.5S)-4-Acetylthio-5-methyl-1-(4-phenoxybenzyl)pyrrolidin-2-one (1) Similarly to Example 20 and starting from 2.34 g (15.0 mmol) of L-alanine methyl ester hydrochloride, 3.14 ml (22.5 mmol) of triethylamine and 2.63 ml (15.0 mmol) of 4-phenoxybenzaldehyde, 4.31 g (quantitative yield) of N-(4-phenoxybenzy)-L-alanine methyl ester was obtained as a colorless oil.
$^1$H-NMR (300 MHz, CDCl$_3$)
δ: 7.27–7.37 (4H, m), 7.09 (1H, m), 6.98 (4H, m), 3.77 (1H, d, J=12.8 Hz), 3.74 (3H, s), 3.64 (1H, d, J=12.8 Hz), 3.40 (1H, q, J=6.8 Hz), 1.33 (3H, d, J=6.8 Hz)

(2) Starting from 4.21 g (14.8 mmol) of N-(4-phenoxybenzy)-L-alanine methyl ester, 2.48 ml (17.8 mmol) of triethylamine and 2.28 ml (17.8 mmol) of ethylmalonyl chloride, 5.11 g (yield: 86%) of N-(ethylmalonyl)-N-(4-phenoxybenzyl)-L-alanine methyl ester was obtained as a colorless oil.
$^1$H-NMR (300 MHz, CDCl$_3$)
δ:7.20–7.40 (4H, m), 7.13 (1H, m), 6.97–7.04 (4H, m), 4.66 (1H, q, J=7.2 Hz), 65 (1H, d, J=17.3 Hz), 4.50 (1H, d, J=17.3 Hz), 4.19 (1H, q; J=7.2 Hz), 3.69 (3H, s) 3.47 (1H, d, J=15.5 Hz), 3.39 (1H, d, J=15.5 Hz), 1.41 (3H, d, J=7.2 Hz), 1.28 (3H, t, J=7.2 Hz)

(3) 5.00 g (12.5 mmol) of N-(ethylmalonyl)-N-(4-phenoxybenzyl)-L-alanine methyl ester and 4.91 ml (12.5 mmol) of a 20% solution of sodium ethoxide in ethanol were treated and decarboxylated, and then 473 mg (12.5 mmol) of sodium borohydride was used to obtain 3.61 g (yield: 97%) of (5S)-4-hydroxy-5-methyl-1-(4-phenoxybenzyl)pyrrolidin-2-one as a colorless oil.
Major peaks:
$^1$H-NMR, (300 MHz, CDCl$_3$)
δ:7.33 (2H, m), 7.19 (2H, m), 7.10 (1H, m), 6.97–7.03 (4H, m), 4.95 (1H, d, J=15.1 Hz), 4.35 (1H, m), 3.97 (1H, d, J=15.1 Hz), 3.60 (1H, m), 2.70 (1H, dd, J=17.0, 6.6 Hz), 2.47 (1H, dd, J=17.0, 3.4 Hz), 1.22 (3H, d, J=6.8 Hz)

(4) Starting from 3.50 g (11.8 mmol) of (5S)-4-hydroxy-5-methyl-1-(4-phenoxybenzyl)pyrrolidin-2-one, 3.28 ml (23.5 mmol) of triethylamine and 1.81 ml (23.5 mmol) of methanesulfonyl chloride, 3.87 g (yield: 87%) of (5S)-4-methanesulfonyloxy-5-methyl-1-(4-phenoxybenzyl)pyrrolidin-2-one was obtained as a colorless oil. This product was subjected to fractional high pressure liquid chromatography (column: YMC Pack S-363 I-15 ODS, Mobile phase: 42% acetonitrile/0.01 M phosphate buffer, pH 6.3, flow rate: 20 ml/min, detection: 214 nm), and each of the fractions of 2 peaks was concentrated and extracted twice with ethyl acetate. The ethyl acetate layer was washed with water and saturated brine, dried over anhydrous sodium sulfate and concentrated to obtain 1.20 g (recovery: 31%) of (4H, 5S)-4-methanesulfonyloxy-5-methyl-1-(4-phenoxybenzyl)pyrrolidin-2-one as a colorless oil and 2.08 g (recovery: 54%) of (4S, 5S)-4-methanesulfonyloxy-5-methyl-1-(4-phenoxybenzyl)pyrrolidin-2-one as a white powder.

(4R, 5S)-4-Methanesulfonyloxy-5-methyl-1-(4-phenoxybenzyl)pyrrolidin-2-one $^1$H-NMR (300 MHz, CDCl$_3$)
δ:7.34 (2H, m), 7.21 (2H, d, J=8.7 Hz), 7.11 (1H, m), 6.98 (4H, m), 4.97 (1H, d, J=15.1 Hz), 4.90 (1H, m), 3.98 (1H, d, J=15.1 Hz), 3.73 (1H, dq, J=1.5, 6.8 Hz), 2.97 (3H, s), 2.95 (1H, dd, J=18.1, 6.8 Hz), 2.66 (1H, dd, J=18.1, 2.3 Hz), 1.23 (3H, d, J=6.8 Hz)

(4S, 5S)-4-Methanesulfonyloxy-5-methyl-1-(4-phenoxybenzyl)pyrrolidin-2-one $^1$H-NMR (300 MHz, CDCl$_3$)
δ:7.35 (2H, m), 7.18 (2H, d, J=8.3 Hz), 7.12 (1H, m), 7.01 (2H, m), 6.95 (2H, d, J=8.3 Hz), 5.21 (1H, m), 4.98 (1H, d, J=15.1 Hz), 3.96 (1H, d, J=15.1 Hz), 3.80 (1H, m), 3.06 (3H, s), 2.83 (1H, dd, J=17.3, 6.4 Hz), 2.74 (1H, dd, J=17.3, 4.0 Hz), 1.28 (3H, d, J=6.4 Hz)

(5) 1.00 g (2.66 mmol) of (4R, 5S)-4-methanesulfonyloxy-5-methyl-1-(4-phenoxybenzyl)pyrrolidin-2-one was dissolved in 30 ml of ethanol, treated with 608 mg (5.33 mmol) of potassium thioacetate, and heated under reflux for 13 hours with stirring. The reaction mixture was concentrated, treated with in ethyl acetate, washed with water and saturated brine, and dried over anhydrous sodium sulfate. After concentrating, the residue was subjected to column chromatography on silica gel eluting with hexane: ethyl acetate (60:40), concentrated into dryness to obtain 207 mg (yield: 22%) of (4S, 5S)-4-acetylthio-5-methyl-1-(4-phenoxybenzyl)pyrrolidin-2-one as a colorless oil.
$^1$H-NMR (300 MHz, CDCl$_3$)
δ:7.34 (2H, m), 7.20 (2H, d, J=8.3 Hz), 7.11 (1H, m), 7.01 (2H, m), 6.96 (2H, m), 4.93 (1H, d, J=15.1 Hz), 4.18 (1H, m), 3.96 (1H, d, J=15.1 Hz), 3.84 (1H, m), 2.82 (1H, dd, J=17.0, 8.3 Hz), 2.45 (1H, dd, J=17.0, 9.1 Hz), 2.34 (3H, s), 1.13 (3H, d, J=6.4 Hz)

Example 176

(4S, 5S)-4-Mercapto-5-methyl-1-(4-phenoxybenzyl)pyrrolidin-2-one 120 mg (0.338 mmol) of (4S, 5S)-4-acetylthio-5-methyl-1-(4-phenoxybenzyl)pyrrolidin-2-one obtained in Example 175 was processed similarly to Example 31 to obtain 81.2 mg (yield: 77%) of (4S, 5S)-4-mercapto-5-methyl-1-(4-phenoxybenzyl)pyrrolidin-2-one as a colorless oil.
$^1$H-NMR (300 MHz, CDC$_3$)
δ:7.34 (2H, m), 7.20 (2H, d, J=8.3 Hz), 7.11 (1H, m), 7.00 (2H, m), 6.96 (2H, d, J=8.3 Hz), 4.96 (1H, d, J=15.1 Hz), 3.95 (1H, d, J=15.1 Hz), 3.65 (1H, m), 3.58 (1H, m), 2.84 (1H, dd, J=17.0, 7.5 Hz), 2.46 (1H, dd, J=17.0, 7.7 Hz), 1.52 (1H, d, J=7.5 Hz), 1.23 (3H, d, J=6.4 Hz)

Example 177

(4R, 5S)-4-Acetylthio-5-methyl-1-(4-phenoxybenzyl)pyrrolidin-2-one 1.50 g (4.00 mmol) of (4S, 5S)-4-methanesulfonyloxy-5-methyl-1-(4-phenoxybenzyl)pyrrolidin-2-one obtained in Example 175 and 914 mg (8.00 mmol) of potassium thioacetate were processed similarly to Example 175 to obtain 596 mg (yield: 42%) of (4R, 5S)-4-acetylthio-5-methyl-1-(4-phenoxybenzyl)pyrrolidin-2-one as a colorless oil.
¹H-NMR (300 MHz, CDCl₃)
δ:7.34 (2H, m), 7.19 (2H, d, J=8.3 Hz), 7.11 (1H, m), 7.00 (2H, m), 6.96 (2H, m), 4.95 (1H, d, J=15.1 Hz), 3.95 (1H, d, J=15.1 Hz), 3.68 (1H, m), 3.39 (1H, m), 3.02 (1H, dd, J=17.7, 8.9 Hz), 2.39 (1H, dd, J=17.7, 5.7 Hz), 2.31 (3H, s), 1.26 (3H, d, J=6.4 Hz)

Example 178

(4R, 5S)-4-Mercapto-5-methyl-1-(4-phenoxybenzyl)pyrrolidin-2-one 301 mg (0.847 mmol) of (4R, 5S)-4-acetylthio-5-methyl-1-(4-phenoxybenzyl)pyrrolidin-2-one obtained in Example 177 was processed similarly to Example 31 to obtain 210 mg (yield: 79%) of (4R, 5S)-4-mercapto-5-methyl-1-(4-phenoxybenzyl)pyrrolidin-2-one as a colorless oil.
¹H-NMR (300 MHz, CDCl₃)
δ:7.34 (2H, m), 7.21 (2H, d, J=8.7 Hz), 7.11 (1H, m), 7.00 (2H, m), 96 (2H, d, J=8.7 Hz), 4.96 (1H, d, J=15.1 Hz), 3.96 (1H, d, J=15.1 Hz), 3.33 (1H, m), 3.03 (1H, m), 2.95 (1H, m), 2.39 (1H, dd, J=16.2, 6.8 Hz), 1.75 (1H, d, J=6.8 Hz), 1.25 (3H, d, J=6.4 Hz)

Example 179 trans-4-Acetylthio-5-isobutyl-1-(4-phenoxybenzyl)pyrrolidin-2-one (1) Similarly to Example 20 and starting from 6.56 g (50.0 mmol) of D,L-leucine, 50 ml of methanol and 13.0 ml (180 mmol) of thionyl chloride, 8.93 g (yield: 98%) of D,L-leucine methyl ester hydrochloride was obtained as a white powder.
¹H-NMR (300 MHz, D₂O)
δ:4.17 (1H, t, J=6.8 Hz), 3.87 (3H, s), 1.90 (1H, m), 1.78 (2H, m), 00 (3H, d, J=6.0 Hz), 0.99 (3H, d, J=6.0 Hz)

(2) Starting from 2.73 g (15.0 mmol) of D,L-leucine methyl ester hydrochloride, 3.14 ml (22.5 mmol) of triethylamine, 2.63 ml (15.0 mmol) of 4-phenoxybenzaldehyde and 420 mg (11.1 mmol) of sodium borohydride, 4.34 g (yield: 88%) of N-(4-phenoxybenzyl)-D,L-leucine methyl ester was obtained as a colorless oil.
¹H-NMR (300 MHz, CDCl₃)
δ:7.30 (4H, m), 7.08 (1H, m), 6.97 (4H, m), 3.78 (1H, d, J=12.8 Hz), 3.73 (3H, s), 3.58 (1H, d, J=12.8 Hz), 3.31 (1H, t, J=7.2 Hz), 1.78 (1H, m), 1.48 (2H, t, J=7.2 Hz), 0.92 (3H, d, J=6.8 Hz), 0.85 (3H, d, J=6.4 Hz)

(3) Starting from 4.34 g (13.3 mmol) of N-(4-phenoxybenzyl)-D,L-leucine methyl ester, 2.22 ml (16.0 mmol) of triethylamine and 2.05 ml (16.0 mmol) of ethylmalonyl chloride, 5.24 g (yield: 89%) of N-(ethylmalonyl)-N-(4-phenoxybenzyl)-D,L-leucine methyl ester was obtained as a colorless oil.
Major peaks:
¹H-NMR (300 MHz, CDC₃)
δ:7.21–7.38 (4H, m), 7.12 (1H, m), 6.91–7.03 (4H, m), 4.86 (1H, m), 4.63 (1H, d, J=17.3 Hz), 4.50 (1H, d, J=17.3 Hz), 4.19 (2H, q, J=7.2 Hz), 3.62 (3H, s), 3.47 (1H, d, J=15.5 Hz), 3.42 (1H, d, J=15.5 Hz), 1.88 (1H, m), 1.60 (2H, m), 1.28 (3H, t, J=7.2 Hz), 0.91 (3H, d, J=6.4 Hz), 0.84 (3H, d, J=6.0 Hz)

(4) 5.24 g(11.9 mmol) of N-(ethylmalonyl)-N-(4-phenoxybenzyl)-D,L-leucine methyl ester was treated with 4.66 ml (11.9 mmol) of a 20% solution of sodium ethoxide in ethanol, decarboxylated and reacted with 450 mg (11.9 mmol) of sodium borohydride to obtain 3.52 g (yield: 87%) of 4-hydroxy-5-isobutyl-1-(4-phenoxybenzyl)pyrrolidine-2-one as a colorless oil.
Major peaks:
¹H-NMR (300 MHz, CDCl₃)
δ:7.33 (2H, m), 7.18 (2H, d, J=8.7 Hz), 7.10 (1H, m), 6.97 (4H, m), 4.96 (1H, d, J=15.3 Hz), 4.37 (1H, m), 3.97 (1H, d, J=15.3 Hz), 3.49 (1H, m), 2.67 (1H, dd, J=17,0, 5.9 Hz), 2.47 (1H, dd, J=17.0, 1.9 Hz), 1.70 (2H, m), 1.40 (1H, m), 0.94 (3H, d, J=6.4 Hz), 0.81 (3H, d, J=6.4 Hz)

(5) 3.30 g (9.72 mmol) of 4-hydroxy-5-isobutyl-1-(4-phenoxybenzyl)pyrrolidine-2-one was reacted with 2.71 ml (19.4 mmol) of triethylamine and 1.50 ml (19.4 mmol) of methanesulfonyl chloride, and subjected similarly to Example 175 to fractional high pressure liquid chromatography to obtain 2.63 g (yield: 65%) of cis-5-isobutyl-4-methanesulfonyloxy-1-(4-phenoxybenzyl)pyrrolidin-2-one as a white powder.
¹H-NMR (300 MHz, CDCl₃)
δ: 7.34 (2H, m), 7.17 (2H, d, J=8.7 Hz), 7.11 (1H, m), 6.98 (4H, m), 5.26 (1H, m), 5.02 (1H, d, J=15.3 Hz), 3.96 (1H, d, J=15.3 Hz), 3.68 (1H, m), 3.06 (3H, s), 2.82 (1H, dd, J=17.9, 2.8 Hz), 2.75 (1H, dd, J=17.9, 5.5 Hz), 1.70 (1H, m), 1.67 (1H, m), 1.47 (1H, m), 0.94 (3H, d, J=6.4 Hz), 0.79 (3H, d, J=6.4 Hz)

(6) Starting from 1.00 g (2.40 mmol) of cis-5-isobutyl-4-methanesulfonyloxy-1-(4-phenoxybenzyl)pyrrolidin-2-one and 548 mg (4.80 mmol) of potassium thioacetate, 227 mg (yield: 24%) of trans-4-acetylthio-5-isobutyl-1-(4-phenoxybenzyl)pyrrolidin-2-one as a colorless oil.
¹H-NMR (300 MHz, CDCl₃)
δ: 7.34 (2H, m), 7.19 (2H, d, J=8.7 Hz), 7.11 (1H, m), 6.99 (4H, m), 5.02 (1H, d, J=15.3 Hz), 3.86 (1H, d, J=15.3 Hz), 3.81 (1H, m), 3.30 (1H, m), 3.09 (1H, dd, J=17.7 7.9 Hz), 2.37 (1H, dd, J=17.7, 2.3 Hz), 2.29 (3H, s), 1.77 (1H, m), 1.42 (2H, m), 0.92 (3H, d, J=6.8 Hz), 0.80 (3H, d, J=6.8 Hz)

Example 180 trans-5-Isobutyl-4-mercapto-1-(4-phenoxybenzyl)pyrrolidin-2-one 227 mg (0.571 mmol) of trans-4-acetylthio-5-isobutyl-1-(4-phenoxybenzyl)pyrrolidin-2-one obtained in Example 179 was processed similarly to Example 31 to obtain 165 mg (yield: 81%) of trans-5-isobutyl-4-mercapto-1-(4-phenoxybenzyl)pyrrolidin-2-one as a colorless oil.
¹H-NMR (300 MHz, CDCl₃)
δ: 7.34 (2H, m), 7.24 (2H, d, J=8.3 Hz), 7.11 (1H, m), 6.99 (4H, m), 5.03 (1H, d, J=15.1 Hz), 3.88 (1H, d, J=15.1 Hz), 3.29 (1H, m), 3.23 (1H, m), 3.03 (1H, dd, J=17.3 7.9 Hz), 2.38 (1H, dd, J=17.3, 2.6 Hz), 1.78 (1H, d, J=6.8 Hz), 1.68 (1H, m), 1.48 (1H, m), 1.28 (1H, m), 0.93 (3H, d, J=6.8 Hz), 0.85 (3H, d, J=6.4 Hz)

Example 181 trans-4-Acetylthio-5-benzyl-1-(4-phenoxybenzyl)pyrrolidin-2-one (1) Similarly to Example 20 and starting from 8.26 g (50.0 mmol) of D,L-phenylalanine, 50 ml of methanol and 13.0 ml (180 mmol) of thionyl chloride, 10.6 g (yield: 98%) of D,L-phenylalanine methyl ester hydrochloride was obtained as a white powder.
¹H-NMR (300 MHz, D₂O)
δ: 7.45 (3H, m), 7.34 (2H, m), 4.46 (1H, m), 3.87 (3H, s), 3.39 (1H, dd, J=14.3 5.9 Hz), 3.27 (1H, dd, J=14.3, 7.5 Hz)

(2) Starting from 3.24 g (15.0 mmol) of D,L-phenylalanine methyl ester hydrochloride, 3.14 ml (22.5 mmol) of triethylamine, 2.63 ml (15.0 mmol) of 4-phenoxybenzaldehyde and 496 mg (13.1 mmol) of sodium borohydride, 4.05 g (yield: 75%) of N-(4-phenoxybenzyl)-D,L-phenylalanine methyl ester was obtained as a colorless oil.

$^1$H-NMR (300 MHz, CDCl$_3$)

δ: 7.21–7.36 (5H, m), 7.14–7.20 (4H, m), 7.09 (1H, m), 6.99 (2H, m), 6.92 (2H, d, J=8.3 Hz), 3.78 (1H, d, J=12.8 Hz), 3.66 (3H, s), 3.60 (1H, d, J=12.8 Hz), 3.54 (1H, t, J=6.8 Hz), 2.99 (1H, dd, J=13.6, 6.4 Hz), 2.94 (1H, dd, J=13.6, 7.5 Hz)

(3) Starting from 4.05 g (11.2 mmol) of N-(4-phenoxybenzyl)-D,L-phenylalanine methyl ester, 1.87 ml (13.4 mmol) of triethylamine and 1.72 ml (13.4 mmol) of ethylmalonyl chloride, 5.34 g (yield: 100%) of N-(ethylmalonyl)-N-(4-phenoxybenzyl)-D,L-phenylalanine methyl ester was obtained as a colorless oil.

Major peaks:

$^1$H-NMR (300 MHz, CDCl$_3$)

δ: 7.23–7.38 (6H, m), 7.06–7.19 (4H, m), 6.99 (2H, m), 6.90 (2H, d, J=8.7 Hz) 4.41 (1H, d, J=16.8 Hz), 4.28 (1H, dd, J=9.4, 5.7 Hz), 4.21 (2H, q, J=7.2 Hz), 3.83 (1H, d, J=16.8 Hz), 3.66 (3H, s), 3.46 (1H, d, J=14.9 Hz), 3.38 (1H, d, J=14.9 Hz), 3.36 (1H, m), 3.25 (1H, m), 1.29 (3H, t, J=7.2 Hz)

(4) 5.34 g(11.2 mmol) of N—(ethylmalonyl)—N—(4-phenoxybenzyl)-D, L-phenylalanine methyl ester was treated with 4.39 ml (11.2 mmol) of a 20% solution of sodium ethoxide in ethanol, decarboxylated and reacted with 424 mg (11.2 mmol) of sodium borohydride to obtain 3.93 g (yield: 94%) of 5-benzyl-4-hydroxy-1-(4-phenoxybenzyl) pyrrolidine-2-one as a colorless oil.

Major peaks:

$^1$H-NMR (300 MHz, CDCl$_3$)

δ: 7.20–7.38 (5H, m), 7.08–7.19 (5H, m), 7.01 (2H, m), 6.96 (2H, d, J=8.7 Hz), 5.02 (1H, d, J=15.1 Hz), 4.22 (1H, m), 3.93 (1H, d, J=15.1 Hz), 3.73 (1H, dt, J=5.3, 7.5 Hz), 3.00 (2H, d, J=7.5 Hz), 2.63 (1H, dd, J=17.0, 6.4 Hz), 2.44 (1H, dd, J=17.0, 3.4 Hz), 1.84 (1H, d, J=4.5 Hz)

(5) 3.70 g (9.91 mmol) of 5-benzyl-4-hydroxy-1-(4-phenoxybenzyl)pyrrolidine-2-one was reacted with 2.76 ml (19.8 mmol) of triethylamine and 1.53 ml (19.8 mmol) of methanesulfonyl chloride, and subjected similarly to Example 175 to fractional high pressure liquid chromatography to obtain 1.65 g (yield: 37%) of cis-5-benzyl-4-methanesulfonyloxy-1-(4-phenoxybenzyl)pyrrolidin-2-one as a white powder.

$^1$H-NMR (300 MHz, CDCl$_3$)

δ:7.22–7.39 (5H, m), 7.14 (3H, m), 7.02 (4H, m), 6.94 (2H, d, J=8.7 Hz), 5.09 (1H, m), 5.06 (1H, d, J=15.1 Hz), 4.01 (1H, m), 3.75 (1H, d, J=15.1 Hz), 3.05 (2H, d, J=6.8 Hz), 2.87 (3H, s), 2.74 (2H, d, J=6.0 Hz)

(6) Starting from 1.35 g (2.99 mmol) of cis-5-benzyl-4-methanesulfonyloxy-1-(4-phenoxybenzyl)pyrrolidin-2-one and 683 mg (5.98 mmol) of potassium thioacetate, 327 mg (yield: 25%) of trans-4-acetylthio-5-benzyl-1-(4-phenoxybenzyl)pyrrolidin-2-one as a colorless oil.

Elemental analysis (%): C$_{26}$H$_{25}$NO$_3$S.0.2H$_2$O

Calcd.: C, 71.76;H, 5.88;N, 3.22

Found: C, 71.71;H, 6.02;N, 2.97

Example 182 trans-5-Benzyl-4-mercapto-1-(4-phenoxybenzyl) pyrrolidin-2-one 185 mg (0.429 mmol) of trans-4-acetylthio-5-benzyl-1-(4-phenoxybenzyl)pyrrolidin-2-one obtained in Example 181 was processed similarly to Example 31 to obtain 135 mg (yield: 81%) of trans-5-benzyl-4-mercapto-1-(4-phenoxybenzyl)pyrrolidin-2-one as a colorless oil.

Elemental analysis (%): C$_{24}$H$_{23}$NO$_2$S.0.2H$_2$O

Calcd.: C, 73.33;H, 6.00;N, 3.56

Found: C, 73.41;H, 6.16;N, 3.56

Example 183 trans-4-Acetylthio-5-propylaminocarbonyloxymethyl-1-(4-phenoxybenzyl)pyrrolidin-2-one 122 mg (1.43 mmol) of propyl isocyanate was dissolved in 20 ml of chloroform, 0.36 ml (1.43 mmol) of a 4N solution of hydrogen chloride in ethyl acetate was added, and then 280 mg (0.72 mmol) of cis-5-hydroxymethyl-4-methanesulfonyloxy-1-(4-phenoxybenzyl)pyrrolidin-2-one obtained in Example 20 was added with stirring. After stirring at room temperature overnight, the reaction mixture was subjected to column chromatography on silica gel eluting with methanol: chloroform (3:97) to obtain 320 mg (yield: 94%) of cis-4-methanesulfonyloxy-5-propylaminocarbonyloxymethyl-1-(4-phenoxybenzyl)pyrrolidin-2-one as a colorless oil.

300 mg (0.63 mmol) of the cis-mesylate thus obtained was dissolved in 15 ml of ethanol, treated with 360 mg (3.15 mmol) of potassium thioacetate and then stirred at 90° C. for 3 hours. The reaction mixture was concentrated, and the residue was extracted with ethyl acetate and water, and the ethyl acetate layer was washed with water and concentrated, and the residue was subjected to column chromatography on silica gel eluting with ethyl acetate: n-hexane (30:70) to obtain 31 mg (yield: 22%) of trans-4-acetylthio-5-propylaminocarbonyloxymethyl-1-(4-phenoxybenzyl) pyrrolidin-2-one as a colorless oil.

$^1$H-NMR (200 MHz, CDCl$_3$)

δ: 7.40–6.90 (9H, m), 5.01 (1H, d, J=15.7 Hz), 4.87–4.65 (1H, m), 4.42–4.32 (1H, m) 4.21–3.95 (3H, m), 3.52–3.45 (1H, m), 3.20–3.08 (2H, m), 3.05 (1H, dd, J=8.9 17.8 Hz) 2.37 (1H, dd, J=4.0, 22.0 Hz), 2.30 (3H, s), 1.60–1.45 (2H, m), 0.92 (3H, t, J=7.5 Hz).

Example 184 trans-4-Mercapto-5-propylaminocarbonyloxymethyl-1-(4-phenoxybenzyl)pyrrolidin-2-one 57 mg (0.13 mmol) of trans-4-acetylthio-5-propylaminocarbonyloxymethyl-1-(4-phenoxybenzyl) pyrrolidin-2-one obtained in Example 183 was dissolved in 5 ml of methanol, treated with 24 μl (0.13 mmol) of a 28% solution of sodium methoxide in methanol and stirred at room temperature for 30 minutes. The reaction mixture was concentrated, and the residue was extracted with ethyl acetate and dilute hydrochloric acid, and the ethyl acetate layer was washed with water and concentrated, and the residue was subjected to column chromatography on silica gel eluting with ethyl acetate: n-hexane (30:70) to obtain 23 mg (yield: 44%) of trans-4-mercapto-5-propylaminocarbonyloxymethyl-1-(4-phenoxybenzyl) pyrrolidin-2-one as a colorless oil.

$^1$H-NMR (200 MHz, CDCl$_3$)

δ: 7.40–6.90 (9H, m), 5.02 (1H, d, J=15.0 Hz), 4.87–4.65 (1H, m), 4.30–4.10 (2H, m) 3.99 (1H, d, J=15.0 Hz), 3.51–3.35 (2H, m), 3.19–3.08 (2H, m), 3.00 (1H, dd, J=8.3, 16.0 Hz), 2.39 (1H, dd, J=5.2, 16.0 Hz), 1.87 (1H, d, J=6.9 Hz), 1.60–1.43 (2H, m), 0.92 (3H, t, J=7.4 Hz)

Example 185 trans-4-Acetylthio-5-(tetrahydro-2H,-pyran-2-yl)oxymethyl-1-(4-phenoxybenzyl)pyrrolidin-2-one 200 mg (0.51 mmol) of cis-5-hydroxymethyl-4-methanesulfonyloxy-1-(4-phenoxybenzyl)pyrrolidin-2-one obtained in Example 20 was dissolved in 5 ml of chloroform, treated with 51 mg (0.61 mmol) of dihydropyran and 1 drop of conc. hydrochloric acid and stirred at room temperature for 3 hours.

The reaction mixture was extracted with a saturated aqueous solution of sodium hydrogen sulfate, and the chloroform layer was washed with water and concentrated, and the residue was subjected to column chromatography on silica gel eluting with chloroform to obtain 210 mg (yield: 87%) of 5-(tetrahydro-2H,-pyran-2-yl)oxymethyl product as a colorless oil.

200 mg (0.42 mmol) of 5-(tetrahydro-2H,-pyran-2-yl)oxymethyl product thus obtained and 240 mg (2.10 mmol) of potassium thioacetate were subjected to a method similar to that in Example 183 to obtain 40 mg (yield: 21%) of trans-4-acetylthio-5-tetrahydro-2H,-pyran-2-yl)oxymethyl-1-(4-phenoxybenzyl)pyrrolidin-2-one as a colorless oil.
$^1$H-NMR (200 MHz, CDCl$_3$)
d: 7.40–6.90 (18H, m), 5.09 (1H, d, J=15.2 Hz), 4.83 (1H, d, J=15.1 Hz), 4.66–4.63 (1H, m), 4.39–4.35 (1H, m), 4.19 (1H, d, J=15.0 Hz), 4.05–3.40 (12H, m), 3.21–3.06 (2H, m), 2.40–2.39 (2H, m), 2.30 (3H, s), 2.29 (3H, s), 1.80–1.45 (12H, m).

Example 186 trans-4-Acetylthio-5-ethoxycarbonylmethylaminocarbonyl-1-(4-phenoxybenzyl)pyrrolidin-2-one 500 mg (1.28 mmol) of cis-5-hydroxymethyl-4-methanesulfonyloxy-1-(4-phenoxybenzyl)pyrrolidin-2-one obtained in Example 20 was dissolved in 20 ml of acetone, treated dropwise with Jones reagent with cooling on ice and stirring until the orange color of the reaction mixture was observed stably, and then the stirring was continued further for 2 hours with cooling on ice. 1 ml of 2-propanol was added, and the mixture was extracted with ethyl acetate and water. The ethyl acetate layer was washed with water and concentrated, and the residue was treated with ethyl acetate and n-hexane to effect a precipitation, whereby obtaining 450 mg (yield: 87%) of a 5-carboxylic acid product as a white powder.

300 mg (0.74 mmol) of the carboxylic acid product thus obtained was dissolved in 15 ml of N,N-dimethylformamide, and treated with 153 mg (0.80 mmol) of 1-ethyl-3-(3-dimethylaminopropyl)carbodiimide and 108 mg (0.80 mmol) of hydroxybenzotriazole and stirred at room temperature for 15 minutes. To this reaction mixture, a solution of 112 mg (0.80 mmol) of glycine ethyl ester hydrochloride and 81 mg (0.80 mmol) of triethylamine dissolved in 3 ml of (0.35 mmol) dimethylformamide was added dropwise at room temperature, and the mixture was stirred for 3 hours. The reaction mixture was extracted with ethyl acetate and diluted hydrochloric acid, and the ethyl acetate layer was washed with water and concentrated, and the residue was subjected to column chromatography on silica gel eluting with chloroform:methanol (98:2) to obtain 160 mg (yield: 44%) of a 5-ethoxycarbonylmethylaminocarbonyl product as a colorless oil.

170 mg (0.35 mmol) of the 5-ethoxycarbonylmethylaminocarbonyl product thus obtained and 198 mg (1.73 mmol) of potassium thioacetate were subjected to a method similar to that in Example 183 to obtain U.S. patent application Ser. No. 10/161,289 41 mg (yield: 25%) of trans-4-acetylthio-5-ethoxycarbonylmethylaminocarbonyl-1-(4-phenoxybenzyl)pyrrolidin-2-one as a colorless oil.
$^1$H-NMR (200 MHz, CDCl$_3$) d: 7.40–6.90 (10H, m), 5.17 (1H, d, J=15.1 Hz), 4.26–3.80 (5H, m), 4.24 (211, q, J=7.2 Hz), 3.05 (1H, dd, J=8.1, 18.0 Hz), 2.34 (1H, dd, J=1.5, 18.0 Hz), 2.33 (3H, s), 1.30 (3H, t, J=7.2 Hz)

Example 187 trans-5-Aminocarbonyl-4-acetylthio-1-(4-phenoxybenzyl)pyrrolidin-2-one

Similarly to Example 186 and starting from 578 mg (1.43 mmol) of a carboxylic acid product and conc. aqueous ammonia, 220 mg (yield: 46%) of an amide product was obtained. 220 mg (0.54 mmol) of the amide product thus obtained and 310 mg (2.72 mmol) of potassium thioacetate were then used to produce 28 mg (yield: 14%) of trans-5-aminocarbonyl-4-acetylthio-1-(4-phenoxybenzyl)pyrrolidin-2-one as a white powder.
$^1$H-NMR (200 MHz, CDCl$_3$)
d: 7.40–6.90 (9H, m), 6.73 (1H, brs), 5.66 (1H, brs), 5.19 (1H, d, J=15.3 Hz), 3.98 (1H, d, J=8.9 Hz), 3.85 (1H, d, J=15.4 Hz), 3.77 (1H, s), 3.05 (1H, dd, J=9.0, 17.8 Hz), 2.35 (1H, dd, J=1.4, 18.0 Hz), 2.33 (3H, s)

Example 188 trans-5-Aminocarbonyl-4-mercapto-1-(4-phenoxybenzyl)pyrrolidin-2-one 57 mg (0.13 mmol) of trans-5-aminocarbonyl-4-acetylthio-1-(4-phenoxybenzyl)pyrrolidin-2-one obtained in Example 187 was subjected to a method similar to that in Example 184 to obtain 23 mg (yield: 44%) of trans-5-aminocarbonyl-4-mercapto-1-(4-phenoxybenzyl)pyrrolidin-2-one as a colorless oil.
$^1$H-NMR (200 MHz, CDCl$_3$)
d: 7.40–6.90 (9H, m), 5.84 (1H, brs), 5.68 (1H, brs), 5.14 (1H, d, J=14.8 Hz), 3.88 (1H, d, J=14.7 Hz), 3.72 (1H, d, J=4.1 Hz), 3.62–3.48 (1H, m), 3.07 (1H, dd, J=8.2, 18.0), 2.39 (1H, dd, J=5.0, 18.0 Hz), 2.04 (1H, d, J=7.2 Hz)

Example 189 trans-4-Acetylthio-5-(2-hydroxyethyl)aminocarbonyl-1-(4-phenoxybenzyl)pyrrolidin-2-one Similarly to Example 186 and starting from 700 mg (1.73 mmol) of a carboxylic acid product and 2-aminoethanol, 180 mg (yield: 23%) of an amide product was obtained. 160 mg (0.36 mmol) of the amide product thus obtained and 163 mg (1.43 mmol) of potassium thioacetate were then used to produce 52 mg (yield: 34%) of trans-4-acetylthio-5-(2-hydroxyethyl)aminocarbonyl-1-(4-phenoxybenzyl)pyrrolidin-2-one as a white powder.
$^1$H-NMR (200 MHz, CDCl$_3$)
d: 7.40–6.85 (10H, m), 5.11 (1H d, J=15.1 Hz), 4.00–3.94 (1H, m), 3.86 (1H, d, J=15.4 Hz), 3.80–3.70 (3H, m), 3.60–3.30 (2H, m), 3.08 (1H, dd, J=8.0, 18.0 Hz), 2.34 (1H, dd, J=2.0, 18.0 Hz), 2.32 (3H, s)

Example 190 trans-5-(2-Hydroxyethyl)aminocarbonyl-4-mercapto-1-(4-phenoxybenzyl)pyrrolidin-2-one 25 mg (0.058 mmol) of trans-4-acetylthio-5-(2-hydroxyethyl)aminocarbonyl-1-(4-phenoxybenzyl)

pyrrolidin-2-one obtained in Example 189 was subjected to a method similar to that in Example 184 to obtain 5 mg (yield: 22%) of trans-5-(2-hydroxyethyl)aminocarbonyl-4-mercapto-1-(4-phenoxybenzyl)pyrrolidin-2-one as a colorless oil.
$^1$H-NMR (200 MHz, CDCl$_3$)
d: 7.42–6.89 (9H, m), 6.30–6.17 (1H, m), 5.07 (1H, d, J=14.7 Hz), 3.91 (1H, d, J=14.7 Hz), 3.78–3.30 (6H, m), 3.08 (1H, dd, J=8.0, 18.0 Hz), 2.38 (1H, dd, J=5.2, 18.0 Hz), 2.03 (1H, d, J=7.0 Hz)

Example 191 trans-4-Acetylthio-5-(4-pyridylmethyl)aminocarbonyl-1-(4-phenoxybenzyl)pyrrolidin-2-one Similarly to Example 186 and starting from 600 mg (1.48 mmol) of a carboxylic acid product and 4-aminomethylpyridine, 320 mg (yield: 44%) of an amide product was obtained. 300 mg (0.61 mmol) of the amide product thus obtained and 346 mg (3.00 mmol) of potassium thioacetate were then used to produce 98 mg (yield: 34%) of trans-4-acetylthio-5-(4-pyridylmethyl)aminocarbonyl-1-(4-phenoxybenzyl)pyrrolidin-2-one as a colorless oil.
$^1$H-NMR (200 MHz, CDCl$_3$)
d: 8.60–8.57 (2H, n), 7.40–6.90 (12H, m), 5.14 (1H, d, J=15.4 Hz), 4.51 (1H, d, J=6.1 Hz), 3.93 (1H, d, J=8.8 Hz), 3.89 (1H, d, J=15.3 Hz), 3.76 (1H, s), 3.06 (1H, dd, J=9.1, 18.0 Hz), 2.36 (1H, dd, J=1.5, 18.0 Hz), 2.34 (3H, s)

Example 192 trans-4-Mercapto-5-(4-pyridylmethyl)aminocarbonyl-1-(4-phenoxybenzyl)pyrrolidin-2-one 50 mg (0.11 mmol) of trans-4-acetylthio-5-(4-pyridylmethyl)aminocarbonyl-1-(4-phenoxybenzyl)pyrrolidin-2-one obtained in Example 191 was subjected to a method similar to that in Example 184 to obtain 23 mg (yield: 48%) of trans-4-mercapto-5-(4-pyridylmethyl)aminocarbonyl-1-(4-phenoxybenzyl)pyrrolidin-2-one as a colorless oil.
$^1$H-NMR (200 MHz, CDCl$_3$)
d: 8.59–8.50 (2H, m), 7.40–6.90 (11H, m), 6.88–6.65 (1H, m), 5.04 (1H, d, J=15.0 Hz), 4.46 (2H, d, J=6.2 Hz), 3.87 (1H, d, J=14.6 Hz), 3.75 (1H, d, J=4.3 Hz), 3.62–3.45 (1H, m), 3.04 (1H, dd, J=8.2, 18.0 Hz), 2.36 (1H, dd, J=5.4, 18.0 Hz), 2.05–1.95 (1H, m)

Example 193

4-Acetylthio-1-[(1-benzoyl-4-piperidyl)methyl]pyrrolidin-2-one 2.28 g (0.02 mol) of 4-aminomethylpiperidine and 2.12 g (0.02 mol) of benzaldehyde were dissolved in 20 ml of toluene, and heated under reflux for 2 hours with dehydrating. The reaction mixture was concentrated, treated with 20 ml of chloroform and 2.23 g (0.022 mol) of triethylamine, stirred with cooling on ice while being treated dropwise with 2.81 g (0.022 mol) of benzoyl chloride. After stirring for 2 hours, the reaction mixture was concentrated, treated with 30 ml of acetic acid and 10 ml of water, and stirred at room temperature for 30 minutes. The reaction mixture was concentrated and partitioned between diethyl ether and water, and the aqueous layer was made basic with an aqueous solution of sodium hydroxide, and then extracted with chloroform. The chloroform layer was washed with water and concentrated to obtain 2.71 g (yield: 62.1%) of 1-benzoyl-4-aminomethylpiperidine as a colorless oil.

1-Benzoyl-4-aminomethylpiperidine thus obtained was subjected to a method similar to that in Example 123 to obtain 4-acetylthio-1-[(1-benzoyl-4-piperidyl)methyl]pyrrolidin-2-one.
$^1$H-NMR (200 MHz, CDCl$_3$)
d: 7.39 (5H, s), 4.81–4.55 (1H, m), 4.13–4.00 (1H, m), 4.00–3.62 (1H, m), 3.89 (1H, dd, J=7.3, 12.0 Hz), 3.31 (1H, dd, J=4.5, 12.0 Hz), 3.35–3.01 (2H, m), 3.00–2.75 (2H, m), 2.87 (1H, dd, J=8.8, 18.0 Hz), 2.38 (1H, dd, J=5.6, 18.0 Hz), 2.35 (3H, s), 2.13–1.80 (1H, m), 1.80–1.50 (2H, m), 1.40–1.15 (2H, m).

Example 194 trans-4-Acetylthio-3-methyl-1-(4-phenoxybenzyl)pyrrolidin-2-one 0.70 g (2.0 mmol) of the pyrrolidin-2-one product obtained in Example 15 was dissolved in 15 ml of acetonitrile, treated with 0.5 ml of water, and stirred at 90° C. for 20 minutes. The reaction mixture was concentrated, treated with 15 ml of tetrahydrofuran and 0.32 g (2.2 mmol) of 1,1-diethoxytrimethylamine, and stirred at 80° C. for 30 minutes.

The reaction mixture was concentrated, and the residue was treated with 15 ml of 2-propanol, and stirred at room temperature while being treated with 0.15 g (4.0 mmol) of sodium borohydride. After stirring for 1 hour, the reaction mixture was concentrated, and the residue was extracted with ethyl acetate and saturated aqueous sodium hydrogen carbonate. The ethyl acetate layer was washed with water, concentrated, and subjected to column chromatography on silica gel eluting with methanol: chloroform (3:97) to obtain 0.41 g (yield: 68.1%) of an alcohol product as a colorless oil.

0.36 g (1.2 mmol) of the alcohol product thus obtained was dissolved in 10 ml of pyridine, treated with 0.28 g (2.4 mmol) of methanesulfonyl chloride, and stirred at 50° C. for 2 hours. The reaction mixture was concentrated, and the residue was made acidic with 2N hydrochloric acid, and then extracted with ethyl acetate. The ethyl acetate layer was concentrated and subjected to column chromatography on silica gel eluting with ethyl acetate: n-hexane (60:40) to obtain 0.12 g (yield: 26.2%) of a cis-mesylate product as a colorless oil.

38 mg (0.1 mmol) of the cis-mesylate product thus obtained was dissolved in 2 ml of N,N-dimethylformamide, treated with 57 mg (0.5 mmol) of potassium thioacetate and stirred at 45° C. overnight. The reaction mixture was extracted with ethyl acetate and water, and the ethyl acetate layer was washed with water and concentrated, and the residue was subjected to column chromatography on silica gel eluting with ethyl acetate: n-hexane (30:70) to obtain 24 mg (yield: 68%) of trans-4-acetylthio-3-methyl-1-(4-phenoxybenzyl)pyrrolidin-2-one as a colorless oil.
$^1$H-NMR (200 MHz, CDCl$_3$)
d: 7.40–6.90 (9H, m), 4.49 (1H, d, J=14.7 Hz), 4.37 (1H, d, J=14.7 Hz), 4.30–4.20 (1H, m), 3.66 (1H, dd, J=10.7, 6.6 Hz), 3.12 (1H, dd, J=10.7, 4.3 Hz), 2.92–2.78 (1H, m), 2.33 (3H, s), 1.20 (3H, d, J=7.3 Hz)

Example 195 trans-4-Mercapto-3-methyl-1-(4-phenoxybenzyl)pyrrolidin-2-one

Starting from 20 mg (0.056 mmol) of trans-4-acetylthio-3-methyl-1-(4-phenoxybenzyl)pyrrolidin-2-one obtained in Example 194 and similarly to Example 17, 17 mg (yield: 97%) of trans-4-mercapto-3-methyl-1-(4-phenoxybenzyl) pyrrolidin-2-one was obtained as a colorless oil.
$^1$H-NMR (200 MHz, CDCl$_3$)
d: 7.40–6.90 (9H, m), 4.52 (1H, d, J=14.6 Hz), 4.37 (1H, d, J=14.7 Hz), 3.71–3.56 (2H, m), 3.19–3.05 (1H, m), 2.80–2.67 (1H, m), 1.44 (1H, d, J=7.9 Hz), 1.26 (3H, d, J=7.3 Hz)

Example 196

S—[5-Oxo-1-(4-phenoxybenzoyl)-3-pyrrolidinyl]ethanethioate 3.0 g (29.67 mmol) of 4-hydroxy-2-pyrrolidone and 5050 mg (74.18 mmol) of imidazole were dissolved in 15 ml of DMF, treated with 5366 mg (35.60 mmol) of tert-butyldimethylchlorosilane, and stirred at room temperature for 24 hours. The reaction mixture was treated with ethyl acetate, washed 4 times with water and then with saturated brine, and dried over anhydrous sodium sulfate. After concentrating under reduced pressure, the mixture was precipitated from n-hexane: ethyl acetate (1:1) to obtain (yield: 89%) 400 mg (1.86 mmol) of 4-{[tert-butyl(dimethyl)silyl]oxy}-2-pyrrolidinone, which was then dissolved in 4 ml of THF and treated with 89 mg (2.23 mmol) of 60% sodium hydride at 0° C. and stirred at the same temperature for 15 minutes, and immediately after being treated with a solution of 4-phenoxybenzoyl chloride prepared from 477 mg (2.23 mmol) of 4-phenoxybenzoic acid, 389 µl (4.46 mmol) of oxalyl chloride and 5 µl (catalytic amount) of DMF in 4 ml of THF, the mixture was allowed to warm to room temperature and then stirred for 2 hours. The reaction mixture was concentrated under reduced pressure, dissolved in ethyl acetate, washed with water, a saturated aqueous solution of sodium hydrogen carbonate and saturated brine, and dried over anhydrous sodium sulfate. After concentrating under reduced pressure, the residue was purified by preparative thin layer chromatography (eluent: n-hexane: ethyl acetate (3:1)) and dissolved in ethyl acetate, washed three times with a saturated aqueous solution of sodium hydrogen carbonate and then with saturated brine, and dried over anhydrous sodium sulfate. The mixture was concentrated under reduced pressure to obtain (yield: 26%) 100 mg (0.244 mmol) of 1-(4-phenoxybenzoyl)-4-{[tert-butyl(dimethyl)silyl]oxy}-2-pyrrolidinone, which was then dissolved in 1 ml of THF, treated with 244 µl (0.24 mmol) of a 1M solution of tetrabutylammonium fluoride in THF at 0° C. and stirred at the same temperature for 15 minutes. The reaction mixture was concentrated under reduced pressure and purified by preparative thin layer chromatography (eluent: n-hexane: ethyl acetate (1:2)) to obtain (yield: 78%) 30mg (0.10 mmol) of 4-hydroxy-1-(4-phenoxybenzoyl)-2-pyrrolidinone which was dissolved in 0.5 ml of toluene together with 26.1 mg (0.15 mmol) of N,N,N',N'-tetramethylazodicarboxamide and 38 µl (0.15 mmol) of tributylphosphine, treated with 7.2 µl (0.10 mmol) of thiolacetic acid at 0° C., and then allowed immediately to warm to room temperature, and stirred for 20 hours. 7.2 µl (0.10 mmol) of thiolacetic acid was added again and the mixture was stirred for 24 hours. The reaction mixture was concentrated under reduced pressure, dissolved in ethyl acetate, washed twice with water and then with saturated brine, and dried over anhydrous sodium sulfate. After concentrating under reduced pressure, the residue was purified by preparative thin layer chromatography (eluent: n-hexane: ethyl acetate (1:1)) to obtain 7 mg (yield: 19%) of the title compound as a yellow oil.
$^1$H-NMR (300 MHz, CDCl$_3$)
δ: 7.65–6.95 (9H, m), 4.33 (1H, dd, J=11.9, 6.9 Hz), 4.23–4.14 (1H, m), 3.86 (1H, dd, J=11.9, 5.0 Hz), 3.09 (1H, dd, J=18.2, 8.2 Hz), 2.61 (1H, dd, J=18.1, 5.8 Hz), 2.38 (3H, s)

Example 197

S—((3R)-5-Oxo-1-{4-[(phenylsulfonyl)amino]benzyl}pyrrolidinyl)ethanethioate

To a mixture of 4.8 g (25.44 mmol) of 4-nitrobenzylamine hydrochloride, 4.4 g(27.98 mmol) of (S)—(—)—O-acetylmalic anhydride and 40 ml of acetonitrile was treated dropwise with a solution of 3547 µl (25.44 mmol) of triethylamine in 20 ml of THF at 0° C. Immediately after completion of the dropwise addition, the mixture was allowed to warm to room temperature, and stirred for 1.5 hours. The reaction mixture was concentrated under reduced pressure, dissolved in 50 ml of acetyl chloride, and stirred at 60° C. for 2 hours. The reaction mixture was concentrated under reduced pressure, dissolved in ethyl acetate, washed with water, a saturated aqueous solution of sodium hydrogen carbonate and saturated brine, and dried over anhydrous sodium sulfate. After concentrating under reduced pressure, the residue was purified by column chromatography on silica gel, and the fraction eluted with n-hexane: ethyl acetate (3:1 to 2:3) was concentrated to obtain (yield: 51%) 2.0 g (6.84 mmol) of (3S)-1-(4-nitrobenzyl)-2,5-dioxopyrrolidinylacetate, which was dissolved in a solvent mixture of 11.5 ml of ethanol and 23 ml of THF, treated with 259 mg (6.84 mmol) of sodium borohydride at −10° C., and stirred at −13 to −10° C. for 1 hour.259 mg (6.84 mmol) of sodium borohydride was added again, and the mixture was further stirred at −13 to −10° C. for 2.5 hours, and treated with a saturated aqueous solution of sodium hydrogen carbonate, ethyl acetate and saturated brine to effect a partition, and the aqueous layer was extracted twice with ethyl acetate and the organic layers were combined and dried over anhydrous sodium sulfate. After concentrating under reduced pressure, the residue was dissolved in 15 ml of trifluoroacetic acid, treated with 1093 µl (6.84 mmol) of triethylsilane and stirred at room temperature for 10 minutes. The reaction mixture was concentrated under reduced pressure, dissolved in ethyl acetate, washed twice with a saturated aqueous solution of sodium hydrogen carbonate, twice with a saturated aqueous solution of sodium hydrogen carbonate, and then with 0.1 N hydrochloric acid and saturated brine, and dried over anhydrous sodium sulfate. The mixture was concentrated under reduced pressure, dissolved in 10 ml of chloroform, treated with 1292 µl (13.67 mmol) of acetic anhydride and 1107 µl (13.67 mmol) of pyridine and stirred at room temperature for 5 hours. The reaction mixture was concentrated under reduced pressure, dissolved in ethyl acetate, washed twice with 1N hydrochloric acid and then with saturated brine, and dried over anhydrous sodium sulfate. After concentrating under reduced pressure, the residue was purified by column chromatography on silica gel, and the fraction eluted with n-hexane: ethyl acetate (33:67) was concentrated to obtain (3 steps, yield: 48%) 200 mg (0.72 mmol) of (3S)-1-(4-nitrobenzyl)-5-oxopyrrolidinyl acetate, which was stirred vigorously in the presence of 258 mg of 10% Pd/C in a solvent mixture of 1 ml of formic acid and 2ml of a iN solution of hydrochloric acid in ethyl acetate under hydrogen atmosphere for 1 hour, and the reaction mixture was filtered through Celite, concentrated under reduced pressure, dissolved in ethyl acetate, washed with a saturated aqueous solution of sodium hydrogen carbonate and saturated brine, and dried over anhydrous sodium sulfate.0.5 ml of a 4N solution of hydrochloric acid in ethyl acetate was added, and the mixture was concentrated under reduced pressure to obtain (yield: 82%) 167 mg (0.59 mmol) of (3S)-1-(4-aminobenzyl)-5-oxopyrrolidinyl acetate hydrochloride, which was then dissolved in 2 ml of chloroform together with 82 μl (0.64 mmol) of benzenensulfonyl chloride, and treated dropwise with 172 μl (1.23 mmol) of triethylamine at 0° C. After completion of the dropwise addition, the mixture was stirred at 0° C. for 30 minutes. The reaction mixture was concentrated under reduced pressure, dissolved in ethyl acetate, washed with 0.1 N hydrochloric acid and saturated brine, and dried over anhydrous sodium sulfate. After concentrating under reduced pressure, the residue was purified by preparative thin layer chromatography (eluent: n-hexane: ethyl acetate (1:2)) to obtain (yield: 71%) 130 mg (0.37 mmol) of (3S)-5-oxo-1-{4-[(phenylsulfonyl)amino]benzyl}pyrrolidinyl acetate, which was then dissolved in a solution prepared previously by adding 519 μl (7.3 mmol) of acetyl chloride dropwise to 1 ml of ethanol, and stirred at 50° C. for 1.5 hours. The reaction mixture was concentrated under reduced pressure to obtain (yield: 92%) 116 mg (0.335 mmol) of N-(4-{[(4S)-4-hydroxy-2-oxypyrrolidinyl]methyl}phenyl)benzenesulfonamide, which was dissolved in 1 ml of acetonitrile together with 44 μl (0.57 mmol) of methanesulfonyl chloride, and treated dropwise with a solution of 79.4 μl (1.07 mmol) of triethylamine in 1 ml of acetonitrile at 0° C. After completion of the dropwise addition, the mixture was stirred at 0° C. for 10 minutes, and treated dropwise again with 44 μl (0.57 mmol) of methanesulfonyl chloride and a solution of 79.4 μl (1.07 mmol) of triethylamine in 0.5 ml of acetonitrile. After completion of the dropwise addition followed by stirring at 0° C. further for 10 minutes, the reaction mixture was concentrated under reduced pressure, dissolved in ethyl acetate, washed with water and saturated brine, and dried over anhydrous sodium sulfate. After concentrating under reduced pressure, the residue was purified by preparative thin layer chromatography (eluent: chloroform: methanol (10:1)) to obtain (yield: 9%) 13 mg (0.03 mmol) of (3S)-5-oxo-1-{4-[(phenylsulfonyl)amino]benzyl}pyrrolidinyl methanesulfonate, which was dissolved in 1 ml of DMF, treated with 8 mg (0.02 mmol) of cesium carbonate and a solution of 11 μl (0.15 mmol) of thioacetic acid in 1 ml of DMF, and stirred under nitrogen atmosphere at room temperature for 24 hours. 10 mg (0.03 mmol) of cesium carbonate and a solution of 4 μl (0.06 mmol) of thioacetic acid in 1 ml of DMF were added again, and the mixture was stirred under nitrogen atmosphere at room temperature for 11 days. The reaction mixture was treated with ethyl acetate, washed three times with water and then with saturated brine, and dried over anhydrous sodium sulfate. After concentrating under reduced pressure, the residue was purified by preparative thin layer chromatography (eluent: n-hexane: ethyl acetate (1:2)) to obtain 1.6 mg (yield: 13%) of the title compound as a colorless oil.

$^1$H-NMR (300 MHz, CDCl$_3$)

δ: 7.88–7.01 (9H, m), 6.74 (1H, m), 4.51–4.06 (2H, m), 4.08–3.99 (1H, m), 3.82–3.67 (1H, m), 3.23–3.08 (1H, m), 2.90 (1H, dd, J=17.4, 8.9 Hz), 2.52–2.35 (1H, m), 2.31 (3H, s)

Example 198

S—{(3R)-1-{4-(1,3-benzodioxol-5-yloxy)benzyl]-5-oxopyrrolidinyl}ethanethioate 3.0 g (24.17 mmol) of 4-fluorobenzaldehyde, 3.3 g (24.17 mmol) of 3,4-methylenedioxyphenol and 3.3 g (24.17 mmol) of potassium carbonate were stirred in 20 ml of DMF at 120° C. for 22 hours, and the reaction mixture was treated with ethyl acetate and washed 4 times with water and then with saturated brine and dried over anhydrous sodium sulfate. After concentrating under reduced pressure, the residue was purified by column chromatography on silica gel, and the fraction eluted with n-hexane: ethyl acetate (92:8) was concentrated to obtain (yield: 25%) 2.9 g (11.95 mmol) of 4-(1,3-benzodioxol-5-yloxy)benzaldehyde, which was stirred together with 1030 mg (14.82 mmol) of hydroxylamine hydrochloride and 1486 mg (17.57 mmol) of sodium hydrogen carbonate in a solvent mixture of 41 ml of ethanol and 6 ml of water at 60° C. for 1 hour, and the reaction mixture was concentrated under reduced pressure, dissolved in ethyl acetate, washed twice with water and with saturated brine, and dried over anhydrous sodium sulfate. After concentrating under reduced pressure, the residue was stirred vigorously together with 684 μl (11.95 mmol) of acetic acid in the presence of 258 mg of 10% Pd/C in 55 ml of methanol under hydrogen atmosphere for 2 hours, and the reaction mixture was filtered through Celite, concentrated under reduced pressure, treated with ethyl acetate, treated dropwise with 3 ml of a 4N solution of hydrochloric acid in ethyl acetate, concentrated under reduced pressure, precipitated from ethyl acetate to obtain (2 steps, yield: 77%) 2.0 g (7.15 mmol) of 4-(1,3-benzodioxol-5-yloxy)benzylamine hydrochloride, which was treated with 1244 mg (7.87 mmol) of (S)—(—)—O—acetylmalic anhydride and 10 ml of acetonitrile and then treated dropwise with a solution of 996 μl (7.15 mmol) of triethylamine in 5 ml of THF at 0° C. After completion of the dropwise addition, the mixture was allowed immediately to warm to room temperature, and stirred for 2 hours. The reaction mixture was concentrated under reduced pressure, dissolved in 20 ml of acetyl chloride, and stirred at 60° C. for 30 minutes. The reaction mixture was concentrated under reduced pressure, dissolved in ethyl acetate, washed with water, a saturated aqueous solution of sodium hydrogen carbonate and saturated brine, and dried over anhydrous sodium sulfate. After concentrating under reduced pressure, the residue was purified by column chromatography on silica gel, and the fraction eluted with n-hexane: ethyl acetate (3:1) was concentrated to obtain (yield: 92%) 1592 mg (4.15 mmol) of (3S)-1-{4-(1,3-benzodioxol-5-yloxy)benzyl]-2,5-dioxopyrrolidinyl acetate, which was dissolved in a solvent mixture of 7 ml of ethanol and 14 ml of THF, treated with 314 mg (8.30 mmol) of sodium borohydride at −14° C., and stirred at −14 to −10° C. for 3 hours. The reaction mixture was treated with a saturated aqueous solution of sodium hydrogen carbonate, ethyl acetate and saturated brine to effect a partition, and the aqueous layer was extracted twice with ethyl acetate and the organic layers were combined and dried over anhydrous sodium sulfate. After concentrating under reduced pressure, the residue was dissolved in 9 ml of trifluoroacetic acid, treated with 663 μl (4.15 mmol) of triethylsilane and stirred at room temperature for 30 minutes. The reaction mixture was concentrated under reduced pressure, dissolved in ethyl acetate, washed with a saturated aqueous solution of sodium hydrogen carbonate and saturated brine, and dried over anhydrous sodium sulfate. After concentrating under reduced pressure, the residue was dissolved in a solution prepared by adding 639 μl (83 mmol) of acetyl chloride dropwise to 15 ml of ethanol, and stirred at 50° C. for 1.5 hours. The reaction mixture was concentrated under reduced pressure, and purified by column chromatography on silica gel, and the fraction eluted with n-hexane: acetone (55:45) was concentrated to obtain (3 steps, yield: 34%) 250 mg (0.76 mmol) of (4S)-1-[4-(1,3-benzodioxol-5-yloxy) benzyl]-4-hydroxy-2-pyrrolidinone, which was dissolved in 2 ml of chloroform together with 82 μl (1.07 mmol) of methanesulfonyl chloride, and treated dropwise with a solution of 149 μl (1.07 mmol) of triethylamine in 1 ml of chloroform at 0° C. over a period of 10 minutes. After completion of the dropwise addition, the mixture was stirred at 0° C. for 10 minutes. The reaction mixture was concentrated under reduced pressure, dissolved in ethyl acetate, washed with water and saturated brine, and dried over anhydrous sodium sulfate. The mixture was concentrated under reduced pressure to obtain (quantitative) 200 mg (0.53 mmol) of (3S)-1-[4-(1,3-benzodioxol-5-yloxy)benzyl]-5-oxopyrrolidinyl methanesulfonate, which was dissolved in 1 ml of DMF, treated with 22 mg (0.37 mmol) of cesium carbonate and a solution of 191 μl (2.67 mmol) of thiolacetic acid in 1 ml of DMF, and stirred under nitrogen atmosphere at room temperature for 48 hours. The reaction mixture was treated with ethyl acetate, washed 5 times with water and then with saturated brine, and dried over anhydrous sodium sulfate. After concentrating under reduce pressure, the residue was purified by preparative thin layer chromatography (eluent: n-hexane: ethyl acetate (1:1)) to obtain 88 mg (yield: 43%) of the title compound as a brown oil.
$^1$H-NMR (300 MHz, CDCl$_3$)
δ: 7.17–6.47 (7H, m), 5.97 (2H, s), 4.44 (1H, d, J=14.6 Hz), 4.38 (1H, d, J=14.7 Hz), 4.09–4.00 (1H, m), 3.74 (1H, dd, J=10.6, 7.5 Hz), 3.15 (1H, dd, J=10.6, 4.9 Hz), 2.91 (1H, dd, J=17.4, 9.0 Hz), 2.41 (1H, dd, J=17.4, 6.0 Hz), 2.31 (3H, s)

Example 199

(R)-4-Acetylthio-1-[4-(4'-bromophenoxy)benzyl] pyrrolidin-2-one

Using a method similar to that in Example 125 and starting from 4-(4'-bromophenoxy)benzylamine prepared from 4-fluorobenzaldehyde and 4-bromophenol and (S)—O-acetylmalic anhydride, (R)-4-acetylthio-1-[4-(4'-bromophenoxy)benzyl]pyrrolidin-2-one was obtained as a pale orange powder.
$^1$H-NMR (200 MHz, CDCl$_3$)
δ:7.44 (2H, d, J=9.0 Hz), 7.20 (2H, d, J=8.7 Hz), 6.96 (2H, d, J=8.7 Hz), 6.89 (2H, d, J=9.0 Hz), 4.43 (2H, s), 4.14–3.98 (1H, m), 3.76 (1H, dd, J=10.6, 7.5 Hz), 3.17 (1H, dd, J=10.6, 5.0 Hz), 2.92 (1H, dd, J=17.4, 8.9 Hz), 2.43 (1H, dd, J=17.4, 6.0 Hz), 2.32 (3H, s)

Example 200

(R)-4-Mercapto-1-[4-(4'-bromophenoxy)benzyl] pyrrolidin-2-one

Using a method similar to that in Example 126 and starting from 200 mg (0.48 mmol) of (R)-4-acetylthio-1-[4-(4'-bromophenoxy)benzyl]pyrrolidin-2-one obtained in Example 199, 180 mg (yield: 77%) of (R)-4-mercapto-1-[4-(4'-bromophenoxy)benzyl]pyrrolidin-2-one was obtained as a pale pinkish oil.
$^1$H-NMR (200 MHz, CDCl$_3$)
δ: 7.44 (2H, d, J=9.0 Hz), 7.23 (2H d, J=8.7 Hz), 6.96 (6H, d, J=8.7 Hz), 6.88 (2H, d, J=9.0 Hz), 4.49 (1H, d, J=14.9 Hz), 4.37 (1H, d, J=14.9 Hz), 3.66 (1H, dd, J=9.8, 7.2 Hz), 3.55–3.46 (1H, m), 3.17 (1H, dd, J=9.8, 4.8 Hz), 2.93 (1H, dd, J=17.2, 8.0 Hz), 2.43 (1H, dd, J=17.2, 6.1 Hz), 1.87 (1H, d, J=6.7 Hz)

Example 201

4-Acetylthio-1-(2-dibenzofuranmethyl)pyrrolidin-2-one (1) 10.0 g (60 mmol) of dibenzofuran was dissolved in 300 ml of chloroform, and stirred with cooling on ice. 9.8 ml (89 mmol) of titanium tetrachloride was added dropwise over a period of 30 minutes, and the mixture was stirred further for 1.5 hours with cooling on ice. To this solution, 8.1 ml (89 mmol) of dichloromethyl methyl ether was added dropwise over a period of 30 minutes, and the mixture was stirred further for 2.5 hours with cooling on ice. Ice was added slowly to the reaction mixture, which was then allowed to warm to room temperature with stirring for 1 hour. After concentrating under reduced pressure followed by extracting twice with ethyl acetate, the organic layer obtained was washed with water and saturated brine, and dried over anhydrous sodium sulfate. After concentrating under reduced pressure, the residue was subjected to column chromatography on silica gel eluting with hexane: ethyl acetate (95:5) to obtain 3.50 g (yield: 30%) of 2-dibenzofuran carboxyaldehyde as an orange powder.
$^1$H-NMR (300 MHz, CDCl$_3$)
δ: 10.14 (1H, s), 8.51 (1H, d, J=1.4 Hz), 8.03 (1H, d, J=8.5 Hz), 8.03 (1H, dd, J=8.2, 1.0 Hz), 7.70 (1H, d, J=8.5 Hz), 7.63 (1H, d, J=8.2 Hz), 7.54 (1H, ddd, J=7.2, 7.2, 1.4 Hz), 7.42 (1H, ddd, J=7.4, 7.4, 1.0 Hz)

(2) Then using a method similar to that in Example 30 and starting from 1.22 g (5.6 mmol) of 2-chloromethyldibenzofuran and 1.16 g (6.7 mmol) of 4-trimethylsilyloxypyrrolidin-2-one, 537 mg (yield: 29%) of 4-acetylthio-1-(2-dibenzofuranmethyl)pyrrolidin-2-one was obtained as a brown oil.
$^1$H-NMR (300 MHz, CDCl$_3$)
δ: 7.95 (1H, d, J=7.4 Hz), 7.84 (1H, d, J=1.4 Hz), 7.57 (1H, d, J=8.2 Hz), 7.53 (1H, d, J=8.4 Hz), 7.47 (1H, ddd, J=7.4, 7.4, 1.4 Hz), 7.35 (2H, m), 4.67 (1H, d, J=14.6 Hz), 4.56 (1H, d, J=14.6 Hz), 4.06 (1H, m), 3.78 (1H, dd, J=10.7, 7.5 Hz), 3.19 (1H, dd, J=10.7, 4.8 Hz), 2.95 (1H, dd, J=17.5, 9.0 Hz), 2.46 (1H, dd, J=17.5, 5.9 Hz), 2.28 (3H, s)

Example 202

4-Mercapto-1-(2-dibenzofuranmethyl)pyrrolidin-2-one

Using a method similar to that in Example 31 and starting from 282 mg (0.80 mmol) of 4-acetylthio-1-(2-dibenzofuranmethyl)pyrrolidin-2-one obtained in Example 201, 207 mg (yield: 87%) of 4-mercapto-1-(2-dibenzofuranmethyl)pyrrolidin-2-one was obtained as a colorless oil.
$^1$H-NMR (300 MHz, CDCl$_3$)
δ: 7.95 (1H, d, J=7.4 Hz), 7.85 (1H, d, J=1.4 Hz), 7.57 (1H, d, J=8.2 Hz), 7.53 (1H, d, J=8.5 Hz), 7.47 (1H, ddd, J=7.4, 7.3, 1.4 Hz), 7.35 (2H, m), 4.66 (1H, d, J=14.6 Hz), 4.59 (1H, d, J=14.6 Hz), 3.68 (1H, dd, J=10.2, 7.2 Hz), 3.54 (1H, m), 3.19 (1H, dd, J=10.2, 5.1 Hz), 2.95 (1H, dd, J=17.1, 8.2 Hz), 2.45 (1H, dd, J=17.1, 6.1 Hz), 1.85 (1H, d, J=6.8 Hz)

Example 203

4-Acetylthio-1-[4-(N-phenyl-N-p-toluenesulfonyl) aminobenzyl]pyrrolidin-2-one (1) 20.0 g (148 mmol) of acetoanilide and 13.9 g (76.5 mmol) of 4-bromobenzonitrile were dissolved under nitrogen atmosphere at 120° C. and treated with 23.0 g (161 mmol) of copper (I) oxide and 18.0 g (130 mmol) of potassium carbonate and then stirred under nitrogen atmosphere at 200° C. for 18 hours. The reaction mixture was treated with ethyl acetate and filtered, and the ethyl acetate layer was washed with water and saturated brine and dried over anhydrous sodium sulfate. After concentrating under reduced pressure, the residue was subjected to column chromatography on silica gel, and the fraction eluted with hexane: ethyl acetate (80:20) was concentrated under reduced pressure and crystallized from hexane-ethyl acetate to obtain 5.51 g (yield: 37%) of 4-cyano-N-phenylaniline as a pale yellow needle.

$^1$H-NMR (300 MHz, CDCl$_3$)

δ: 7.48 (2H, d, J=8.7 Hz), 7.36 (2H, m), 7.17 (2H, m), 7.12 (1H, m), 6.97 (2H, d, J=8.7 Hz), 6.07 (1H, s)

(2) 1.00 g (5.15 mmol) of 4-cyano-N-phenylaniline was dissolved in 40 ml of toluene, treated with 618 mg (15.5 mmol) of 60% sodium hydride and 2.95 g (15.5 mmol) of p-toluenesulfonyl chloride, and heated at 100° C. for 3 days with stirring. The reaction mixture was treated with water and extracted twice with ethyl acetate, and the ethyl acetate layer was washed with water and saturated brine, and dried over anhydrous sodium sulfate. After concentrating under reduced pressure, the residue was subjected to column chromatography on silica gel eluting with hexane: ethyl acetate (80:20) to recover 510 mg of the starting material 4-cyano-N-phenylaniline and then obtain as an intended substance 4-cyano-N-phenyl-N-p-toluenesulfonylaniline. The recovered starting material was subjected to the same reaction and combined with 4-cyano-N-phenyl-N-p-toluenesulfonylaniline to give 1.47 g (yield: 82%) in total as a pale yellow powder.

$^1$H-NMR (300 MHz, CDCl$_3$)

δ:7.61 (2H, d, J=8.3 Hz), 7.56 (2H, d, J=8.7 Hz), 7.38 (3H, m), 7.34 (2H, d, J=8.7 Hz), 7.30 (2H, d, J=8.3 Hz), 7.21 (2H, m), 2.44 (3H, s)

(3) 1.26 g (3.62 mmol) of 4-cyano-N-phenyl-N-p-toluenesulfonylaniline was dissolved in a mixture of 36.2 ml of toluene and 7.24 ml of dichloromethane under argon atmosphere and cooled to −78° C. and treated with 5.43 ml (5.43 mmol) of a 1M solution of diisobutylaluminium hydride in toluene. After stirring at −78° C. for 0.5 hour, the mixture was stirred further for 2 hours at room temperature. The reaction mixture was treated with 7.24 ml of methanol and 7.24 ml of 2N aqueous hydrochloric acid and extracted twice with ethyl acetate, and the ethyl acetate layer was washed twice with water and once with saturated brine, and dried over anhydrous sodium sulfate. After concentrating under reduced pressure, the residue was subjected to column chromatography on silica gel, and the fraction eluted with hexane: ethyl acetate (80:20–70:30) was concentrated under reduced pressure to obtain 1.04 g (yield: 82%) of 4-formyl-N-phenyl-N-p-toluenesulfonylaniline as a pale yellow powder.

$^1$H-NMR (300 MHz, CDCl$_3$)

δ: 9.94 (1H, s), 7.79 (2H, d, J=8.3 Hz), 7.62 (2H, d, J=8.3 Hz), 7.40 (2H, d, J=8.3 Hz), 7.36 (3H, m), 7.29 (2H, d, J=8.3 Hz), 7.25 (2H, m), 2.44 (3H, s)

(4) 1.00 g (2.85 mmol) of 4-formyl-N-phenyl-N-p-toluenesulfonylaniline was dissolved in 200 ml of methanol, treated with 108 mg (2.85 mmol) of sodium borohydride and stirred at room temperature for 0.5 hours. The reaction mixture was concentrated under reduced pressure, treated with ethyl acetate, washed with water and saturated brine, and dried over anhydrous sodium sulfate. The mixture was concentrated under reduced pressure to obtain 1.05 g (quantitative yield) of 4-hydroxymethyl-N-phenyl-N-p-toluenesulfonylaniline as a colorless oil.

$^1$H-NMR (300 MHz, CDCl$_3$)

δ: 7.58 (2H, d, J=8.3 Hz), 7.20–7.35 (11H, m), 4.67 (2H, d, J=5.8 Hz), 2.43 (3H, s), 1.69 (1H, t, J=5.8 Hz)

(5) 1.05 g (2.85 mmol) of 4-hydroxymethyl-N-phenyl-N-p-toluenesulfonylaniline, 231 μl (2.85 mmol) of pyridine and 229 μl (3.14 mmol) of thionyl chloride were processed similarly to Example 159 to obtain 1.05 g (quantitative yield) of 4-chloromethyl-N-phenyl-N-p-toluenesulfonylaniline as a colorless oil.

$^1$H-NMR (300 MHz, CDCl$_3$)

δ: 7.59 (2H, d, J=8.3 Hz), 7.21–7.36 (11H, m), 4.54 (2H, s), 2.44 (3H, s)

(6) Similarly to Example 30 and starting from 1.05 g (2.82 mmol) of 4-chloromethyl-N-phenyl-N-p-toluenesulfonylaniline, 494 mg (2.85 mmol) of 4-trimethylsilyloxypyrrolidin-2-one and 160 mg (2.85 mmol) of powdered potassium hydroxide, 439 mg (yield: 35%) of 4-hydroxy-1-[4-(N-phenyl-N-p-toluenesulfonylamino)benzyl]pyrrolidin-2-one as a tan oil.

$^1$H-NMR (300 MHz, CDCl$_3$)

δ: 7.57 (2H, d, J=8.3 Hz), 7.15–7.35 (11H, m), 4.50 (1H, m), 4.48 (1H, d, J=15.1 Hz), 4.40 (1H, d, J=15.1 Hz), 3.51 (1H, dd, J=10.9, 5.5 Hz), 3.19 (1H, dd, J=10.9, 1.9 Hz), 2.73 (1H, dd, J=17.3, 6.4 Hz), 2.44 (3H, s), 2.42 (1H, dd, J=17.3, 2.3 Hz)

(7) Starting from 390 mg (0.893 mmol) of 4-hydroxy-1-[4-(N-phenyl-N-p-toluenesulfonylamino)benzyl]pyrrolidin-2-one, 374 μl (2.68 mmol) of triethylamine and 208 μl (2.68 mmol) of methanesulfonyl chloride, 419 mg (yield: 91%) of 4-methanesulfonyloxy-1-[4-(N-phenyl-N-p-toluenesulfonylamino)benzyl]pyrrolidin-2-one was obtained as a colorless oil.

$^1$H-NMR (300 MHz, CDCl$_3$)

δ: 7.57 (2H, d, J=8.3 Hz), 7.15–7.35 (11H, m), 5.28 (1H, m), 4.48 (1H, d, J=15.6 Hz), 4.42 (1H, d, J=15.6 Hz), 3.65 (1H, dd, J=12.1, 5.5 Hz), 3.50 (1H, dd, J=12.1, 1.9 Hz), 2.98 (3H, s), 2.86 (1H, dd, J=17.9, 6.8 Hz), 2.70 (1H, dd, J=17.9, 2.3 Hz), 2.44 (3H, s)

(8) Starting from 350 mg (0.680 mmol) of 4-methanesulfonyloxy-1-[4-(N-phenyl-N-p-toluenesulfonylamino)benzyl]pyrrolidin-2-one and 155 mg (1.36 mmol) of potassium thioacetate, 268 mg (yield: 80%) of 4-acetylthio-1-[4-(N-phenyl-N-p-toluenesulfonylamino)benzyl]pyrrolidin-2-one was obtained as a colorless oil.

$^1$H-NMR (300 MHz, CDCl$_3$)

δ: 7.57 (2H, d, J=8.3 Hz), 7.20–7.36 (9H, m), 7.16 (2H, d, J=8.3 Hz), 4.45 (1H, d J=15.1 Hz), 4.39 (1H, d, J=15.1 Hz), 4.05 (1H, m), 3.74 (1H, dd, J=10.6, 7.7 Hz), 3.16 (1H, dd, J=10.6, 4.9 Hz), 2.90 (1H, dd, J=17.5, 8.9 Hz), 2.44 (3H, s), 2.40 (1H, m), 2.31 (3H, s)

Example 204

4-Mercapto-1-[4-(N-phenyl-N-p-toluenesulfonylamino)benzyl]pyrrolidin-2-one

Starting from 120 mg (0.234 mmol) of 4-acetylthio-1-[4-(N-phenyl-N-p-toluenesulfonylamino)benzyl]pyrrolidin-2-one obtained in Example 203 and 345 μl (4.85 mmol) of acetyl chloride and by a method similar to that in Example 126, 65.3 mg (yield:59%) of 4-mecapto-1-[4-(N-phenyl-N-p-toluenesulfonylamino)benzyl]pyrrolidin-2-one was obtained as a white powder.

$^1$H-NMR (300 MHz, CDCl$_3$)

δ: 7.57 (2H, d, J=8.3 Hz), 7.15–7.36 (11H, m), 4.45 (1H, d, J=15.5 Hz), 4.40 (1H, d, J=15.5 Hz), 3.64 (1H, dd, J=10.2, 7.4 Hz), 3.54 (1H, m), 3.16 (1H, dd, J=10.2, 4.9 Hz), 2.90 (1H, dd, J=17.3, 8.1 Hz), 2.44 (3H, s), 2.40 (1H, dd, J=17.3, 6.0 Hz), 1.86 (1H, d, J=6.4 Hz)

Experiment 1

Production of Recombinant Human MMP-13 Enzyme

Based on the sequence described in the literature by Freije, J. M. et al (Journal of Biological Chemistry, 269: 16766–16773, 1994) and using a PCR method known per se, a human MMP-13 cDNA was obtained.

A pBlueBac4 (Invitrogen) and a Baculovirus vector Bac-N-Blue (Invitrogen) to each of which the human MMP-13 cDNA obtained above was integrated were co-transfected to an Sf9 cell to obtain a MMP-13-expressing recombinant virus.

The recombinant virus thus obtained was infected to a High-Five cell (Invitrogen), and the culture supernatant after three days was employed as an enzyme solution. Experiment 2 Assay of MMP-13 inhibiting activity 75 µl of a sample containing the recombinant human MMP-13, 200 mM sodium chloride, 20 mM calcium chloride, 0.1% Brij 35, 1 mM 2-mercantoethanol, 200 mM tris-HCl buffer solution (pH 7.5) and a test substance at various concentrations was treated with 25 µl of 40 µM MOCAc-Pro-Leu-Gly-Leu-$A_2$pr(DNP)-Ala-Arg-$NH_2$ (PEPTIDE KENKYUSHO) to initiate a reaction and kept at 37° C. for 2 hours, and then 100 µl of 500 mM sodium acetate-HCl buffer solution (pH 3.0) was added to terminate the reaction.

The level of liberated MOCAc-Pro-Leu-Gly was determined using a fluorophotometer (MTP-32/F2: CORONA DENKI) at the excitation wavelength of 330 nm and the fluorescent wavelength of 405 nm. The fluorescent level of the reaction in the absence of a test substance was regarded as 100%, and the concentration of each test substance required for achieving 50% inhibition was indicated as $IC_{50}$.

The followings are the structures of the compositions of Examples together with their $IC_{50}$s.

TABLE 1

| Example | m | R1 | $IC_{50}$ (µM) |
|---|---|---|---|
| 1 | 0 | H | 0.005 |
| 2 | 0 | $C_2H_5$ | >10 |
| 3 | 0 | $C_2H_4CO_2Et$ | >10 |
| 4 | 0 | $CH_2Ph$ | >10 |
| 5 | 0 | $COCH_3$ | 0.03 |
| 6 | 0 | COPh | 0.002 |
| 10 | 1 | $COCH_3$ | 0.4 |
| 11 | 0 | (tetrahydrofurfuryl-S-CH$_2$) | 0.1 |

TABLE 2

| Example | R1 | Y | $IC_{50}$ (µM) |
|---|---|---|---|
| 7 | $COCH_3$ | $CH_3$ | 0.05 |
| 8 | H | $CH_3$ | 0.02 |
| 9 | $C_2H_4CO_2Et$ | OH | 1 |

TABLE 3

| Example | R1 | * | $IC_{50}$ (µM) |
|---|---|---|---|
| 15 | $COCH_3$ | | 0.01 |
| 16 | COPh | | 0.002 |
| 17 | H | | 0.005 |
| 18 | $CH_2OCOBu^t$ | | 0.03 |
| 21 | $COCH_3$ | (S) | 4 |
| 22 | H | (S) | 0.3 |
| 24 | $COCH_3$ | (R) | 0.009 |
| 25 | H | (R) | 0.003 |
| 49 | $H_2NCO-$ | | 0.00065 |
| 50 | MeNHCO— | | 0.003 |
| 51 | EtNHCO— | | 0.001 |
| 52 | n-PrNHCO— | | 0.002 |
| 53 | PhNHCO— | | 0.001 |
| 54 | $PhCH_2NHCO-$ | | 0.0015 |
| 55 | MeCONHCO— | | 0.0013 |
| 56 | PhCONHCO— | | 0.0014 |
| 57 | EtOOCNHCO— | | 0.00081 |
| 58 | $EtOOCCH_2NHCO-$ | | 0.0007 |
| 59 | $HOOCCH_2NHCO-$ | | 0.002 |
| 60 | $EtOOCCH_2CH_2NHCO-$ | | 0.0009 |
| 61 | $HOOCCH_2CH_2NHCO-$ | | 0.0018 |
| 62 | $(CH_3)_2NCO-$ | | 3 |
| 63 | (morpholinyl-CO-) | | 2 |
| 64 | EtCO— | | 0.0032 |
| 65 | n-PrCO– | | 0.0013 |
| 66 | n-BuCO— | | 0.001 |
| 67 | iso-PrCO– | | 0.011 |
| 68 | $PhCH_2CO-$ | | 0.002 |
| 69 | 4-Cl—$PhCH_2CO-$ | | 0.02 |
| 70 | $Ph_2CHCO-$ | | 0.002 |
| 71 | $EtOOCCH_2CO-$ | | 0.00089 |
| 72 | $tert-BuOOCCH_2CO-$ | | 0.0024 |
| 73 | $HOOCCH_2CO-$ | | 0.011 |
| 74 | $EtOOCCH_2CH_2CO-$ | | 0.0054 |
| 75 | $HOOCCH_2CH_2CO-$ | | 0.008 |
| 76 | MeNHCS— | | 0.0012 |
| 77 | EtNHCS— | | 0.0016 |
| 78 | MeOOCS— | | >10 |
| 79 | EtS— | | 0.1 |
| 80 | $n-C_6H_{13}S-$ | | 1.0 |
| 81 | tert-BuS— | | 1 |
| 82 | $EtOOCCH_2S-$ | | 0.05 |
| 83 | $HOOCCH_2S-$ | | 0.4 |
| 84 | $EtOOCCH_2CH_2S-$ | | 0.032 |
| 85 | $HOOCCH_2CH_2S-$ | | 0.46 |
| 86 | 2-(HOOC)—PhS— | | 0.5 |

TABLE 3-continued

Structure: R1-S-[pyrrolidinone with *]-N-CH2-C6H4-O-C6H5 (para-phenoxy)

| Example | R1 | * | IC$_{50}$ ($\mu$M) |
|---|---|---|---|
| 87 | 2-(O$_2$N)—PhS— | | 0.6 |
| 88 | [4-amino-2-methylpyrimidin-5-ylmethyl-N(CHO)-N=C(Me)-C(Me)=CH-CH2-CH2-OH group] | | 0.67 |
| 89 | Me— | | 0.7 |
| 90 | HOCH$_2$CH$_2$— | | 5 |
| 91 | HOOCCH$_2$— | | 1 |
| 92 | EtOOCCH$_2$CH$_2$— | | 2 |
| 93 | HOOCCH$_2$CH$_2$— | | 6 |
| 94 | 4-Br—PhCH$_2$— | | 0.3 |
| 95 | 4-(MeOOC)—PhCH$_2$— | | 0.4 |
| 96 | 4-(HOOC)—PhCH$_2$— | | 0.7 |
| 97 | PhSO$_2$CH$_2$CH$_2$— | | 2 |
| 98 | MeOCH$_2$— | | 0.2 |
| 99 | [3-methyl-isobenzofuran-1(3H)-one] | | 0.007 |
| 100 | MeCONHCH$_2$— | | 2 |
| 101 | tert-BuCONHCH$_2$— | | 3 |
| 102 | PhCONHCH$_2$— | | 0.1 |
| 103 | EtOOCNHCH$_2$— | | 0.3 |
| 104 | [N-ethyl-phthalimide] | | 0.2 |
| 105 | [3-methyl-pyrrolidine-2,5-dione] | | 0.04 |
| 106 | [1,3-dimethyl-pyrrolidine-2,5-dione] | | 0.02 |
| 107 | EtOOC— | | 0.03 |

TABLE 4

Structure: R1-S-[pyrrolidinone]-N-CH2-C6H4-O-C6H5 (meta-phenoxy)

| Example | R1 | IC$_{50}$ ($\mu$M) |
|---|---|---|
| 40 | COCH$_3$ | 1 |
| 41 | H | 0.2 |

TABLE 5

Structure: R1-S-[pyrrolidinone with * and Y substituent]-N-CH2-C6H4-O-C6H5 (para-phenoxy)

| Example | relative configuration | R1 | Y | IC$_{50}$ ($\mu$M) |
|---|---|---|---|---|
| 20 | | COCH$_3$ | CH$_2$OH | 0.01 |
| 38 | | COCH$_3$ | CH$_2$OCH$_2$Ph | 0.005 |
| 39 | | H | CH$_2$OCH$_2$Ph | 0.009 |
| 175 | cis | Ac | Me | 0.1 |
| 175 | cis | H | Me | 0.05 |
| 177 | trans | Ac | Me | 0.002 |
| 178 | trans | H | Me | 0.005 |
| 179 | trans | Ac | iso-Bu | 0.009 |
| 180 | trans | H | iso-Bu | 0.02 |
| 181 | trans | Ac | PhCH$_2$ | 0.008 |
| 182 | trans | H | PhCH$_2$ | 0.02 |
| 183 | trans | Ac | n-PrNHCOOCH$_2$ | 0.012 |
| 184 | trans | H | n-PrNHCOOCH$_2$ | 0.0023 |
| 185 | trans | Ac | [2-ethoxy-tetrahydropyran] | 0.006 |
| 186 | trans | Ac | EtOOCCH$_2$NHCO | 0.05 |
| 187 | trans | Ac | H$_2$NCO | 0.36 |
| 188 | trans | H | H$_2$NCO | 0.013 |
| 189 | trans | Ac | HOCH$_2$CH$_2$NHCO | 0.089 |
| 190 | trans | H | HOCH$_2$CH$_2$NHCO | 0.025 |
| 191 | trans | Ac | [N-(pyridin-4-ylmethyl)acetamide] | 0.12 |

TABLE 5-continued

| Example | relative configuration | R1 | Y | IC$_{50}$ ($\mu$M) |
|---|---|---|---|---|
| 192 | trans | H | (pyridin-4-yl-CH$_2$-NH-C(=O)-) | 0.019 |

TABLE 6

| Example | relative configuration | R1 | Y | IC$_{50}$ ($\mu$M) |
|---|---|---|---|---|
| 194 | trans | Ac | Me— | 0.03 |
| 195 | trans | H | Me— | 0.006 |

TABLE 7

| Example | m | Q | * | Y | IC$_{50}$ ($\mu$M) |
|---|---|---|---|---|---|
| 12 | 0 | S-S | | =O | 0.009 |
| 13 | 1 | S-S | | =O | >10 |
| 14 | 0 | S | | =O | 0.1 |
| 19 | 0 | S-S | | H | 0.2 |
| 23 | 0 | S-S | (S,S) | H | >10 |
| 26 | 0 | S-S | (R,R) | H | 0.07 |

TABLE 8

| Example | R1 | IC$_{50}$ ($\mu$M) |
|---|---|---|
| 27 | COCH$_3$ | >10 |
| 28 | COPh | 1 |
| 29 | H | 2 |

TABLE 9

| Example | R1 | R$^c$ | R$^d$ | R$^e$ | R$^f$ | R$^g$ | IC$_{50}$ ($\mu$M) |
|---|---|---|---|---|---|---|---|
| 30 | Ac | H | H | H | H | F | 0.01 |
| 31 | H | H | H | H | H | F | 0.003 |
| 32 | Ac | H | H | H | H | Cl | 0.008 |
| 33 | H | H | H | H | H | Cl | 0.005 |
| 34 | Ac | H | H | H | H | Br | 0.01 |
| 35 | H | H | H | H | H | Br | 0.006 |
| 36 | Ac | H | H | H | H | OCH$_3$ | 0.05 |
| 37 | H | H | H | H | H | OCH$_3$ | 0.005 |
| 112 | Ac | H | H | F | H | H | 0.02 |
| 113 | H | H | H | F | H | H | 0.004 |
| 114 | Ac | H | H | H | F | H | 0.01 |
| 115 | H | H | H | H | F | H | 0.004 |
| 116 | Ac | H | H | H | H | F | 7 |
| 117 | Ac | H | H | H | H | F | 0.007 |
| 118 | H | H | H | H | H | F | 0.002 |
| 119 | Ac | H | H | F | H | F | 0.01 |
| 120 | H | H | H | F | H | F | 0.007 |
| 121 | Ac | H | H | H | F | F | 0.02 |
| 122 | H | H | H | H | F | F | 0.02 |
| 123 | Ac | H | H | H | H | Me | 0.0089 |
| 124 | Ac | H | H | H | H | Et | 0.0070 |
| 125 | Ac | H | H | H | H | Cl | 0.0061 |
| 126 | H | H | H | H | H | Cl | 0.0017 |
| 127 | Ac | H | H | H | H | Me | 0.01 |

TABLE 9-continued

| Example | R1 | R$^c$ | R$^d$ | R$^e$ | R$^f$ | R$^g$ | IC$_{50}$ ($\mu$M) |
|---|---|---|---|---|---|---|---|
| 128 | H | H | H | H | H | Me | 0.007 |
| 129 | Ac | H | H | H | H | CF$_3$ | 0.03 |

TABLE 9-continued

| Example | R1 | $R^c$ | $R^d$ | $R^e$ | $R^f$ | $R^g$ | $IC_{50}$ ($\mu M$) |
|---|---|---|---|---|---|---|---|
| 130 | H | H | H | H | H | $CF_3$ | 0.01 |
| 131 | Ac | H | H | H | H | COOEt | 0.02 |
| 132 | H | H | H | H | H | COOEt | 0.0033 |
| 133 | Ac | H | H | H | H | COOH | >10 |
| 134 | Ac | H | H | H | H | $CONH_2$ | 0.029 |
| 135 | H | H | H | H | H | $CONH_2$ | 0.0092 |
| 136 | Ac | H | H | H | H | OH | 0.009 |
| 137 | H | H | H | H | H | OH | 0.003 |
| 138 | Ac | H | H | H | H | OEt | 0.02 |
| 139 | H | H | H | H | H | OEt | 0.006 |
| 140 | Ac | H | H | H | H | $OCF_3$ | 0.02 |
| 141 | H | H | H | H | H | $OCF_3$ | 0.01 |
| 142 | Ac | H | H | H | H | $NO_2$ | 0.053 |
| 143 | H | H | H | H | H | $NO_2$ | 0.011 |
| 144 | Ac | H | H | H | H | NHCOMe | 0.0027 |
| 145 | H | H | H | H | H | NHCOMe | 0.0013 |
| 146 | Ac | H | H | H | H | $NHSO_2Me$ | 0.025 |
| 147 | H | H | H | H | H | $NHSO_2Me$ | 0.0012 |
| 148 | Ac | H | H | H | H | NHCONHEt | 0.025 |
| 149 | H | H | H | H | H | NHCONHEt | 0.0035 |
| 150 | Ac | $NO_2$ | H | H | H | H | 5.5 |
| 151 | Ac | H | $NO_2$ | H | H | H | >10 |
| 152 | Ac | H | $NHSO_2Me$ | H | H | H | >10 |
| 153 | H | H | $NHSO_2Me$ | H | H | H | 4 |
| 199 | Ac | H | H | H | H | Br | 0.006 |
| 200 | H | H | H | H | H | Br | 0.002 |

TABLE 10

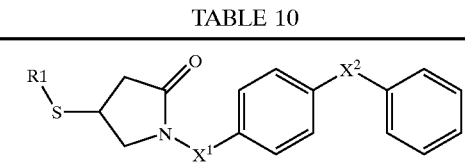

| Example | R1 | $X^1$ | $X^2$ | $IC_{50}$ ($\mu M$) |
|---|---|---|---|---|
| 154 | Ac | $CH_2$ | S | 0.02 |
| 155 | H | $CH_2$ | S | 0.007 |
| 159 | Ac | $CH_2$ | $CH_2$ | 0.5 |
| 160 | H | $CH_2$ | $CH_2$ | 0.09 |
| 161 | Ac | $CH_2$ | CO | 0.2 |
| 162 | H | $CH_2$ | CO | 0.02 |
| 163 | Ac | $CH_2$ | $OCH_2$ | 0.5 |
| 164 | H | $CH_2$ | $OCH_2$ | 0.08 |
| 165 | Ac | $CH_2$ | $CH_2O$ | 1 |
| 166 | H | $CH_2$ | $CH_2O$ | 0.1 |
| 167 | Ac | $CH_2$ | $CH_2CH_2$ | 0.4 |
| 168 | H | $CH_2$ | $CH_2CH_2$ | 0.07 |
| 169 | Ac | $CH_2CH_2$ | O | 7 |
| 170 | H | $CH_2CH_2$ | O | 0.5 |
| 171 | Ac | $CH_2$ | SO | >10 |
| 172 | H | $CH_2$ | SO | >10 |
| 173 | Ac | $CH_2$ | $SO_2$ | >10 |
| 174 | H | $CH_2$ | $SO_2$ | 0.51 |
| 196 | Ac | CO | O | >10 |

TABLE 11

| Example | R1 | T | $IC_{50}$ ($\mu M$) |
|---|---|---|---|
| 156 | Ac | 4-methylphenoxy-2-pyridyl | 0.7 |
| 157 | Ac | 4-methylphenoxy-3-thienyl | 0.006 |
| 158 | H | 4-methylphenoxy-3-thienyl | 0.004 |
| 193 | Ac | 4-methyl-1-(benzoyl)piperidinyl | >10 |
| 198 | Ac | (4-methylphenyl)(benzo[1,3]dioxol-5-yl)methanone | 0.012 |
| 201 | Ac | 2-methyldibenzofuran-yl | 0.3 |
| 202 | H | 2-methyldibenzofuran-yl | 0.1 |
| 203 | Ac | N-phenyl-N-(4-methylphenyl)-4-methylbenzenesulfonamide | >10 |
| 204 | H | N-phenyl-N-(4-methylphenyl)-4-methylbenzenesulfonamide | 3.9 |

TABLE 12

| Example | $R^h$ | $R^i$ | $IC_{50}$ (µM) |
|---|---|---|---|
| 108 | H | AcS | 0.3 |
| 109 | H | HS | 0.06 |
| 110 | AcS | H | 0.25 |
| 111 | HS | H | 0.017 |

TABLE 13

| Example | R1 | Y | $R^g$ | $IC_{50}$ (µM) |
|---|---|---|---|---|
| 42 | COCH₃ | =O | H | 0.07 |
| 43 | COCH₃ | =O | Br | 0.02 |
| 44 | COPh | =O | H | 0.01 |
| 45 | H | =O | H | 0.04 |
| 46 | COCH₃ | H | H | >10 |
| 47 | COPh | H | H | 4 |
| 48 | H | H | H | 5 |

Example 3

Assay of Cartilage Collagen Degradation Inhibiting Activity

A nasal cartilage was isolated aseptically from a sacrificed cow, and preincubated in a Dulbecco's modified eagle medium containing 5% heat-inactivated fetal bovine serum, 100 units/ml of penicillin G and 100 units/ml of streptomycin at 37° C. under 5% $CO_2$ and 95% air for 3 days. After completing the preincubation, a cartilage piece weighing about 10 mg was prepared and placed in 100 µl of a medium supplemented with a human recombinant interleukin-1β (IL-1β: *ZENZYME*) and a test compound. After incubating for 3 weeks in total during which the culture medium was replaced on the weekly basis, the total amount of hydroxyproline liberated into the culture medium and the amount of hydroxyproline remaining in the cartilage piece were determined and % collagen degradation was calculated. The collagen degradation inhibiting activity of a test compound was determined according to the following equation.

Equation: Collagen degradation inhibiting activity (%) =100×(Ci−Cs)/(Ci−Cc)

wherein Cc is % collagen degradation in the absence of both of IL-1β and compound, Ci is % collagen degradation in the presence of IL-1β, and Cs is a % collagen degradation in the presence of both of IL-1β and a test compound.

The followings are the collagen degradation inhibiting activities of the compounds of Examples.

TABLE 14

Cartilage collagen degradation inhibiting activity
(degradation inhibiting activity at 1 µM of compound)

| Example | % Inhibition |
|---|---|
| 24 | 91 |
| 25 | 88 |
| 39 | 39 |
| 126 | 70 |
| 156 | 84 |

INDUSTRIAL APPLICABILITY

Since an inventive compound (I) or a salt thereof has an excellent MMP inhibiting effect, especially MMP-13 inhibiting effect, it is useful as a safe prophylactic and therapeutic agent for osteoarthritis, rheumatoid arthritis, osteoporosis, cancer, periodontosis, corneal ulcer, pathologic bone resorption (such as Behcet's disease), nephritis, arteriosclerosis, pulmonary emphysema, cirrhosis, autoimmune disease (Crohn's disease and Sjögren's disease), cancer metastasis, contraception, etc.

What is claimed is:

1. A compound represented by Formula:

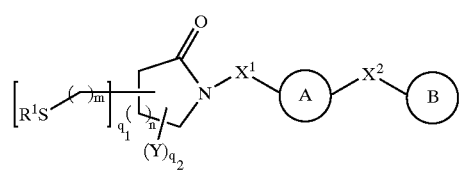

wherein ring A and ring B may be same or different and each is an optionally substituted homocyclic or heterocyclic ring,
wherein the substituents on ring A and ring B may be bound to each other and taken together with ring A, ring B and $X^2$ to form a condensed ring,
each $R^1$ may be same or different and is a hydrogen atom, an optionally substituted hydrocarbon group, an acyl group, an optionally substituted heterocyclic group or $SR^2$,
(wherein $R^2$ is a hydrogen atom, an optionally substituted hydrocarbon group, an acyl group or an optionally substituted heterocyclic group),
$X^1$ is a bond, an optionally substituted divalent $C_{1-3}$ aliphatic hydrocarbon group or —$NR^3$—,
(wherein $R^3$ is a hydrogen atom, an optionally substituted hydrocarbon group or an acyl group),
$X^2$ is a bond, an optionally substituted divalent $C_{1-3}$ aliphatic hydrocarbon group, —$NR^4$—, —O— or —$S(O)_p$—
wherein $R^4$ is a hydrogen atom, an optionally substituted hydrocarbon group or an acyl group,
and wherein p is 0, 1 or 2,
each Y may be same or different and is a hydrogen atom, an optionally substituted hydrocarbon group, a halogen atom, a carboxyl group, an acyl group, an optionally substituted hydroxy group, an optionally substituted amino group, $SR^5$, an oxo group, a thioxo group, an optionally substituted imino group, a nitro group or a cyano group,
wherein $R^5$ is a hydrogen atom, an optionally substituted hydrocarbon group, an acyl group or an optionally substituted heterocyclic group, each m may be same or different and is 0 or 1,
n is 2,
$q_1$ is an integer of 1 to 2n+4,
$q_2$ is an integer of 0 to 2n+3,
and the sum of $q_1$ and $q_2$ is 2n+4,
provided that when ring B is a nitrogen-containing heterocyclic ring then $X^2$ binds to a position capable of being substituted except for a nitrogen atom on ring B, or a salt thereof.

2. A compound according to claim 1 wherein each of ring A and ring B is an optionally substituted benzene ring.

3. A compound according to claim 1 wherein each $R^1$ may be same or different and is a hydrogen atom, an optionally substituted lower alkyl group, —(C=O)—$R^6$ or $SR^2$ wherein $R^6$ is a hydrogen atom, an optionally substituted hydrocarbon group, an optionally substituted amino group or an optionally substituted hydroxy group, and wherein $R^2$ has a meaning defined in claim 1.

4. A compound according to claim 1 wherein each $R^1$ may be same or different and is represented by Formula:

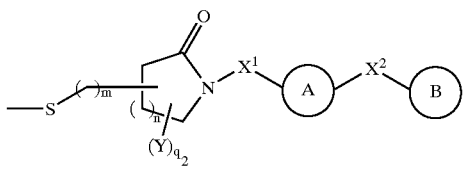

wherein each symbol has a meaning defined in claim 1, or by formula:

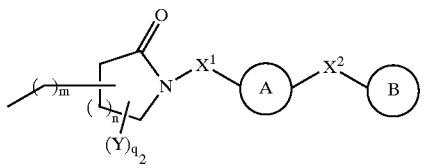

wherein each symbol has a meaning defined in claim 1.

5. A compound according to claim 1 wherein $X^1$ is an optionally substituted methylene group.

6. A compound according to claim 1 wherein $X^2$ is —O—.

7. A compound according to claim 1 wherein the group represented by Formula:

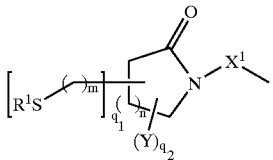

in Formula I is a group represented by Formula:

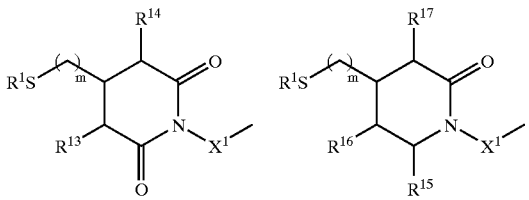

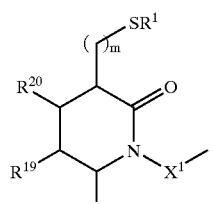 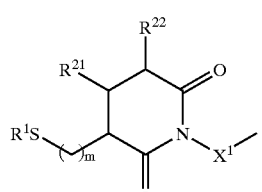

or 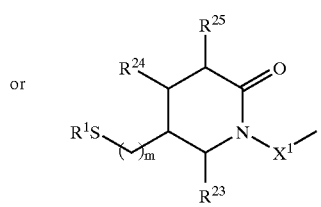

wherein each of $R^{13}$ to $R^{25}$ maybe same or different and each is a hydrogen atom, an optionally substituted lower alkyl group, an optionally substituted hydroxy group, an optionally substituted amino group or $SR^{12}$ wherein $R^{12}$ is a hydrogen atom, an optionally substituted hydrocarbon group, an acyl group or an optionally substituted heterocyclic group and each of other symbols has a meaning defined in claim 1.

8. A compound according to claim 1 wherein m is 0.

9. A method for producing a compound represented by Formula:

[I]

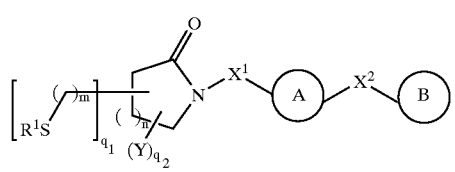

wherein each symbol has a meaning defined in claim 1 or a salt thereof, comprising reacting a compound represented by Formula:

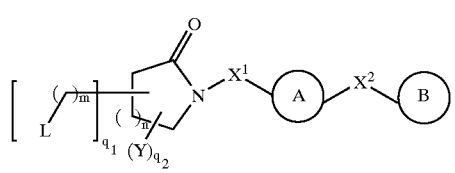

wherein L is a leaving group and each of other symbols has a meaning defined in claim 1 or a salt thereof with a compound represented by Formula:

$R^1SH$ wherein $R^1$ has a meaning defined in claim 1 or a salt thereof.

10. A method for producing a compound represented by Formula:

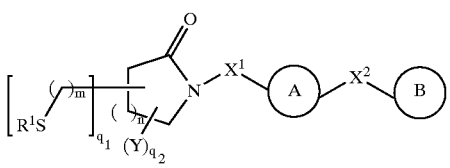

wherein each symbol has a meaning defined in claim 1 or a salt thereof, comprising reacting a compound represented by Formula:

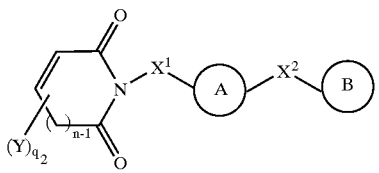

wherein each symbol has a meaning defined in claim 1 or a salt thereof, or a compound represented by Formula:

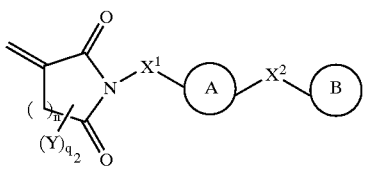

wherein each symbol has a meaning defined in claim 1 or a salt thereof, with a compound represented by Formula:

$R^1SH$ wherein $R^1$ has a meaning defined in claim 1 or a salt thereof.

11. A pharmaceutical composition comprising a compound represented by Formula:

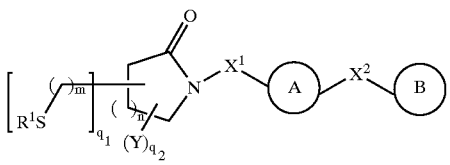

wherein ring A and ring B may be same or different and each is an optionally substituted homocyclic or heterocyclic ring,
wherein the substituents on ring A and ring B may be bound to each other and taken together with ring A, ring B and $X^2$ to form a condensed ring,
each $R^1$ may be same or different and is a hydrogen atom, an optionally substituted hydrocarbon group, an acyl group, an optionally substituted heterocyclic group or $SR^2$ wherein $R^2$ is a hydrogen atom, an optionally substituted hydrocarbon group, an acyl group or an optionally substituted heterocyclic group,
$X^1$ is a bond, an optionally substituted divalent $C_{1-3}$ aliphatic hydrocarbon group or —$NR^3$—wherein $R^3$ is a hydrogen atom, an optionally substituted hydrocarbon group or an acyl group, $X^2$ is a bond, an optionally substituted divalent $C_{1-3}$ aliphatic hydrocarbon group, —$NR^4$—, —O— or —$S(O)_p$—
wherein $R^4$ is a hydrogen atom, an optionally substituted hydrocarbon group or an acyl group,
and wherein p is 0, 1 or 2,
each Y may be same or different and is a hydrogen atom, an optionally substituted hydrocarbon group, a halogen atom, a carboxyl group, an acyl group, an optionally substituted hydroxy group, an optionally substituted amino group, $SR^5$, an oxo group, a thioxo group, an optionally substituted imino group, a nitro group or a cyano group,
wherein $R^5$ is a hydrogen atom, an optionally substituted hydrocarbon group, an acyl group or an optionally substituted heterocyclic group,
each m may be same or different and is 0 or 1,
n is 2,
$q_1$ is an integer of 1 to 2n+4,
$q_2$ is an integer of 0 to 2n+3,
and the sum of $q_1$ and $q_2$ is 2n+4
or a salt thereof
and a pharmaceutically acceptable carrier.

12. A matrix metalloprotease inhibitor comprising a pharmaceutical composition of a compound represented by Formula:

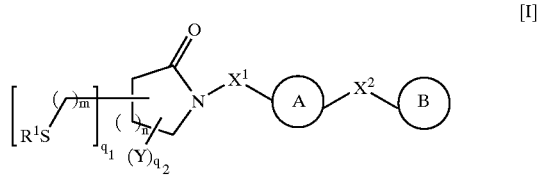

wherein ring A and ring B may be same or different and each is an optionally substituted homocyclic or heterocyclic ring,
wherein the substituents on ring A and ring B may be bound to each other and taken to 2ether with ring A, ring B and $X^2$ to form a condensed ring,
each $R^1$ may be same or different and is a hydrogen atom, an optionally substituted hydrocarbon group, an acyl group, an optionally substituted heterocyclic group or $SR^2$,
wherein $R^2$ is a hydrogen atom, an optionally substituted hydrocarbon group, an acyl group or an optionally substituted heterocyclic group,
$X^1$ is a bond, an optionally substituted divalent $C_{1-3}$ aliphatic hydrocarbon group or —$NR^3$—,
wherein $R^3$ is a hydrogen atom, an optionally substituted hydrocarbon group or an acyl group,
$X^2$ is a bond, an optionally substituted divalent $C_{1-3}$ aliphatic hydrocarbon group, —$NR^4$—, —O— or —$S(O)_p$—,
wherein $R^4$ is a hydrogen atom, an optionally substituted hydrocarbon group or an acyl group
wherein p is 0, 1 or 2,
each Y may be same or different and is a hydrogen atom, an optionally substituted hydrocarbon group, a halogen atom, a carboxyl group, an acyl group, an optionally substituted hydroxy group, an optionally substituted amino group, $SR^5$, an oxo group, a thioxo group, an optionally substituted imino group, a nitro group or a cyano group, wherein $R^5$ is a hydrogen atom, an optionally substituted hydrocarbon group, an acyl group or an optionally substituted heterocyclic group each m may be same or different and is 0 or 1, n is 2, $q_1$ is an integer of 1 to 2n+4, $q_2$ is an integer of 0 to 2n+3, and the sum of $q_1$ and $q_2$ is 2n+4 or a salt thereof and a pharmaceutically acceptable carrier.

13. A prophylactic and therapeutic agent against osteoarthritis, rheumatoid arthritis, osteoporosis, cancer, periodontosis or corneal ulcer comprising a a pharmaceutical composition of a compound represented by Formula:

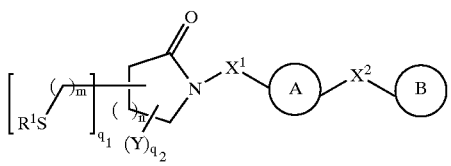

[I]

wherein ring A and ring B may be same or different and each is an optionally substituted homocyclic or heterocyclic ring, wherein the substituents on ring A and ring B may be bound to each other and taken together with ring A, ring B and $X^2$ to form a condensed ring, each $R^1$ may be same or different and is a hydrogen atom, an optionally substituted hydrocarbon group, an acyl group, an optionally substituted heterocyclic group or $SR^2$, wherein $R^2$ is a hydrogen atom, an optionally substituted hydrocarbon group, an acyl group or an optionally substituted heterocyclic group, $X^1$ is a bond, an optionally substituted divalent $C_{1-3}$ aliphatic hydrocarbon group or —$NR^3$—, wherein $R^3$ is a hydrogen atom, an optionally substituted hydrocarbon group or an acyl group, $X^2$ is a bond, an optionally substituted divalent $C_{1-3}$ aliphatic hydrocarbon group, —$NR^4$—, —O— or —$S(O)_p$—, wherein $R^4$ is a hydrogen atom, an optionally substituted hydrocarbon group or an acyl group wherein p is 0, 1 or 2, each Y may be same or different and is a hydrogen atom, an optionally substituted hydrocarbon group, a halogen atom, a carboxyl group, an acyl group, an optionally substituted hydroxy group, an optionally substituted amino group, $SR^5$, an oxo group, a thioxo group, an optionally substituted imino group, a nitro group or a cyano group, wherein $R^5$ is a hydrogen atom, an optionally substituted hydrocarbon group, an acyl group or an optionally substituted heterocyclic group each m may be same or different and is 0 or 1, n is 2, $q_1$ is an integer of 1 to 2n+4, $q_2$ is an integer of 0 to 2n+3, and the sum of $q_1$ and $q_2$ is 2n+4 or a salt thereof and a pharmaceutically acceptable carrier.

14. A method for treating osteoarthritis, rheumatoid arthritis, osteoporosis, periodontosis or corneal ulcer comprising administering a composition according to claim 11 or a salt thereof.

* * * * *